(12) United States Patent  
Siegel et al.

(10) Patent No.: US 8,940,776 B2  
(45) Date of Patent: Jan. 27, 2015

(54) 2-ACYLAMINOPROPOANOL-TYPE GLUCOSYLCERAMIDE SYNTHASE INHIBITORS

(75) Inventors: Craig Siegel, Woburn, MA (US); Cecilia M. Bastos, South Grafton, MA (US); David J. Harris, Lexington, MA (US); Angeles Dios, Waltham, MA (US); Edward Lee, Sudbury, MA (US); Richard Silva, Needham, MA (US); Lisa M. Cuff, Leominster, MA (US); Mikaela Levine, Swampscott, MA (US); Cassandra A. Celatka, Hull, MA (US); Frederic Vinick, Lexington, MA (US); Thomas H. Jozefiak, Belmont, MA (US); Yibin Xiang, Acton, MA (US); John Kane, Maynard, MA (US); Junkai Liao, Tewksbury, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 13/595,349

(22) Filed: Aug. 27, 2012

(65) Prior Publication Data

US 2012/0322787 A1    Dec. 20, 2012

Related U.S. Application Data

(63) Continuation of application No. 12/601,871, filed as application No. PCT/US2008/006906 on May 30, 2008, now Pat. No. 8,304,447.

(60) Provisional application No. 60/932,370, filed on May 31, 2007, provisional application No. 60/997,846, filed on Oct. 5, 2007.

(51) Int. Cl.
| | |
|---|---|
| A61K 31/42 | (2006.01) |
| A61K 31/4245 | (2006.01) |
| A61K 31/427 | (2006.01) |
| A61K 31/428 | (2006.01) |
| A61K 31/4025 | (2006.01) |

(Continued)

(52) U.S. Cl.  
CPC .......... C07D 295/125 (2013.01); C07D 319/18 (2013.01); C07D 405/06 (2013.01); C07D 405/12 (2013.01); C07D 407/12 (2013.01); C07D 409/12 (2013.01); C07D 409/14 (2013.01); C07D 411/12 (2013.01); C07D 413/12 (2013.01); C07D 413/14 (2013.01)  
USPC .......... 514/364; 514/365; 514/367; 514/380; 514/422; 514/424; 514/428; 548/131; 548/159; 548/204; 548/245; 548/518; 548/526; 548/527; 548/541; 548/571

(58) Field of Classification Search  
USPC ......... 514/364, 365, 367, 380, 422, 424, 428; 548/131, 159, 204, 245, 518, 526, 527, 548/541, 571  
See application file for complete search history.

(56) References Cited

U.S. PATENT DOCUMENTS

| 4,065,562 A | 12/1977 | Ohata et al. |
| 4,182,767 A | 1/1980 | Murai et al. |

(Continued)

FOREIGN PATENT DOCUMENTS

| EP | 126974 A1 | 12/1984 |
| EP | 0 144 290 A | 6/1985 |

(Continued)

OTHER PUBLICATIONS

Notice of Allowance and Fee(s) Due for U.S. Appl. No. 13/055,036; titled: "Glucosylceramide Synthase Inhibition for the Treatment of Collapsing Glomerulopathy and Other Glomerular Disease" Date Mailed: Oct. 31, 2012.

Qian, Q., et al., "Treatment prospects for autosomal-dominant polysystic kidney disease", *Kidney International*, vol. 59, pp. 2005-2002 (2001).

Non-Final Office Action for U.S. Appl. No. 12/681,291 dated Dec. 10, 2012, "Method of Treating Polycystic Kidney Diseases with Ceramide Derivatives".

(Continued)

*Primary Examiner* — Samantha Shterengarts  
(74) *Attorney, Agent, or Firm* — Hamilton, Brook, Smith & Reynolds, P.C.

(57) ABSTRACT

A compound is represented by Structural Formula (I):

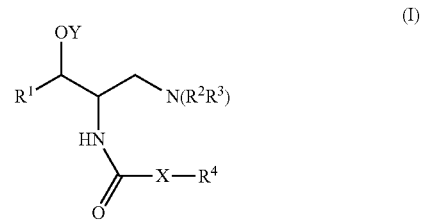

or a pharmaceutically acceptable salt thereof. A pharmaceutical composition comprises a compound represented by Structural Formula (I) or a pharmaceutically acceptable salt thereof. A method of treating a subject in need thereof comprises administering to the subject a therapeutically effective amount of a compound represented by Structural Formula (I) or a pharmaceutically acceptable salt thereof. The subject has type 2 diabetes; renal hypertrophy or hyperplasia associated with diabetic nephropathy; Tay-Sachs; Gaucher's; or Fabry's disease. Methods of decreasing plasma TNF-α, lowering blood glucose levels, decreasing glycated hemoglobin levels, inhibiting glucosylceramide synthase, and lowering glycosphingolipid concentrations in a subject in need thereof respectively comprise administering to the subject a therapeutically effective amount of a compound represented by Structural Formula (I) or a pharmaceutically acceptable salt thereof.

19 Claims, No Drawings

(51) Int. Cl.
*A61K 31/40* (2006.01)
*C07D 277/20* (2006.01)
*C07D 277/62* (2006.01)
*C07D 261/06* (2006.01)
*C07D 405/02* (2006.01)
*C07D 271/06* (2006.01)
*C07D 207/04* (2006.01)
*C07D 295/125* (2006.01)
*C07D 319/18* (2006.01)
*C07D 405/06* (2006.01)
*C07D 405/12* (2006.01)
*C07D 407/12* (2006.01)
*C07D 409/12* (2006.01)
*C07D 409/14* (2006.01)
*C07D 411/12* (2006.01)
*C07D 413/12* (2006.01)
*C07D 413/14* (2006.01)

(56) References Cited

U.S. PATENT DOCUMENTS

| | | | |
|---|---|---|---|
| 4,533,668 | A | 8/1985 | Matsumura et al. |
| 4,639,436 | A | 1/1987 | Junge et al. |
| 5,041,441 | A | 8/1991 | Radin et al. |
| 5,302,609 | A | 4/1994 | Shayman et al. |
| 5,472,969 | A | 12/1995 | Platt et al. |
| 5,525,616 | A | 6/1996 | Platt et al. |
| 5,631,394 | A | 5/1997 | Wei et al. |
| 5,707,649 | A | 1/1998 | Inokuchi et al. |
| 5,763,438 | A | 6/1998 | Inokuchi et al. |
| 5,849,326 | A | 12/1998 | Inokuchi et al. |
| 5,907,039 | A | 5/1999 | Jinbo et al. |
| 5,916,911 | A | 6/1999 | Shayman et al. |
| 5,945,442 | A | 8/1999 | Shayman et al. |
| 5,952,370 | A | 9/1999 | Shayman et al. |
| 5,972,928 | A | 10/1999 | Chatterjee |
| 6,030,995 | A | 2/2000 | Shayman et al. |
| 6,040,332 | A | 3/2000 | Shayman et al. |
| 6,051,598 | A | 4/2000 | Shayman et al. |
| 6,228,889 | B1 | 5/2001 | Chatterjee |
| 6,255,336 | B1 | 7/2001 | Shayman et al. |
| 6,335,444 | B1 | 1/2002 | Jimbo et al. |
| 6,407,064 | B2 | 6/2002 | Masuda et al. |
| 6,511,979 | B1 | 1/2003 | Chatterjee |
| 6,569,889 | B2 | 5/2003 | Shayman et al. |
| 6,610,703 | B1 | 8/2003 | Jacob et al. |
| 6,660,749 | B2 | 12/2003 | Butters et al. |
| 6,835,831 | B2 | 12/2004 | Hirth |
| 6,855,830 | B2 | 2/2005 | Hirth et al. |
| 6,890,949 | B1 | 5/2005 | Shayman et al. |
| 6,916,802 | B2 | 7/2005 | Shayman et al. |
| 7,148,251 | B2 | 12/2006 | Shayman |
| 7,196,205 | B2 | 3/2007 | Siegel et al. |
| 7,253,185 | B2 | 8/2007 | Shayman et al. |
| 7,265,228 | B2 | 9/2007 | Hirth et al. |
| 7,335,681 | B2 | 2/2008 | Shayman et al. |
| 7,615,573 | B2 | 11/2009 | Siegel et al. |
| 7,763,738 | B2 | 7/2010 | Hirth et al. |
| 8,003,617 | B2 | 8/2011 | Cheng et al. |
| 8,304,447 | B2 | 11/2012 | Siegel et al. |
| 8,309,593 | B2 | 11/2012 | Siegel et al. |
| 8,389,517 | B2 | 3/2013 | Ibraghimov-Beskrovnaya et al. |
| 8,716,327 | B2 | 5/2014 | Zhao et al. |
| 8,729,075 | B2 | 5/2014 | Ibraghimov-Beskrovnaya et al. |
| 2001/0003741 | A1 | 6/2001 | Masuda et al. |
| 2002/0156107 | A1 | 10/2002 | Shayman et al. |
| 2002/0198240 | A1 | 12/2002 | Shayman et al. |
| 2003/0050299 | A1 | 3/2003 | Hirth et al. |
| 2003/0073680 | A1 | 4/2003 | Shayman et al. |
| 2004/0260099 | A1 | 12/2004 | Shayman |
| 2005/0009872 | A1 | 1/2005 | Hirth et al. |
| 2005/0049235 | A1 | 3/2005 | Shayman et al. |
| 2005/0222244 | A1 | 10/2005 | Siegel et al. |
| 2005/0239862 | A1 | 10/2005 | Shayman et al. |
| 2005/0267094 | A1 | 12/2005 | Shayman et al. |
| 2006/0058349 | A1 | 3/2006 | Ali et al. |
| 2006/0074107 | A1 | 4/2006 | Butters et al. |
| 2006/0217560 | A1 | 9/2006 | Shayman |
| 2007/0066581 | A1 | 3/2007 | Aerts |
| 2007/0072916 | A1 | 3/2007 | Shayman |
| 2007/0112028 | A1 | 5/2007 | Orchard |
| 2007/0203223 | A1 | 8/2007 | Siegel et al. |
| 2008/0146533 | A1 | 6/2008 | Shayman et al. |
| 2009/0312392 | A1 | 12/2009 | Shayman et al. |
| 2010/0256216 | A1 | 10/2010 | Siegel et al. |
| 2010/0298317 | A1 | 11/2010 | Natoli et al. |
| 2011/0166134 | A1 | 7/2011 | Ibraghimov-Beskrovnaya et al. |
| 2011/0184021 | A1 | 7/2011 | Siegel et al. |
| 2012/0022126 | A1 | 1/2012 | Cheng et al. |
| 2012/0322786 | A1 | 12/2012 | Siegel et al. |
| 2013/0225573 | A1 | 8/2013 | Ibraghimov-Beskrovnaya et al. |

FOREIGN PATENT DOCUMENTS

| | | | |
|---|---|---|---|
| EP | 0 765 865 A1 | 4/1997 | |
| EP | 1 384 719 A1 | 1/2004 | |
| EP | 1 528 056 A1 | 5/2005 | |
| EP | 1 576 894 A1 | 9/2005 | |
| GB | 2054371 | 2/1981 | |
| JP | 35-5798 | 5/1960 | |
| JP | 9-169664 | 6/1997 | |
| JP | 9216856 A1 | 8/1997 | |
| JP | 10-324671 | 12/1998 | |
| JP | 10338636 A | 12/1998 | |
| JP | 2003-238410 A | 8/2003 | |
| WO | WO 97/10817 | 3/1997 | |
| WO | WO 98/52553 | 11/1998 | |
| WO | WO 01/04108 A1 | 1/2001 | |
| WO | WO 01/54654 A2 | 8/2001 | |
| WO | WO 01/80852 A1 | 11/2001 | |
| WO | WO 02/50019 A2 | 6/2002 | |
| WO | WO 02/055498 A1 | 7/2002 | |
| WO | WO 02/062777 A2 | 8/2002 | |
| WO | WO 03/008399 A1 | 1/2003 | |
| WO | WO 03/057874 A1 | 7/2003 | |
| WO | WO 03/068255 A1 | 8/2003 | |
| WO | WO 2004/007453 A1 | 1/2004 | |
| WO | WO 2004/056748 A1 | 7/2004 | |
| WO | WO 2004/078193 A1 | 9/2004 | |
| WO | WO 2005/039578 A2 | 5/2005 | |
| WO | WO 2005/040118 A1 | 5/2005 | |
| WO | WO 2005/063275 A1 | 7/2005 | |
| WO | WO 2005/087023 A1 | 9/2005 | |
| WO | WO 2005/108600 A1 | 11/2005 | |
| WO | WO 2005/123055 A2 | 12/2005 | |
| WO | WO 2006/023827 A2 | 3/2006 | |
| WO | WO 2006/053043 A2 | 5/2006 | |
| WO | WO 2006/053043 A3 | 5/2006 | |
| WO | WO 2007/022518 A2 | 2/2007 | |
| WO | WO 2007/134086 A2 | 11/2007 | |
| WO | WO 2007/134086 A3 | 11/2007 | |
| WO | WO 2008/011478 A2 | 1/2008 | |
| WO | WO 2008/011487 A2 | 1/2008 | |
| WO | WO 2008/012555 A2 | 1/2008 | |
| WO | WO 2008/024337 A2 | 2/2008 | |
| WO | WO 2008/150486 A2 | 12/2008 | |
| WO | WO 2009/045503 A1 | 4/2009 | |
| WO | WO 2009/117150 A2 | 9/2009 | |

OTHER PUBLICATIONS

Notice of Allowance and Fee(s) Due for U.S. Appl. No. 12/601,871; "2- Acylaminopropoanol-Type Glucosylceramide Synthase Inhibitors" Date Mailed: Aug. 9, 2012.

Final Office Action for U.S. Appl. No. 12/227,076 dated Mar. 20, 2012.

Non-Final Office Action for U.S. Appl. No. 13/122,135 mailed on Apr. 27, 2012.

Abdel-Magid, A., et al., "Metal-Assisted Aldol Condensation of Chiral α-Halogenated Imide Enolates: A Stereocontrolled Chiral Epoxide Syntheses,"*J. Am. Chem Soc.*, 108: 4595-4602 (1986).

(56) References Cited

OTHER PUBLICATIONS

Abe, A., et al., "Improved Inhibitors of Glucosylceramide Synthase," *J. Biochem.*, 111:191-196 (1992).

Abe, A., et al., "Induction of Glucosylceramide Synthase by Synthase Inhibitors and Ceramide," *Biochim. Biophys. Acta*, 1299: 333-341 (1996).

Abe, A., et al., "Metabolic Effects of Short-Chain Ceramide and Glucosylceramide on Sphingolipids and Protein Kinase C," *Eur. J. Biochem*, 210: 765-773 (1992).

Abe, A., et al., "Reduction of Globotriasylceramide in Fabry Disease mice by substrate deprivation", *J. Clin Invest.* 105(11): 1563-1571, (2000).

Abe, A., et al., "Structural and stereochemical studies of potent inhibitors of glucosylceramide synthase and tumor cell growth," *J. Lipid Research*, 36:611-621 (1995).

Adams, L.A., et al., "Nonalcoholic Fatty Liver Disease," *CMAJ*, 172(7):899-905 (2005).

Alberti, C., et al., "Chloramphenicol. XII and XIII. Chloramphenicol analogs. p-Nitrophenyldiaminopropanols", *Chemical Abstracts Service*, XP002495477 retrieved from CAPLUS Database accession No. 1957:17088 (abstract).

Alker, D., et al., "Application of Enantiopure Templated Azomethine Ylids to β-Hydroxy-α-amino Acid Syntheses," *Tetrahedron*, 54: 6089-6098 (1998).

Alon, R., et al., "Glycolipid Ligands for Selectins Support Leukocyte Tethering and Rolling Under Physiologic Flow Conditions," *J. Immunol.*, 154: 5356-5366 (1995).

Ames, Bruce N., "Assay of Inorganic Phosphate, Total Phosphate and Phosphatases," *Methods Enzymol.*, 8: 115-118 (1996).

Asano, N., "Glycosidase Inhibitors: Update and Perspectives on Practical Use," *Glycobiology*, 13(10):93R-104R (2003).

Bielawska, A., et al., "Ceramide-Mediated Biology: Determination of Structural and Stereospecific Requirements Through the Use of N-Acyl-Phenylaminoalcohol Analogs," *J. Biol. Chem.*, 267: 18493-18497 (1992).

Bielawska, et al., "Modulation of Cell Growth and Differentiation by Ceramide," *FEBS Letters*, 307(2): 211-214 (1992).

Blobe, G.C., et al., "Regulation of Protein Kinase C and its Role in Cancer Biology," *Cancer Metastasis Rev.*, 13: 411-431 (1994).

Brenkert, A., et al., "Synthesis of Galactosyl Ceramide and Glucosyl Ceramide by Rat Brain: Assay Procedures and Changes with Age," *Brain Res.*, 36: 183-193 (1972).

CAPLUS Listing of Accession No. 1985:221199, Keith McCullagh, et al., "Carboxyalkyl peptide derivatives."

Carson, K.G., et al., "Studies on Morpholinosphingolipids: Potent Inhibitors of Glucosylceramide Synthase," *Tetrahedron Letters*, 35(17): 2659-2662 (1994).

Chatterjee, S., et al., "Oxidized Low Density Lipoprotein Stimulates Aortic Smooth Muscle Cell Proliferation", *Glycobiology*, 6(3): 303-311 (1996).

Chatterjee, S., et al., "Role of lactosylceramide and MAP kinase in the proliferation of proximal tubular cells in human polycystic kidney disease", *Journal of Lipid Research*, 37(6): 1334-1344 (1996).

Clark, J.M., et al., "Nonalcoholic Fatty Liver Disease, An Underrecognized Cause of Cryptogenic Cirrhosis," *JAMA*, 289(22):3000-3004 (2003).

Comuzzie, A.G., et al., "The Baboon as a Nonhuman Primate Model for the Study of the Genetics of Obesity", *Obesity Research*, 11(1):75-80 (2003).

Dellaria, Jr., J.F., et al., "Enantioselective Synthesis of α-Amino Acid Derivatives via the Stereoselective Alkylation of a Homochiral Glycine Enolate Synthon," *J. Org. Chem.*, 54: 3916-3926 (1989).

Dickie, P., et al., "HIV-Associated Nephropathy in Transgenic Mice Expressing HIV-1 Genes," *Virology*, 185:109-119, 1991.

Dittert, L.W., et al., "Acetaminophen Prodrugs I-Synthesis, Physicochemical Properties and Analgesic Activity", *J. Pharm. Sci.* 57(5), pp. 774-780 (1968).

Elbein, A.D., "Glycosidase Inhibitors: Inhibitors of N-linked Oligosaccharide Processing," *The FASEB Journal*, 5:3055-3063 (1991).

European Search Report, European Application No. 09003291.3 dated Apr. 29, 2009.

Evans, D.A., et al., "Stereoselective Aldol Condensations Via Boron Enolates," *J. Am. Chem. Soc.*, 103: 3099-3111 (1981).

Fan, J-G., et al., "Preventie Effects of Metformin on Rats with Non-alcoholic Steatohepatitis," *Hepatology*, 34(4)(1), p. 501A (2003).

Felding-Habermann, B., et al., "A Ceramide Analog Inhibits T Cell Proliferative Response Through Inhibition of Glycosphingolipid Synthesis and Enhancement of N,N-Dimethylsphingosins Synthesis," *Biochemistry*, 29: 6314-6322 (1990).

Folch, J., et al., "A Simple Method for the Isolation and Purification of Total Lipids from Animal Tissues", *J. Biol. Chem.*, 226:497-509, 1956.

Freireich, E., et al., "Quantitative Comparison of Toxicity of Anticancer Agents in Mouse, Rat, Hampster, Dog, Monkey, and Man", *Cancer Chemother. Reports* 50(4):219 (1996).

Gatt, S., et al., "Assay of Enzymes of Lipid Metabolism with Colored and Fluorescent Derivatives of Natural Lipids," *Meth. Enzymol.*, 72: 351-375 (1981).

Gill-Randall, R.J., et al., "Is human Type 2 diabetes maternally inherited? Insights from an animal model", Diabet. Med. 21 (7):759 (2004).

Hakomori, S. "New Directions in Cancer Therapy Based on Aberrant Expression of Glycosphingolipids: Anti-adhesion and Ortho-Signaling Therapy," *Cancer Cells* 3(12): 461-470 (1991).

Hammett, L.P. *Physical Organic Chemistry*, (NY: McGraw), (1940).

Harwood, L.M., et al., "Asymmetric Cycloadditions of Aldehydes to Stabilized Azomethine Ylids: Enantiocontrolled Construction of β-Hydroxy-α-amino acid Derivitives," *Tetrahedron: Asymmetry*, 3(9): 1127-1130 (1992).

Harwood, L.M., et al., "Double diastereocontrol in the synthesis of enantiomerically pure polyoxamic acid," *Chem. Commun.*, 2641-2642 (1998).

Högberg, T. and ULF Norinder, "Theoretical and Experimental Methods in Drug Design Applied on Antipsychotic Dopamine Antagonists" *Textbook of Drug Design and Development*, pp. 55-91 (1991).

Hospattankar, A.V., et al., "Changes in Liver Lipids After Administration of 2-Decanoylamino-3-morpholinopropiophenone and Chlorpromazine," *Lipids*, 17(8): 538-543 (1982).

Inokuchi, et al., "Amino Alcohol Esters as Ceramide Analogs and Pharmaceuticals Containing Them for Treatment of Nerve Diseases," Abstract of CAPLUS Accession No. 1998: 786189, JP 10324671 (1998).

Inokuchi, et al., (1996): SNT International HCAPLUS database, Columbus (OH), accession No. 1996: 214749.

Inokuchi, J. et al., "Antitumor Activity Via Inhibition of Glycosphingolipid Biosynthesis," *Cancer Lett.*, 38:23-30(1987).

Inokuchi, J., et al., "Preparation of the Active Isomer of 1-phenyl-2-decanoylamino-3-morpholino-1-propanol, Inhibitor of Murine Clucocerebroside Synthetase," *Journal of Lipid Research*, 28:565-571 (1987).

Inokuchi, J., et al., "Inhibition of Experimental Metastasis of Murine Lewis Lung Carcinoma by an Inhibitor of Glucosylceramide Synthase and Its Possible Mechanism of Action", *Cancer Research*, 50:6731-6737 (1990).

Inokuchi, et al., "Aminoalcohol derivatives for treatment of abnormal proliferative diseases", *Chemical Abstracts Service*, XP002495476 retrieved from CAPLUS Database accession No. 1998:816280 (abstract).

International Preliminary Examination Report issued in International Application PCT/US2000/18935, titled: "Amino Ceramide-Like Compounds and Therapeutic Methods of Use" (WO 01/04108) dated Jul. 20, 2001.

International Preliminary Examination Report for International Application No. PCT/US2002/022659, titled: "Synthesis of UDP-Glucose: N-Acylsphingosine Glucosyltransferase Inhibitors" dated Jul. 24, 2003.

International Preliminary Report on Patentability for International Application No. PCT/US2008/011450, titled: "Method of Treating Polycystic Kidney Diseases With Ceramide Derivatives" dated Apr. 7, 2010.

(56) References Cited

OTHER PUBLICATIONS

International Preliminary Report on Patentability for International Application No. PCT/US2009/001773, titled: Method of Treating Lupus with Ceramide Derivatives: dated Sep. 21, 2010.
International Preliminary Report on Patentability issued in International Application PCT/US2007/068521, titled: "Methods of Treating Fatty Liver Disease" dated Nov. 11, 2008.
International Preliminary Report on Patentability issued in International Application PCT/US2005/040596, titled: "Methods of Treating Diabetes Mellitus" dated May 15, 2007.
International Preliminary Examination Report issued in International Application PCT/US2002/00808, titled: "Amino Ceramide-Like Compounds and Therapeutic Methods of Use", dated Jan. 10, 2003.
International Search Report for PCT/US2000/018935, titled: "Amino Ceramide-Like Compounds and Therapeutic Methods of Use" dated Nov. 28, 2000.
International Search Report for PCT/US2002/00808, titled: "Amino Ceramide-Like Compounds and Therapeutic Methods of Use", dated Oct. 1, 2002.
International Search Report for PCT/US2002/022659, titled: "Synthesis of UDP-Glucose: N-Acylsphingosine Glucosyltransferase Inhibitors" dated Nov. 5, 2002.
Jaffrézou, Jr., et al, "Inhibition of Lysosomal Acid Sphingomyelinase by Agents which Reverse Multidrug Resistance," *Biochim. Biophys. Acta*, 1266: 1-8 (1995).
Jankowski, K., "Microdetermination of phosphorus in organic materials from polymer industry by microwave-induced plasma atomic emission spectrometry after microwave digestion", *Microchem. J.*, 70:41-49, 2001.
Jimbo, M., et al., "Development of a New Inhibitor of Glucosylceramide Synthase", *J. Biochem*, 127: 485-491 (2000).
Kabayama, K., et al., "TNFα-induced Insulin Resistance in Adipocytes as a Membrane Microdomain Disorder: Involvement of Ganglioside GM3," *Glycobiology*, 15(1): 21-29 (2005).
Kalén, A., et al., "Elevated Ceramide Levels in $GH_4C_1$ Cells Treated with Retinoic Acid," *Biochim. Biophys. Acta*, 1125: 90-96 (1992).
Kopaczyk, K., C., et al., "In Vivo Conversions of Cerebroside and Ceramide in Rat Brain," *J. Lipid Res.*, 6: 140-145 (1965).
Kurosawa, M., et al., "$C^{14}$-Labeling of Novel Atypical β-Adrenoceptor Agonist, SM-11044," *Journal of Labelled Compounds and Radiopharmaceuticals*, 38(3): 285-297 (1996).
Lee, L., et al. "Improved Inhibitors of Glucosylceramide Synthase", *J. Bio Chem.*, 274(21): 14662-14669 (1999).
Masson, E., et al., "a-Series Gangliosides Mediate the Effects of Advanced Glycation End Products on Pericyte and Mesangial Cell Proliferation—A Common Mediator for Retinal and Renal Microangiopathy?," *Diabetes*, 54:220-227 (2005).
Mitchell, S., et al., "Glycosyltransferase Inhibitors: Synthesis of D-*threo*-PDMP, L-*threo*- PDMP, and Other Brain Glucosylceramide Synthase Inhibitors from D- or L-Serine," *J. Org. Chem.*, 63: 8837-8842 (1998).
Miura, T., et al., "Synthesis and Evaluation of Morpholino and Pyrrolidinosphingolipids as Inhibitors of Glucosylceramide Synthase", *Bioorganic and Medicinal Chemistry*, (6) 1481-1489 (1998).
Nakamura, K., et al., "Coomassie Brilliant Blue Staining of Lipids on Thin-Layer Plates," *Anal. Biochem.*, 142: 406-410 (1984).
Nicolaou, K., et al., "A Practical and Enantioselective Synthesis of Glycosphingolipids and Related Compounds. Total Synthesis of Globotriasylceramide (Gb3)," *J. Am. Chem., Soc.*, 110: 7910-7912 (1988).
Nishida, A., et al., "Practical Synthesis of *threo*-(1S, 2S)- and *erythro*-(1R, 2S)-1-Phenyl- 2-palmitoylamino-3-morpholino-l-propanol (PPMP) from L-Serine,"*Synlett*, 389-390(1998).
Nojiri, H., et al., "Ganglioside GM3: An acidic membrane component that increases during macrophage-like cell differentiation can induce monocytic differentiation of human myeloid and monoctyoid leukemic cell lines HL-60 and U937", *Proc. Natl. Acad. Sci.*, 83:782-786 (1986).

International Preliminary Report on Patentability for International Application No. PCT/US2008/006906, titled: "2-Acylaminopropoanol-Type Glucosylceramide Synthase Inhibitors" Dated Dec. 1, 2009.
International Preliminary Report on Patentability for International Application No. PCT/US2009/051864, titled "Glucosylceramide Synthase Inhibition for the Treatment of Collapsing Glomerulopathy and Other Glomerular Diseases" dated Feb. 1, 2011.
Notification of Transmittal of the International Search Report and Written Opinion of the International Searching Authority from International Application No. PCT/US2008/006906, titled: "2-Acylaminopropoanol-Type Glucosylceramide Synthase Inhibitors" dated Dec. 4, 2008.
Notification of Transmittal of the International Search Report and Written Opinion of the International Searching Authority from International Application No. PCT/US2008/011450, titled "Method of Treating Polycystic Kidney Diseases with Ceramide Derivatives" dated Jan. 21, 2009.
Notification of Transmittal of the International Search Report and Written Opinion of the International Searching Authority for International Application No. PCT/US2009/001773, titled "Method of Treating Lupus with Ceramide Derivatives", dated Nov. 11, 2009.
Notification of Transmittal of the International Search Report and the Written Opinion of the International Searching Authority for International Application No. PCT/US2009/051864, titled "Glucosylceramide Synthase Inhibition for the Treatment of Collapsing Glomerulopathy and Other Glomerular Diseases" dated Nov. 3, 2009.
Notification of Transmittal of the International Search Report and the Written Opinion of the International Searching Authority for International Application No. PCT/US2009/005435, titled: "2-Acylaminopropoanol-Type Glucosylceramide Synthase Inhibitors", dated Feb. 12, 2010.
Notification of Transmittal of the International Search Report and Written Opinion of the International Searching Authority from International Application No. PCT/US2007/068521, titled: "Methods of Treating Fatty Liver Disease" dated Nov. 21, 2007.
Ogawa, S., et al., "Synthesis and Biological Evaluation of Four Stereoisomers of PDMP-Analogue, N-(2-Decylamino-3-Hydroxy-3-Phenylprop-1-YL)-β-Valienamine, and Related Compounds," *Bioorganic & Medicinal Chemistry Letters*, 7(14):1915-1920 (1997).
Overkleeft, H.S., et al., "Generation of Specific Deoxynojirimycin-type Inhibitors of the Non-lysosomal Glucosylceramidase," *The Journal of Biological Chemistry*, 273(41):26522-26527 (1998).
Preiss, J., et al., "Quantitative Measurement of *sn*-1,2-Diaclglycerols Present in Platelets, Hepatocytes, and *ras*-and *sis*- Transformed Normal Rat Kidney Cells," *J. Biol.Chem.*, 261(19): 8597-8600 (1986).
Radin, N.S., "Killing Cancer Cells by Poly-drug Elevation of Ceramide Levels, A Hypothesis Whose Time has Come:," *Eur. I Biochem*. 268(2): 193-204 (2001).
Radin, N.S., et al., "Metabolic Effects of Inhibiting Glucosylceramide Synthesis with PDMP and Other Substances."*Advances in Lipid Research: Sphingolipid, Part B.*, R.M. Bell et al., Eds. (San Diego: Academic Press), 26: 183-213 (1993).
Radin, N.S., et al., "Ultrasonic Baths as Substitutes for Shaking Incubator Baths," *Enzyme*, 45: 867-70(1991).
Radin, N.S., et al., "Use of an Inhibitor of Glucosylceramide Synthesis, D-1-Phenyl-2-decanoylamino-3-morpholino-1-propanol," In *NeuroProtocols: A Companion to Methods in Neurosciences*, S.K. Fisher, et al., Eds., (San Diego: Academic Press) 3: 145-155 (1993).
Rosenwald, A.G., et al., "Effects of a Sphingolipid Synthesis Inhibitor on Membrane Transport Through the Secretory Pathway," *Biochemistry*, 31: 3581-3590 (1992).
Rosenwald, A.G., et al., "Effects of the Glucosphingolipid Synthesis Inhibitor, PDMP, on Lysosomes in Cultured Cells," *J. Lipid Res.*, 35: 1232-1240 (1994).
Rubino, Md., F., et al., "Letter to the Editor," *Annals of Surgery*, 240(2):389-390 (2004).
Sandhoff, K., et al., "Biosynthesis and Degradation of Mammalian Glycosphingolipids," *Phil. Trans. R. Soc. Lond*, B 358:847-861 (2003).

(56) References Cited

OTHER PUBLICATIONS

Sasaki, A., et al., "Overexpression of Plasma Membrane-Associated Sialidase Attenuates Insulin Signaling in Transgenic Mice," *The Journal of Biological Chemistry*, 278(30):27896-27902 (2003).
Shayman, J.A., et al., "Glucosphingolipid Dependence of Hormone-Stimulated Inositol Trisphophate Formation," *J. Biol. Chem.*, 265(21): 12135-12138 (1990).
Shayman, J.A., et al., "Modulation of Renal Epithelial Cell Growth by Glucosylceramide," *The Journal of Biological Chemistry*, 266(34):22968-22974 (1991).
Shukla, A., et al., "Metabolism of D-[$^3$H]*threo*-1-phenyl-2-decanoylamino-3-morpholino-1-propanol, an inhibitor of glucosylceramide synthesis and the synergistic action of an inhibitor of microsomal momooxygenase," *J. Lipid Research*, 32: 713-722 (1991).
Shukla, G., et al., "Rapid Kidney Changes Resulting From Glycosphingolipid Depletion by Treatment with a Glucosyltransferase Inhibitor," *Biochim. Biophys. Acta*, 1083: 101-108 (1991).
Shukla, G.S., et al., "Glucosylceramide Synthase of Mouse Kidney: Further Characterization with an Improved Assay Method," *Arch. Biochem. Biophys.*, 283(2): 372-378 (1990).
Skehan, P., et al., "New Colorimetric Cytotoxicity Assay for Anticancer-Drug Screening," *J. Natl. Cancer Inst.*, 82(13): 1107-1112 (1990).
Strum, J.C., et al.,"1-β-$_D$-Arabinofuranosylcytosine Stimulates Ceramide and Diglyceride Formation in HL-60-Cells," *J. Biol. Chem.*, 269(22): 15493-15497 (1994).
Svensson, M., et al., "Epithelial Glucosphingolipid Express as a Determinant of Bacterial Adherence and Cytokine Production", *Infection and Immunity*, 62:10 pp. 4404-4410 (1994).
Tagami, S., et al., "Ganglioside GM3 Participates in the Pathological Conditions of Insulin Resistance", *The Journal of Biological Chemistry*, 227(5):3085-3092 (2002).
Tang, W., et al., "Phorbol Ester Inhibits 13-Cis-Retinoic Acid-Induced Hydrolysis of Phosphatidylinositol 4,5-Biophosphate in cultured Murine Keratinocytes: A Possible Negative Feedback Via Protein Kinase C-Activation," *Cell Bioch. Funct.*, 9: 183-191 (1991).
Uemura, K., et al., "Effect of an Inhibitor of Glucosylceramide Synthesis on Cultured Rabbit Skin Fibroblasts," *J. Biochem.*, (Tokyo) 108(4): 525-530 (1990).
Vunnum, R.,R., et al.., "Analogs of Ceramide That Inhibit Glucocerebroside Synthetase in Mouse Brain," *Chemistry and Physics of Lipids*, LD. Bergelson, et al., eds. (Elsevier/North-Holland Scientific Publishers Ltd.), 26: 265-278 (1980).
Wermuth, C.G., et al., "Designing Prodrug and Bioprecursors I: Carrier Prodrug", *The Practice of Medicinal Chemistry*, C.G., Wermuth, ed.(CA: Academic Press Limited), pp. 671-696 (1996).
Wong, C-H., et al.., "Synthesis and Evaluation of Homoazasugars as Glycosidase Inhibitors," *J. Org. Chem.*, 60:1492-1501, (1995).
Yamashita, T., et al., "Enhanced insulin sensitivity in mice lacking ganglioside GM3", *Proc. Natl. Acad. Sci.*, 100(6): 3445-3449 (2003).
Zador, I., et al. "A Role for Glycosphingolipid Accumulation in the Renal Hypertrophy of Streptozotocin-induced Diabetes Mellitus", *J. Clin. Invest.*, 91: 797-803 (1993).
Zhao, H., et al., "Inhibiting glycosphingolipid systhesis improves glycemic control and insulin sensitivity in animal models of type 2 diabetes.", *Diabetes*, 56(5): 1210-1218 (2007).
Ziche, M. et al., "Angiogenesis Can Be Stimulated or Repressed in Vivo by a Change in GM3 :GD3 Ganglioside Ratio," *Lab. Invest.*, 67:711-715 (1992).
Notice of Allowance and Fee(s) Due for U.S. Appl. No. 11/667,224; Date Mailed: Apr. 22, 2011, titled: "Method of Treating Diabetes Mellitus".
Tay-Sachs, URL: http://www.ninds.nih.gov/disorders/taysachs/taysachs.htm. National Institute of Health of Neurological Disorders and Stroke. Accessed online Sep. 9, 2011.
Office Action for U.S. Appl. No. 12/601,871 dated Sep. 21, 2011, Titled: "2-Acylaminopropoanol-Type Glucosylceramide Synthase Inhibitors".
Non-Final Office Action for U.S. Appl. No. 12/227,076 mailed on Nov. 23, 2011, titled: "Methods of Treating Fatty Liver Disease".
Ong, et al., "Nonalcoholic Fatty Liver Disease and the epidemic of Obesity", *Cleveland Clinic Journal of Medicine*, 71(8): 657-664 (Aug. 2004).
Nicolaus, B.J.R., "Symbiotic Approach to Drug Design", *Decision Making in Drug Research*, XP-001111439, p. 1-14 (1983).
Schwimmer, J.B., et al., "Obesity, Insulin Resistance, and and Other Clinicopathological Correlates of Pediatric Nonalcoholic Fatty Liver Disease", *Journal of Pediatrics*, 143(4): 500-505 (2003).
Office Action dated Mar. 29, 2012 for U.S. Appl. No. 12/601,871, Titled: "2-Acylaminopropoanol-Type Glucosylceramide Synthase Inhibitors".
Abe, A., et al., "Use of Sulfobutyl Ether β-Cyclodextrin as a Vehicle for *d-threo*-1-Phenyl-2-decanoylamino-3-morpholinopropanol-Related Glucosylceramide Synthase Inhibitors", *Analytical Biochemistry*, vol. 287, pp. 344-347 (2000).
Levery, S.B., et al., "Disruption of the glucosylceramide biosynthetic pathway in *Aspergillus nidulans* and *Aspergillus futnigatus* by inhibitors of UDP-Glc:ceramide glucosyltransferase strongly affects spore germination, cell cycle, and hyphal growth", *FEBS Letters*, vol. 525, pp. 59-64 (2002).
Office Action for U.S. Appl. No. 12/227,076 dated Mar. 20, 2012, titled: "Methods of Treating Fatty Liver Disease".
Notification Concerning Transmittal of International Preliminary Report on Patentability for International Application No. PCT/US2009/005435 dated Apr. 5, 2011.
Natoli, T.A., et al., "Inhibition of glucosylceramide accumulation results in effective blockade of polysystic kidney disease in mouse models" and supplemental information, *Nature Medicine*, 16(7): 788-792 (Jul. 2010).
Husain, A., and Ganem, B., "*syn*-Selective additions to Garner aldehyde: synthesis of a potent glucosylceramide synthase inhibitor", *Tetrahedron Letters*, 43: 8621-8623 (2002).
Koga, K., and Yamada, S., "Stereochemical Studies. X. Effects of Neighboring Functional Groups on 1,2-Asymmetric Induction in the Reduction of Propiophenone Derivatives with Sodium Borohydride", *Chemical and Pharmaceutical Bulletin*, 20(3): 526-538 (1972).
European Search Report for EP Patent Application No. 12007327.5, "Method of Treating Polycystic Kidney Diseases With Ceramide Derivatives" dated Apr. 11, 2013.
Office Action dated May 28, 2013 for U.S.Appl. No. 13/762,102; titled: "Glucosylceramide Synthase Inhibition for the Treatment of Collapsing Glomerulopathy and Other Glomerular Disease".
Notice of Allowance and Fee(s) Due for U.S. Appl. No. 12/227,076; titled: "Methods of Treating Fatty Liver Disease" Date Mailed: Jun. 4, 2013.
European Search Report, European Application No. 13154970.1, "2-Acylaminopropoanol-Type Glucosylceramide Synthesis Inhibitors" dated Jul. 10, 2013.
European Search Report, European Application No. 13154967.7, "2-Acylaminopropoanol-Type Glucosylceramide Synthase Inhibitors" dated Jul. 18, 2013.
European Search Report, European Application No. 13154949.5, "2-Acylaminopropoanol-Type Glucosylceramide Synthase Inhibitors" dated Jul. 12, 2013.
European Search Report, European Application No. 13154955.2, "2-Acylaminopropoanol-Type Glucosylceramide Synthase Inhibitors" dated Jul. 10, 2013.
Notice of Allowance and Fee(s) Due for U.S. Appl. No. 12/227,076; titled: "Methods of Treating Fatty Liver Disease" Date Mailed: Oct. 9, 2012.
Belikov., V.G., "Pharmaceutical Chemistry, Moscow", *Vysshaya Shkola Publishers*, pp. 43-47 (1993).
Kharkevich, D.A., "Pharmacology", M., Medicament, 47-48 (1987).
Yew, N.S., et al., "Increased Hepatic Insulin Action in Diet-Induced Obese Mice Following Inhibition of Glucosylceramide Synthase" PLoS one, 5(6): 1-9 (Jun. 2010).

(56) References Cited

OTHER PUBLICATIONS

Zhao, H., et al., "Inhibiting Glycosphingolipid Synthesis Ameliorates Hepatic Steatosis in Obese Mice" Hepatology, pp. 85-93 (Jul. 2009)).

Non-Final Office for U.S. Appl. No. 12/681,291, titled "Method of Treating Polycystic Kidney Diseases with Ceramide Derivatives", dated: Oct. 18, 2013.

Notice of Allowance and Fee(s) Due for U.S. Appl. No. 12/227,076; titled: "Methods of Treating Fatty Liver Disease" Date Mailed: Dec. 23, 2013.

Notice of Allowance and Fee(s) Due for U.S. Appl. No. 13/762,102; titled: "Glucosylceramide Synthase Inhibition for the Treatment of Collapsing Glomerulopathy and Other Glomerular Disease" Date Mailed: Jan. 9, 2014.

Non-Final Office for U.S. Appl. No. 13/193,990, titled "Method of Treating Diabetes Mellitus", dated: Feb. 20, 2014.

2-ACYLAMINOPROPOANOL-TYPE GLUCOSYLCERAMIDE SYNTHASE INHIBITORS

RELATED APPLICATION(S)

This application is a continuation of U.S. application Ser. No. 12/601,871, filed on May 6, 2010, now U.S. Pat. No. 8,304,447, issued Nov. 6, 2012, which is the U.S. National Stage of International Application No. PCT/US2008/006906, filed May 30, 2008, which designates the U.S., published in English, and claims the benefit of U.S. Provisional Application No. 60/932,370, filed May 31, 2007, and U.S. Provisional Application No. 60/997,846, filed on Oct. 5, 2007. The entire teachings of the above applications are incorporated herein by reference.

BACKGROUND OF THE INVENTION

Gangliosides, such as GM1, GM2 and GM3, are glycosphingolipids (GSLs) comprised of ceramide and at least one acidic sugar. Gangliosides are generally found in the outer leaflet of the plasma membrane (Nojri et al., Proc. Natl. Acad. Sci. USA 83:782 (1986)). Gangliosides are involved in cell signaling and act as modulators of receptor activity (Yamashita et al., *Proc. Natl. Acad. Sci. USA* 100(6):3445 (2003)). A number of GSLs are derived from glucosylceramide, which is enzymatically formed from ceramide and UDP-glucose. The formation of glucosylceramide is catalyzed by glucosylceramide synthase.

It has been found that the level of GSLs controls a variety of cell functions, such as growth, differentiation, adhesion between cells or between cells and matrix proteins, binding of microorganisms and viruses to cells, and metastasis of tumor cells. In addition, the glucosylceramide precursor, ceramide, may cause differentiation or inhibition of cell growth and be involved in the functioning of vitamin $D_3$, tumor necrosis factor-α, interleukins, and apoptosis. Sphingols, precursors of ceramide, and products of ceramide catabolism have also been shown to influence many cell systems, possibly by inhibiting protein kinase C.

Defects in GSL metabolizing enzymes can cause serious disorders. For example, Tay-Sachs, Gaucher's, and Fabry's diseases result from enzymatic defects in the GSL degradative pathway and the accumulation of GSL. In particular, GM1 accumulates in the nervous system leading to mental retardation and liver enlargement. In Tay-Sachs, GM2 accumulates in brain tissue leading to mental retardation and blindness. These observations suggest that inhibitors of glycosylceramide synthase can be effective in treating lysosomal diseases such as Tay-Sachs, Gaucher's, and Fabry's diseases. Indeed, glucosylceramide synthase inhibitors have been described for this purpose (see U.S. Pat. Nos. 6,569,889; 6,255,336; 5,916,911; 5,302,609; 6,660,749; 6610,703; 5,472,969; and 5,525,616).

Recently it has been disclosed that the interruption of the insulin induced signaling cascade may be associated with elevated levels of GM3. It has also been suggested that the cytokine tumor necrosis factor-α (TNF-α), implicated in insulin resistance, results in increased expression of GM3 (Tagami et al., *J. Biol. Chem.* 277(5):3085 (2002)). Also, it has been disclosed that mutant mice lacking GM3 synthase, and thus lacking in GM3, are protected from insulin resistance caused by a high-fat diet (Yamashita et al., *Proc. Natl. Acad. Sc. USA* 100:3445-3449 (2003)). These observations suggest that inhibitors of glycosylceramide synthase can be effective in treating diabetes. Indeed, inhibitors of glucosylceramide synthase have been proposed for treating Type 2 diabetes (see WO 2006/053043).

Therefore, agents which inhibit glucosylceramide synthesis, or reduce intracellular content of GSLs, such as GM3, have the potential to treat conditions associated with altered GSL levels and/or GSL precursor levels. There is a need for additional agents which can act as glucosylceramide synthase inhibitors.

SUMMARY OF THE INVENTION

It has now been discovered that 2-acylaminopropoanol derivatives represented by Structural Formula (I) below can effectively inhibit glycosphingolipid synthesis, such as GM3 synthesis. As such, these compounds can be used for treating diabetes or lysosomal storage diseases, such as Tay-Sachs, Gaucher's or Fabry's disease. In addition, a number of these compounds were tested and found to significantly inhibit glycosphingolipid synthesis in animal tissues and to have high metabolic stability at the liver. Based upon this discovery, novel 2-acylaminopropoanol derivatives, pharmaceutical compositions comprising the 2-acylaminopropoanol derivatives, and methods of treatment using the 2-acylaminopropoanol derivatives are disclosed herein.

In one embodiment, the present invention is directed to compounds represented by Structural Formula (I):

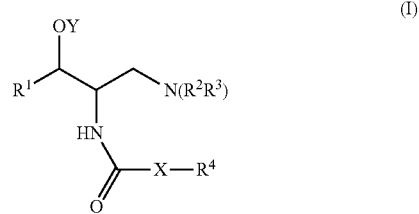

and pharmaceutically acceptable salts thereof, wherein:
$R^1$ is a substituted or unsubstituted aryl group;
Y is —H, a hydrolyzable group, or a substituted or unsubstituted alkyl group.
$R^2$ and $R^3$ are each independently —H, a substituted or unsubstituted aliphatic group, or a substituted or unsubstituted aryl group, or $R^2$ and $R^3$ taken together with the nitrogen atom of $N(R^2R^3)$ form a substituted or unsubstituted non-aromatic heterocyclic ring;
X is —$(CR^5R^6)_n$-Q-; Q is —O—, —S—, —C(O)—, —C(S)—, —C(O)O—, —C(S)O—, —C(S)S—, —C(O)NR$^7$—, —NR$^7$—, —NR$^7$C(O)—, —NR$^7$C(O)NR$^7$—, —OC(O)—, —SO$_3$—, —SO—, —S(O)$_2$—, —SO$_2$NR$^7$—, or —NR$^7$SO$_2$—; and $R^4$ is —H, a substituted or unsubstituted aliphatic group, or a substituted or unsubstituted aryl group;
Alternatively, X is —O—, —S— or —NR$^7$—; and $R^4$ is a substituted or unsubstituted aliphatic group, or substituted or unsubstituted aryl group;
Alternatively, X is —$(CR^5R^6)_n$—; and $R^4$ is a substituted or unsubstituted cyclic alkyl group, or a substituted or unsubstituted cyclic alkenyl group, a substituted or unsubstituted aryl group, —CN, —NCS, —NO$_2$ or a halogen;
Alternatively, X is a covalent bond; and $R^4$ is a substituted or unsubstituted aryl group;
$R^5$ and $R^6$ are each independently —H, —OH, —SH, a halogen, a substituted or unsubstituted lower alkoxy group, a substituted or unsubstituted lower alkylthio group, or a substituted or unsubstituted lower aliphatic group;
n is 1, 2, 3, 4, 5 or 6;

Each $R^7$ is independently —H, a substituted or unsubstituted aliphatic group, or a substituted or unsubstituted aryl group, or $R^7$ and $R^4$ taken together with the nitrogen atom of $NR^7R^4$ form a substituted or unsubstituted non-aromatic heterocyclic group.

In another embodiment, the present invention is directed to a pharmaceutical composition comprising a pharmaceutically acceptable carrier and a compound represented by Structural Formula (1) or a pharmaceutically acceptable salt thereof.

In yet another embodiment, the present invention is directed to a method of treating a subject having type 2 diabetes, comprising administering to the subject a therapeutically effective amount of a compound represented by Structural Formula (I) or a pharmaceutically acceptable salt thereof.

A method of treating a subject having renal hypertrophy or hyperplasia associated with diabetic nephropathy is also included in the invention. The method comprises administering to the subject a therapeutically effective amount of a compound represented by Structural Formula (I) or a pharmaceutically acceptable salt thereof.

A method of decreasing plasma TNF-α in a subject in need thereof is also included in the present invention. The method comprises administering to the subject a therapeutically effective amount of a compound represented by Structural Formula (I) or a pharmaceutically acceptable salt thereof A method of lowering blood glucose levels in a subject in need thereof is also included in the present invention. The method comprises administering to the subject a therapeutically effective amount of a compound represented by Structural Formula (I) or a pharmaceutically acceptable salt thereof.

A method of decreasing glycated hemoglobin levels in a subject in need thereof is also included in the present invention. The method comprises administering to the subject a therapeutically effective amount of a compound represented by Structural Formula (I) or a pharmaceutically acceptable salt thereof.

A method of inhibiting glucosylceramide synthase or lowering glycosphingolipid concentrations in a subject in need thereof is also included in the present invention. The method comprises administering to the subject a therapeutically effective amount of a compound represented by Structural Formula (I) or a pharmaceutically acceptable salt thereof.

A method of treating a subject with Tay-Sachs, Gaucher's or Fabry's disease is also included in the present invention. The method comprises administering to the subject a therapeutically effective amount of a compound represented by Structural Formula (I) or a pharmaceutically acceptable salt thereof.

Also, included in the present invention is the use of a compound represented by Structural Formula (I) or a pharmaceutically acceptable salt thereof for the manufacture of a medicament. The medicament is for treating a subject having type 2 diabetes; for treating a subject having renal hypertrophy or hyperplasia associated with diabetic nephropathy; for decreasing plasma TNF-α in a subject in need thereof; for lowering blood glucose levels in a subject in need thereof; for decreasing glycated hemoglobin levels in a subject in need thereof; for inhibiting glucosylceramide synthase or lowering glycosphingolipid concentrations in a subject in need thereof; or for treating a subject with Tay-Sachs, Gaucher's or Fabry's disease.

The compounds of the invention are inhibitors of glucosylceramide synthesis. As such, they can be used for treating various disorders associated with GSL metabolism, including diabetes and lysosomal storage diseases. The compounds of the invention can effectively inhibit glucosylceramide synthesis and at the same time have high metabolic stability at the liver. For example, the compounds of the invention can have a clearance value of less than 50%, and commonly less than 30%, at the liver relative to hepatic blood flow.

DETAILED DESCRIPTION OF THE INVENTION

In one embodiment, the invention is directed to a compound represented by Structural Formula (I), or a pharmaceutically acceptable salt thereof. A first set of values and preferred values for the variables in Structural Formula (I) is provided in the following paragraphs:

$R^1$ is a substituted or unsubstituted aryl group, such as a substituted or unsubstituted phenyl group. Preferably, $R^1$ is an aryl group optionally substituted with one or more substituents selected from halogen, alkyl, haloalkyl, $Ar^1$, —$OR^{30}$, —O(haloalkyl), —$SR^{30}$, —$NO_2$, —CN, —NCS, —$N(R^{31})_2$, —$NR^{31}C(O)R^{30}$, —$NR^{31}C(O)OR^{32}$, —$N(R^{31})C(O)N(R^{31})_2$, —$C(O)R^{30}$, —$C(S)R^{30}$, —$C(O)OR^{30}$, —$OC(O)R^{30}$, —$C(O)N(R^{31})_2$, —$S(O)_2R^{30}$, —$SO_2N(R^{31})_2$, —$S(O)R^{32}$, —$SO_3R^{30}$, —$NR^{31}SO_2N(R^{31})_2$, —$NR^{31}SO_2R^{32}$, —$V_o$—$Ar^1$, —$V_o$—$OR^{30}$, —$V_o$—O(haloalkyl), —$V_o$—$SR^{30}$, —$V_o$—$NO_2$, —$V_o$—CN, —$V_o$—$N(R^{31})_2$, —$V_o$—$NR^{31}C(O)R^{30}$, —$V_o$—$NR^{31}CO_2R^{32}$, —$V_o$—$N(R^{31})C(O)N(R^{31})_2$, —$V_o$—$C(O)R^{30}$, —$V_o$—$C(S)R^{30}$, —$V_o$—$CO_2R^{30}$, —$V_o$—$OC(O)R^{30}$, —$V_o$—$C(O)N(R^{31})_2$—, —$V_o$—$S(O)_2R^{30}$, —$V_o$—$SO_2N(R^{31})_2$, —$V_o$—$S(O)R^{32}$, —$V_o$—$SO_3R^{30}$, —$V_o$—$NR^{31}SO_2N(R^{31})_2$, —$V_o$—$NR^{31}SO_2R^{32}$, —O—$V_o$—$Ar^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —$NR^{31}C(O)$—$V_o$—$N(R^{31})_2$, —$NR^{31}C(O)$—$V_o$—$Ar^1$, —C(O)—$V_o$—$N(R^{31})_2$, —C(O)—$V_o$—$Ar^1$, —C(S)—$V_o$—$N(R^{31})_2$, —C(S)—$V_o$—$Ar^1$, —C(O)O—$V_1$—$N(R^{31})_2$, —C(O)O—$V_o$—$Ar^1$, —O—C(O)—$V_1$—$N(R^{31})_2$, —O—C(O)—$V_o$—$Ar^1$, —C(O)$N(R^{31})$—$V_1$—$N(R^{31})_2$, —C(O)$N(R^{31})$—$V_o$—$Ar^1$, —$S(O)_2$—$V_o$—$N(R^{31})_2$, —$S(O)_2$—$V_o$—$Ar^1$, —$SO_2N(R^{31})$—$V_1$—$N(R^{31})_2$, —$SO_2N(R^{31})$—$V_o$—$Ar^1$, —S(O)—$V_o$—$N(R^{31})_2$, —S(O)—$V_o$—$Ar^1$, —$S(O)_2$—O—$V_1$—$N(R^{31})_2$, —$S(O)_2$—O—$V_o$—$Ar^1$, —$NR^{31}SO_2$—$V_o$—$N(R^{31})_2$, —$NR^{31}SO_2$—$V_o$—$Ar^1$, —O—$[CH_2]_p$—O—, —S—$[CH_2]_p$—S—, or —$[CH_2]_q$—. More preferably, $R^1$ is an aryl group, such as a phenyl group, optionally substituted with one or more halogen, cyano, nitro, C1-C6 alkyl, C1-C6 haloalkyl, —$OR^{30}$, —$SR^{30}$, —$N(R^{31})_2$, $Ar^1$, —$V_o$—$OR^{30}$, —$V_o$—$N(R^{31})_2$, —$V_o$—$Ar^1$, —O—$V_o$—$Ar^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —O—$[CH_2]_p$—O—, —S—$[CH_2]_p$—S—, or —$[CH_2]_q$—. More preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, —O—$[CH_2]_p$—O—, and —$[CH_2]_q$—. Even more preferably, $R^1$ is a phenyl group optionally substituted with —OH, —$OCH_3$, —$OC_2H_5$ or —O—$[CH_2]_p$—O—. Even more preferably, $R^1$ is

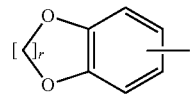

where r is 1, 2, 3 or 4, preferably 1 or 2.

Y is —H, a hydrolyzable group, or a substituted or unsubstituted alkyl group. Examples of hydrolyzable groups include —C(O)R, —C(O)OR, —C(O)NRR', C(S)R, —C(S)OR, —C(O)SR or —C(S)NRR'. Preferably, Y is —H, —C(O)R, —C(O)OR or —C(O)NRR'; more preferably, —H.

$R^2$ and $R^3$ are each independently —H, a substituted or unsubstituted aliphatic group, or a substituted or unsubstituted aryl group, or $R^2$ and $R^3$ taken together with the nitrogen atom of $N(R^2R^3)$ form a substituted or unsubstituted non-aromatic heterocyclic ring. Preferably, $R^2$ and $R^3$ taken together with the nitrogen atom of $N(R^2R^3)$ form a 5- or 6-membered, optionally-substituted non-aromatic heterocyclic ring. More preferably, —$N(R^2R^3)$ is an optionally substituted pyrrolidinyl, azetidinyl, piperidinyl, piperazinyl or morpholinyl group. Even more preferably, —$N(R^2R^3)$ is an unsubstituted pyrrolidinyl, azetidinyl, piperidinyl, piperazinyl or morpholinyl group, preferably an unsubstituted pyrrolidinyl group.

Suitable substituents for the aliphatic and aryl groups represented by $R^2$ and $R^3$, and suitable substituents for the non-aromatic heterocyclic ring represented by $N(R^2R^3)$ each independently include halogen, alkyl, haloalkyl, —$OR^{40}$, —O(haloalkyl), —$SR^{40}$, —$NO_2$, —CN, —$N(R^{41})_2$, —$NR^{41}C(O)R^{40}$, —$NR^{41}C(O)OR^{42}$, —$N(R^{41})C(O)N(R^{41})_2$, —$C(O)R^{40}$, —$C(S)R^{40}$, —$C(O)OR^{40}$, —$OC(O)R^{40}$, —$C(O)N(R^{41})_2$, —$S(O)_2R^{40}$, —$SO_2N(R^{41})_2$, —$S(O)R^{42}$, —$SO_3R^{40}$, $Ar^2$, $V_2$—$Ar^2$, —$V_2$—$OR^{40}$, —$V_2$—O(haloalkyl), —$V_2$—$SR^{40}$, —$V_2$—$NO_2$, —$V_2$—CN, —$V_2$—$N(R^{41})_2$, —$V_2$—$NR^{41}C(O)R^{40}$, —$V_2$—$NR^{41}CO_2R^{42}$, —$V_2$—$N(R^{41})C(O)N(R^{41})_2$, —$V_2$—$C(O)R^{40}$, —$V_2$—$C(S)R^{40}$, —$V_2$—$CO_2R^{40}$, —$V_2$—$OC(O)R^{40}$, —$V_2$—$C(O)N(R^{41})_2$—, —$V_2$—$S(O)_2R^{40}$, —$V_2$—$SO_2N(R^{41})_2$, —$V_2$—$S(O)R^{42}$, —$V_2$—$SO_3R^{40}$, —O—$V_2$—$Ar^2$ and —S—$V_2$—$Ar^2$. Preferably, suitable substituents for the aliphatic and aryl groups represented by $R^2$ and $R^3$, and suitable substituents for the non-aromatic heterocyclic ring represented by $N(R^2R^3)$ each independently include halogen, alkyl, haloalkyl, —$OR^{40}$, —O(haloalkyl), —$SR^{40}$, —$NO_2$, —CN, —$N(R^{41})_2$, —$C(O)R^{40}$, —$C(S)R^{40}$, —$C(O)OR^{40}$, —$OC(O)R^{40}$, —$C(O)N(R^{41})_2$, $Ar^2$, $V_2$—$Ar^2$, —$V_2$—$OR^{40}$, —$V_2$—O(haloalkyl), —$V_2$—$SR^{40}$, —$V_2$—$NO_2$, —$V_2$—CN, —$V_2$—$N(R^{41})_2$, —$V_2$—$C(O)R^{40}$, —$V_2$—$C(S)R^{40}$, —$V_2$—$CO_2R^{40}$, —$V_2$—$OC(O)R^{40}$, —O—$V_2$—$Ar^2$ and —S—$V_2$—$Ar^2$. More preferably, suitable substituents for the aliphatic and aryl groups represented by $R^2$ and $R^3$, and suitable substituents for the non-aromatic heterocyclic ring represented by $N(R^2R^3)$ each independently include halogen, C1-C10 alkyl, C1-C10 haloalkyl, —O(C1-C10 alkyl), —O(phenyl), —O(C1-C10 haloalkyl), —S(C1-C10 alkyl), —S(phenyl), —S(C1-C10 haloalkyl), —$NO_2$, —CN, —NH(C1-C10 alkyl), —N(C1-C10 alkyl)$_2$, —NH(C1-C10 haloalkyl), —N(C1-C10 haloalkyl)$_2$, —NH(phenyl), —N(phenyl)$_2$, —C(O)(C1-C10 alkyl), —C(O)(C1-C10 haloalkyl), —C(O)(phenyl), —C(S)(C1-C10 alkyl), —C(S)(C1-C10 haloalkyl), —C(S)(phenyl), —C(O)O(C1-C10 alkyl), —C(O)O(C1-C10 haloalkyl), —C(O)O(phenyl), phenyl, —$V_2$-phenyl, —$V_2$—O-phenyl, —$V_2$—O(C1-C10 alkyl), —$V_2$—O(C1-C10 haloalkyl), —$V_2$-S-phenyl, —$V_2$—S(C1-C10 alkyl), —$V_2$—S(C1-C10 haloalkyl), —$V_2$—$NO_2$, —$V_2$—CN, —$V_2$—NH(C1-C10 alkyl), —$V_2$—N(C1-C10 alkyl)$_2$, —$V_2$—NH(C1-C10 haloalkyl), —$V_2$—N(C1-C10 haloalkyl)$_2$, —$V_2$—NH(phenyl), —$V_2$—N(phenyl)$_2$, —$V_2$—C(O)(C1-C10 alkyl), —$V_2$—C(O)(C1-C10 haloalkyl), —$V_2$—C(O)(phenyl), —$V_2$—C(S)(C1-C10 alkyl), —$V_2$—C(S)(C1-C10 haloalkyl), —$V_2$—C(S)(phenyl), —$V_2$—C(O)O(C1-C10 alkyl), —$V_2$—C(O)O(C1-C10 haloalkyl), —$V_2$—C(O)O(phenyl), —$V_2$—OC(O)(C1-C10 alkyl), —$V_2$—OC(O)(C1-C10 haloalkyl), —$V_2$—OC(O)(phenyl), —O—$V_2$-phenyl and —S—$V_2$-phenyl. Even more preferably, suitable substituents for the aliphatic and aryl groups represented by $R^2$ and $R^3$, and suitable substituents for the non-aromatic heterocyclic ring represented by $N(R^2R^3)$ each independently include halogen, C1-C5 alkyl, C1-C5 haloalkyl, hydroxy, C1-C5 alkoxy, nitro, cyano, C1-C5 alkoxycarbonyl, C1-C5 alkylcarbonyl, C1-C5 haloalkoxy, amino, C1-C5 alkylamino and C1-C5 dialkylamino.

X is —$(CR^5R^6)_n$-Q-; Q is —O—, —S—, —C(O)—, —C(S)—, —C(O)O—, —C(S)O—, —C(S)S—, —C(O)NR$^7$—, —NR$^7$—, —NR$^7$C(O)—, —NR$^7$C(O)NR$^7$—, —OC(O)—, —$SO_3$—, —SO—, —$S(O)_2$—, —$SO_2$NR$^7$—, or —NR$^7SO_2$—; and $R^4$ is —H, a substituted or unsubstituted aliphatic group, or a substituted or unsubstituted aryl group. Preferably, Q is —O—, —S—, —C(O)—, —C(S)—, —C(O)O—, —C(S)O—, —C(S)S—, —C(O)NR$^7$—, —NR$^7$C(O)NR$^7$—, —OC(O)—, —$SO_3$—, —SO—, —$S(O)_2$—, —$SO_2$NR$^7$— or —NR$^7SO_2$—. More Preferably, Q is —O—, —S—, —C(O)—, —C(S)—, —C(O)O—, —C(S)O—, —C(S)S—, —C(O)NR$^7$— or —OC(O)—. Even more preferably, Q is —O—, —S—, —C(O)— or —C(S)—.

Alternatively, X is —O—, —S— or —NR$^7$—; and $R^4$ is a substituted or unsubstituted aliphatic group, or substituted or unsubstituted aryl group.

In another alternative, X is —$(CR^5R^6)_n$—; and $R^4$ is a substituted or unsubstituted cyclic alkyl (e.g., C3-C8) group, or a substituted or unsubstituted cyclic alkenyl (C3-C8) group, a substituted or unsubstituted aryl group, —CN, —NCS, —$NO_2$ or a halogen.

In another alternative, X is a covalent bond; and $R^4$ is a substituted or unsubstituted aryl group.

Preferably, $R^4$ is an optionally substituted aliphatic, such as a lower alkyl, or aryl group. More preferably, $R^4$ is an optionally substituted aryl or lower arylalkyl group. Even more preferably, $R^4$ is selected from the group consisting of:

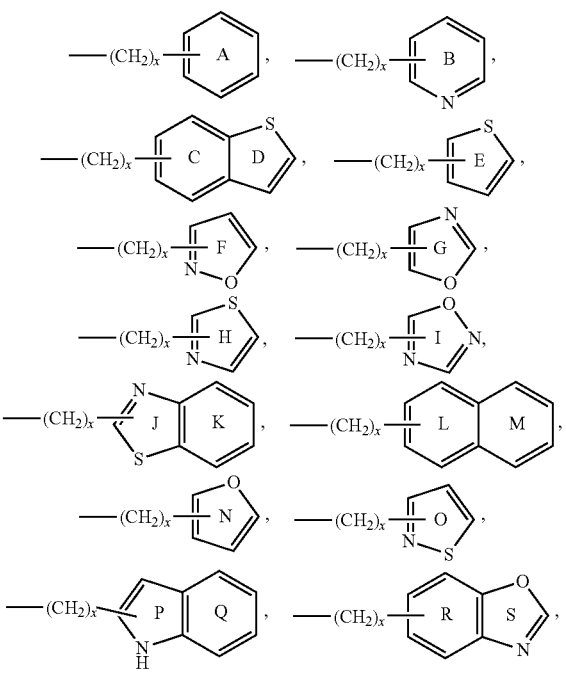

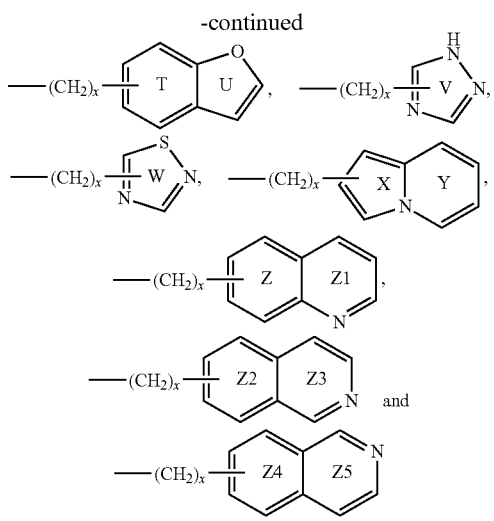

wherein each of rings A-Z5 is optionally and independently substituted; and each x is independently 0 or 1, specifically x is 0. Even more preferably, R⁴ is an optionally substituted

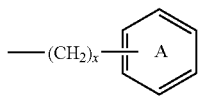

group. Alternatively, R⁴ is an optionally substituted phenyl group. Alternatively, R⁴ is an aryl group substituted with Ar³, such as a phenyl group substituted with Ar³. It is noted that, as shown above, rings A-Z5 can be attached to variable "X" of Structural Formula (I) through —(CH₂)ₓ— at any ring carbon of rings A-Z5 which is not at a position bridging two aryl groups. For example, R⁴ represented by

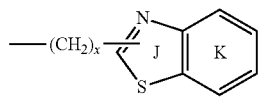

means that R⁴ is attached to variable "X" through either ring J or ring K.

Preferred substituents for each of the aliphatic group and the aryl group represented by R⁴, including lower alkyl, arylalkyl and rings A-Z5, include halogen, alkyl, haloalkyl, Ar³, Ar³—Ar³, —OR⁵⁰, —O(haloalkyl), —SR⁵⁰, —NO₂, —CN, —NCS, —N(R⁵¹)₂, —NR⁵¹C(O)R⁵⁰, —NR⁵¹C(O)OR⁵², —N(R⁵¹)C(O)N(R⁵¹)₂, —C(O)R⁵⁰, —C(S)R⁵⁰, —C(O)OR⁵⁰, —OC(O)R⁵⁰, —C(O)N(R⁵¹)₂, —S(O)₂R⁵⁰, —SO₂N(R⁵¹)₂, —S(O)R⁵², —SO₃R⁵⁰, —NR⁵¹SO₂N(R⁵¹)₂, —NR⁵¹SO₂R⁵², —V₄—Ar³, —V—OR⁵⁰, —V₄—O(haloalkyl), —V₄—SR⁵⁰, —V₄—NO₂, —V₄—CN, —V₄—N(R⁵¹)₂, —V₄—NR⁵¹C(O)R⁵⁰, —V₄—NR⁵¹CO₂R⁵², —V₄—N(R⁵¹)C(O)N(R⁵¹)₂, —V₄—C(O)R⁵⁰, —V₄—C(S)R⁵⁰, —V₄—CO₂R⁵⁰, —V₄—OC(O)R⁵⁰, —V₄—C(O)N(R⁵¹)₂—, —V₄—S(O)₂R⁵⁰, —V₄—SO₂N(R⁵¹)₂, —V₄—S(O)R⁵², —V₄—SO₃R⁵⁰, —V₄—NR⁵¹SO₂N(R⁵¹)₂, —V₄—NR⁵¹SO₂R⁵², —O—V₄—Ar³, —O—V₅—N(R⁵¹)₂, —S—V₄—Ar³, —S—V₅—N(R⁵¹)₂, —N(R⁵¹)—V₄—Ar³, —N(R⁵¹)—V₅—N(R⁵¹)₂, —NR⁵¹C(O)—V₄—N(R⁵¹)₂, —NR⁵¹C(O)—V₄—Ar³, —C(O)—V₄—N(R⁵¹)₂, —C(O)—V₄—Ar³, —C(S)—V₄—N(R⁵¹)₂, —C(S)—V₄— Ar³, —C(O)O—V₅—N(R⁵¹)₂, —C(O)O—V₄—Ar³, —O—C(O)—V₅—N(R⁵¹)₂, —O—C(O)—V₄—Ar³, —C(O)N(R⁵¹)—V₅—N(R⁵¹)₂, —C(O)N(R⁵¹)—V₄—Ar³, —S(O)₂—V₄—N(R⁵¹)₂, —S(O)₂—V₄—Ar³, —SO₂N (R⁵¹)—V₅—N(R⁵¹)₂, —SO₂N(R⁵¹)—V₄—Ar³, —S(O)—V₄—N(R⁵¹)₂, —S(O)—V₄—Ar³, —S(O)₂—O—V₅—N(R⁵¹)₂, —S(O)₂—O—V₄—Ar³, —NR⁵¹SO₂—V₄—N(R⁵¹)₂, —NR⁵¹SO₂—V₄—Ar³, —O—[CH₂]ₚ—O—, —S—[CH₂]ₚ—S—, and —[CH₂]q—. More preferably, substituents for each of the aliphatic group and the aryl group represented by R⁴, including lower alkyl, arylalkyl and rings A-Z5, include halogen, C1-C10 alkyl, C1-C10 haloalkyl, Ar³, Ar³—Ar³, —OR⁵⁰, —O(haloalkyl), —SR⁵⁰, —NO₂, —CN, —N(R⁵¹)₂, —NR⁵¹C(O)R⁵⁰, —C(O)R⁵⁰, —C(O)OR⁵⁰, —OC(O)R⁵⁰, —C(O)N(R⁵¹)₂, —V₄—Ar³, —V—OR⁵⁰, —V₄—O(haloalkyl), —V₄—SR⁵⁰, —V₄—NO₂, —V₄—CN, —V₄—N(R⁵¹)₂, —V₄—NR⁵¹C(O)R⁵⁰, —V₄—C(O)R⁵⁰, —V₄—CO₂R⁵⁰, —V₄—OC(O)R⁵⁰, —V₄—C(O)N(R⁵¹)₂—, —O—V₄—Ar³, —O—V₅—N(R⁵¹)₂, —S—V₄—Ar³, —S—V₅—N(R⁵¹)₂, —N(R⁵¹)—V₄—Ar³, —N(R⁵¹)—V₅—N(R⁵¹)₂, —NR⁵¹C(O)—V₄—N(R⁵¹)₂, —NR⁵¹C(O)—V₄—Ar³, —C(O)—V₄—N(R⁵¹)₂, —C(O)—V₄—Ar³, —C(O)O—V₅—N(R⁵¹)₂, —C(O)O—V₄—Ar³, —O—C(O)—V₅—N(R⁵¹)₂, —O—C(O)—V₄—Ar³, —C(O)N(R⁵¹)—V₅—N(R⁵¹)₂, —C(O)N(R⁵¹)—V₄—Ar³, —O—[CH₂]ₚ—O— and —[CH₂]q—. More preferably, substituents for each of the aliphatic group and the aryl group represented by R⁴, including lower alkyl, arylalkyl and rings A-Z5, include halogen, cyano, nitro, C1-C10 alkyl, C1-C10 haloalkyl, amino, C1-C10 alkylamino, C1-C10 dialkylamino, aryl, aryloxy, hydroxy, C1-10 alkoxy, —O—[CH₂]ₚ—O— or —[CH₂]q—. Even more preferably, substituents for each of the aliphatic group and the aryl group represented by R⁴, including lower alkyl, arylalkyl and rings A-Z5, include halogen, cyano, amino, nitro, Ar³, C1-C6 alkyl, C1-C6 haloalkyl, C1-C6 alkoxy, hydroxy and C1-C6 haloalkoxy. Even more preferably, substituents for each of the aliphatic and aryl groups represented by R⁴, including lower alkyl, arylalkyl and rings A-Z5, include —OH, —OCH₃, —OC₂H₅ and —O—[CH₂]ₚ—O—. Preferably, phenyl ring A is optionally substituted with one or more substituents selected from the group consisting of halogen, cyano, nitro, C1-C10 alkyl, C1-C10 haloalkyl, amino, C1-C10 alkylamino, C1-C10 dialkylamino, —OR⁵⁰, —Ar³, —V₄—Ar³, —V—OR⁵⁰, —O(C1-C10 haloalkyl), —V₄—O(C1-C10 haloalkyl), —O—V₄—Ar³, —O—[CH₂]ₚ—O— and —[CH₂]q—. More preferably, phenyl ring A is optionally substituted with one or more substituents selected from the group consisting of halogen, cyano, nitro, C1-C10 alkyl, C1-C10 haloalkyl, amino, C1-C10 alkylamino, C1-C10 dialkylamino, aryl, aryloxy, hydroxy, C1-10 alkoxy, —O—[CH₂]ₚ—O— and —[CH₂]q—. Even more preferably, phenyl ring A is optionally substituted with one or more substituents selected from the group consisting of —OH, —OCH₃ and —OC₂H₅. Specifically, when R⁴ is phenyl ring A, at least one of the substituents of ring A is at the para position.

R⁵ and R⁶ are each independently —H, —OH, —SH, a halogen, a substituted or unsubstituted lower alkoxy group, a substituted or unsubstituted lower alkylthio group, or a substituted or unsubstituted lower aliphatic group. Preferably, R⁵ and R⁶ are each independently —H; —OH; a halogen; or a lower alkoxy or lower alkyl group. More preferably, R⁵ and R⁶ are each independently —H, —OH or a halogen. Even more preferably, R⁵ and R⁶ are each independently —H.

Each R⁷ is independently —H, a substituted or unsubstituted aliphatic group, or a substituted or unsubstituted aryl group, or R⁷ and R⁴ taken together with the nitrogen atom of $NR^7R^4$ form a substituted or unsubstituted non-aromatic heterocyclic group. Preferably, each $R^7$ is independently —H, an aliphatic group or phenyl. Even more preferably, each $R^7$ is independently —H or C1-C6 alkyl.

Each n is independently 1, 2, 3, 4, 5 or 6. Preferably, each n is independently 1, 2, 3 or 4. Alternatively, each n is independently 2, 3, 4 or 5.

Each p is independently 1, 2, 3 or 4, preferably 1 or 2.

Each q is independently 3, 4, 5 or 6, preferably 3 or 4.

Each p' is independently 1, 2, 3 or 4, preferably 1 or 2.

Each q' is independently 3, 4, 5 or 6, preferably 3 or 4.

Each $V_o$ is independently a C1-C10 alkylene group, preferably C1-C4 alkylene group.

Each $V_1$ is independently a C2-C10 alkylene group, specifically C2-C4 alkylene group.

Each $V_2$ is independently a C1-C4 alkylene group.

Each $V_4$ is independently a C1-C10 alkylene group, preferably a C1-C4 alkylene group.

Each $V_5$ is independently a C2-C10 alkylene group, preferably a C2-C4 alkylene group.

Each $Ar^1$ is an aryl group optionally and independently substituted with one or more substituents selected from the group consisting of halogen, alkyl, amino, alkylamino, dialkylamino, alkoxy, nitro, cyano, hydroxy, haloalkoxy and haloalkyl. Preferably, $Ar^1$ is an aryl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. More preferably, $Ar^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $Ar^2$ is an aryl group optionally and independently substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

Each $Ar^3$ is independently an aryl group, such as phenyl, each optionally substituted with one or more substituents selected from the group consisting of halogen, alkyl, amino, alkylamino, dialkylamino, alkoxy, nitro, cyano, hydroxy, haloalkoxy and haloalkyl. Preferably, $Ar^3$ is independently an aryl group each optionally substituted with one or more substituents selected from the group consisting of halogen, C1-C10 alkyl, C1-C10 haloalkyl, hydroxy, C1-C10 alkoxy, nitro, cyano, C1-C10 alkoxycarbonyl, C1-C10 alkylcarbonyl, C1-C10 haloalkoxy, amino, C1-C10 alkylamino and C1-C10 dialkylamino. Even more preferably, $Ar^3$ is independently an aryl group each optionally substituted with one or more substituents selected from the group consisting of halogen, C1-C4 alkyl, C1-C4 haloalkyl, hydroxy, C1-C4 alkoxy, nitro, cyano, C1-C4 alkoxycarbonyl, C1-C4 alkylcarbonyl, C1-C4 haloalkoxy, amino, C1-C4 alkylamino and C1-C4 dialkylamino Each $R^{30}$ is independently hydrogen; an aryl group optionally substituted with one or more substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or an alkyl group optionally substituted with one or more substituents selected from the group consisting of halogen, amino, alkylamino, dialkylamino, alkoxy, nitro, cyano, hydroxy, haloalkoxy, alkoxycarbonyl and alkylcarbonyl. Preferably, each $R^{30}$ is independently hydrogen; an aryl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or an C1-C10 alkyl group optionally substituted with one or more substituents selected from the group consisting of halogen, amino, C1-C6 alkylamino, C1-C1 dialkylamino, C1-C6 alkoxy, nitro, cyano, hydroxy, C1-C6 haloalkoxy, C1-C6 alkoxycarbonyl and C1-C6 alkylcarbonyl. More preferably, each $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or an C1-C10 alkyl group optionally substituted with one or more substituents selected from the group consisting of halogen, amino, C1-C6 alkylamino, C1-C1 dialkylamino, C1-C6 alkoxy, nitro, cyano, hydroxy, C1-C6 haloalkoxy, C1-C6 alkoxycarbonyl and C1-C6 alkylcarbonyl.

Each $R^{31}$ is independently $R^{30}$, —$CO_2R^{30}$, —$SO_2R^{30}$ or —$C(O)R^{30}$; or —$N(R^{31})_2$ taken together is an optionally substituted non-aromatic heterocyclic group. Preferably, each $R^{31}$ is independently $R^{30}$, or —$N(R^{31})_2$ is an optionally substituted non-aromatic heterocyclic group.

Each $R^{32}$ is independently an aryl group optionally substituted with one or more substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or an alkyl group optionally substituted with one or more substituents selected from the group consisting of halogen, amino, alkylamino, dialkylamino, alkoxy, nitro, cyano, hydroxy, haloalkoxy, alkoxycarbonyl and alkylcarbonyl. Preferably, each $R^{32}$ is independently an aryl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C1 dialkylamino, C1-C6 alkoxy, nitro, cyano, hydroxy, C1-C6 haloalkoxy, C1-C6 alkoxycarbonyl and C1-C6 alkylcarbonyl. More preferably, each $R^{32}$ is independently a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy and C1-C6 haloalkyl; or a C1-C10 alkyl group optionally substituted with one or more substituents selected from the group consisting of halogen, amino, C1-C6 alkylamino, C1-C1 dialkylamino, C1-C6 alkoxy, nitro, cyano, hydroxy, C1-C6 haloalkoxy, C1-C6 alkoxycarbonyl and C1-C6 alkylcarbonyl.

Each $R^{40}$ is independently hydrogen; an aryl group, such as a phenyl group, optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino; or a C1-C10 alkyl group optionally substituted with one or more substituents selected from the group consisting of halogen, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

Each $R^{41}$ is independently $R^{40}$, —$CO_2R^{40}$, —$SO_2R^{40}$ or —$C(O)R^{40}$; or —$N(R^{41})_2$ taken together is an optionally substituted non-aromatic heterocyclic group.

Each $R^{42}$ is independently an aryl group, such as a phenyl group, optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino; or a C1-C10 alkyl group optionally substituted with one or more substituents selected from the group consisting of halogen, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

Each $R^{50}$ is independently hydrogen; an aryl group optionally substituted with one or more substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or an alkyl group optionally substituted with one or more substituents selected from the group consisting of halogen, amino, alkylamino, dialkylamino, alkoxy, nitro, cyano, hydroxy, haloalkoxy, alkoxycarbonyl, alkylcarbonyl and haloalkyl. Preferably, each $R^{50}$ is independently hydrogen; an aryl group, such as a phenyl group, optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino; or a C1-C10 alkyl group optionally substituted with one or more substituents selected from the group consisting of halogen, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

Each $R^{51}$ is independently $R^{50}$, —$CO_2R^{50}$, —$SO_2R^{50}$ or —$C(O)R^{50}$, or —$N(R^{51})_2$ taken together is an optionally substituted non-aromatic heterocyclic group. Preferably, each $R^{51}$ is independently $R^{50}$, or —$N(R^{31})_2$ is an optionally substituted non-aromatic heterocyclic group.

Each $R^{52}$ is independently an aryl group optionally substituted with one or two substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or an alkyl group optionally substituted with one or more substituents selected from the group consisting of halogen, amino, alkylamino, dialkylamino, alkoxy, nitro, cyano, hydroxy, haloalkoxy, alkoxycarbonyl, alkylcarbonyl and haloalkyl. Preferably, each $R^{52}$ is independently an aryl group, such as a phenyl group, optionally substituted with one or more substituents selected from the group consisting of halogen, C1-C6 alkyl, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino; or a C1-C10 alkyl group optionally substituted with one or more substituents selected from the group consisting of halogen, C1-C6 haloalkyl, hydroxy, C1-C6 alkoxy, nitro, cyano, C1-C6 alkoxycarbonyl, C1-C6 alkylcarbonyl, C1-C6 haloalkoxy, amino, C1-C6 alkylamino and C1-C6 dialkylamino.

R and R' are each independently —H; a lower aliphatic group optionally substituted with one or more substituents selected from the group consisting of halogen, —OH, —CN, —NCS, —$NO_2$, —$NH_2$, lower alkoxy, lower haloalkoxy and aryl; or an aryl group optionally substituted with one or more substituents selected from the group consisting of halogen, —OH, —CN, —NCS, —$NO_2$, —$NH_2$, lower alkoxy, lower haloalkoxy, lower aliphatic group and lower haloaliphatic group; or R and R' taken together with the nitrogen atom of NRR' form a non-aromatic heterocyclic ring optionally substituted with one or more substituents selected from the group consisting of: halogen; —OH; —CN; —NCS; —$NO_2$; —$NH_2$; lower alkoxy; lower haloalkoxy; lower aliphatic group optionally substituted with one or more substituents selected from the group consisting of halogen, —OH, —CN, —NCS, —$NO_2$, —$NH_2$, lower alkoxy, lower haloalkoxy and aryl; and aryl group optionally substituted with one or more substituents selected from the group consisting of halogen, —OH, —CN, —NCS, —$NO_2$, —$NH_2$, lower alkoxy, lower haloalkoxy, lower aliphatic group and lower haloaliphatic group. Preferably, R and R' are each independently —H; a lower aliphatic group; a lower aliphatic group substituted with phenyl; or an aryl group. More preferably, R and R' are each independently —H, C1-C4 alkyl, phenyl or benzyl.

A second set of values for the variables in Structural Formula (I) is provided in the following paragraphs:

Y is —H, —C(O)R, —C(O)OR or —C(O)NRR', preferably —H.

$R^1$ is an aryl group optionally substituted with one or more substituents selected from the group consisting of halogen, alkyl, haloalkyl, $Ar^1$, —$OR^{30}$, —O(haloalkyl), —$SR^{30}$, —$NO_2$, —CN, —NCS, —$N(R^{31})_2$, —$NR^{31}C(O)R^{30}$, —$NR^{31}C(O)OR^{32}$, —$N(R^{31})C(O)N(R^{31})_2$, —$C(O)R^{30}$, —$C(S)R^{30}$, —$C(O)OR^{30}$, —$OC(O)R^{30}$, —$C(O)N(R^{31})_2$, —$S(O)_2R^{30}$, —$SO_2N(R^{31})_2$, —$S(O)R^{32}$, —$SO_3R^{30}$, —$NR^{31}SO_2N(R^{31})_2$, —$NR^{31}SO_2R^{32}$, —$V_o$—$Ar^1$, —$V_o$—$OR^{30}$, —$V_o$—O(haloalkyl), —$V_o$—$SR^{30}$, —$V_o$—$NO_2$, —$V_o$—CN, —$V_o$—$N(R^{31})_2$, —$V_o$—$NR^{31}C(O)R^{30}$, —$V_o$—$NR^{31}CO_2R^{32}$, —$V_o$—$N(R^{31})C(O)N(R^{31})_2$, —$V_o$—$C(O)R^{30}$, —$V_o$—$C(S)R^{30}$, —$V_o$—$CO_2R^{30}$, —$V_o$—$OC(O)R^{30}$, —$V_o$—$C(O)N(R^{31})_2$—, —$V_o$—$S(O)_2R^{30}$, —$V_o$—$SO_2N(R^{31})_2$, —$V_o$—$S(O)R^{32}$, —$V_o$—$SO_3R^{30}$, —$V_o$—$NR^{31}SO_2N(R^{31})_2$, —$V_o$—$NR^{31}SO_2R^{32}$, —O—$V_o$—$Ar^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —$NR^{31}C(O)$—$V_o$—$N(R^{31})_2$, —$NR^{31}C(O)$—$V_o$—$Ar^1$, —$C(O)$—$V_o$—$N(R^{31})_2$, —$C(O)$—$V_o$—$Ar^1$, —$C(S)$—$V_o$—$N(R^{31})_2$, —$C(S)$—$V_o$—$Ar^1$, —$C(O)O$—$V_1$—$N(R^{31})_2$, —$C(O)O$—$V_o$—$Ar^1$, —O—$C(O)$—$V_1$—$N(R^{31})_2$, —O—$C(O)$—$V_o$—$Ar^1$, —$C(O)N(R^{31})$—$V_1$—$N(R^{31})_2$, —$C(O)N(R^{31})$—$V_o$—$Ar^1$, —$S(O)_2$—$V_o$—$N(R^{31})_2$, —$S(O)_2$—$V_o$—$Ar^1$, —$SO_2N(R^{31})$—$V_1$—$N(R^{31})_2$, —$SO_2N(R^{31})$—$V_o$—$Ar^1$, —$S(O)$—$V_o$—$N(R^{31})_2$, —$S(O)$—$V_o$—$Ar^1$, —$S(O)_2$—O—$V_1$—$N(R^{31})_2$, —$S(O)_2$—O—$V_o$—$Ar^1$, —$NR^{31}SO_2$—$V_o$—$N(R^{31})_2$, —$NR^{31}SO_2$—$V_o$—$Ar^1$, —O—$[CH_2]_p$—O—, —S—$[CH_2]_p$—S— and —$[CH_2]_q$—.

Values and preferred values for the remainder of the variables of Structural Formula (I) are each independently as described above for the first set of values.

A third set of values for the variables in Structural Formula (I) is provided in the following four paragraphs.

Y is —H, —C(O)R, —C(O)OR or —C(O)NRR', preferably —H.

$R^1$ is an aryl group optionally substituted with one or more substituents selected from the group consisting of halogen, alkyl, haloalkyl, $Ar^1$, —$OR^{30}$, —O(haloalkyl), —$SR^{30}$, —$NO_2$, —CN, —NCS, —$N(R^{31})_2$, —$NR^{31}C(O)R^{30}$, —$NR^{31}C(O)OR^{32}$, —$N(R^{31})C(O)N(R^{31})_2$, —$C(O)R^{30}$, —$C(S)R^{30}$, —$C(O)OR^{30}$, —$OC(O)R^{30}$, —$C(O)N(R^{31})_2$, —S(O)$_2$R$^{30}$, —SO$_2$N(R$^{31}$)$_2$, —S(O)R$^{32}$, —SO$_3$R$^{30}$, —NR$^{31}$SO$_2$N(R$^{31}$)$_2$, —NR$^{31}$SO$_2$R$^{32}$, —V$_o$—Ar$^1$, —V$_o$—OR$^{30}$, —V$_o$—O(haloalkyl), —V$_o$—SR$^{30}$, —V$_o$—NO$_2$, —V$_o$—CN, —V$_o$—N(R$^{31}$)$_2$, —V$_o$—NR$^{31}$C(O)R$^{30}$, —V$_o$—NR$^{31}$CO$_2$R$^{32}$, —V$_o$—N(R$^{31}$)C(O)N(R$^{31}$)$_2$, —V$_o$—C(O)R$^{30}$, —V$_o$—C(S)R$^{30}$, —V$_o$—CO$_2$R$^{30}$, —V$_o$—OC(O)R$^{30}$, —V$_o$—C(O)N(R$^{31}$)$_2$—, —V$_o$—S(O)$_2$R$^{30}$, —V$_o$—SO$_2$N(R$^{31}$)$_2$, —V$_o$—S(O)R$^{32}$, —V$_o$—SO$_3$R$^{30}$, —V$_o$—NR$^{31}$SO$_2$N(R$^{31}$)$_2$, —V$_o$—NR$^{31}$SO$_2$R$^{32}$, —O—V$_o$—Ar$^1$, —O—V$_1$—N(R$^{31}$)$_2$, —S—V$_o$—Ar$^1$, —S—V$_1$—N(R$^{31}$)$_2$, —N(R$^{31}$)—V$_o$—Ar$^1$, —N(R$^{31}$)—V$_1$—N(R$^{31}$)$_2$, —NR$^{31}$C(O)—V$_o$—N(R$^{31}$)$_2$, —NR$^{31}$C(O)—V$_o$—Ar$^1$, —C(O)—V$_o$—N(R$^{31}$)$_2$, —C(O)—V$_o$—Ar$^1$, —C(S)—V$_o$—N(R$^{31}$)$_2$, —C(S)—V$_o$—Ar$^1$, —C(O)O—V$_1$—N(R$^{31}$)$_2$, —C(O)O—V$_o$—Ar$^1$, —O—C(O)—V$_1$—N(R$^{31}$)$_2$, —O—C(O)—V$_o$—Ar$^1$, —C(O)N(R$^{31}$)—V$_1$—N(R$^{31}$)$_2$, —C(O)N(R$^{31}$)—V$_o$—Ar$^1$, —S(O)$_2$—V$_o$—N(R$^{31}$)$_2$, —S(O)$_2$—V$_o$—Ar$^1$, —SO$_2$N(R$^{31}$)—V$_1$—N(R$^{31}$)$_2$, —SO$_2$N(R$^{31}$)—V$_o$—Ar$^1$, —S(O)—V$_o$—N(R$^{31}$)$_2$, —S(O)—V$_o$—Ar$^1$, —S(O)$_2$—O—V$_1$—N(R$^{31}$)$_2$, —S(O)$_2$—O—V$_o$—Ar$^1$, —NR$^{31}$SO$_2$—V$_o$—N(R$^{31}$)$_2$, —NR$^{31}$SO$_2$—V$_o$—Ar$^1$, —O—[CH$_2$]$_p$—O—, —S—[CH$_2$]$_p$—S— and —[CH$_2$]$_q$—.

R$^2$ and R$^3$ taken together with the nitrogen atom of N(R$^2$R$^3$) form a 5- or 6-membered, optionally-substituted non-aromatic heterocyclic ring. Examples of suitable substituents for the non-aromatic heterocyclic ring represented by —NR$^2$R$^3$ are as described in the first set of values for Structural Formula (I).

Values and preferred values for the remainder of the variables of Structural Formula (I) are as described above for the first set of values.

A fourth set of values for the variables in Structural Formula (I) is provided in the following paragraphs:

Y is —H, —C(O)R, —C(O)OR or —C(O)NRR', preferably —H.

R$^1$ is an aryl group optionally substituted with one or more substituents selected from the group consisting of halogen, alkyl, haloalkyl, Ar$^1$, —OR$^{30}$, —O(haloalkyl), —SR$^{30}$, —NO$_2$, —CN, —NCS, —N(R$^{31}$)$_2$, —NR$^{31}$C(O)R$^{30}$, —NR$^{31}$C(O)OR$^{32}$, —N(R$^{31}$)C(O)N(R$^{31}$)$_2$, —C(O)R$^{30}$, —C(S)R$^{30}$, —C(O)OR$^{30}$, —OC(O)R$^{30}$, —C(O)N(R$^{31}$)$_2$, —S(O)$_2$R$^{30}$, —SO$_2$N(R$^{31}$)$_2$, —S(O)R$^{32}$, —SO$_3$R$^{30}$, —NR$^{31}$SO$_2$N(R$^{31}$)$_2$, —NR$^{31}$SO$_2$R$^{32}$, —V$_o$—Ar$^1$, —V$_o$—OR$^{30}$, —V$_o$—O(haloalkyl), —V$_o$—SR$^{30}$, —V$_o$—NO$_2$, —V$_o$—CN, —V$_o$—N(R$^{31}$)$_2$, —V$_o$—NR$^{31}$C(O)R$^{30}$, —V$_o$—NR$^{31}$CO$_2$R$^{32}$, —V$_o$—N(R$^{31}$)C(O)N(R$^{31}$)$_2$, —V$_o$—C(O)R$^{30}$, —V$_o$—C(S)R$^{30}$, —V$_o$—CO$_2$R$^{30}$, —V$_o$—OC(O)R$^{30}$, —V$_o$—C(O)N(R$^{31}$)$_2$—, —V$_o$—S(O)$_2$R$^{30}$, —V$_o$—SO$_2$N(R$^{31}$)$_2$, —V$_o$—S(O)R$^{32}$, —V$_o$—SO$_3$R$^{30}$, —V$_o$—NR$^{31}$SO$_2$N(R$^{31}$)$_2$, —V$_o$—NR$^{31}$SO$_2$R$^{32}$, —O—V$_o$—Ar$^1$, —O—V$_1$—N(R$^{31}$)$_2$, —S—V$_o$—Ar$^1$, —S—V$_1$—N(R$^{31}$)$_2$, —N(R$^{31}$)—V$_o$—Ar$^1$, —N(R$^{31}$)—V$_1$—N(R$^{31}$)$_2$, —NR$^{31}$C(O)—V$_o$—N(R$^{31}$)$_2$, —NR$^{31}$C(O)—V$_o$—Ar$^1$, —C(O)—V$_o$—N(R$^{31}$)$_2$, —C(O)—V$_o$—Ar$^1$, —C(S)—V$_o$—N(R$^{31}$)$_2$, —C(S)—V$_o$—Ar$^1$, —C(O)O—V$_1$—N(R$^{31}$)$_2$, —C(O)O—V$_o$—Ar$^1$, —O—C(O)—V$_1$—N(R$^{31}$)$_2$, —O—C(O)—V$_o$—Ar$^1$, —C(O)N(R$^{31}$)—V$_1$—N(R$^{31}$)$_2$, —C(O)N(R$^{31}$)—V$_o$—Ar$^1$, —S(O)$_2$—V$_o$—N(R$^{31}$)$_2$, —S(O)$_2$—V$_o$—Ar$^1$, —SO$_2$N(R$^{31}$)—V$_1$—N(R$^{31}$)$_2$, —SO$_2$N(R$^{31}$)—V$_o$—Ar$^1$, —S(O)—V$_o$—N(R$^{31}$)$_2$, —S(O)—V$_o$—Ar$^1$, —S(O)$_2$—O—V$_1$—N(R$^{31}$)$_2$, —S(O)$_2$—O—V$_o$—Ar$^1$, —NR$^{31}$SO$_2$—V$_o$—N(R$^{31}$)$_2$, —NR$^{31}$SO$_2$—V$_o$—Ar$^1$, —O—[CH$_2$]$_p$—O—, —S—[CH$_2$]$_p$—S— and —[CH$_2$]$_q$—.

R$^2$ and R$^3$ taken together with the nitrogen atom of N(R$^2$R$^3$) form a 5- or 6-membered, optionally-substituted non-aromatic heterocyclic ring.

R$^5$ and R$^6$ are each independently —H, —OH, a halogen, a lower alkoxy group or a lower alkyl group.

Values and preferred values of the remainder of the variables of Structural Formula (I) are each independently as described above for the first set of values.

A fifth set of values for the variables in Structural Formula (I) is provided in the following paragraphs:

Y is —H, —C(O)R, —C(O)OR or —C(O)NRR', preferably —H.

R$^1$ is an aryl group optionally substituted with one or more substituents selected from the group consisting of halogen, alkyl, haloalkyl, Ar$^1$, —OR$^{30}$, —O(haloalkyl), —SR$^{30}$, —NO$_2$, —CN, —NCS, —N(R$^{31}$)$_2$, —NR$^{31}$C(O)R$^{30}$, —NR$^{31}$C(O)OR$^{32}$, —N(R$^{31}$)C(O)N(R$^{31}$)$_2$, —C(O)R$^{30}$, —C(S)R$^{30}$, —C(O)OR$^{30}$, —OC(O)R$^{30}$, —C(O)N(R$^{31}$)$_2$, —S(O)$_2$R$^{30}$, —SO$_2$N(R$^{31}$)$_2$, —S(O)R$^{32}$, —SO$_3$R$^{30}$, —NR$^{31}$SO$_2$N(R$^{31}$)$_2$, —NR$^{31}$SO$_2$R$^{32}$, —V$_o$—Ar$^1$, —V$_o$—OR$^{30}$, —V$_o$—O(haloalkyl), —V$_o$—SR$^{30}$, —V$_o$—NO$_2$, —V$_o$—CN, —V$_o$—N(R$^{31}$)$_2$, —V$_o$—NR$^{31}$C(O)R$^{30}$, —V$_o$—NR$^{31}$CO$_2$R$^{32}$, —V$_o$—N(R$^{31}$)C(O)N(R$^{31}$)$_2$, —V$_o$—C(O)R$^{30}$, —V$_o$—C(S)R$^{30}$, —V$_o$—CO$_2$R$^{30}$, —V$_o$—OC(O)R$^{30}$, —V$_o$—C(O)N(R$^{31}$)$_2$—, —V$_o$—S(O)$_2$R$^{30}$, —V$_o$—SO$_2$N(R$^{31}$)$_2$, —V$_o$—S(O)R$^{32}$, —V$_o$—SO$_3$R$^{30}$, —V$_o$—NR$^{31}$SO$_2$N(R$^{31}$)$_2$, —V$_o$—NR$^{31}$SO$_2$R$^{32}$, —O—V$_o$—Ar$^1$, —O—V$_1$—N(R$^{31}$)$_2$, —S—V$_o$—Ar$^1$, —S—V$_1$—N(R$^{31}$)$_2$, —N(R$^{31}$)—V$_o$—Ar$^1$, —N(R$^{31}$)—V$_1$—N(R$^{31}$)$_2$, —NR$^{31}$C(O)—V$_o$—N(R$^{31}$)$_2$, —NR$^{31}$C(O)—V$_o$—Ar$^1$, —C(O)—V$_o$—N(R$^{31}$)$_2$, —C(O)—V$_o$—Ar$^1$, —C(S)—V$_o$—N(R$^{31}$)$_2$, —C(S)—V$_o$—Ar$^1$, —C(O)O—V$_1$—N(R$^{31}$)$_2$, —C(O)O—V$_o$—Ar$^1$, —O—C(O)—V$_1$—N(R$^{31}$)$_2$, —O—C(O)—V$_o$—Ar$^1$, —C(O)N(R$^{31}$)—V$_1$—N(R$^{31}$)$_2$, —C(O)N(R$^{31}$)—V$_o$—Ar$^1$, —S(O)$_2$—V$_o$—N(R$^{31}$)$_2$, —S(O)$_2$—V$_o$—Ar$^1$, —SO$_2$N(R$^{31}$)—V$_1$—N(R$^{31}$)$_2$, —SO$_2$N(R$^{31}$)—V$_o$—Ar$^1$, —S(O)—V$_o$—N(R$^{31}$)$_2$, —S(O)—V$_o$—Ar$^1$, —S(O)$_2$—O—V$_1$—N(R$^{31}$)$_2$, —S(O)$_2$—O—V$_o$—Ar$^1$, —NR$^{31}$SO$_2$—V$_o$—N(R$^{31}$)$_2$, —NR$^{31}$SO$_2$—V$_o$—Ar$^1$, —O—[CH$_2$]$_p$—O—, —S—[CH$_2$]$_p$—S— and —[CH$_2$]$_q$—.

R$^2$ and R$^3$ taken together with the nitrogen atom of N(R$^2$R$^3$) form a 5- or 6-membered, optionally-substituted non-aromatic heterocyclic ring.

R$^4$ is an aliphatic or aryl group each optionally substituted with one or more substituents. Examples of suitable substituents are as described above for the first set of values.

R$^5$ and R$^6$ are each independently —H, —OH, a halogen, a lower alkoxy group or a lower alkyl group.

Values and preferred values of the remainder of the variables of Structural Formula (I) are each independently as described above for the first set of values.

A sixth set of values for the variables in Structural Formula (I) is provided in the following paragraphs:

Y is —H, —C(O)R, —C(O)OR or —C(O)NRR', preferably —H.

R$^1$ is an aryl group optionally substituted with one or more substituents selected from the group consisting of halogen, alkyl, haloalkyl, Ar$^1$, —OR$^{30}$, —O(haloalkyl), —SR$^{30}$, —NO$_2$, —CN, —NCS, —N(R$^{31}$)$_2$, —NR$^{31}$C(O)R$^{30}$, —NR$^{31}$C(O)OR$^{32}$, —N(R$^{31}$)C(O)N(R$^{31}$)$_2$, —C(O)R$^{30}$, —C(S)R$^{30}$, —C(O)OR$^{30}$, —OC(O)R$^{30}$, —C(O)N(R$^{31}$)$_2$, —S(O)$_2$R$^{30}$, —SO$_2$N(R$^{31}$)$_2$, —S(O)R$^{32}$, —SO$_3$R$^{30}$, —NR$^{31}$SO$_2$N(R$^{31}$)$_2$, —NR$^{31}$SO$_2$R$^{32}$, —V$_o$—Ar$^1$, —V$_o$—OR$^{30}$, —V$_o$—O(haloalkyl), —V$_o$—SR$^{30}$, —V$_o$—NO$_2$, —V$_o$—CN, —V$_o$—N(R$^{31}$)$_2$, —V$_o$—NR$^{31}$C(O)R$^{30}$, —V$_o$—NR$^{31}$CO$_2$R$^{32}$, —V$_o$—N(R$^{31}$)C(O)N(R$^{31}$)$_2$, —V$_o$—C(O)R$^{30}$, —V$_o$—C(S)R$^{30}$, —V$_o$—CO$_2$R$^{30}$, —V$_o$—OC(O)R$^{30}$, —V$_o$—C(O)N(R$^{31}$)$_2$—, —V$_o$—S(O)$_2$R$^{30}$, —V$_o$—SO$_2$N(R$^{31}$)$_2$, —V$_o$—S(O)R$^{32}$, —V$_o$—SO$_3$R$^{30}$, —V$_o$—NR$^{31}$SO$_2$N(R$^{31}$)$_2$, —V$_o$—NR$^{31}$SO$_2$R$^{32}$, —O—V$_o$—Ar$^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —$NR^{31}C(O)$—$V_o$—$N(R^{31})_2$, —$NR^{31}C(O)$—$V_o$—$Ar^1$, —C(O)—$V_o$—$N(R^{31})_2$, —C(O)—$V_o$—$Ar^1$, —C(S)—$V_o$—$N(R^{31})_2$, —C(S)—$V_o$—$Ar^1$, —C(O)O—$V_1$—$N(R^{31})_2$, —C(O)O—$V_o$—$Ar^1$, —O—C(O)—$V_1$—$N(R^{31})_2$, —O—C(O)—$V_o$—$Ar^1$, —C(O)$N(R^{31})$—$V_1$—$N(R^{31})_2$, —C(O)$N(R^{31})$—$V_o$—$Ar^1$, —$S(O)_2$—$V_o$—$N(R^{31})_2$, —$S(O)_2$—$V_o$—$Ar^1$, —$SO_2N(R^{31})$—$V_1$—$N(R^{31})_2$, —$SO_2N(R^{31})$—$V_o$—$Ar^1$, —S(O)—$V_o$—$N(R^{31})_2$, —S(O)—$V_o$—$Ar^1$, —$S(O)_2$—O—$V_1$—$N(R^{31})_2$, —$S(O)_2$—O—$V_o$—$Ar^1$, —$NR^{31}SO_2$—$V_o$—$N(R^{31})_2$, —$NR^{31}SO_2$—$V_o$—$Ar^1$, —O—$[CH_2]_p$—O—, —S—$[CH_2]_p$—S— and —$[CH_2]_q$—.

$R^2$ and $R^3$ taken together with the nitrogen atom of $N(R^2R^3)$ form a 5- or 6-membered, optionally-substituted non-aromatic heterocyclic ring.

$R^4$ is an optionally substituted cyclic alkyl group, or an optionally substituted cyclic alkenyl group, an optionally substituted aryl group, —CN, —NCS, —$NO_2$ or a halogen. Examples of suitable substituents are as described above for the first set.

$R^5$ and $R^6$ are each independently —H, —OH, a halogen, a lower alkoxy group or a lower alkyl group.

Values and preferred values of the remainder of the variables of Structural Formula (I) are each independently as described above for the first set of values.

A seventh set of values and preferred values for the variables in Structural Formula (I) is provided in the following paragraphs:

Values and preferred values of $R^1$, Y, $R^2$, $R^3$, $R^5$ and $R^6$ are each independently as described above for the sixth set.

$R^4$ is an optionally substituted cyclic alkyl group, or an optionally substituted cyclic alkenyl group, or an optionally substituted aryl group, specifically optionally substituted aryl group. Examples of suitable substituents are as described above for the first set.

Values and preferred values of the remainder of the variables of Structural Formula (I) are each independently as described above for the first set of values.

In a second embodiment, the compound of the invention is represented by Structural Formula (II), (III), (IV), (V), (VI), (VII) or (VIII):

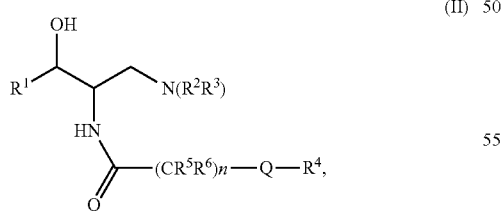
(II)

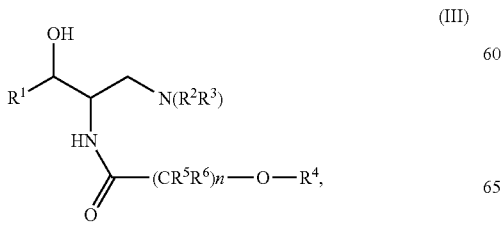
(III)

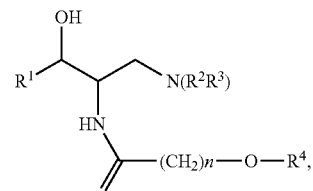
(IV)

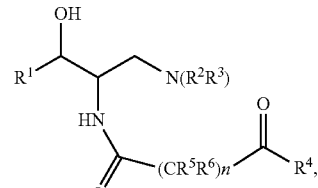
(V)

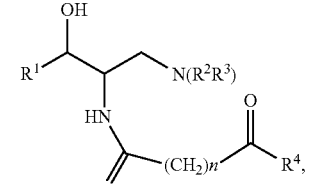
(VI)

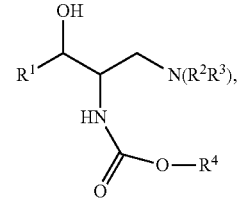
(VII)

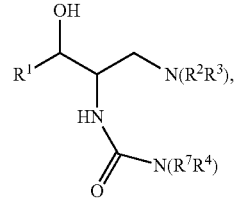
(XIII)

or a pharmaceutically acceptable salt thereof. A first set of values for the variables of Structural Formulas (II)-(VIII) is provided in the following paragraphs:

$R^1$ is a phenyl group optionally substituted with one or more substituents selected from the group consisting of halogen, cyano, nitro, C1-C6 alkyl, C1-C6 haloalkyl, —$OR^{30}$, —$SR^{30}$, —$N(R^{31})_2$, $Ar^1$, —$V_o$—$OR^{30}$, —$V_o$—$N(R^{31})_2$, —$V_o$—$Ar^1$, —O—$V_o$—$Ar^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —O—$[CH_2]_p$—O—, —S—$[CH_2]_p$—S— and —$[CH_2]_q$—. Preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, —O—$[CH_2]_p$—O— and —$[CH_2]_q$—.

$Ar^1$ is an aryl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $Ar^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

$R^{30}$ is independently hydrogen; an aryl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{31}$ is independently $R^{30}$, or $-N(R^{31})_2$ is an optionally substituted non-aromatic heterocyclic group. Examples of suitable substituents are as described above in the first set of values for Structural Formula (I).

$R^2$ and $R^3$ taken together with the nitrogen atom of $N(R^2R^3)$ form a 5- or 6-membered, optionally-substituted non-aromatic heterocyclic ring. Examples of suitable substituents for the non-aromatic heterocyclic ring represented by $-NR^2R^3$ are as described above in the first set of values for Structural Formula (I).

$R^4$ is an aliphatic or aryl group each optionally substituted with one or more substituents described above in the first set of values for Structural Formula (I).

$R^5$ and $R^6$ for Structural Formulas (II), (III) and (V) are each independently —H, —OH, a halogen, a lower alkoxy group or a lower alkyl group.

For Structural Formula (VIII), $R^7$ is —H or C1-C6 alkyl, preferably —H.

Values and preferred values of the remainder of the variables of Structural Formulas (II)-(VIII) are each independently as described above in the first set of values for Structural Formula (I).

A second set of values for the variables in Structural Formulas (II)-(VIII) is provided in the following paragraphs:

$R^1$ is a phenyl group optionally substituted with one or more substituents selected from the group consisting of halogen, cyano, nitro, C1-C6 alkyl, C1-C6 haloalkyl, $-OR^{30}$, $-SR^{30}$, $-N(R^{31})_2$, $Ar^1$, $-V_o-OR^{30}$, $-V_o-N(R^{31})_2$, $-V_o-Ar^1$, $-O-V_1-Ar^1$, $-O-V_1-N(R^{31})_2$, $-S-V_o-Ar^1$, $-S-V_1-N(R^{31})_2$, $-N(R^{31})-V_o-Ar^1$, $-N(R^{31})-V_1-N(R^{31})_2$, $-O-[CH_2]_p-O-$, $-S-[CH_2]_p-S-$, or $-[CH_2]_q-$. Preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, —O—$[CH_2]_p$—O— and —$[CH_2]_q$—.

$Ar^1$ is an aryl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $Ar^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

$R^{30}$ is independently hydrogen; an aryl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{31}$ is independently $R^{30}$, or $-N(R^{31})_2$ is an optionally substituted non-aromatic heterocyclic group.

$-N(R^2R^3)$ is a pyrrolidinyl, azetidinyl, piperidinyl, piperazinyl or morpholinyl group optionally substituted with one or more substituents selected from the group consisting of halogen, C1-C5 alkyl, C1-C5 haloalkyl, hydroxyl, C1-C5 alkoxy, nitro, cyano, C1-C5 alkoxycarbonyl, C1-C5 alkylcarbonyl or C1-C5 haloalkoxy, amino, C1-C5 alkylamino and C1-C5 dialkylamino $R^4$ is an aliphatic or aryl group each optionally substituted with one or more substituents. Examples of suitable substituents are described above in the first set of values for Structural Formula (I).

$R^5$ and $R^6$ for Structural Formulas (II), (III) and (V) are each independently —H, —OH, a halogen, a lower alkoxy group or a lower alkyl group.

For Structural Formula (VIII), $R^7$ is —H or C1-C6 alkyl, preferably —H.

Values and preferred values of the remainder of the variables of Structural Formulas (II)-(VIII) are each independently as described above in the first set of values for Structural Formula (I).

A third set of values for the variables in Structural Formulas (II)-(VIII) is provided in the following paragraphs:

$R^1$ is a phenyl group optionally substituted with one or more substituents selected from the group consisting of halogen, cyano, nitro, C1-C6 alkyl, C1-C6 haloalkyl, $-OR^{30}$, $-SR^{30}$, $-N(R^{31})_2$, $Ar^1$, $-V_o-OR^{30}$, $-V_o-N(R^{31})_2$, $-V_o-Ar^1$, $-O-V_o-Ar^1$, $-O-V_1-N(R^{31})_2$, $-S-V_o-Ar^1$, $-S-V_1-N(R^{31})_2$, $-N(R^{31})-V_o-Ar^1$, $-N(R^{31})-V_1-N(R^{31})_2$, $-O-[CH_2]_p-O-$, $-S-[CH_2]_p-S-$, or $-[CH_2]_q-$. Preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, —O—$[CH_2]_p$—O— and —$[CH_2]_q$—.

Ar¹ is an aryl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, Ar¹ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

$R^{30}$ is independently hydrogen; an aryl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or an C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{31}$ is independently $R^{30}$, or $-N(R^{31})_2$ is an optionally substituted non-aromatic heterocyclic group.

$-N(R^2R^3)$ is a pyrrolidinyl, azetidinyl, piperidinyl, piperazinyl or morpholinyl group optionally substituted with one or more substituents selected from the group consisting of halogen, C1-C5 alkyl, C1-C5 haloalkyl, hydroxyl, C1-C5 alkoxy, nitro, cyano, C1-C5 alkoxycarbonyl, C1-C5 alkylcarbonyl or C1-C5 haloalkoxy, amino, C1-C5 alkylamino and C1-C5 dialkylamino.

$R^4$ is an optionally substituted aryl or an optionally substituted lower arylalkyl group. Example of suitable substituents are as described in the first set of values for Structural Formula (I).

$R^5$ and $R^6$ for Structural Formulas (II), (III) and (V) are each independently —H, —OH, a halogen, a lower alkoxy group or a lower alkyl group.

For Structural Formula (VIII), $R^7$ is —H.

Preferably, Q in Structural Formula (II) is —O—, —S—, —C(O)—, —C(S)—, —NR⁷(CO)— or —C(O)NR⁷—

Values and preferred values of the remainder of the variables of Structural Formulas (II)-(VIII) are each independently as described above in the first set of values for Structural Formula (I). Preferably, for Structural Formula (II), Q is —O—, —S—, —C(O)—, —C(S)—, —NR⁷(CO)— or —C(O)NR⁷—.

A fourth set of values for the variables in Structural Formulas (II)-(VIII) is provided in the following paragraphs:

$R^1$ is a phenyl group optionally substituted with one or more substituents selected from the group consisting of halogen, cyano, nitro, C1-C6 alkyl, C1-C6 haloalkyl, —OR³⁰, —SR³⁰, —N(R³¹)₂, Ar¹, —V₀—OR³⁰, —V₀—N(R³¹)₂, —V₀—Ar¹, —O—V₀—Ar¹, —O—V₁—N(R³¹)₂, —S—V₀—Ar¹, —S—V₁—N(R³¹)₂, —N(R³¹)—V₀—Ar¹, —N(R³¹)—V₁—N(R³¹)₂, —O—[CH₂]ₚ—O—, —S—[CH₂]ₚ—S—, or —[CH₂]_q—. Preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, —O—[CH₂]ₚ—O— and —[CH₂]_q—.

Ar¹ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{31}$ is independently $R^{30}$, or $-N(R^{31})_2$ is an optionally substituted non-aromatic heterocyclic group.

$-N(R^2R^3)$ is a pyrrolidinyl, azetidinyl, piperidinyl, piperazinyl or morpholinyl group, which is optionally substituted with one or more substituents selected from the group consisting of halogen, C1-C5 alkyl, C1-C5 haloalkyl, hydroxyl, C1-C5 alkoxy, nitro, cyano, C1-C5 alkoxycarbonyl, C1-C5 alkylcarbonyl or C1-C5 haloalkoxy, amino, C1-C5 alkylamino and C1-C5 dialkylamino.

$R^4$ is an optionally substituted aryl or an optionally substituted lower arylalkyl group. Examples of suitable substitutents for $R^4$ are as provided above in the first set of values for Structural Formula (I). Preferably, $R^4$ is selected from the group consisting of:

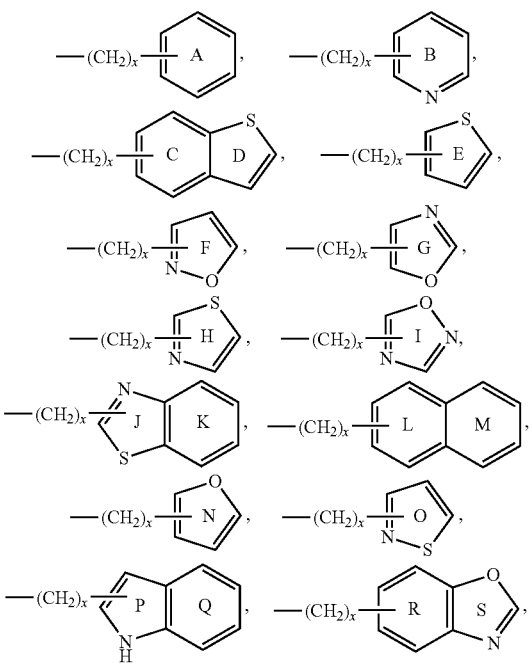

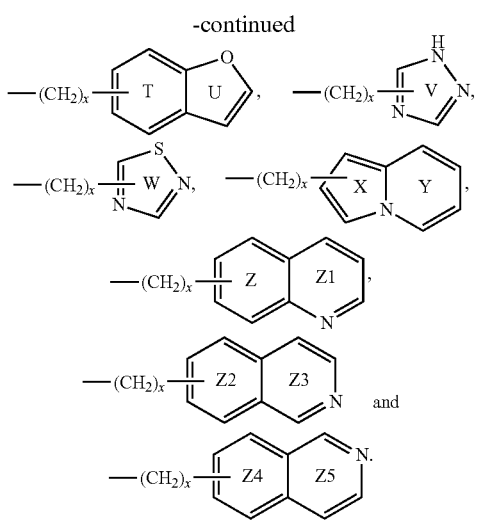

Each of rings A-Z5 is optionally and independently substituted.

For Structural Formula (VIII), $R^7$ is —H.

Values and preferred values of the remainder of the variables of Structural Formulas (II)-(VIII) are each independently as described above in the first set of values for Structural Formula (I). When the compound of the invention is represented by Structural Formula (III) or (IV), or a pharmaceutically acceptable salt thereof, n is 1, 2, 3 or 4. Alternatively, when the compound of the invention is represented by Structural Formula (V) or (VI), or a pharmaceutically acceptable salt thereof, n is 3, 4 or 5.

A fifth set of values for the variables in Structural Formulas (II)-(VIII) independently is as defined in the first set, second set, third set, fourth set, fifth set, sixth set or seventh set of values for the variables for Structural Formula (I).

In a third embodiment, the compound of the invention is represented by Structural Formula (IX) or (X):

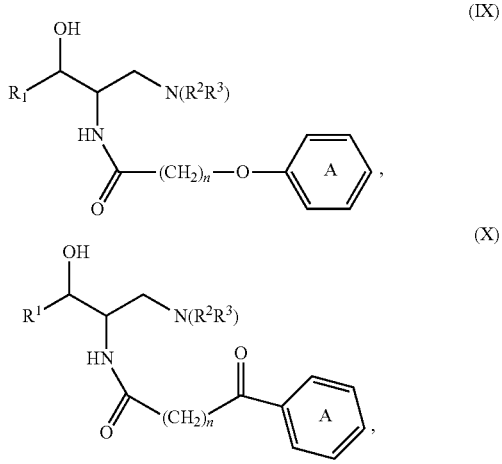

or a pharmaceutically acceptable salt thereof. A first set of values for the variables in Structural Formulas (IX) and (X) is defined in the following paragraphs:

$R^1$ is a phenyl group optionally substituted with one or more substituents. Examples of suitable substituents include halogen, cyano, nitro, C1-C6 alkyl, C1-C6 haloalkyl, —$OR^{30}$, —$SR^{30}$, —$N(R^{31})_2$, $Ar^1$, —$V_o$—$OR^{30}$, —$V_o$—N($R^{31})_2$, —$V_o$—$Ar^1$, —O—$V_o$—$Ar^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —O—$[CH_2]_p$—O—, —S—$[CH_2]_p$—S—, and —$[CH_2]_q$—; preferably, $R^1$ is a phenyl group optionally substituted with one or more substituents selected from the group consisting of —OH, —$OCH_3$, —$OC_2H_5$ and —O—$[CH_2]_p$—O—.

—$N(R^2R^3)$ is a pyrrolidinyl, azetidinyl, piperidinyl, piperazinyl or morpholinyl group, which is optionally substituted with one or more substituents selected from the group consisting of halogen, C1-C5 alkyl, C1-C5 haloalkyl, hydroxyl, C1-C5 alkoxy, nitro, cyano, C1-C5 alkoxycarbonyl, C1-C5 alkylcarbonyl or C1-C5 haloalkoxy, amino, C1-C5 alkylamino and C1-C5 dialkylamino; preferably, —$N(R^2R^3)$ is an unsubstituted pyrrolidinyl, azetidinyl, piperidinyl, piperazinyl or morpholinyl group.

Phenyl ring A is optionally substituted with one or more substituents selected from the group consisting of halogen, cyano, nitro, C1-C10 alkyl, C1-C10 haloalkyl, amino, C1-C10 alkylamino, C1-C10 dialkylamino, —$OR^{50}$, —$Ar^3$, —$V_4$—$Ar^3$, —V—$OR^{50}$, —O(C1-C10 haloalkyl), —$V_4$—O (C1-C10 haloalkyl), —O—$V_4$—$Ar^3$, —O—$[CH_2]_{p'}$—O— and —$[CH_2]_{q'}$—.

$Ar^3$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{50}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or an C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

For Structural Formula (IX), n is 1, 2, 3 or 4. For Structural Formula (X), n is 3, 4 or 5.

Values and preferred values of the remainder of the variables of Structural Formulas (IX) and (X) are each independently as defined above in the first set of values for Structural Formula (I).

A second set of values and preferred values for the variables in Structural Formulas (IX) and (X) is as defined in the following paragraphs:

$R^1$ is a phenyl group optionally substituted with one or more substituents selected from the group consisting of —OH, —$OCH_3$, —$OC_2H_5$ and —O—$[CH_2]_p$—O—.

—$N(R^2R^3)$ is pyrrolidinyl.

Phenyl ring A is optionally substituted with one or more substituents selected from the group consisting of halogen, cyano, nitro, C1-C10 alkyl, C1-C10 haloalkyl, amino, C1-C10 alkylamino, C1-C10 dialkylamino, aryl, aryloxy, hydroxy, C1-C10 alkoxy, —O—$[CH_2]_{p'}$—O— and —$[CH_2]_{q'}$—. Preferably, phenyl ring A is optionally substituted with one or more substituents selected from the group consisting of —OH, —$OCH_3$ or —$OC_2H_5$.

For Structural Formula (IX), n is 1, 2, 3 or 4. For Structural Formula (X), n is 3, 4 or 5.

Values and preferred values of the remaining variables of Structural Formulas (IX) and (X) are each independently as described above in the first set of values for Structural Formula (I).

A third set of values for the variables in Structural Formulas (IX) and (X) independently is as defined in the first set, second set, third set, fourth set or fifth set, of values for Structural Formulas (II)-(VIII).

In a fourth embodiment, the compound of the invention is represented by Structural Formula (XI), (XII) or (XIII):

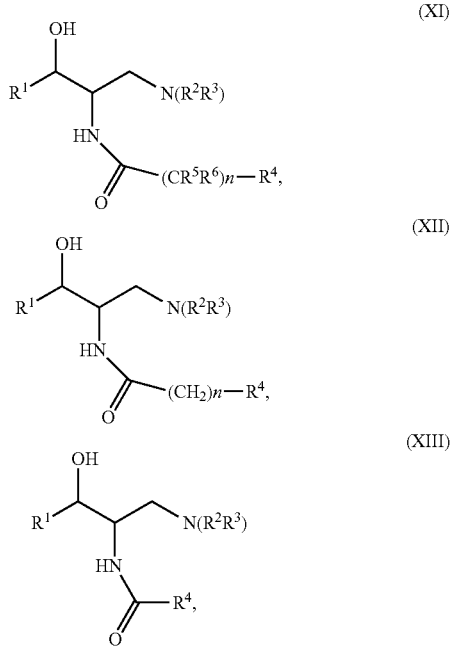

or a pharmaceutically acceptable salt thereof. A first set of values and preferred values for the variables of Structural Formulas (XI)-(XIII) is defined in the following paragraphs:

$R^1$ is a phenyl group optionally substituted with one or more substituents selected from the group consisting of halogen, cyano, nitro, C1-C6 alkyl, C1-C6 haloalkyl, —$OR^{30}$, —$SR^{30}$, —$N(R^{31})_2$, $Ar^1$, —$V_o$—$OR^{30}$, —$V_o$—$N(R^{31})_2$, —$V_o$—$Ar^1$, —O—$V_o$—$Ar^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —O—$[CH_2]_p$—O—, —S—$[CH_2]_q$—, or —$[CH_2]_q$—. Preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, —O—$[CH_2]_p$—O— and —$[CH_2]_q$—.

$Ar^1$ is an aryl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $Ar^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

$R^{30}$ is independently hydrogen; an aryl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{31}$ is independently $R^{30}$, or —$N(R^{31})_2$ is an optionally substituted non-aromatic heterocyclic group. Examples of suitable substituents are as described above in the first set of values for Structural Formula (I).

$R^2$ and $R^3$ taken together with the nitrogen atom of $N(R^2R^3)$ form a 5- or 6-membered, optionally-substituted non-aromatic heterocyclic ring. Examples of suitable substituents for the non-aromatic heterocyclic group represented by —$NR^2R^3$ are as described above in the first set of values for Structural Formula (I).

$R^4$ is an optionally substituted aryl group. Examples of suitable substituents for $R^4$ are as provided above in the first set of values for Structural Formula (I).

$R^5$ and $R^6$ for Structural Formula (XI) are each independently —H, —OH, a halogen, a lower alkoxy group or a lower alkyl group.

Values and preferred values of the remainder of the variables of Structural Formulas (XI)-(XIII) are each independently as described above in the first set of values for Structural Formula (I).

A second set of values and preferred values for the variables of Structural Formulas (XI)-(XIII) is defined in the following paragraphs:

$R^1$ is a phenyl group optionally substituted with one or more substituents selected from the group consisting of halogen, cyano, nitro, C1-C6 alkyl, C1-C6 haloalkyl, —$OR^{30}$, —$SR^{30}$, —$N(R^{31})_2$, $Ar^1$, —$V_o$—$OR^{30}$, —$V_o$—$N(R^{31})_2$, —$V_o$—$Ar^1$, —O—$V_o$—$Ar^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —O—$[CH_2]_p$—O—, —S—$[CH_2]_p$—S—, or —$[CH_2]_q$—. Preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, —O—$[CH_2]_p$—O—, and —$[CH_2]_q$—.

$Ar^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy C1-C6 alkoxycarbonyl, C1-C6 alkylcarbonyl and C1-C6 haloalkyl.

Each $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or an C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; and Each $R^{31}$ is independently $R^{30}$, or $—N(R^{31})_2$ is an optionally substituted non-aromatic heterocyclic group.

$—N(R^2R^3)$ is a pyrrolidinyl, azetidinyl, piperidinyl, piperazinyl or morpholinyl group, which is optionally substituted with one or more substituents selected from the group consisting of halogen, C1-C5 alkyl, C1-C5 haloalkyl, hydroxyl, C1-C5 alkoxy, nitro, cyano, C1-C5 alkoxycarbonyl, C1-C5 alkylcarbonyl or C1-C5 haloalkoxy, amino, C1-C5 alkylamino and C1-C5 dialkylamino.

$R^4$ is an optionally substituted aryl group. Suitable substituents and preferred substituents are as provided above in the first set of values for Structural Formula (I). Preferably, $R^4$ is selected from the group consisting of:

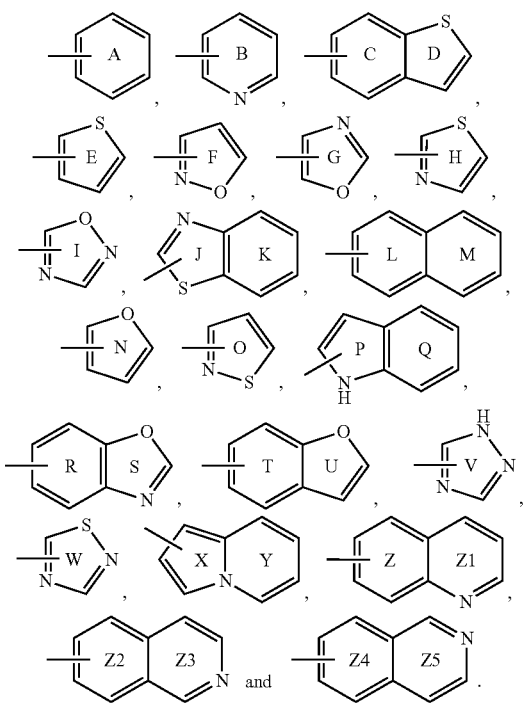

Each of rings A-Z5 is optionally and independently substituted. Preferably, each of rings A-Z5 is optionally and independently substituted with one or more substituents selected from $Ar^3$ and $Ar^3—Ar^3$ wherein values and preferred values of $Ar^3$ are as described above for the first set of values for Structural Formula (I). Preferably, $Ar^3$ is an aryl group each optionally substituted with one or more substituents selected from the group consisting of halogen, C1-C10 alkyl, C1-C10 haloalkyl, hydroxy, C1-C10 alkoxy, nitro, cyano, C1-C10 alkoxycarbonyl, C1-C10 alkylcarbonyl, C1-C10 haloalkoxy, amino, C1-C10 alkylamino and C1-C10 dialkylamino. More preferably, $Ar^3$ is an aryl group each optionally substituted with one or more substituents selected from the group consisting of halogen, C1-C4 alkyl, C1-C4 haloalkyl, hydroxy, C1-C4 alkoxy, nitro, cyano, C1-C4 alkoxycarbonyl, C1-C4 alkylcarbonyl, C1-C4 haloalkoxy, amino, C1-C4 alkylamino and C1-C4 dialkylamino $R^5$ and $R^6$ for Structural Formula (XI) are each independently —H, —OH, a halogen, a lower alkoxy group or a lower alkyl group.

Values and preferred values of the remainder of the variables of Structural Formulas (XI)-(XIII) are each independently as described above in the first set of values for Structural Formula (I).

A third set of values for the variables of Structural Formulas (XI)-(XIII) is defined in the following paragraphs:

$R^1$ is a phenyl group optionally substituted with one or more substituents selected from the group consisting of halogen, cyano, nitro, C1-C6 alkyl, C1-C6 haloalkyl, $—OR^{30}$, $—SR^{30}$, $—N(R^{31})_2$, $Ar^1$, $—V_o—OR^{30}$, $—V_o—N(R^{31})_2$, $—V_o—Ar^1$, $—O—V_o—Ar^1$, $—O—V_1—N(R^{31})_2$, $—S—V_o—Ar^1$, $—S—V_1—N(R^{31})_2$, $—N(R^{31})—V_o—Ar^1$, $—N(R^{31})—V_1—N(R^{31})_2$, $—O—[CH_2]_p—O—$, $—S—[CH_2]_p—S—$, or $—[CH_2]_q—$. Preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, $—O—[CH_2]_p—O—$, and $—[CH_2]_q—$.

$Ar^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy C1-C6 alkoxycarbonyl, C1-C6 alkylcarbonyl and C1-C6 haloalkyl.

Each $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{31}$ is independently $R^{30}$, or $—N(R^{31})_2$ is an optionally substituted non-aromatic heterocyclic group.

$—N(R^2R^3)$ is an unsubstituted pyrrolidinyl, azetidinyl, piperidinyl, piperazinyl or morpholinyl group.

$R^4$ is a biaryl group, such as a biphenyl group, optionally substituted with one or more substituents selected from the group consisting of halogen, cyano, amino, nitro, $Ar^3$, C1-C6 alkyl, C1-C6 haloalkyl, C1-C6 alkoxy, hydroxy and C1-C6 haloalkoxy.

$R^5$ and $R^6$ for Structural Formula (XI) are each independently —H, —OH, a halogen, a lower alkoxy group or a lower alkyl group, preferably —H.

Values and preferred values of the remainder of the variables of Structural Formulas (XI)-(XIII) are each independently as described above in the first set of values for Structural Formula (I).

A fourth set of values for the variables of Structural Formulas (XI)-(XIII) is defined in the following paragraphs:

$R^1$ is a phenyl group optionally substituted with one or more substituents selected from the group consisting of —OH, —OCH$_3$, —OC$_2$H$_5$ and $—O—[CH_2]_q—O—$, Preferably, $R^1$ is

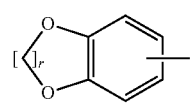

where r is 1, 2, 3 or 4, preferably 1 or 2.

$—N(R^2R^3)$ is an unsubstituted pyrrolidinyl group.

$R^4$ is a biaryl group, such as a biphenyl group, optionally substituted with one or more substituents selected from the group consisting of halogen, cyano, amino, nitro, $Ar^3$, C1-C6 alkyl, C1-C6 haloalkyl, C1-C6 alkoxy, hydroxy and C1-C6 haloalkoxy.

$R^5$ and $R^6$ for Structural Formula (XI) are each independently —H, —OH, a halogen, a lower alkoxy group or a lower alkyl group, preferably —H.

n is an integer from 1 to 4.

Values and preferred values of the remainder of the variables of Structural Formulas (XI)-(XIII) are each independently as described above in the first set of values for Structural Formula (I).

A fifth set of values preferred values for the variables of Structural Formulas (XI)-(XIII) is defined in the following paragraphs:

$R^1$ is a phenyl group optionally substituted with one or more substituents selected from the group consisting of —OH, —OCH$_3$, —OC$_2$H$_5$ and —O—[CH$_2$]$_p$—O—. Preferably $R^1$ is

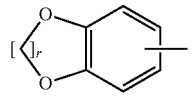

where r is 1, 2, 3 or 4, preferably 1 or 2.

—N($R^2R^3$) is pyrrolidinyl.

$R^4$ is

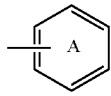

optionally substituted with one or more substituents selected from the group consisting of halogen, cyano, amino, nitro, $Ar^3$, C1-C6 alkyl, C1-C6 haloalkyl, C1-C6 alkoxy, hydroxy and C1-C6 haloalkoxy.

n is 1.

$R^5$ and $R^6$ for Structural Formula (XI) are each independently —H, —OH, a halogen, a lower alkoxy group or a lower alkyl group, preferably —H.

Values and preferred values of the remainder of the variables of Structural Formulas (XI)-(XIII) are each independently as described above in the first set of values for Structural Formula (I).

A sixth set of values for the variables in Structural Formulas (XI)-(XIII) independently is as defined in the first set, second set, third set, fourth set, fifth set, sixth set or seventh set of values for Structural Formula (I).

In a fifth embodiment, the compound of the invention is represented by Structural Formula (XIV) or (XV):

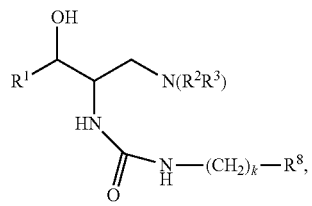

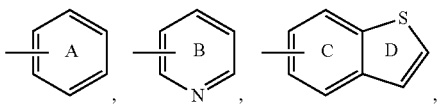

(XV)

or a pharmaceutically acceptable salt thereof. A first set of values and preferred values for the variables in Structural Formulas (XIV) and (XV) is as defined in the following paragraphs:

$R^1$ is a phenyl group optionally substituted with one or more substituents selected from the group consisting of halogen, cyano, nitro, C1-C6 alkyl, C1-C6 haloalkyl, —OR$^{30}$, —SR$^{30}$, —N(R$^{31}$)$_2$, Ar$^1$, —V$_o$—OR$^{30}$, —V$_o$—N(R$^{31}$)$_2$, —V$_o$—Ar$^1$, —O—V$_o$—Ar$^1$, —O—V$_1$—N(R$^{31}$)$_2$, —S—V$_o$—Ar$^1$, —S—V$_1$—N(R$^{31}$)$_2$, —N(R$^{31}$)—V$_o$—Ar$^1$, —N(R$^{31}$)—V$_1$—N(R$^{31}$)$_2$, —O—[CH$_2$]$_p$—O—, —S—[CH$_2$]$_p$—S—, or —[CH$_2$]$_q$—. Preferably, $R^1$ is a phenyl group optionally substituted with one or more substituents selected from the group consisting of halogen, cyano, nitro, C1-C6 alkyl, C1-C6 haloalkyl, C1-C6 alkylamino, C1-C6 dialkylamino, aryl, aryloxy, —OH, C1-C6 alkoxy, —O—[CH$_2$]$_p$—O—, and —[CH$_2$]$_q$—.

Ar$^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy and C1-C6 haloalkyl.

Each R$^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each R$^{31}$ is independently R$^{30}$, or —N(R$^{31}$)$_2$ is an optionally substituted non-aromatic heterocyclic group.

—N($R^2R^3$) is a pyrrolidinyl, azetidinyl, piperidinyl, piperazinyl or morpholinyl group optionally substituted with one or more substituents selected from the group consisting of halogen, C1-C5 alkyl, C1-C5 haloalkyl, hydroxyl, C1-C5 alkoxy, nitro, cyano, C1-C5 alkoxycarbonyl, C1-C5 alkylcarbonyl or C1-C5 haloalkoxy, amino, C1-C5 alkylamino and C1-C5 dialkylamino.

k is 0, 1, 2, 3, 4, 5 or 6.

$R^8$ is —H, or an optionally substituted aryl or an optionally substituted lower alkyl group. Examples of suitable substituents are as described for the first set of values for Structural Formula (I). Preferably, $R^8$ is selected from the group consisting of:

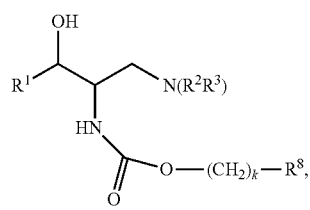

-continued

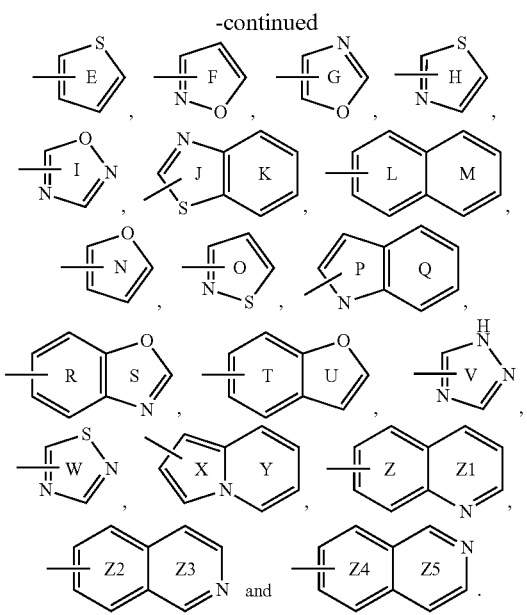

Each of rings A-Z5 is optionally and independently substituted. Examples of suitable substituents for $R^8$ are as provided above in the first set of values for $R^4$ in Structural Formula (I). More preferably, $R^8$ is a

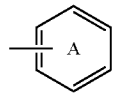

group. Alternatively, $R^8$ is an aryl group substituted with $Ar^3$, such as a phenyl group substituted with $Ar^3$, where values and preferred values of $Ar^3$ are as described above in Structural Formula (I).

Values and preferred values of the remainder of the variables of Structural Formulas (XIV) and (XV) are each independently as described above in the first set of values for Structural Formula (I).

A second set of values for the variables in Structural Formulas (XIV) and (XV) is defined in the following paragraphs:

$R^1$ is a phenyl group optionally substituted with one or more substituents selected from the group consisting of halogen, cyano, nitro, C1-C6 alkyl, C1-C6 haloalkyl, —$OR^{30}$, —$SR^{30}$, —$N(R^{31})_2$, $Ar^1$, —V—$OR^{30}$, —V—$N(R^{31})_2$, —V—$Ar^1$, —O—V—$Ar^1$, —O—$V_1$—$N(R^{31})_2$, —S—V—$Ar^1$, —S—$V_1$—$N(R^{31})_2$, —$N(R^{31})$—V—$Ar^1$, —$N(R^{31})$—$V_1$—$N(R^{31})_2$, —O—$[CH_2]_p$—O—, —S—$[CH_2]_p$—S— and —$[CH_2]_q$—.

$Ar^1$ is a phenyl group each optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or an C1-C10 alkyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl.

Each $R^{31}$ is independently $R^{30}$, or —$N(R^{31})_2$ is an optionally substituted non-aromatic heterocyclic group.

—$N(R^2R^3)$ is an unsubstituted pyrrolidinyl, azetidinyl, piperidinyl, piperazinyl or morpholinyl group, preferably an unsubstituted pyrrolidinyl group.

Values and preferred values for k and $R^8$ are as provided above in the first set of values for Structural Formulas (XIV) and (XV).

Values and preferred values of the remainder of the variables of Structural Formulas (XIV) and (XV) are each independently as described above in the first set of values for Structural Formula (I).

A third set of values for the variables in Structural Formulas (XIV) and (XV) is defined in the following paragraphs:

$R^1$ is a phenyl group optionally substituted with one or more substituents selected from the group consisting of —OH, —$OCH_3$, —$OC_2H_5$ and —O—$[CH_2]_p$—O—. Preferably $R^1$ is

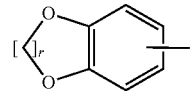

where r is 1, 2, 3 or 4, preferably 1 or 2.

—$N(R^2R^3)$ is pyrrolidinyl.

Values and preferred values for k and $R^8$ are each independently as provided above in the first set of values for Structural Formulas (XIV) and (XV).

Values and preferred values of the remainder of the variables of Structural Formulas (XIV) and (XV) are each independently as described above in the first set of values for Structural Formula (I).

A fourth set of values for the variables in Structural Formulas (XIV)-(XV) is as defined in the first set, second set, third set, fourth set, fifth set, sixth set or seventh set for Structural Formula (I).

In a sixth embodiment, the compound of the invention is represented by Structural Formula (XXI):

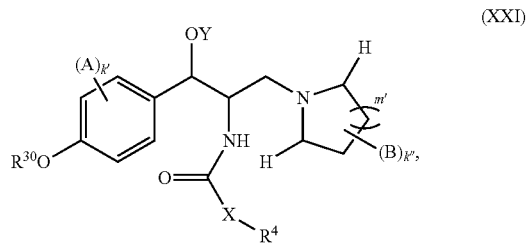

or a pharmaceutically acceptable salt thereof. A first set of values and preferred values for the variables in Structural Formula (XXI) is as defined in the following paragraphs:

Each of A and B independently is halogen, hydroxy, C1-C6 alkyl, C1-C6 haloalkyl, C1-C6 alkoxy or C1-C6 haloalkoxy.

k' is 0, 1 or 2.

k" is 0, 1 or 2. Preferably, k" is 0 or 1. More preferably k" is 1.

m' is 0, 1 or 2. Preferably, m' is 1.

Values and preferred values for the remainder of the variables of Structural Formula (XXI) are each independently as described above in the first set of values for Structural Formula (I).

A second set of values for the variables in Structural Formula (XXI) is provided in the following paragraphs:

Y is —H, —C(O)R, —C(O)OR or —C(O)NRR', preferably —H.

Values and preferred values for A, B, k', k" and m' are each independently as described above in the first set of values for Structural Formula (XXI).

Values and preferred values for the remainder of the variables of Structural Formula (XXI) are each independently as described above in the first set of values for Structural Formula (I).

A third set of values for the variables in Structural Formula (XXI) is provided in the following paragraphs:

$R^{30}$ is independently hydrogen; an aryl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. More preferably, $R^{30}$ is independently hydrogen; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Even more preferably, $R^{30}$ is independently hydrogen, or a C1-C10 alkyl group optionally substituted with one or more substituents selected from the group consisting of halogen, C1-C6 alkoxy, C1-C6 haloalkoxy and hydroxy.

Values and preferred values for A, B, Y, k', k" and m' are each independently as described above in the second set of values for Structural Formula (XXI).

Values and preferred values for the remainder of the variables of Structural Formula (XXI) are each independently as described above in the first set of values for Structural Formula (I).

A fourth set of values for the variables in Structural Formula (XXI) is provided in the following paragraphs:

Y is —H.

Values and preferred values for $R^{30}$, A, B, k', k" and m' are each independently as described above in the third set of values for Structural Formula (XXI).

Values and preferred values for the remainder of the variables of Structural Formula (XXI) are each independently as described above in the first set of values for Structural Formula (I).

In a seventh embodiment, the compound of the invention is represented by Structural Formula (XXII), (XXIII), (XXIV), (XXV), (XXVI), (XXVII), (XXVIII), (XXIX), (XXX) or (XXXI):

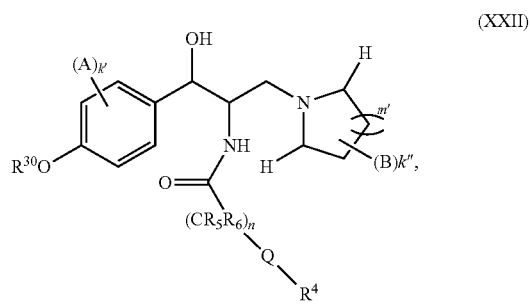

(XXII)

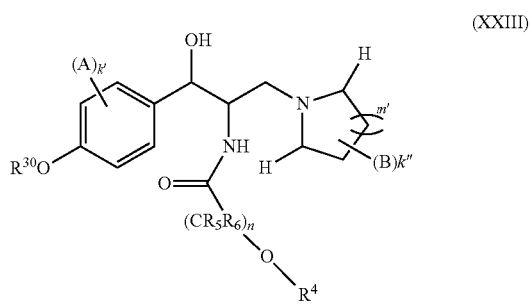

(XXIII)

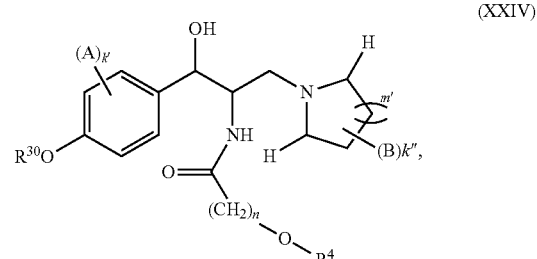

(XXIV)

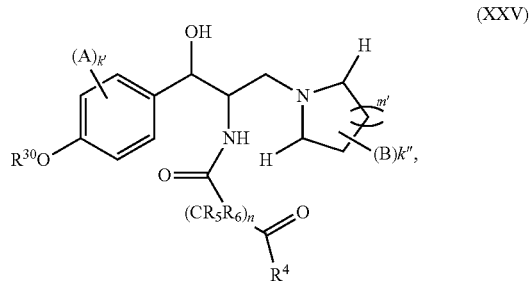

(XXV)

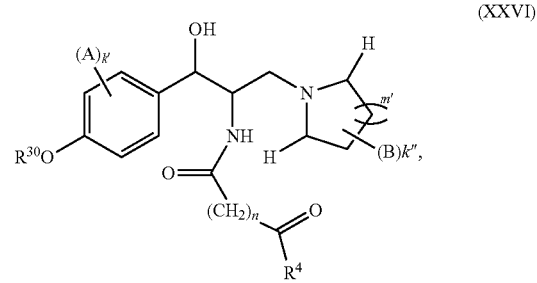

(XXVI)

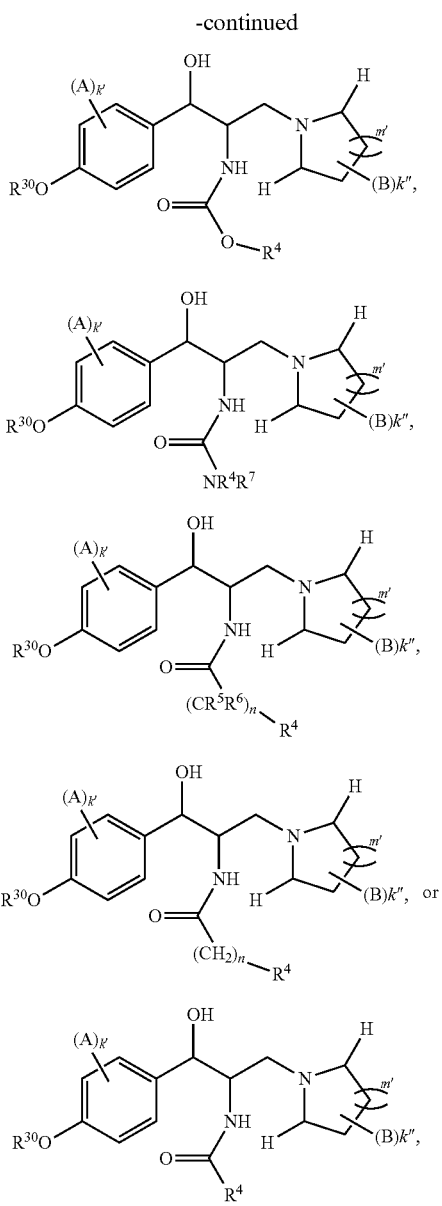

or a pharmaceutically acceptable salt thereof. A first set of values and preferred values for the variables in Structural Formulas (XXII)-(XXXI) is as defined in the following paragraphs:

Each of A and B independently is halogen, hydroxy, C1-C6 alkyl, C1-C6 haloalkyl, C1-C6 alkoxy or C1-C6 haloalkoxy.

Each $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $R^{30}$ is independently hydrogen; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. More preferably, $R^{30}$ is independently hydrogen, or a C1-C10 alkyl group optionally substituted with one or more substituents selected from the group consisting of halogen, C1-C6 alkoxy, C1-C6 haloalkoxy and hydroxy.

Each k' is independently 0, 1 or 2.
Each k" is independently 0, 1 or 2.
Each m' is independently 0, 1 or 2. Preferably, each m' is 1.
Each n is independently 1, 2, 3, 4, 5 or 6. Preferably, each n in Structural Formulas (XXV) and (XXVI) is independently 1, 2, 3 or 4, and each n in Structural Formulas (XXIII) or (XXIV) is independently 2, 3, 4 or 5.

Values and preferred values for the remainder of the variables of Structural Formulas (XXII)-(XXXI) are each independently as described above in the first set of values for Structural Formula (I).

A second set of values for the variables in Structural Formulas (XXII)-(XXXI) is provided in the following paragraphs:

Each $R^4$ in Structural Formulas (XXII)-(XXVIII) is independently an aliphatic or aryl group each optionally substituted with one or more substituents described above in the first set of values for Structural Formula (I). Preferably, each $R^4$ in Structural Formulas (XXII)-(XXVIII) is independently an optionally substituted aryl or an optionally substituted lower arylalkyl group. Examples of suitable substituents are as described in the first set of values for Structural Formula (I).

Each $R^4$ in Structural Formulas (XXIX)-(XXXI) is independently an aryl group optionally substituted with one or more substituents described above in the first set of values for Structural Formula (I).

$R^5$ and $R^6$ in Structural Formulas (XXII), (XXIII), (XV) and (XXIX) are each independently —H, —OH, a halogen, a C1-C6 alkoxy group or a C1-C6 alkyl group.

For Structural Formula (XXVIII), $R^7$ is —H or C1-C6 alkyl, preferably —H.

Values and preferred values for A, B, $R^{30}$, k', k", m' and n are each independently as described above in the first set of values for the variables in Structural Formulas (XXII)-(XXXI). Preferably, each n in Structural Formulas (XXV) and (XXVI) is independently 1, 2, 3 or 4, and each n in Structural Formulas (XXIII) or (XXIV) is independently 2, 3, 4 or 5.

Values and preferred values for the remainder of the variables of Structural Formulas (XXII)-(XXXI) are each independently as described above in the first set of values for Structural Formula (I).

A third set of values for the variables in Structural Formulas (XXII)-(XXXI) is provided in the following paragraphs:

Each $R^4$ in Structural Formulas (XXII)-(XXVIII) is independently an optionally substituted aryl or an optionally substituted lower arylalkyl group. Example of suitable substituents are as described in the first set of values for Structural Formula (I). Each $R^4$ in Structural Formulas (XXIX)-(XXXI) is independently an aryl group optionally substituted with one or more substituents described above in the first set of values for Structural Formula (I).

$R^5$ and $R^6$ for Structural Formulas (XXII), (XXIII), (XXV) and (XXIX) are each independently —H, —OH, a halogen, a lower alkoxy group or a lower alkyl group.

For Structural Formula (XXVIII), $R^7$ is —H.

Q in Structural Formula (XXII) is —O—, —S—, —C(O)—, —C(S)—, —NR$^7$(CO)— or —C(O)NR$^7$—.

Values and preferred values for A, B, R$^{30}$, k', k'', m' and n are each independently as described above in the first set of values for the variables in Structural Formulas (XXII)-(XXXI). Preferably, each n in Structural Formulas (XXV) and (XXVI) is independently 1, 2, 3 or 4, and each n in Structural Formulas (XXIII) or (XXIV) is independently 2, 3, 4 or 5.

Values and preferred values for the remainder of the variables of Structural Formulas (XXII)-(XXXI) are each independently as described above in the first set of values for Structural Formula (I).

A fourth set of values for the variables in Structural Formulas (XXII)-(XXXI) is provided in the following paragraphs:

Each R$^4$ in Structural Formulas (XXII)-(XXVIII) is independently selected from the group consisting of:

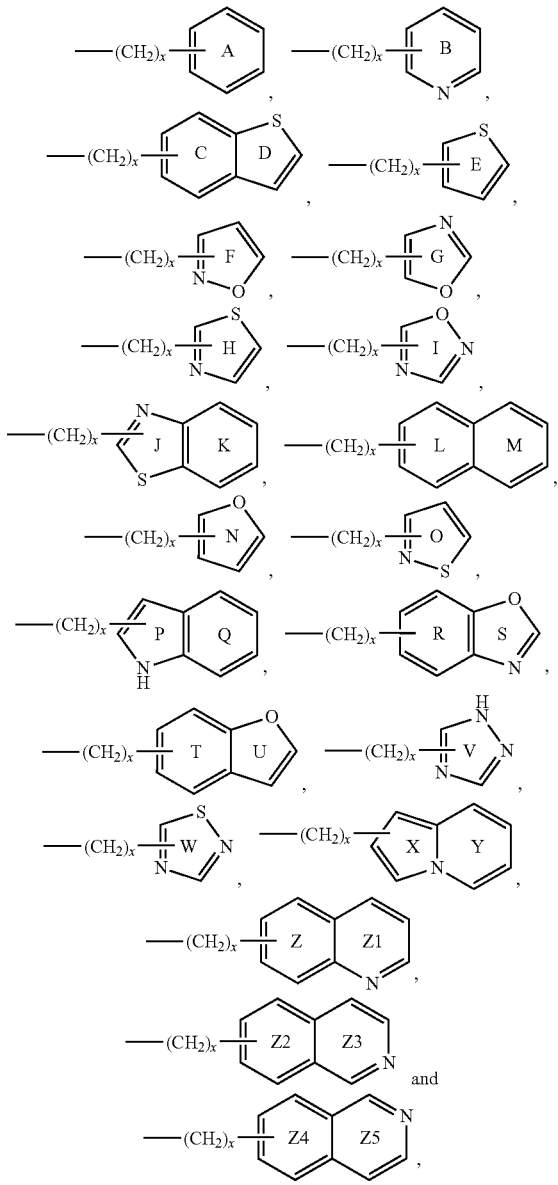

wherein each x is independently 0 or 1, and each of rings A-Z5 is optionally and independently substituted.

Each R$^4$ in Structural Formulas (XXIX)-(XXXI) is independently selected from the group consisting of:

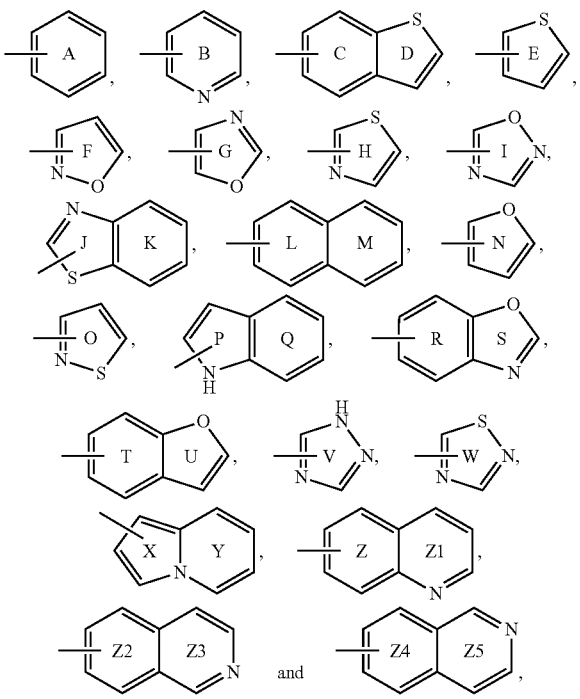

wherein each of rings A-Z5 is optionally and independently substituted. Preferably, each R$^4$ in Structural Formulas (XXII)-(XXXI) is independently monocyclic.

Example of suitable substituents for rings A-Z5 are as described in the first set of values for Structural Formula (I).

Preferably, in Structural Formulas (XXIX)-(XXXI), each of rings A-Z5 is optionally and independently substituted with one or more substituents selected from Ar$^3$ and Ar$^3$—Ar$^3$ wherein values and preferred values of Ar$^3$ are as described above for the first set of values for Structural Formula (I). Preferably, Ar$^3$ is an aryl group each optionally substituted with one or more substituents selected from the group consisting of halogen, C1-C10 alkyl, C1-C10 haloalkyl, hydroxy, C1-C10 alkoxy, nitro, cyano, C1-C10 alkoxycarbonyl, C1-C10 alkylcarbonyl, C1-C10 haloalkoxy, amino, C1-C10 alkylamino and C1-C10 dialkylamino. More preferably, Ar$^3$ is an aryl group each optionally substituted with one or more substituents selected from the group consisting of halogen, C1-C4 alkyl, C1-C4 haloalkyl, hydroxy, C1-C4 alkoxy, nitro, cyano, C1-C4 alkoxycarbonyl, C1-C4 alkylcarbonyl, C1-C4 haloalkoxy, amino, C1-C4 alkylamino and C1-C4 dialkylamino.

Values and preferred values for R$^5$, R$^6$, R$^7$, R$^{30}$, Q, k', k'', m' and n are each independently as described above in the third set of values for the variables in Structural Formulas (XXII)-(XXXII). Preferably, each n in Structural Formulas (XXV) and (XXVI) is independently 1, 2, 3 or 4, and each n in Structural Formulas (XXIII) or (XXIV) is independently 2, 3, 4 or 5.

Values and preferred values for the remainder of the variables of Structural Formulas (XXII)-(XXXI) are each independently as described above in the first set of values for Structural Formula (I).

A fifth set of values for the variables in Structural Formulas (XXII)-(XXXI) is provided in the following paragraphs:

Each R$^4$ in Structural Formulas (XXII)-(XXVIII) is independently

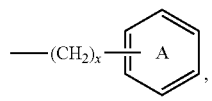

wherein x is 0 or 1.

Each $R^4$ in Structural Formulas (XXIX)-(XXXI) is independently

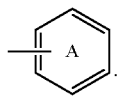

Each ring A is optionally substituted. Example of suitable substituents for rings A are as described in the first set of values for Structural Formula (I). Preferably, ring A is optionally substituted with one or more substituents selected from the group consisting of halogen, cyano, amino, nitro, $Ar^3$, C1-C6 alkyl, C1-C6 haloalkyl, C1-C6 alkoxy, hydroxy and C1-C6 haloalkoxy.

$Ar^3$ is an aryl group each optionally substituted with one or more substituents selected from the group consisting of halogen, C1-C4 alkyl, C1-C4 haloalkyl, hydroxy, C1-C4 alkoxy, nitro, cyano, C1-C4 alkoxycarbonyl, C1-C4 alkyl carbonyl, C1-C4 haloalkoxy, amino, C1-C4 alkylamino and C1-C4 dialkylamino Values and preferred values for A, B, $R^5$, $R^6$, $R^7$, $R^{30}$, Q, k', k'', m' and n are each independently as described above in the fourth set of values for the variables in Structural Formulas (XXII)-(XXXI).

Values and preferred values for the remainder of the variables of Structural Formulas (XXII)-(XXXI) are each independently as described above in the first set of values for Structural Formula (I).

A sixth set of values for the variables other than A, B, k', k'' and m' in Structural Formulas (XXII)-(XXXI) is as defined in the first set, second set, third set, fourth set, fifth set, sixth set or seventh set of values for the variables for Structural Formula (I), and values and preferred values for A, B, k', k'' and m' are each independently as described above in the first set of values for the variables in Structural Formulas (XXII)-(XXXI).

In an eighth embodiment, the compound of the invention is represented by Structural Formula (XXXII) or (XXXIII):

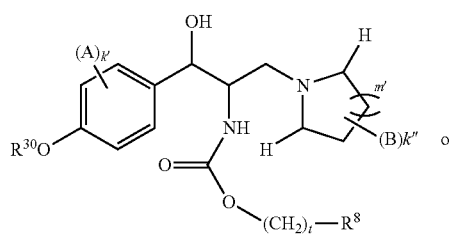

(XXXII)

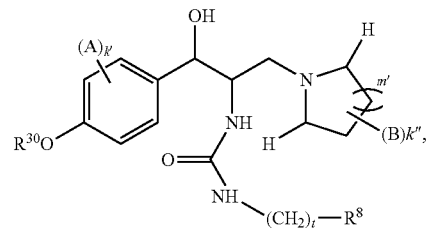

(XXXIII)

or a pharmaceutically acceptable salt thereof. A first set of values and preferred values for the variables in Structural Formulas (XXXII)-(XXXIII) is as defined in the following paragraphs:

Each of A and B independently is halogen, hydroxy, C1-C6 alkyl, C1-C6 haloalkyl, C1-C6 alkoxy or C1-C6 haloalkoxy.

Each $R^{30}$ is independently hydrogen; a phenyl group optionally substituted with one or more substituents selected from the group consisting of halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. Preferably, $R^{30}$ is independently hydrogen; or a C1-C10 alkyl group optionally substituted with one or more substituents selected from the group consisting of halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl and C1-C6 haloalkyl. More preferably, $R^{30}$ is independently hydrogen, or a C1-C10 alkyl group optionally substituted with one or more substituents selected from the group consisting of halogen, C1-C6 alkoxy, C1-C6 haloalkoxy and hydroxy.

Each k' is independently 0, 1 or 2.
Each k'' is independently 0, 1 or 2.
Each m' is independently 0, 1 or 2.
Each q is independently 0, 1, 2, 3, 4, 5 or 6.
Each $R^8$ independently is —H, or an optionally substituted aryl or an optionally substituted lower alkyl group. Examples of suitable substituents are as described for the first set of values for Structural Formula (I). Preferably, each $R^8$ independently is selected from the group consisting of:

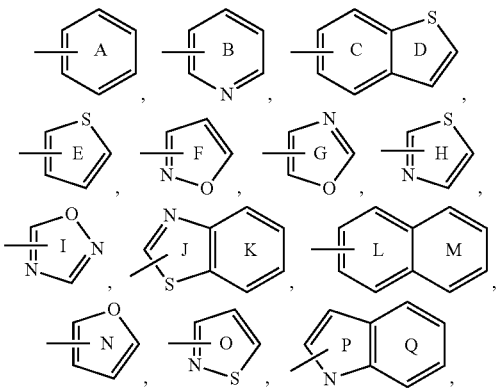

-continued

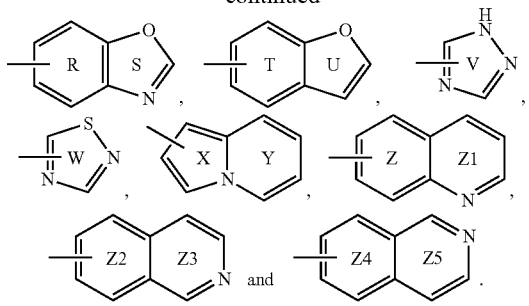

Each of rings A-Z5 is optionally and independently substituted. Examples of suitable substituents for $R^8$ are as provided above in the first set of values for $R^4$ in Structural Formula (I). More preferably, each $R^8$ is independently a

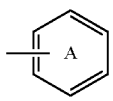

group. Alternatively, each $R^8$ is independently an aryl group substituted with $Ar^3$, such as a phenyl group substituted with $Ar^3$, where values and preferred values of $Ar^3$ are as described above in Structural Formula (I).

Values and preferred values for the remainder of the variables of Structural Formulas (XXXII)-(XXXIII) are each independently as described above in the first set of values for Structural Formula (I).

In one preferred embodiment, each k' in Structural Formulas (XXI)-(XXXIII) is independently 0 or 1. Preferably, when k' is 1, each A independently is positioned at a meta position of the phenyl ring.

In another preferred embodiment, each k" in Structural Formulas (XXI)-(XXXIII) is independently 0 or 1, more preferably 1.

In yet another preferred embodiment, each m' in Structural Formulas (XXI)-(XXXIII) is independently 1.

In yet another preferred embodiment, each k' in Structural Formulas (XXI)-(XXXIII) is independently 0 or 1; and each k" in Structural Formulas (XXI)-(XXXIII) is independently 0 or 1, more preferably 1.

In yet another preferred embodiment, in Structural Formulas (XXI)-(XXXIII):

Each $R^{30}$ is independently hydrogen or a C1-C6 alkyl group optionally substituted with one or more substituents selected from the group consisting of halogen, amino, C1-C3 alkylamino, C1-C3 dialkylamino, C1-C3 alkoxy, nitro, cyano, hydroxy, C1-C3 haloalkoxy, C1-C3 alkoxycarbonyl and C1-C3 alkylcarbonyl;

each k' in Structural Formulas (XXI)-(XXXIV) is independently 0 or 1. Preferably, when k' is 1, each A independently is positioned at a meta position of the phenyl ring; and each k" in Structural Formulas (XXI)-(XXXIV) is independently 0 or 1, preferably 1.

In yet another preferred embodiment, in Structural Formulas (XXI)-(XXXIII):

Each —$OR^{30}$ is independently —OH or —O—C1-C6 alkyl optionally substituted with one or more substituents selected from the group consisting of halogen, C1-C3 C1-C3 alkoxy, hydroxy and C1-C3 haloalkoxy;

each k' in Structural Formulas (XXI)-(XXXIII) is independently 0 or 1. Preferably, when k' is 1, each A is independently positioned at a meta position of the phenyl ring; and each k" in Structural Formulas (XXI)-(XXXIII) is independently 0 or 1, preferably 1.

In one more preferred embodiment, the compound of the invention is represented by Structural Formula (XVIA) or (XVIB):

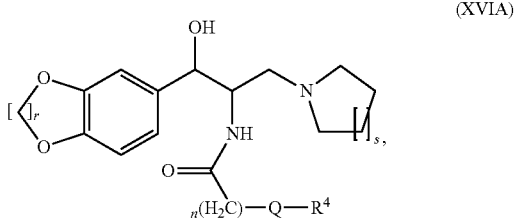

(XVIA)

(XVIB)

or a pharmaceutically acceptable salt thereof, wherein: Q is —O—, —C(O)— or —NH, specifically, —O— or —C(O)—; r and s are each independently 1, 2, 3 or 4; each n independently is 1, 2, 3, 4, 5 or 6; and $R^4$ has values and preferred values provided above in the first set of values for Structural Formula (I).

In another more preferred embodiment, the compound of the invention is represented by Structural Formula (XVIC) or (XVID):

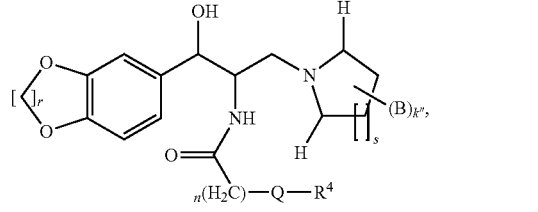

(XVIC)

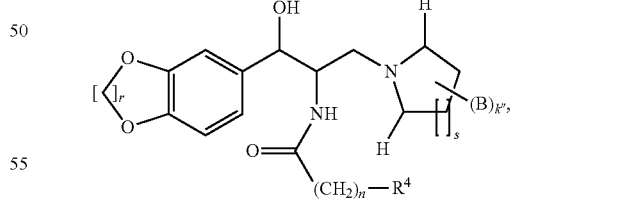

(XVID)

or a pharmaceutically acceptable salt thereof, wherein:
Q is —O—, —C(O)— or —NH, specifically, —O— or —C(O)—;
r and s are each independently 1, 2, 3 or 4;
each n independently is 1, 2, 3, 4, 5 or 6;
$R^4$ has values and preferred values provided above in the first set of values for Structural Formula (I); and
B is halogen, hydroxy, C1-C6 alkyl, C1-C6 haloalkyl, C1-C6 alkoxy or C1-C6 haloalkoxy. Preferably, B is halogen, hydroxy, C1-C5 alkoxy or C1-C5 haloalkoxy.

In another more preferred embodiment, the compound of the invention is represented by Structural Formula (XVII), (XVIII), (XIX) or (XIX):

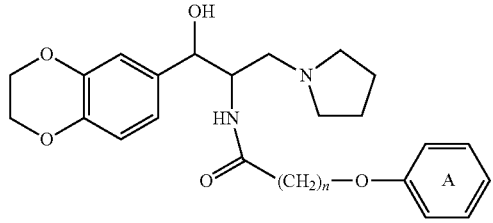

(XVII)

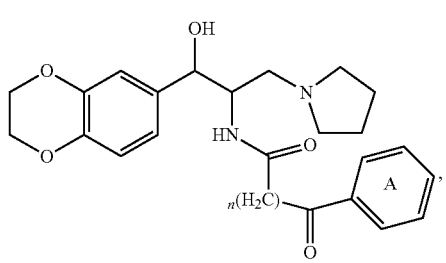

(XVIII)

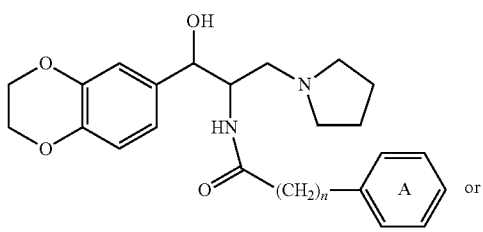

XIX

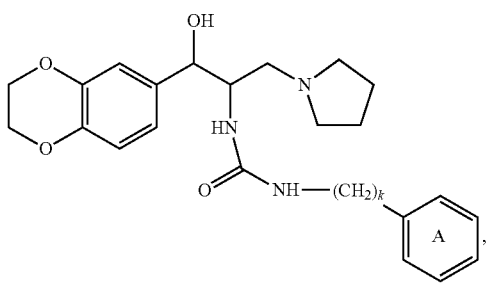

XX or a pharmaceutically acceptable salt thereof, wherein phenyl ring A is optionally substituted; each n is 1, 2, 3, 4, 5, or 6; and k is 0, 1 or 2. Values and preferred values of suitable substituents of phenyl ring A are as described above in the first set of values for Structural Formula (I).

In all of the embodiments described above for Structural Formulas (XXI)-(XXXIII) and (XVIC)-(XVID), the heterocyclic ring represented by

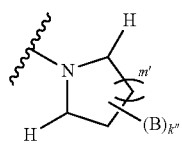

can be replaced with a bridged heterobicyclic ring comprising 5-12 ring carbon atoms and 1 or 2 nitrogen atoms. The invention also includes compounds represented by Structural Formulas (XXI)-(XXXIII) and (XVIC)-(XVID) with this replacement of

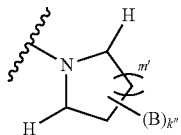

with a bridged heterobicyclic ring comprising 5-12 ring carbon atoms and 1 or 2 nitrogen atoms. Values, including preferred values, for the variables other than B, k" and m' in Structural Formulas (XXI)-(XXXIII) and (XVIC)-(XVID) are as defined above with respect to Structural Formulas (XXI)-(XXXIIII) and (XVIC)-(XVID).

Similarly, in all of the embodiments described above for Structural Formulas (I)-(XX), the non-aromatic heterocyclic ring represented by —NR$^2$R$^3$ can be a bridged heterobicyclic ring comprising 5-12 ring carbon atoms and 1 or 2 nitrogen atoms.

Examples of bridged heterobicyclic ring comprising 5-12 ring carbon atoms and 1 or 2 nitrogen atoms include

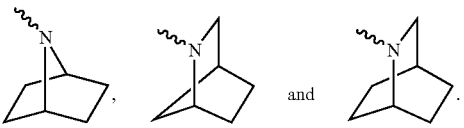

The bridged bicyclic ring carbon atoms can be optionally substituted with one or more substituents selected from the group consisting of halogen, cyano, nitro, —OH, —SH, —O(C1-C6 alkyl), —S(C1-C6 alkyl), —O(C1-C6 haloalkyl), —S(C1-C6 haloalkyl), C1-C6 alkyl, C1-C6 haloalkyl, amino, C1-C6 alkylamino and C1-C6 dialkylamino. Alternatively, the bridged bicyclic ring carbon atoms can be optionally substituted with one or more substituents selected from the group consisting of halogen, —OH, —O(C1-C6 alkyl) and —O(C1-C6 haloalkyl). The bridged bicyclic ring nitrogen atoms can be optionally substituted with one or more substituents selected from the group consisting of C1-C6 alkyl and phenyl, the alkyl being optionally substituted with halogen, cyano, nitro, —OH, —SH, —O(C1-C6 alkyl), —S(C1-C6 alkyl), —O(C1-C6 haloalkyl), —S(C1-C6 haloalkyl), phenyl, amino, C1-C6 alkylamino and C1-C6 dialkylamino, and the phenyl being optionally substituted with halogen, cyano, nitro, —OH, —SH, —O(C1-C6 alkyl), —S(C1-C6 alkyl), —O(C1-C6 haloalkyl), —S(C1-C6 haloalkyl), C1-C6 alkyl, C1-C6 haloalkyl, amino, C1-C6 alkylamino and C1-C6 dialkylamino. Alternatively, the bridged bicyclic ring nitrogen atoms can be optionally substituted with C1-C6 alkyl that is optionally substituted with halogen, —OH, —O(C1-C6 alkyl) and —O(C1-C6 haloalkyl).

In another embodiment, the compound of the invention is represented by a structural formula selected from Structural Formulas (I)-(VIII) and (XI)-(XV), wherein values, including preferred values, of the variables in the structural formulas, other than R$^{30}$, R$^{31}$ and R$^{32}$ for the substituents of R$^1$, are independently as defined in each embodiment described above for Structural Formulas (I)-(VIII) and (XI)-(XV). In this embodiment, each R$^{30}$ is independently: i) hydrogen; ii) an aryl group optionally substituted with one or more substituents selected from the group consisting of halogen, alkyl, amino, alkylamino, dialkylamino, alkoxy, nitro, cyano, hydroxy, haloalkoxy, alkoxycarbonyl, alkylcarbonyl and haloalkyl; or iii) an alkyl group optionally substituted with one or more substituents selected from the group consisting of halogen, amino, nitro, cyano, hydroxy, phenyl, phenylamino, diphenylamino, aryloxy, benzoyl, phenoxycarbonyl, alkylamino, dialkylamino, alkoxy, alkoxycarbonyl and alkylcarbonyl. Each $R^{31}$ is independently $R^{30}$, —$CO_2R^{30}$, —$SO_2R^{30}$ or —$C(O)R^{30}$; or —$N(R^{31})_2$ taken together is an optionally substituted non-aromatic heterocyclic group. Each $R^{32}$ is independently: i) an aryl group optionally substituted with one or more substituents selected from the group consisting of halogen, alkyl, amino, alkylamino, dialkylamino, alkoxy, nitro, cyano, hydroxy, haloalkoxy, alkylcarbonyl and haloalkoxy and haloalkyl; or ii) an alkyl group optionally substituted with one or more substituents selected from the group consisting of halogen, amino, nitro, cyano, hydroxy, phenyl, phenylamino, diphenylamino, aryloxy, benzoyl, phenoxycarbonyl, alkylamino, dialkylamino, alkoxy, alkoxycarbonyl and alkylcarbonyl. Each of the phenyl, phenylamino, diphenylamino, aryloxy, benzoyl, phenoxycarbonyl for the substituents of the alkyl group represented by $R^{30}$ and $R^{32}$ is independently and optionally substituted with one or more substituents selected from the group consisting of halogen, hydroxy, cyano, nitro, amino, C1-C5 alkyl, C1-C5 haloalkyl, C1-C5 alkoxy, C1-C5 haloalkoxy, C1-C5 alkylamino, C1-C5 dialkylamino, (C1-C5 alkoxy)carbonyl and (C1-C5 alkyl)carbonyl. Each of the alkylamino, dialkylamino, alkoxy, alkoxycarbonyl and alkylcarbonyl for the substituents of the alkyl group represented by $R^{30}$ and $R^{32}$ is independently and optionally substituted with one or more substituents selected from the group consisting of halogen, hydroxy, cyano, nitro, amino, phenyl, C1-C5 alkoxy, C1-C5 haloalkoxy, phenylamino, C1-C5 alkylamino, C1-C5 dialkylamino, diphenylamino, (C1-C5 alkoxy)carbonyl, (C1-C5 alkyl)carbonyl, benzoyl and phenoxycarbonyl.

Specific examples of the compounds of the invention are shown below:

(E1)
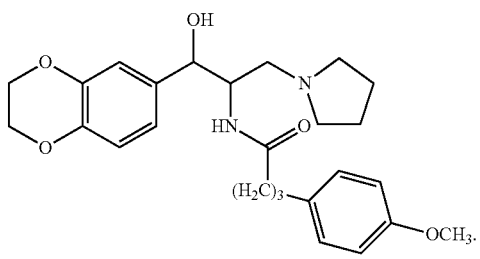

(E2)
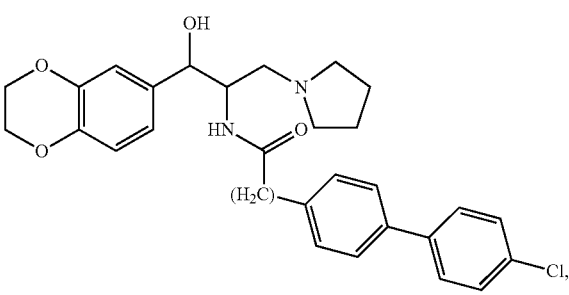

(E3)
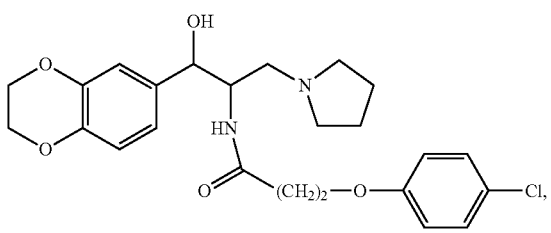

(E4)
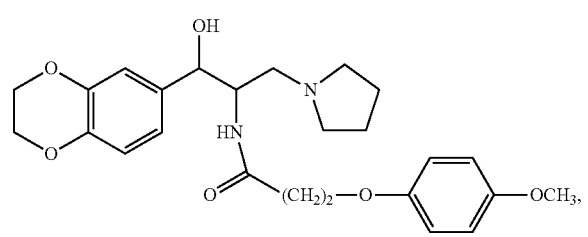

(E5)
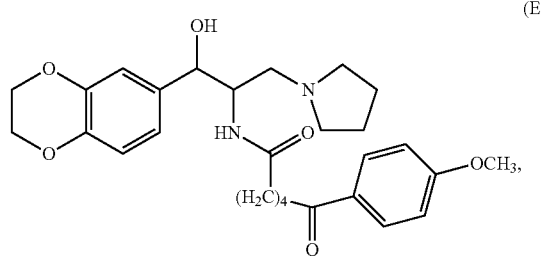

(E6)
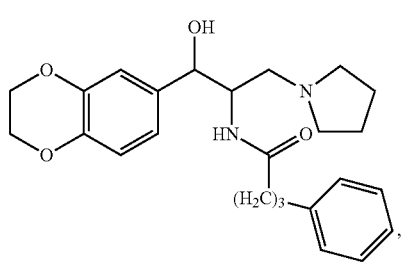

(E7)
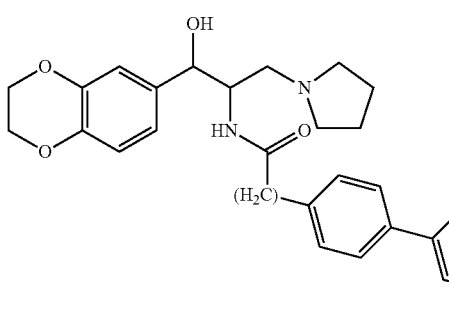

(E8)
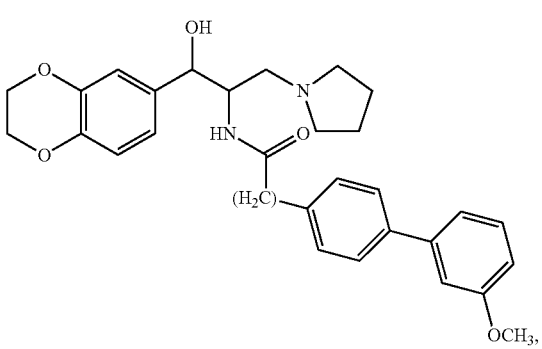

(E9)
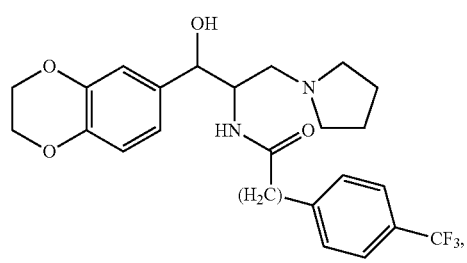
(E10)
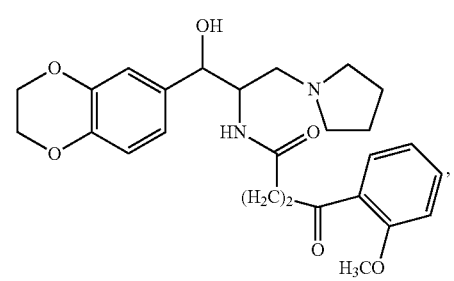
(E11)
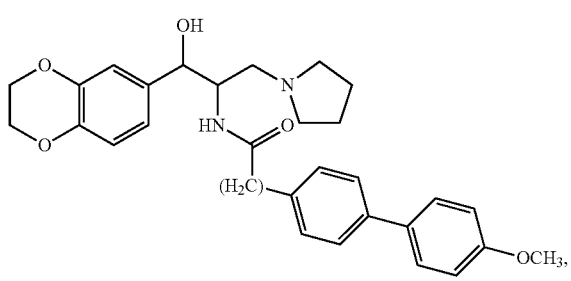
(E12)
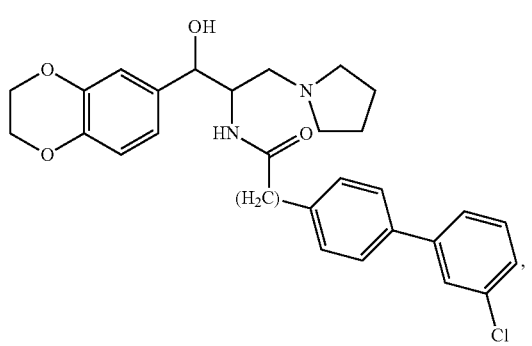
(E13)
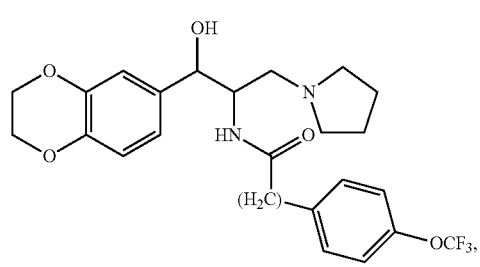
E(14)
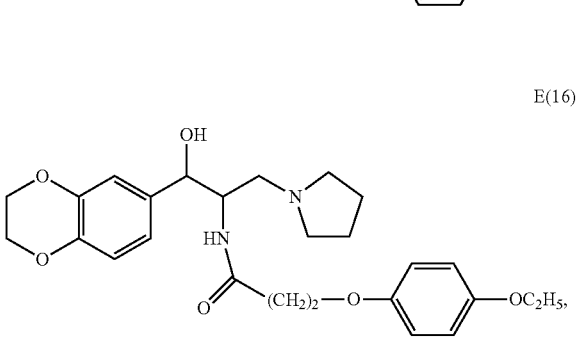
(E15)
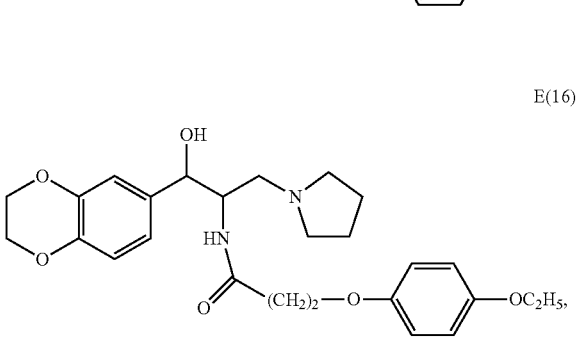
E(16)
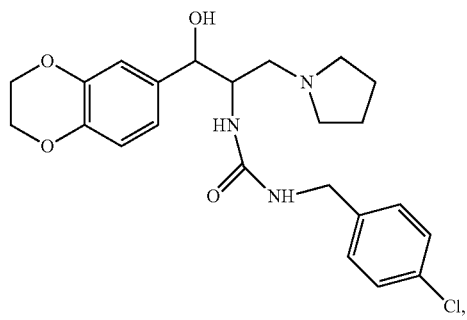
E(17)
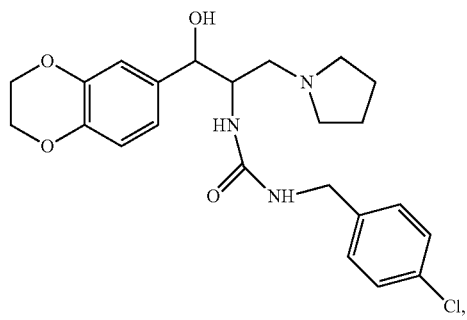
E(18)
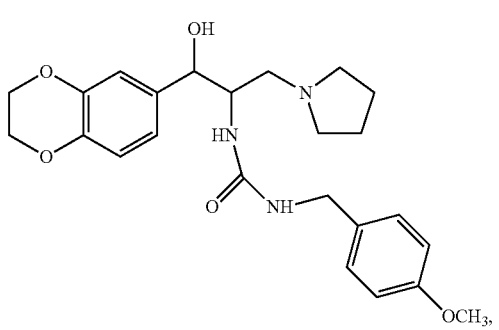

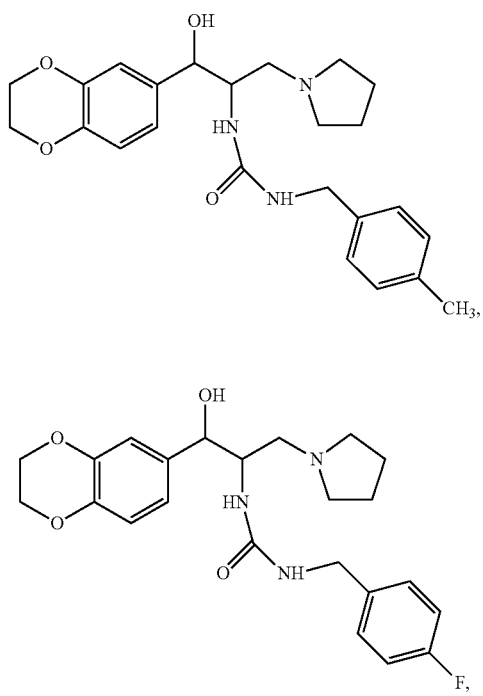

E(19)

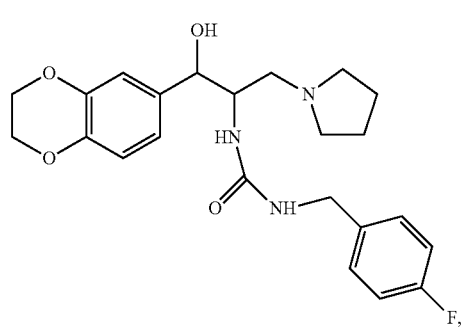

E(20)

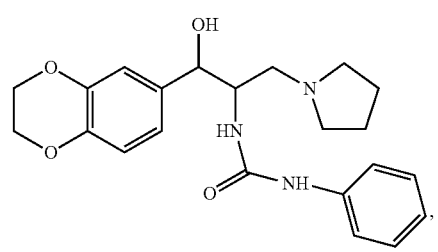

E(21)

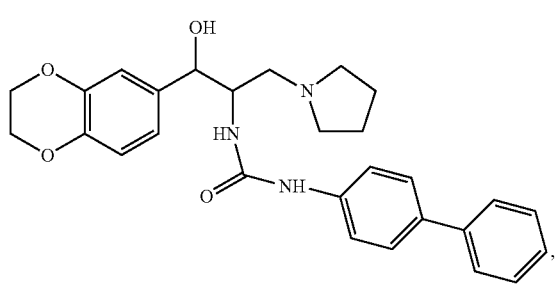

E(22)

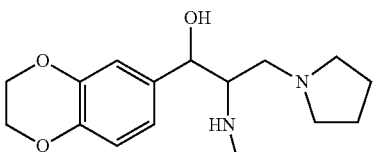

E(23)

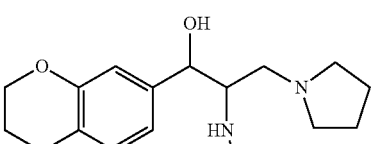

E(24)

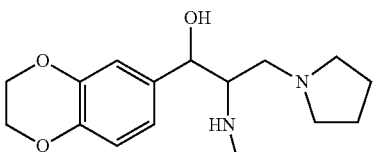 and

E(25)

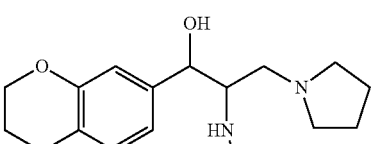

and pharmaceutically acceptable salts thereof.

Other specific examples of the compounds of the invention include compounds shown in Tables 1 and 2 and those exemplified in the examples below, stereoisomers thereof, and pharmaceutically acceptable salts thereof.

Also included are solvates, hydrates or polymorphs of the disclosed compounds herein. Thus, it is to be understood that when any compound is referred to herein by name and structure, solvates, hydrates and polymorphs thereof are included.

The compounds of the invention may contain one or more chiral centers and/or double bonds and, therefore, may exist as stereoisomers, such as double-bond isomers (i.e., geometric isomers), enantiomers, or diastereomers. When compounds of the invention are depicted or named without indicating the stereochemistry, it is to be understood that both stereomerically pure forms (e.g., geometrically pure, enantiomerically pure, or diastereomerically pure) and stereoisomeric mixtures are encompassed. For example, the compound represented by Structural Formula (I) below has chiral centers 1 and 2. Accordingly, the compounds of the invention depicted by Structural Formula (I) include (1R,2R), (1R,2S), (1S,2R) and (1S,2S) stereoisomers and mixtures thereof.

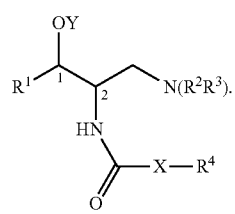

(I)

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the compounds of the invention.

In some preferred embodiments, the compounds of the invention are (1R,2R) stereoisomers.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

Included in the invention are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the invention with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

When the stereochemistry of the disclosed compounds is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

As used herein, the term "hydrolyzable group" means an amide, ester, carbamate, carbonate, ureide, or phosphate analogue, respectively, that either: 1) does not destroy the biological activity of the compound and confers upon that compound advantageous properties in vivo, such as improved water solubility, improved circulating half-life in the blood (e.g., because of reduced metabolism of the prodrug), improved uptake, improved duration of action, or improved onset of action; or 2) is itself biologically inactive but is converted to a biologically active compound. Examples of hydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

An "aliphatic group" is non-aromatic, consists solely of carbon and hydrogen and may optionally contain one or more units of unsaturation, e.g., double and/or triple bonds. An aliphatic group may be straight chained, branched or cyclic. When straight chained or branched, an aliphatic group typically contains between about one and about twenty carbon atoms, typically between about one and about ten carbon atoms, more typically between about one and about six carbon atoms. When cyclic, an aliphatic group typically contains between about three and about ten carbon atoms, more typically between about three and about seven carbon atoms. A "substituted aliphatic group" is substituted at any one or more "substitutable carbon atom". A "substitutable carbon atom" in an aliphatic group is a carbon in an aliphatic group that is bonded to one or more hydrogen atoms. One or more hydrogen atoms can be optionally replaced with a suitable substituent group. A "haloaliphatic group" is an aliphatic group, as defined above, substituted with one or more halogen atoms. Suitable substituents on a substitutable carbon atom of an aliphatic group are the same as those for an alkyl group.

The term "alkyl" used alone or as part of a larger moiety, such as "alkoxy", "haloalkyl", "arylalkyl", "alkylamine", "cycloalkyl", "dialkyamine", "alkylamino", "dialkyamino" "alkylcarbonyl", "alkoxycarbonyl" and the like, includes as used herein means saturated straight-chain, cyclic or branched aliphatic group. As used herein, a C1-C6 alkyl group is referred to "lower alkyl." Similarly, the terms "lower alkoxy", "lower haloalkyl", "lower arylalkyl", "lower alkylamine", "lower cycloalkylalkyl", "lower dialkyamine", "lower alkylamino", "lower dialkyamino" "lower alkylcarbonyl", "lower alkoxycarbonyl" include straight and branched saturated chains containing one to six carbon atoms.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)—R*, wherein R* is alkyl; "alkoxycarbonyl" means —C(O)—OR*, wherein R* is alkyl; and where alkyl is as defined above.

The terms "amine" and "amino" are used interchangeably throughout herein and mean —NH$_2$, —NHR or —NR$_2$, wherein R is alkyl.

"Cycloalkyl" means a saturated carbocyclic ring, with from three to eight carbons.

The terms "haloalkyl" and "haloalkoxy" mean alkyl or alkoxy, as the case may be, substituted with one or more halogen atoms. The term "halogen" means F, Cl, Br or I. Preferably the halogen in a haloalkyl or haloalkoxy is F.

The term "acyl group" means —C(O)R, wherein R is an optionally substituted alkyl group or aryl group (e.g., optionally substituted phenyl). R is preferably an unsubstituted alkyl group or phenyl.

An "alkylene group" is represented by —[CH$_2$]$_z$—, wherein z is a positive integer, preferably from one to eight, more preferably from one to four.

As used herein, the term "alkenyl" refers to a straight or branched hydrocarbon group that contains one or more double bonds between carbon atoms. Suitable alkenyl groups include, e.g., n-butenyl, cyclooctenyl and the like. An alkenyl group may be substituted.

The term "aryl group" used alone or as part of a larger moiety as in "aralkyl", "aralkoxy", or "aryloxyalkyl", includes carbocyclic aromatic rings and heteroaryl rings. The term "aromatic group" may be used interchangeably with the terms "aryl", "aryl ring" "aromatic ring", "aryl group" and "aromatic group". An aromatic group typically has six-fourteen ring atoms. A "substituted aryl group" is substituted at any one or more substitutable ring atom.

Carbocyclic aromatic rings have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to aromatic ring groups having five to fourteen ring atoms selected from carbon and at least one (typically 1-4, more typically 1 or 2) heteroatom (e.g., oxygen, nitrogen or sulfur). They include monocyclic rings and polycyclic rings in which a monocyclic heteroaromatic ring is fused to one or more other carbocyclic aromatic or heteroaromatic rings. Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl(e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heteraryl groups include pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

The term "non-aromatic heterocyclic group", used alone or as part of a larger moiety as in "non-aromatic heterocyclylalkyl group", refers to non-aromatic ring systems typically having five to twelve members, preferably five to seven, in which one or more ring carbons, preferably one or two, are each replaced by a heteroatom such as N, O, or S. A non-aromatic heterocyclic group can be monocyclic or fused bicyclic. A "nitrogen-containing non-aromatic heterocyclic group" is a non-aromatic heterocyclic group with at least one nitrogen ring atom.

Examples of non-aromatic heterocyclic groups include (tetrahydrofuranyl (e.g., 2-tetrahydropyranyl, 3-tetrahydropyranyl, 4-tetrahydropyranyl), [1,3]-dioxalanyl, [1,3]-dithiolanyl, [1,3]-dioxanyl, tetrahydrothienyl (e.g., 2-tetrahydrothienyl, 3-tetrahydrothieneyl), azetidinyl (e.g., N-azetidinyl, 1-azetidinyl, 2-azetidinyl), oxazolidinyl (e.g., N-oxazolidinyl, 2-oxazolidinyl, 4-oxazolidinyl, 5-oxazolidinyl), morpholinyl (e.g., N-morpholinyl, 2-morpholinyl, 3-morpholinyl), thiomorpholinyl (e.g., N-thiomorpholinyl, 2-thiomorpholinyl, 3-thiomorpholinyl), pyrrolidinyl (e.g., N-pyrrolidinyl, 2-pyrrolidinyl, 3-pyrrolidinyl)piperazinyl (e.g., N-piperazinyl, 2-piperazinyl), piperidinyl (e.g., N-piperidinyl), 2-piperidinyl, 3-piperidinyl, 4-piperidinyl), thiazolidinyl (e.g., 4-thiazolidinyl), diazolonyl and N-substituted diazolonyl. The designation "N" on N-morpholinyl, N-thiomorpholinyl, N-pyrrolidinyl, N-piperazinyl, N-piperidinyl and the like indicates that the non-aromatic heterocyclic group is attached to the remainder of the molecule at the ring nitrogen atom.

A "substitutable ring atom" in an aromatic group is a ring carbon or nitrogen bonded to a hydrogen atom. The hydrogen can be optionally replaced with a suitable substituent group. Thus, the term "substitutable ring atom" does not include ring nitrogen or carbon atoms which are shared when two aromatic rings are fused. In addition, "substitutable ring atom" does not include ring carbon or nitrogen atoms when the structure depicts that they are already attached to a moiety other than hydrogen.

An aryl group may contain one or more substitutable ring atoms, each bonded to a suitable substituent. Examples of suitable substituents on a substitutable ring carbon atom of an aryl group include halogen, alkyl, haloalkyl, $Ar^A$, $-OR^A$, $-O(\text{haloalkyl})$, $-SR^A$, $-NO_2$, $-CN$, $-N(R^B)_2$, $-NR^BC(O)R^A$, $-NR^BCO_2R^C$, $-N(R^B)C(O)N(R^B)_2$, $-C(O)R^A$, $-CO_2R^A$, $-S(O)_2R^A$, $-SO_2N(R^B)_2$, $-S(O)R^C$, $-NR^BSO_2N(R^B)_2$, $-NR^BSO_2R^C$, $-V_A-Ar^A$, $-V_A-OR^A$, $-V-O(\text{haloalkyl})$, $-V_A-SR^A$, $-V_A-NO_2$, $-V_A-CN$, $-V_A-N(R^B)_2$, $-V_A-NR^BC(O)R^A$, $-V_A-NR^BCO_2R^C$, $-V_A-N(R^B)C(O)N(R^B)_2$, $-V_A-C(O)R^A$, $-V_A-CO_2R^A$, $-V_A-S(O)_2R^A$, $-V_A-SO_2N(R^B)_2$, $-V_A-S(O)R^C$, $-V_A-NR^BSO_2N(R^B)_2$, $-V_A-NR^BSO_2R^C$, $-O-V_A-Ar^A$, $-O-V_B-N(R^B)_2$, $-S-V_A-Ar^A$, $-S-V_B-N(R^B)_2$, $-N(R^B)-V_B-Ar^A$, $-N(R^B)-V_B-N(R^B)_2$, $-NR^BC(O)-V_A-N(R^B)_2$, $-NR^BC(O)-V_A-Ar^A$, $-C(O)-V_A-N(R^B)_2$, $-C(O)-V_A-Ar^A$, $-CO_2-V_B-N(R^B)_2$, $-CO_2-V_A-Ar^A$, $-C(O)N(R^B)-V_B-N(R^B)_2$, $-C(O)N(R^B)-V_A-Ar^A$, $-S(O)_2-V_A-N(R^B)_2$, $-S(O)_2-V_A-Ar^A$, $-SO_2N(R^B)-V_B-N(R^B)_2$, $-SO_2N(R^b)-V_A-Ar^A$, $-S(O)-V_A-N(R^B)_2$, $-S(O)-V_A-Ar^A$, $-NR^BSO_2-V_A-N(R^B)_2$ or $-NR^BSO_2-V_A-Ar^A$; or two adjacent substituents, taken together, form a methylenedioxy, ethylenedioxy or $-[CH_2]_4-$ group.

Each $V_A$ is independently a C1-C10 alkylene group.

Each $V_B$ is independently a C2-C10 alkylene group.

$Ar^A$ is a monocyclic aromatic group each substituted with zero, one or two groups independently selected from halogen, alkyl, amino, alkylamino, dialkylamino, alkoxy, nitro, cyano, hydroxy, haloalkoxy or haloalkyl.

Each $R^A$ is independently i) hydrogen; ii) an aromatic group substituted with zero, one or two groups represented by halogen, alkyl, amino, alkylamino, dialkylamino, alkoxy, nitro, cyano, hydroxy, haloalkoxy or haloalkyl; or iii) an alkyl group optionally substituted with halogen, hydroxyl, alkoxy, nitro, cyano, alkoxycarbonyl, alkylcarbonyl or haloalkoxy.

Each $R^B$ is independently $R^A$, $-CO_2R^A$, $-SO_2R^A$ or $-C(O)R^A$; or $-N(R^B)_2$ taken together is an optionally substituted non-aromatic heterocyclic group.

Each $R^C$ is independently: i) an aromatic group substituted with zero, one or two groups represented by halogen, alkyl, amino, alkylamino, dialkylamino, alkoxy, nitro, cyano, hydroxy, haloalkoxy or haloalkyl; or ii) an alkyl group optionally substituted with halogen, hydroxyl, alkoxy, nitro, cyano, alkoxycarbonyl, alkylcarbonyl or haloalkoxy.

An alkyl or a non-aromatic heterocyclic group (including, but not limited to, non-aromatic heterocyclic groups represented by $-N(R^{31})_2$, $-N(R^{41})_2$, $-N(R^{51})_2$ and $-N(R^B)_2$) may contain one or more substituents. Examples of suitable substituents for an alkyl or a ring carbon of a non-aromatic heterocyclic group include those listed above for a substitutable carbon of an aryl and the following: $=O$, $=S$, $=NNHR^C$, $=NN(R^C)_2$, $=NNHC(O)R^C$, $=NNHCO_2(\text{alkyl})$, $=NNHSO_2(\text{alkyl})$, $=NR^C$, spiro cycloalkyl group, fused cycloalkyl group or a monocyclic non-aromatic nitrogen-containing heterocyclic group attached by a ring nitrogen atom (e.g., N-piperidinyl, N-pyrrolidinyl, N-azepanyl, N-morpholinyl, N-thiomorphinyl, N-piperazinyl or N-diazepanyl group). Each $R^C$ is independently selected from hydrogen, an unsubstituted alkyl group or a substituted alkyl group. Examples of substituents on the alkyl group represented by $R^C$ include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl. Preferred substituents for an alkyl or a ring carbon of a non-aromatic heterocyclic group include C1-C2 alkyl, —OH, N-pyrrolidinyl, N-piperidinyl, N-(4-alkyl)piperazinyl, N-morpholinyl or N-pyrrolyl.

Suitable substituents on the nitrogen of a non-aromatic heterocyclic group or heteroaryl group include —$R^D$, —N($R^D$)$_2$, —C(O)$R^D$, —CO$_2R^D$, —C(O)C(O)$R^D$, —C(O)CH$_2$C(O)$R^D$, —SO$_2R^D$, —SO$_2$N($R^D$)$_2$, —C(=S)N($R^D$)$_2$, —C(=NH)—N($R^D$)$_2$, and —N$R^D$SO$_2R^D$; wherein $R^D$ is hydrogen, an alkyl group, a substituted alkyl group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the alkyl group or the phenyl ring represented by $R^D$ include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl. Preferred substituents on a substitutable nitrogen atom of a nitrogen-containing heteroaryl or nitrogen-containing non-aromatic heterocyclic group include C1-C2 alkyl, C1-C2 hydroxyalkyl, or benzyl optionally substituted with halogen, nitro, cyano, C1-C2 alkyl, C1-C2 haloalkyl, C1-C2 alkoxy or C1-C2 haloalkoxy.

In some specific embodiments, non-aromatic heterocyclic groups (including, but not limited to, non-aromatic heterocyclic groups represented by —N($R^{31}$)$_2$, —N($R^{41}$)$_2$, —N($R^{51}$)$_2$ and —N($R^B$)$_2$) each independently are optionally substituted with one or more substituents selected from the group consisting of halogen, =O, =S, =N(C1-C6 alkyl), C1-C6 alkyl, C1-C6 haloalkyl, hydroxy, C1-C6 alkoxy, nitro, cyano, (C1-C6 alkoxy)carbonyl, (C1-C6 alkyl)carbonyl, C1-C6 haloalkoxy, amino, (C1-C6 alkyl)amino and (C1-C6 dialkyl) amino. In some more specific embodiments, the non-aromatic heterocyclic groups each independently are optionally substituted with one or more substituents selected from the group consisting of halogen, C1-C6 alkyl, C1-C6 haloalkyl, hydroxy, C1-C6 alkoxy, nitro, cyano, (C1-C6 alkoxy)carbonyl, (C1-C6 alkyl)carbonyl, C1-C6 haloalkoxy, amino, (C1-C6 alkyl)amino and (C1-C6 dialkyl)amino.

Inhibitors of glucosylceramide synthase can be used to treat diabetes, such as type 2 diabetes (see WO 2006/053043, the entire teachings of which are incorporated herein by reference). As such, the disclosed compounds, which are inhibitors of glucosylceramide synthase, can be used to treat diabetes, e.g., type 2 diabetes and renal hypertrophy or hyperplasia associated with diabetic nephropathy, by administration of a therapeutically effective amount of a compound of the invention to a subject in need of such treatment.

Inhibitors of glucosylceramide synthase, such as GM3 synthase, have been shown to be useful for treating lysosomal storage diseases (see, for example, U.S. Pat. Nos. 6,569,889; 6,255,336; 5,916,911; 5,302,609; 6,660,749; 6,610,703; 5,472,969; 5,525,616, the entire teachings of which are incorporated herein by reference). As such, the disclosed compounds, which are inhibitors of glucosylceramide synthase, can be used to treat lysosomal storage diseases, such as Tay-Sachs, Gaucher's or Fabry's disease, by administration of a therapeutically effective amount of a compound of the invention to a subject in need of such treatment.

In an alternative embodiment of the present invention, the compounds of the present invention can be used for: treating disorders involving cell growth and division, including cancer, collagen vascular diseases, atherosclerosis, and the renal hypertrophy of diabetic patients (see U.S. Pat. Nos. 6,916,802 and 5,849,326, the entire teachings of which are incorporated herein by reference); inhibiting the growth of arterial epithelial cells (see U.S. Pat. Nos. 6,916,802 and 5,849,326); treating patients suffering from infections (see Svensson, M. et al., "Epithelial Glucosphingolipid Expression as a Determinant of Bacterial Adherence and Cytokine Production," Infect. and Immun., 62:4404-4410 (1994), the entire teachings of which are incorporated herein by reference); preventing the host, i.e., patient, from generating antibodies against the tumor (see Inokuchi, J. et al., "Antitumor Activity in Mice of an Inhibitor of Glycosphingolipid Biosynthesis," Cancer Lett., 38:23-30 (1987), the entire teachings of which are incorporated herein by reference); and treating tumors (see Hakomori, S. "New Directions in Cancer Therapy Based on Aberrant Expression of Glycosphingolipids: Anti-adhesion and Ortho-Signaling Therapy," Cancer Cells 3:461-470 (1991), Inokuchi, J. et al., "Inhibition of Experimental Metastasis of Murine Lewis Long Carcinoma by an Inhibitor of Glucosylceramide Synthase and its Possible Mechanism of Action," Cancer Res., 50:6731-6737 (1990) and Ziche, M. et al., "Angiogenesis Can Be Stimulated or Repressed in In Vivo by a Change in GM3: GD3 Ganglioside Ratio," Lab. Invest., 67:711-715 (1992), the entire teachings of which are incorporated herein by reference).

In an alternative embodiment, the compounds of the invention can be used for a vaccine-like preparation (see, for example, U.S. Pat. Nos. 6,569,889; 6,255,336; 5,916,911; 5,302,609; 6,660,749; 6,610,703; 5,472,969; 5,525,616). Here, cancer cells are removed from the patient (preferably as completely as possible), and the cells are grown in culture in order to obtain a large number of the cancer cells. The cells are then exposed to the inhibitor for a time sufficient to deplete the cells of their GSLs (generally 1 to 5 days) and are reinjected into the patient. These reinjected cells act like antigens and are destroyed by the patient's immunodefense system. The remaining cancer cells (which could not be physically removed) will also be attacked by the patient's immunodefense system. In a preferred embodiment, the patient's circulating gangliosides in the plasma are removed by-plasmapheresis, since the circulating gangliosides would tend to block the immunodefense system.

As used herein a subject is a mammal, preferably a human, but can also be an animal in need of veterinary treatment, such as a companion animal (e.g., dogs, cats, and the like), a farm animal (e.g., cows, sheep, pigs, horses, and the like) or a laboratory animal (e.g., rats, mice, guinea pigs, and the like). Subject and patient are used interchangeably. A subject "in need of treatment" includes a subject with chronic renal failure.

"Treatment" or "treating" refers to both therapeutic and prophylactic treatment.

An "effective amount" of a pharmaceutical composition disclosed above is a quantity that results in a beneficial clinical outcome of or exerts an influence on, the condition being treated with the pharmaceutical composition compared with the absence of treatment. The administering amount of a pharmaceutical composition disclosed above to the subject will depend on the degree, severity, and type of the disease or condition, the amount of therapy desired, and the release characteristics of the pharmaceutical composition. It will also depend on the subject's health, size, weight, age, sex, and tolerance to drugs. Typically, the pharmaceutical compositions of the invention are administered for a sufficient period of time to achieve the desired therapeutic effect. Dosages may range from 0.1 to 500 mg/kg body weight per day. In one embodiment, the dosing range is 1-20 mg/kg/day. The compound of the invention may be administered continuously or at specific timed intervals. For example, the compound of the invention may be administered 1, 2, 3, or 4 times per day, such as, e.g., a daily or twice-daily formulation. Commercially available assays may be employed to determine optimal dose ranges and/or schedules for administration. For example, assays for measuring blood glucose levels are commercially available (e.g., OneTouch® Ultra®, Lifescan, Inc. Milpitas, Calif.). Kits to measure human insulin levels are also commercially available (Linco Research, Inc. St. Charles, Mo.). Additionally, effective doses may be extrapolated from dose-response curves obtained from animal models (see, e.g., Comuzzie et al., Obes. Res. 11 (1):75 (2003); Rubino et al., Ann. Surg. 240(2):389 (2004); Gill-Randall et al., Diabet. Med. 21 (7):759 (2004), the entire teachings of which are incorporated herein by reference). Therapeutically effective dosages achieved in one animal model can be converted for use in another animal, including humans, using conversion factors known in the art (see, e.g., Freireich et al., Cancer Chemother. Reports 50(4):219 (1996), the entire teachings of which are incorporated herein by reference) and Table A below for equivalent surface area dosage factors.

| From: | Mouse (20 g) | Rat (150 g) | Monkey (3.5 kg) | Dog (8 kg) | Human (60 kg) |
|---|---|---|---|---|---|
| To: Mouse | 1 | ½ | ¼ | ⅙ | 1/12 |
| To: Rat | 2 | 1 | ½ | ¼ | 1/7 |
| To: Monkey | 4 | 2 | 1 | ⅗ | ⅓ |
| To: Dog | 6 | 4 | ⅗ | 1 | ½ |
| To: Human | 12 | 7 | 3 | 2 | 1 |

Typically, the pharmaceutical compositions of the invention can be administered before or after a meal, or with a meal. As used herein, "before" or "after" a meal is typically within two hours, preferably within one hour, more preferably within thirty minutes, most preferably within ten minutes of commencing or finishing a meal, respectively.

In one embodiment, the method of the present invention is a mono-therapy where the pharmaceutical compositions of the invention are administered alone. Accordingly, in this embodiment, the compound of the invention is the only pharmaceutically active ingredient in the pharmaceutical compositions.

In another embodiment, the method of the invention is a co-therapy with other therapeutically active drugs known in the art for treating the desired diseases or indications, such as one or more known drugs for treating, diabetes, lysosomal diseases, tumors, etc.

In a particular embodiment, the method of the invention is a combination therapy for treating diabetes, such as Type 2 diabetes. The combination therapy comprise any of the compounds of the invention described herein and at least one other compound suitable for treating diabetes. Examples of drugs or compounds used to treat type 2 diabetes include: insulin (e.g., Novolin®, Novolog®, Velosulin®); sulfonylureas (e.g., Diabinese®, Glucotrol®, Glucotrol XL®, (Diabeta®, Amaryl®, Orinase®, Tolinase®, Micronase® and Glynase®); metformin; [alpha]-glucosidase inhibitors (e.g., Glyset®); thiazolidinediones (e.g., Actos® and Avandia®); nateglinide (Starlix®); repaglinide (Prandin®) and combination drugs such as Avandamet® (Avandia® and metformin).

The pharmaceutical compositions of the invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)).

The carriers, diluents and/or excipients are "acceptable" in the sense of being compatible with the other ingredients of the pharmaceutical composition and not deleterious to the recipient thereof. The pharmaceutical compositions can conveniently be presented in unit dosage form and can be prepared by any suitable method known to the skilled artisan. In general, the pharmaceutical compositions are prepared by uniformly and intimately bringing into association the compounds disclosed herein with the carriers, diluents and/or excipients and then, if necessary, dividing the product into unit dosages thereof.

The pharmaceutical compositions of the invention can be formulated as a tablet, sachet, slurry, food formulation, troche, capsule, elixir, suspension, syrup, wafer, chewing gum or lozenge. A syrup formulation will generally consist of a suspension or solution of the compounds of the invention described herein or salt in a liquid carrier, for example, ethanol, glycerine or water, with a flavoring or coloring agent. Where the composition is in the form of a tablet, one or more pharmaceutical carriers routinely used for preparing solid formulations can be employed. Examples of such carriers include magnesium stearate, starch, lactose and sucrose. Where the composition is in the form of a capsule, the use of routine encapsulation is generally suitable, for example, using the aforementioned carriers in a hard gelatin capsule shell. Where the composition is in the form of a soft gelatin shell capsule, pharmaceutical carriers routinely used for preparing dispersions or suspensions can be considered, for example, aqueous gums, celluloses, silicates or oils, and are incorporated in a soft gelatin capsule shell.

Though the above description is directed toward routes of oral administration of pharmaceutical compositions consistent with embodiments of the invention, it is understood by those skilled in the art that other modes of administration using vehicles or carriers conventionally employed and which are inert with respect to the compounds of the invention may be utilized for preparing and administering the pharmaceutical compositions. For example, the pharmaceutical compositions of the invention may also be formulated for rectal administration as a suppository or retention enema, e.g., containing conventional suppository bases such as cocoa butter or other glycerides. Also, the pharmaceutical compositions of the invention can be formulated for injection, or for transdermal or transmucosal administration. Illustrative of various modes of administration methods, vehicles and carriers are those described, for example, in Remington's Pharmaceutical Sciences, 18$^{th}$ ed. (1990), the disclosure of which is incorporated herein by reference.

The invention is illustrated by the following examples which are not intended to be limiting in any way.

EXEMPLIFICATION

Example 1

General Methods for the Preparation of Compounds of the Invention

A general method for the synthesis of final compounds is depicted in Scheme 1. A general method for the preparation of the compounds of the invention involves the reaction of the amine of type EVII with the appropriate reagent. The amine type EVII, such as (1R,2R)-2-amino-(2,3-dihydrobenzo[β][1,4]dioxin-6-yl)-3-(pyrrolidin-1-yl) propan-1-ol, can be prepared according to the preparation of intermediate 4 of U.S. Pat. No. 6,855,830 (the entire teachings of which are incorporated herein by reference), or by using the general synthetic procedures depicted in schemes 2-5. Final amide compounds, EIX can be prepared by reaction of the amine EVII with the corresponding acylating agent using standard reaction conditions for the formation of an amide. The urea compounds, EIIX can be prepared by reaction of the amine EVII with the corresponding isocyanate. The carbamates, EX can be prepared by reaction of the amine EVII with the corresponding chloroformate.

lidin-1-yl)propan-1-ol, prepared according to the preparation of intermediate 4 of U.S. Pat. No. 6,855,830 (the entire teachings of which are incorporated herein by reference) or using the methods depicted in schemes 2, 3, 4 and 5, an acid and DCC (dicyclohexylcarbodiimide, 1.2 mmol) was dissolved in $CHCl_3$ (5 ml). The mixture was placed in the microwave reactor (T=120° C., time=1 min) and it was then filtered and purified by column chromatography using, for example, a mixture of ($CH_2Cl_2$/MeOHN$H_4$OH).

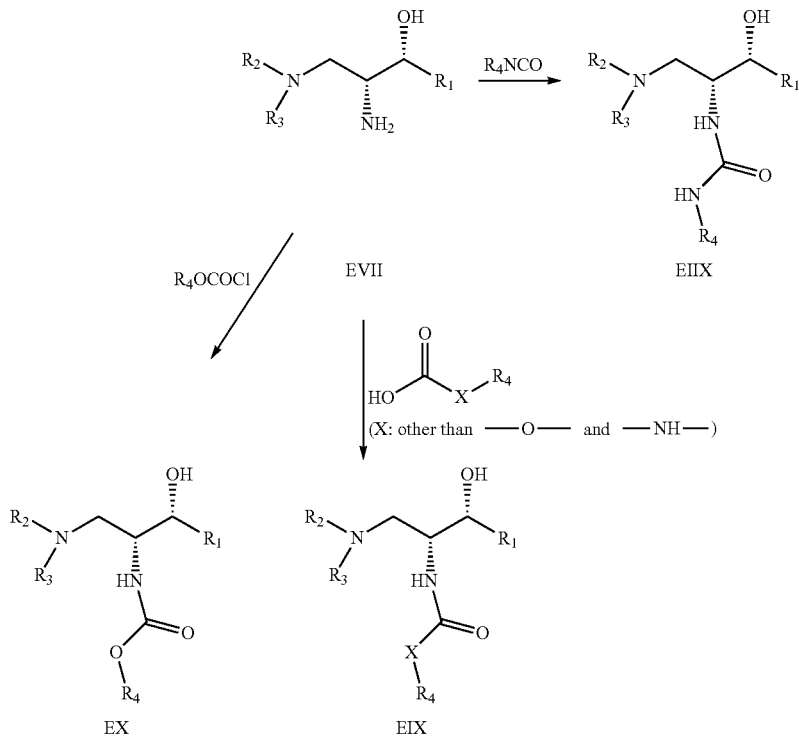

Scheme 1

Example 1A

Synthesis of the Compounds of the Invention

General Methods for the Preparation of Amide Analogs

Method 1

A mixture of Compound EVII (1 mmol), such as (1R,2R)-2-amino-1-(2,3-dihydrobenzo[β][1,4]dioxin-6-yl)-3-(pyrrolidin-1-yl)propan-1-ol, prepared according to the preparation of intermediate 4 of U.S. Pat. No. 6,855,830 (the entire teachings of which are incorporated herein by reference) or using the methods depicted in schemes 2, 3, 4 and 5, an acid (1.2 mmol), DCC (dicyclohexylcarbodiimide, 1.2 mmol) and HOBT (1-hydroxy benzotriazole, 1.2 mmol) was dissolved in $CH_2Cl_2$ (5 ml). The mixture was stirred at room temperature and monitored by TLC (thin liquid chromatography) for completion. After completion the mixture was filtered and purified by column chromatography using, for example, a mixture of ($CH_2Cl_2$/MeOH/$NH_4$OH).

Method 2

A mixture of Compound EVII (1 mmol), such as (1R,2R)-2-amino-1-(2,3-dihydrobenzo[β][1,4]dioxin-6-yl)-3-(pyrro- Method 3

A mixture of Compound EVII (1 mmol), such as (1R,2R)-2-amino-1-(2,3-dihydrobenzo[β][1,4]dioxin-6-yl)-3-(pyrrolidin-1-yl)propan-1-ol, prepared according to the preparation of intermediate 4 of U.S. Pat. No. 6,855,830 (the entire teachings of which are incorporated herein by reference) or using the methods depicted in schemes 2, 3, 4 and 5, an acid chloride (1.2 mmol) and $K_2CO_3$ (2 mmol) was suspended in THF (5 ml). The mixture was stirred at room temperature and monitored by TLC for completion. After completion, the mixture was filtered and purified by column chromatography using, for example, a mixture of ($CH_2Cl_2$/MeOH/$NH_4$OH).

Method 4

Compound EVII such as (1R,2R)-2-amino-1-(2,3-dihydro-benzo[1,4]dioxin-6-yl)-3-pyrrolidin-1-yl-propan-1-ol, prepared according to the preparation of intermediate 4 of U.S. Pat. No. 6,855,830 (the entire teachings of which are incorporated herein by reference) or using the methods depicted in schemes 2, 3, 4 and 5, was coupled with a variety of N-hydroxysuccinamide esters in methylene chloride under an atmosphere of nitrogen, for example, for 18 to 24 hours depending on the ester used.

Preparation of N-hydroxysuccinamide Esters

Various mono- and di-keto acids were coupled with N-hydroxysuccinamide in the presence of N,$N^1$-dicyclohexylcarbodiimide in ethyl acetate under an atmosphere of nitrogen for 18 hours. The products were filtered to remove the dicyclohexylurea. The identity of these esters was confirmed by $^1$H NMR and the crude material was then used in the preparation of amide analogs without further purification.

Example 1B

Alternative Synthetic Method for the Preparation of Intermediate EVII

Synthetic Route 1

An alternative general synthesis of Compound EVII is depicted in Scheme 2. Treatment of (R)-2-(benzyloxycarbonylamino)-3-hydroxypropanoic acid with EDCI and N,O-dimethylhydroxyamine gave the weinreb amide EI in excellent yield. The primary alcohol was protected as the TBDMS ether EII in excellent yield by reaction with TBDMSCl in DMF. Reaction of EII with a grignard at low temperature gave EIII in good to excellent yields. Steroselective reduction of EIII and with L-selectride at −70 C gave EIV in good to excellent yield and selectivity. Compound EV was obtained in good to excellent yields after deprotection with acetic acid. Reaction with mesylate chloride and a suitable amine produced EVI in good to excellent yield. Finally, deprotection to the primary amine EVII was done in the microwave oven using NaOH aqueous solution in methanol at 150° C. for one to three minutes depending on the specific compound.

Scheme 2

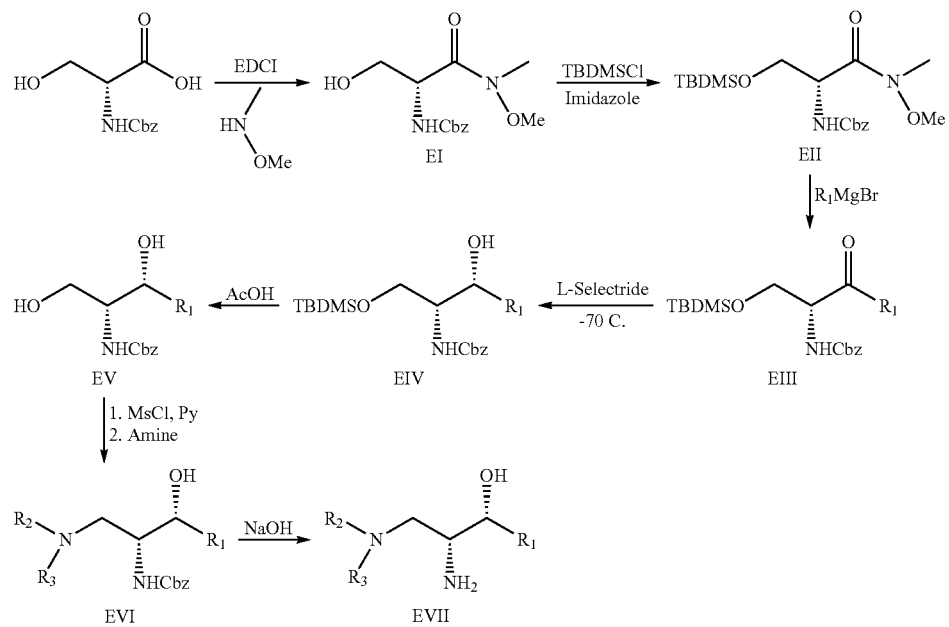

Example 1B

Alternative Synthetic Method for the Preparation of Intermediate EVII

Synthetic Route 2

An alternative general synthesis of Compound EVII is depicted in Scheme 3. Intermediate AI was obtained with excellent diastereoselectivity (96:4) by reduction of compound A with LiAlH$_4$ followed by reaction with an aldehyde in the presence of CuI and Me$_2$S. Mesylate intermediate AIII was obtained by reaction with Amberlyst 15 followed by reaction with MsCl in pyridine. The final compound EVII was obtained by reaction with pyrrolidine and removal of the CBz by hydrogenation.

Scheme 3

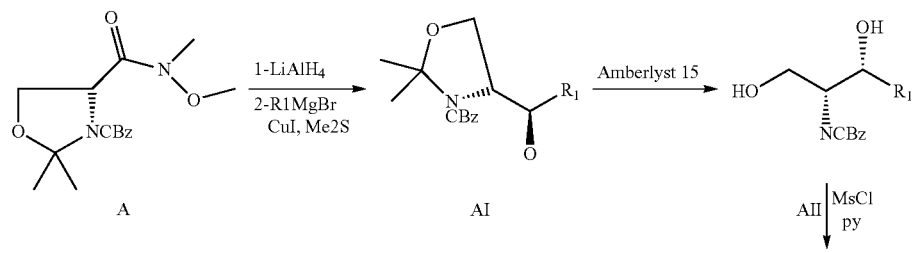

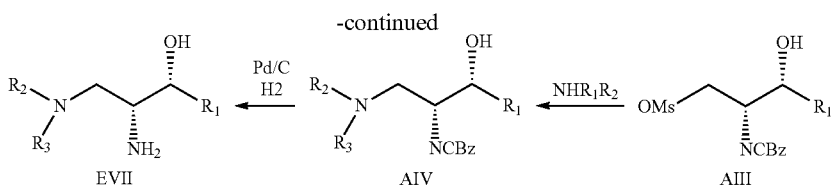

Example 1B

Alternative Synthetic Method for the Preparation of Intermediate EVII

Synthetic Route 3

A general alternative route for synthesis of compound EVII is depicted in Scheme 4. Intermediate EIV was obtain as shown in Scheme 4 was cycled into oxazolidinone B using sodium hydride in a DMF/THF solution. Deprotection of the primary alcohol by reaction with nBu₄NF, followed by formation of the tosylate by reaction with tosyl chloride in pyridine, finally, displacement of the tosylate by an appropriate amine afforded compound B1 in good to excellent yield. Hydrolysis of the oxazolidinone with LiOH in a water ethanol mixture gave compound EVII.

Scheme 4

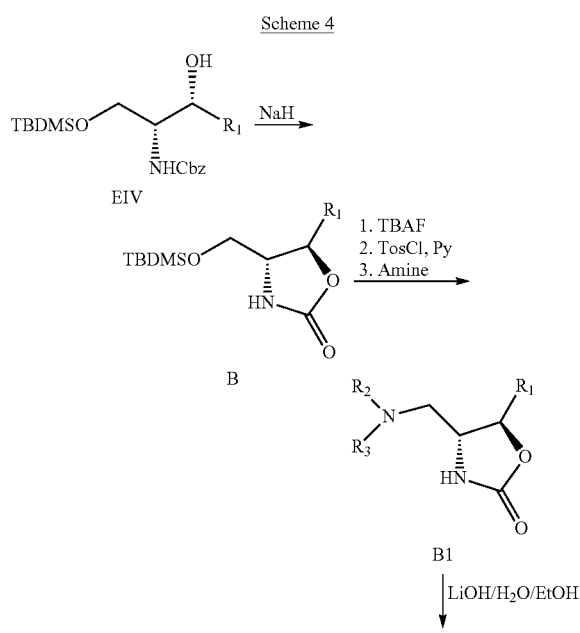

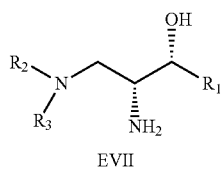

EVII

Example 1B

Alternative Synthetic Method for the Preparation of Intermediate EVII

Synthetic Route 4

An alternative general synthesis of Compound EVII is depicted in Scheme 5. An aldehyde (2 equiv) is condensed with the chiral morpholinone in toluene with removal of water to provide the fused cycloadduct 2. Treatment of 2 with hydrogen chloride in an alcohol solvent such as methanol provides amino acid 3. Removal of the N-benzyl functionality can be accomplished with hydrogen in the presence of a palladium catalyst to afford 4. Cyclization of 4 with triphosgene and base provides ester 5. The ester functionality can be reduced with sodium borohydride, and the resulting alcohol converted to an appropriate leaving group (i.e. tosylate or iodide). Reaction of 6 with a suitable amine in the presence of excess base (e.g. $K_2CO_3$) in a polar solvent (e.g. DMSO or $CH_3CN$) affords 7. Final deprotection under basic conditions affords Compound EVII analogs suitable for conversion to the desired amide final products.

Scheme 5

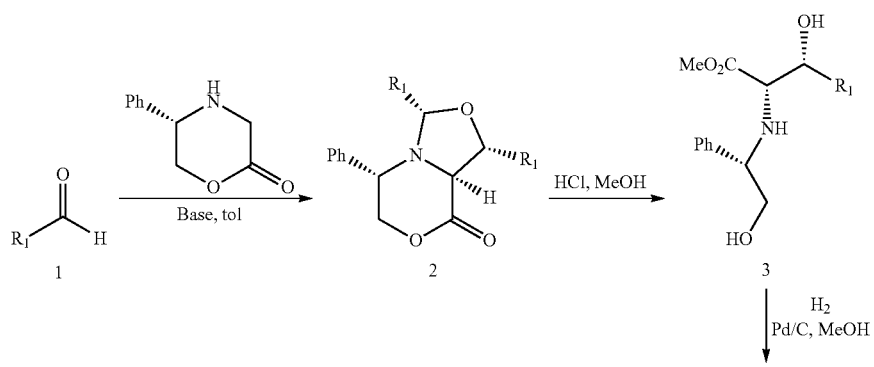

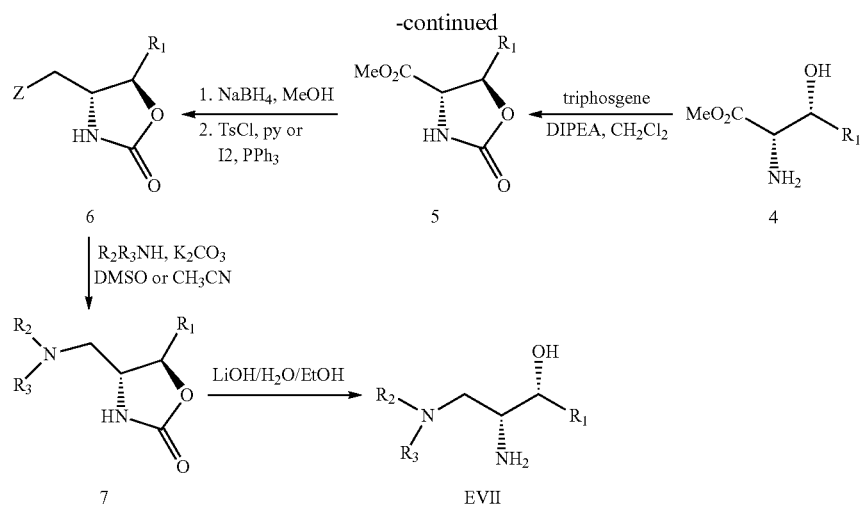

Example 1C

Preparation of Compound EVII Using Scheme 2

Preparation of EII (R)-benzyl 3,8,8,9,9-pentamethyl-4-oxo-2,7-dioxa-3-aza-8-siladecan-5-ylcarbamate Imidazole (1.8 g, 26.5 mmol) was added to a solution of (R)-benzyl 3-hydroxy-1-(methoxy(methyl)amino)-1-oxopropan-2-ylcarbamate (3 g, 10.6 mmol) in DMF (dimethyl formamide, 15 mL) followed by TBDMSiCl (tert-butyldimethylsilyl chloride, 2.4 g, 15.95 mmol). The reaction stirred for 12 hrs at room temperature under nitrogen atmosphere and was quenched with aqueous ammonium chloride (100 ml). The aqueous layer was extracted with methylene chloride (200 mL) and ethyl acetate (100 mL) and the organic layers were washed with brine and concentrated. The crude product was purified by column chromatography using 10% EtOAc (ethylacetate)-hexanes to give an oil (3 g, 74% yield). $^1$H NMR (400 MHz, CDCl$_3$) δ=0 (s, 6H), 0.9 (s, 9H), 3.2 (s, 3H), 3.8 (s, 3H), 3.8-3.9 (m, 2H), 4.8 (broad s, 1H), 5.1 (q, 2H), 5.7 (d, 1H), 7.2-7.4 (m, 5H).

Preparation of EIII (R)-benzyl 3-(tert-butyldimethylsilyloxy)-1-(2,3-dihydrobenzo[β][1,4]dioxin-6-yl)-1-oxopropan-2-ylcarbamate (2,3-dihydrobenzo[β][1,4]dioxin-6-yl)magnesium bromide (26 g, 78 mmol) dissolved in 40 mL of THF (tetrahydrofuran) under a nitrogen atmosphere was cooled down to −70° C. and (R)-benzyl 3,8,8,9,9-pentamethyl-4-oxo-2,7-dioxa-3-aza-8-siladecan-5-ylcarbamate (12.3 g, 31 mmol) dissolved in THF (13 ml) were added dropwise. The reaction mixture was allowed to warm up to −15° C. and left to react for 12 hrs followed by stirring at room temperature for 2 hrs. After cooling the reaction mixture to −40° C. it was quenched using aqueous ammonium chloride and the aqueous layer was extracted with EtOAc dried over magnesium sulfate and concentrated. The crude product was purified by column chromatography using 25% EtOAc-hexanes to give pure product (13 g, 88% yield). $^1$H NMR (400 MHz, CDCl$_3$) δ=0 (d, 6H), 0.9 (s, 9H), 4.0-4.2 (m, 2H), 4.4 (s, 2H), 4.5 (s, 2H), 5.2 (s, 2H), 5.4 (m, 1H), 6.1 (d, 1H), 7 (d, 1H), 7.4-7.7 (m, 7H).

Preparation of EIV

Benzyl (1R,2R)-3-(tert-butyldimethylsilyloxy)-1-(2,3-dihydrobenzo[β][1,4]dioxin-6-yl)-1-hydroxypropan-2-ylcarbamate (R)-benzyl 3-(tert-butyldimethylsilyloxy)-1-(2,3-dihydrobenzo[β][1,4]dioxin-6-yl)-1-oxopropan-2-ylcarbamate (3.1 g, 6.6 mmol) were dissolved in THF (25 ml) and cooled down to −70° C. under nitrogen atmosphere. L Selectride (13.2 ml of 1M solution in THF, 13 mmol) was added dropwise while keeping the temperature at −70° C. After 1 hour, the reaction was quenched with a 1M aqueous solution of potassium tartrate (13 ml) and extracted with EtOAc. The organic layer was evaporated down and the product was purified by column chromatography using 2.5% EtOAc-2% acetone-methylene chloride. The desired diastereomer was obtained in 80% yield (2.5 g). $^1$H NMR (400 MHz, CDCl$_3$) δ=0 (d, 6H), 0.9 (s, 9H), 3.5 (broad s, 1H), 3.7-3.9 (m, 2H), 4.2 (s, 4H), 4.9 (broad s, 1H), 5.0 (d, 2H), 5.4 (d, 1H), 6.8 (s, 2H), 6.9 (s, 1H), 7.2-7.4 (m, 5H).

Preparation of EV

Benzyl (1R,2R)-1-(2,3-dihydrobenzo[β][1,4]dioxin-6-yl)-1,3-dihydroxypropan-2-ylcarbamate Benzyl (1R,2R)-3-(tert-butyldimethylsilyloxy)-1-(2,3-dihydrobenzo[β][1,4]dioxin-6-yl)-1-hydroxypropan-2-ylcarbamate (0.5 g) was dissolved in a 4 ml mixture of Acetic acid/THF/water (3/1/1) and left to stir over night. The crude was evaporated down and the product azeotropically dried with EtOAc (10 ml). The crude product was purified by column chromatography using 50% EtOAc-hexane. The pure product was obtained in 74% yield (0.28 g). $^1$H NMR (400 MHz, CDCl$_3$) δ=3.4-3.8 (m, 4H), 4.1 (broad s, 4H), 4.8 (s, 1H), 4.9 (broad s, 2H), 5.7 (broad s, 1H), 6.8 (s, 2H), 6.9 (s, 1H), 7.2-7.4 (m, 5H).

General Procedure for Preparation of EVI and EVII

Benzyl (1R,2R)-1-(2,3-dihydrobenzo[β][1,4]dioxin-6-yl)-1,3-dihydroxypropan-2-ylcarbamate was dissolved in excess pyridine, cooled to −15° C. and one equivalent of methanosulfonyl chloride was added to the mixture. Mixture was stirred about half an hour, and ten equivalents of the amine were added. The reaction mixture was allowed to warm up to room temperature and then heated at 50° C. overnight. The crude was evaporated down and the product was purified by column chromatography using a mixture of methanol/methylene chloride/ammonium hydroxide. The pure compound EVI was then de-protected by hydrolysis in the microwave, using aqueous NaOH (40% in weight)/methanol solution as solvent and heating the mixture to 150° C. for about 15 minutes to give the free amines of the type EVI. The final product was purified by silica-gel column chromatography using a mixture of methanol/methylene chloride/ammonium hydroxide.

Examples of EVII Compounds i) (1R,2R)-2-amino-1-(2,3-dihydrobenzo[β][1,4]dioxin-6-yl)-3-morpholinopropan-1-ol

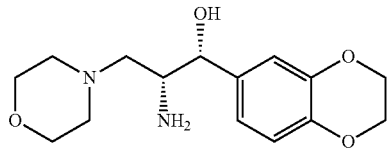 [SMILES: N[C@H](CN1CCOCC1)[C@H](O)c1ccc2c(c1)OCCO2]

$^1$H NMR (400 MHz, CDCl$_3$) δ=2.3 (dd, 2H), 2.4 (dd, 2H), 2.5-2.6 (m, 2H), 3.2 (m, 1H), 3.6-3.7 (m, 4H), 4.2 (s, 4H), 4.4 (d, 1H), 6.5-6.9 (m, 3H); MS for C$_{15}$H$_{22}$N$_2$O$_4$ m/z 294.8 [M+H].

ii) (1R,2R)-2-amino-1-(2,3-dihydrobenzo[β][1,4]dioxin-6-yl)-3-(piperidin-1-yl)propan-1-ol

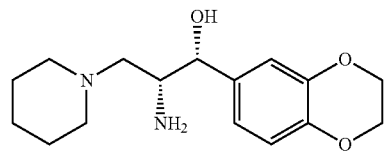 [SMILES: N[C@H](CN1CCCCC1)[C@H](O)c1ccc2c(c1)OCCO2]

$^1$H NMR (400 MHz, CDCl$_3$) δ=1.4 (broad s, 2H), 1.7 (m, 4H), 2.2-2.6 (m, 6H), 3.2 (m, 1H), 4.2 (s, 4H), 4.5 (s, 1H), 6.7-6.9 (m, 3H).

Example 1D

Preparation of Substituted Phenoxy Propionic Acids

Example 1D1

Preparation of 3-(4-methoxyphenoxy)propionic acid i) 3-(4-methoxyphenoxy)propionitrile A 740 g (5.96 mol, 1 eq.) sample of 4-methoxyphenol was charged to a 3 necked 5 L flask under nitrogen. Triton B (50 mL of a 30% wt. solution in methanol) was charged to the flask, and stirring initiated via an overhead stirrer. Acrylonitrile (2365 mL, 35.76 mol, 6 eq.) was then charged to the reaction flask in a single portion, and the reaction mixture heated at 78° C. for 36 h. HPLC analysis indicated that the reaction was complete at this point. Solvents were removed via rotary evaporation, and the resulting oil was chased with toluene to remove excess acrylonitrile. The crude material was recrystallized from TBME (tert-butyl methyl ether) 10 volumes relative to the crude weight), and dried in a vacuum oven to give 945 g of 3-(4-methoxyphenoxy)propionitrile as white crystals (Yield: 89.48%). $^1$H NMR (450 MHz, CDCl$_3$): δ=2.72 (t, 2H; CH$_2$CN); δ=3.83 (s, 3H; OCH$_3$); δ=4.05 (t, 2H; OCH$_2$); δ=6.70 (m, 4H; Ar—H); $^{13}$C NMR (112.5 MHz, CDCl$_3$): δ=18.843 (CH$_2$CN); 55.902 (OCH$_3$); 63.699 (OCH$_2$); 114.947 (CH$_3$OCCH); 116.183 (CH$_2$OCCH); 117.716 (CN); 151.983 (CH$_3$OC); 154.775 (CH$_2$OC).

ii) 3-(4-methoxyphenoxy)propionic acid

A 945 g (5.34 mol, 1 eq.) sample of 1 (3-(4-methoxyphenoxy)propionitrile was charged to a 22 L round bottom flask equipped with an overhead stirrer under N$_2$. To the stirred solids, 4 L of concentrated HCl was slowly added, followed by 2 L of H$_2$O. The reaction mixture was heated to 100° C. for 3.5 h, at which point the reaction was complete by HPLC analysis. The reaction was cooled to 10° C. by the addition of ice to the reaction mixture, and was filtered. The dried solids gave 920 g of crude 3-(4-methoxyphenoxy)propionic acid. The crude material was dissolved in 5 L of 6 wt. % sodium carbonate (such that pH=9), and 2 L of DCM (dichloromethane) was added to the reaction vessel. After stirring thoroughly, the organic layer was separated and discarded via a separatory funnel, and the aqueous layer charged back into the 22 L flask. The pH of the aqueous layer was carefully adjusted to 4.0, by slow addition of 6 M HCl. The precipitated solids were filtered, and dried in a vacuum oven to give 900 g of 3-(4-methoxyphenoxy)propionic acid as a white solid (Yield: 86.04%). $^1$H NMR (450 MHz, CDCl$_3$); δ=2.78 (t, 2H; CH$_2$COOH); 3.70 (s, 3H; OCH$_3$); 4.18 (t, 2H; OCH$_2$); 6.78 (m, 4H; Ar—H); $^{13}$C NMR (112.5 MHz, CDCl$_3$): δ=34.703 (CH$_2$COOH); 55.925 (OCH$_3$); 64.088 (OCH$_2$); 114.855 (CH$_3$OCCH); 115.984 (CH$_2$OCCH); 152.723 (CH$_3$OC); 154.302 (CH$_2$OC); 177.386 (COOH).

Example 1D2

Preparation of 3-(4-(3-oxobutyl)phenoxy)propanoic acid

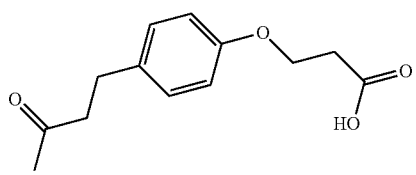 [SMILES: CC(=O)CCc1ccc(OCCC(=O)O)cc1]

Step 1: a mixture of 4-(p-hydroxyphenol)-2-butanone (1.032 g), triton B (400 μL), acrylonitrile (4 mL) and MeOH (0.8 mL) was heated at 70° C. for 20 hours. The mixture was cooled to room temperature and the solvent was removed to dryness. 3-(4-(3-oxobutyl)phenoxy)propanenitrile was obtained as a white solid (0.572 g) after purification by column chromatography using ethyl acetate/hexane.

Step 2: 3-(4-(3-oxobutyl)phenoxy)propanenitrile (0.478 g) was suspended in HCl (37%, 5 mL) and placed in the microwave reactor (T=110° C., 5 min). The mixture was poured onto iced water (20 g), filtered, and the solid was washed with water (2×5 mL). After column chromatography purification using a mixture of methylene chloride/methanol, 3-(4-(3-oxobutyl)phenoxy)propanoic acid was obtained as a white solid (0.3 g). ¹H NMR (CDCl₃, 400 mHz, ppm); 2.2 (s, 3H), 2.7 (t, 2H), 2.85 (m, 4H), 4.25 (t, 2H), 6.8 (d, 2H), 7.1 (d, 2H).

Example 1D3

Preparation of
3-(4-(2-methoxyethyl)phenoxy)propanoic acid

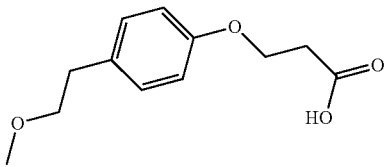 [SMILES: COCCc1ccc(OCCC(=O)O)cc1]

Step 1: a mixture of 4-(2-methoxy ethyl)phenol (1.547 g, 10.3 mmol), propiolic acid tert-butyl ester (1.367 g, 10.8 mmol) and N-methyl morpholine (1.18 mL, 10.8 mmol) in CH₂Cl₂ (15 mL) was stirred at room temperature for 24 hours. The mixture was absorbed on SiO₂ (20 g) and purified by column chromatography using a mixture of methylene chloride/hexane. The product was obtained as a two to one mixture of (E)/(Z)-tert-butyl 3-(4-(2-methoxyethyl)phenoxy) acrylate isomers (2.0 g).

Step 2: (E)/(Z)-tert-butyl 3-(4-(2-methoxyethyl)phenoxy) acrylate (0.57 g) was suspended in a mixture of THF (5 mL)/HCl (2 M, 5 mL) and placed in the microwave reactor (T=100° C., 15 sec). THF was removed by rotary evaporation and the mixture was extracted with CH₂Cl₂ (10 mL). (E)/(Z)-3-(4-(2-methoxyethyl)phenoxy)acrylic acid was obtained as a white solid after purification by column chromatography using a mixture of hexane/ethyl acetate.

Step 3: (E)/(Z)-3-(4-(2-methoxyethyl)phenoxy)acrylic acid (0.3 g) was dissolved in EtOH (10 mL) and Pd/C (5%, degussa type E101, 40 mg) was added. The mixture was hydrogenated at atmospheric pressure for 2 hours and then filtered and the solvent removed to dryness. After purification by column chromatography using a mixture of hexane/ethyl acetate, 3-(4-(2-methoxyethyl)phenoxy)propanoic acid was obtained as a white solid (0.236 g). ¹H NMR (CDCl₃, 400 mHz, ppm); 2.85 (t, 4H), 3.35 (s, 3H), 3.55 (t, 2H), 4.25 (t, 2H), 6.85 (d, 2H), 7.1 (d, 2H).

Example 1D4

Preparation of
3-(4-(3-methylbutanoyl)phenoxy)propanoic acid

Step 1: 3-phenoxypropionic acid (5.0 g, 30 mmol) was dissolved in MeOH (12 mL) and H₂SO₄ (18 M, 3 drops) was added. The mixture was place in the microwave reactor (T: 140° C., t: 5 min). The solvent was evaporated, the mixture was partitioned in EtOAc (30 mL) and NaOH (2N, 20 mL). The organic phase was dried over MgSO₄, filtered, and evaporated to give methyl 3-phenoxypropanoate (5.0 g, 27.7 mmol, 92.5%).

Step 2: aluminum chloride (1.1 g, 8.34 mmol) was added to a cold solution (0° C.) solution of methyl 3-phenoxypropanoate (1.0 g, 5.56 mmol) and tert-butylacetyl chloride (1.25 mL, 8.34 mmol) in CH₂Cl₂ (9 mL) and the reaction mixture was stirred overnight. The mixture was evaporated and the residue was diluted with EtOAc (30 mL) and then washed with water (2×20 mL). The organic phase was removed and purified with silica chromatography using of a gradient hexanes/EtOAc (100:0→0:100) to give methyl 3-phenoxypropanoate (600 mg, 2.27 mmol, 40%).

Step 3: a solution of methyl 3-phenoxypropanoate (200 mg, 0.76 mmol) in 2 mL of HCl (37%) was placed in a microwave reactor (T: 120° C., t: 5 min). The mixture was poured into iced water (2 g) and washed with EtOH (3×10 mL). The organic phase was combined and evaporated. The crude product was purified with silica gel chromatography using of a gradient hexanes/EtOAc (100:0→0:100) to give 3-(4-(3-methylbutanoyl)phenoxy)propanoic acid (120 mg, 0.48 mmol, 63%).

Example 2

Preparation of Compounds of the Invention

The exemplary compounds shown in Example 2 and Tables 1-3 can be prepared by following scheme 1 described above, Detailed synthetic description of certain compounds also are described below as examples.

Example 2E1

Preparation of Hemi-Hydrate of Compound 163
N-[2-Hydroxy-2-(2,3-dihydrobenzo[β][1,4]dioxin-6-yl)-1-pyrrolidin-1-ylmethyl-ethyl]-3-(4-methoxyphenoxy)-propionamide

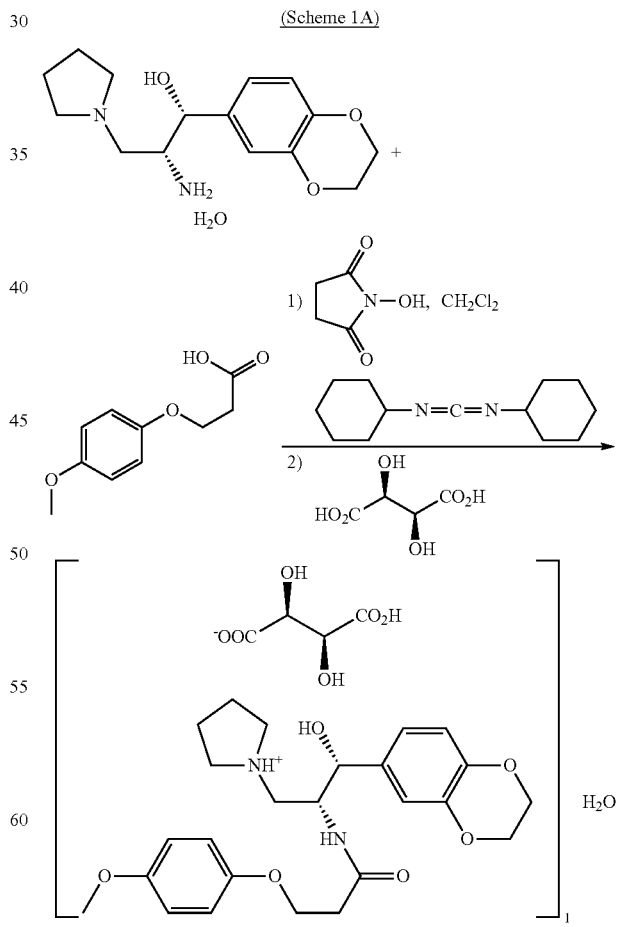

Compound 163 was prepared by following Scheme 1A above. 3-(4-methoxyphenoxy)propanoic acid (see Example 1D1, 34.47 g, 169 mmol, 96% purity by HPLC), DCC (34.78 g, 169 mmol) and N-hydroxysuccinimide (19.33, 169 mmol) were combined as dry powders and methylene chloride (500 mL) was added. The suspension was mechanically stirred overnight, ambient temperature, under a nitrogen atmosphere. HPLC analysis showed complete conversion of the acid to the NHS ester (N-hydroxy succinyl ester). To the mixture was added (1R,2R)-2-amino-1-(2,3-dihydro-benzo[1,4]dioxin-6-yl)-3-pyrrolidin-1-yl-propan-1-ol (50 g, 169 mmol) and stirring continued for 2.5 hours. HPLC showed conversion to the product and loss of both the NHS ester and step 5 amine. The reaction mixture was vacuum filtered on a Büchner funnel to remove DCC urea. The solid urea was washed with 500 mL of methylene chloride. The organic layers were combined, placed in a separatory funnel, and treated with 500 mL of 1.0M NaOH. The layers were separated, and the cloudy organic layer was recharged into a separatory funnel and treated with a 6% HCl solution (adjusted to pH=0.03-0.34, 100 mL of solution). Two clear layers formed. The resultant biphasic solution was poured into an Erlenmeyer flask and cautiously neutralized to a pH of 7.2-7.4 with a saturated solution of sodium bicarbonate (approx 200 mL of solution). The organic layer was separated from the aqueous layer, dried over sodium sulfate and evaporated to yield 83.6 g of yellow oil (theoretical yield: 77.03 g). The oil was dissolved in isopropyl alcohol (500 mL) with heating and transferred to a 1 L round bottom flask equipped with a mechanical stirrer and heating mantel. The solution was heated to 50° C. and the mechanical stirrer was set to a rate of 53-64 rpm. Tartaric acid (25.33 g, 168 mmol) was dissolved in deionized water (50 mL) and added to the stirred solution at 50° C. Once the solution turned from milky white to clear, seed crystals were added to the mixture and crystallization immediately began (temperature jumped to 56° C.). After 20 minutes, the mixture was set to cool to a temperature of 35° C. (cooling took 1.15 hours). Heating was removed and the solution was allowed to stir for 12 hours. The resulting thick slurry was filtered on a Büchner funnel. Any remaining solid in the flask was washed onto the funnel using ice-cold isopropyl alcohol (100 mL). The material was transferred to a drying tray and heated to 48° C. under vacuum for 3 days (after two days the material weighed 76 g and after three days it weighed 69.3 g). The solid was analyzed by LC and shown to be 98.1% pure (AUC), the residual solvent analysis showed the material to possess 3472 ppm of isopropyl alcohol, and the DSC (differential scanning calroimetery) showed a melting point of 134.89° C. A total of 69.3 g of white solid was collected (65.7% overall yield). $^1$H NMR (400 MHz, CDCl$_3$) δ=1.8 (M, 4H), 2.4-2.6 (m, 4H), 2.6 (m, 1H), 2.85 (m, 2H), 3.0 (m, 1H), 3.65 (s, 3H), 3.8 (m, 2H), 3.86 (2, 2H), 4.18 (br s, 5H), 4.6 (s, 1H), 6.6-6.8 (m, 7H), 7.8 (d, 1H); MS for $C_{29}H_{40}N_2O_{13}$ m/z 457.3 [M+H] for main peak (free-base).

Example 2E2

Preparation of Compound 247

N-((1R,2R)-1-hydroxy-1-(4-methoxyphenyl)-3-(pyrrolidin-1-yl)propan-2-yl)-3-(p-tolyloxy)propanamide Compound 247 was prepared by reaction of (1R,2R)-2-amino-1-(4-methoxyphenyl)-3-(pyrrolidin-1-yl)propan-1-ol as the amine, prepared according to scheme 3 with 3-(4-methylphenoxy)propionic acid using method 1.

Preparation of A (R)-benzyl 4-formyl-2,2-dimethyloxazolidine-3-carboxylate

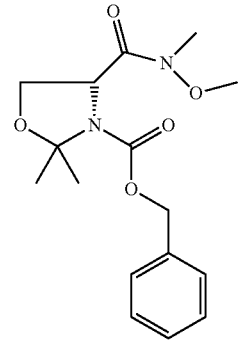

N,O-dimethylhydroxylamine hydrochloride (45 g, 0.46 mmol, 1.5 eq) and N-methyl morpholine (84 mL, 0.765 mol, 2.5 eq.) were added slowly to a cold (−15° C.) suspension of d-CBz serine (73.0 g, 0.305 mol) in CH$_2$Cl$_2$ (560 mL) keeping the temperature below −5° C. The mixture was cooled back to ~−15° C. and EDCI (62 g, 0.323 mol, 1.05 eq) was added. The mixture was stirred for 5 hours keeping the temperature below 5° C. The solvent was removed by rotary evaporation and the mixture was partitioned between HCl (1 M, 300 mL) and EtOAc (500 mL). The organic layer was separated and washed with HCl (1 M, 2×100 mL) and then sat. NaHCO$_3$ (2×150 mL) The mixture was dried over MgSO$_4$, filtered and then the solvent was removed by rotary evaporation. (R)-benzyl 3-hydroxy-1-(methoxy(methyl)amino)-1-oxopropan-2-ylcarbamate was re-dissolved in a mixture of acetone (375 mL) and 2,2-dimethoxy propane (375 mL) and boron trifluoride ethereate (3 mL) was added. The mixture was stirred at room temperature for 5 hours and then triethyl amine (3 mL) was added. The solvent was removed to dryness and (R)-benzyl 4-(methoxy(methyl)carbamoyl)-2,2-dimethyloxazolidine-3-carboxylate was obtained as a white solid (73.0 g, 74% yield from both steps) after purification by column chromatography using a mixture of hexane/EtOAc/acetone.

$^1$H NMR (CDCl$_3$, 400 mHz, ppm); 1.5 (s, 2H), 1.6 (s, 3H), 1.7 (s, 2H), 1.75 (s, 3H), 3.14 (s, 3H), 3.24 (2H), 3.4 (3H), 3.76 (s, 2H), 4.0 (m, 1.7H), 4.16 (m, 1H), 4.2 (m, 1.7), 4.78 (m, 1H), 4.88 (m, 0.6H), 5.06 (q, 2H), 5.18 (q, 1H), 7.4 (m, 8H).

Preparation of AI (R)-benzyl 4-((R)-hydroxy(4-methoxyphenyl)methyl)-2,2-dimethyloxazolidine-3-carboxylate

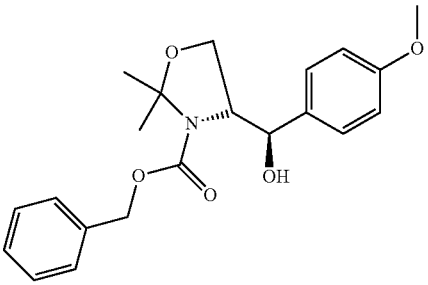

A solution of LiALH$_4$ (1 M, 20 mL, 20 mmol) was added dropwise to a cold (−15° C.) solution of (R)-benzyl 4-(methoxy(methyl)carbamoyl)-2,2-dimethyloxazolidine-3-carboxylate (12.2 g, 37.9 mmol) in THF (75 mL) The mixture was stirred for 30 min keeping the temperature below 0° C. A saturated solution of $KHSO_4$ (100 mL) was added slowly to the mixture and it was warmed to room temperature. The mixture was filtered and the solvent was removed to dryness. (R)-benzyl 4-formyl-2,2-dimethyloxazolidine-3-carboxylate was obtained as a clear oil (9.161 g, 92% yield) after purification by column chromatography ($SiO_2$, using a mixture of hexane/EtOAc).

$^1$H NMR ($CDCl_3$, 400 mHz, ppm); 1.7 (m, 6H), 4.15 (m, 2H), 4.4 (m, 1H), 5.15, (s, 1H), 5.2 (m, 1H), 7.3 (m, 5H), 9.6 (m, 1H).

1,2-dibromoethane (0.2 mL) was added slowly to a hot (65° C.) solution of magnesium turnings (0.91 g, 37 mmol) in THF (14 mL), followed by the dropwise addition of a solution of 4-bromo anisole (4 mL, 32 mmol) in THF (14 mL). The mixture was refluxed for 2 hours and then cooled to room temperature. The grignard solution was added dropwise to a suspension of CuI (6.8 g, 36 mmol) in a mixture of $Me_2S$ (20 mL)/THF (100 mL) at −78° C. The mixture was warmed slowly to −45° C. and stirred for 30 min keeping the temperature between −45 to −35° C. The mixture was cooled back to −78° C., and a solution of the Garner's aldehyde [(R)-benzyl 4-formyl-2,2-dimethyloxazolidine-3-carboxylate] (3.20 g, 12.6 mmol) in THF (15 mL) was added dropwise. The mixture was stirred at low temperature overnight (15 h, T max=10° C.). The reaction mixture was quenched with $NH_4Cl$ (sat. 100 mL) and extracted with EtOAc (50 mL). The solvent was removed to dryness and the mixture was purified by column chromatography ($SiO_2$, using a mixture of hexane/EtOAc/acetone) and the product was obtained as a colorless oil (1.697 g, 36% yield).

Preparation of AII benzyl (1R,2R)-1,3-dihydroxy-1-(4-methoxyphenyl)propan-2-ylcarbamate

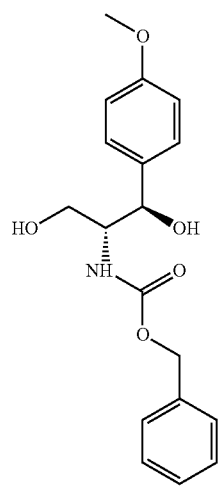 [SMILES: COc1ccc([C@@H](O)[C@@H](CO)NC(=O)OCc2ccccc2)cc1]

A mixture of benzyl 4-(hydroxy-(4-methoxyphenyl)methyl)-2,2-dimethyloxazolidine-3-carboxylate (1.679 g, 4.5 mmol) and amberlyst 15 (1.85 g) in MeOH (20 mL) was stirred at room temperature for 2 days. The mixture was centrifuged and the solid was washed with MeOH (2×40 mL). The solvent was removed to dryness and after purification by column chromatography ($SiO_2$ using a mixture of $CH_2Cl_2$/EtOAc) the product was obtained as a white solid (1.26 g, 84% yield).

Preparation of AIV

Synthesis of Compound 289 benzyl (1R,2R)-1-hydroxy-1-(4-methoxyphenyl)-3-(pyrrolidin-1-yl)propan-2-ylcarbamate

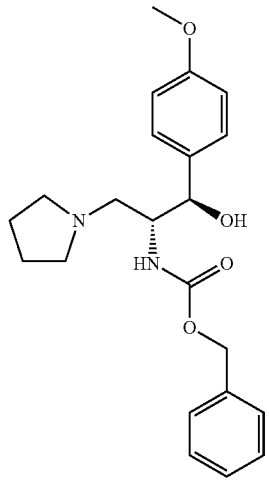 [SMILES: COc1ccc([C@@H](O)[C@@H](CN2CCCC2)NC(=O)OCc2ccccc2)cc1]

Mesityl chloride (0.28 mL, 3.6 mmol) was added slowly to a cold (−10° C.) solution of benzyl (1R,2R)-1,3-dihydroxy-1-(4-methoxyphenyl)propan-2-ylcarbamate (1.07 g, 3.23 mmol) in pyridine (1.5 mL). The mixture was stirred for 30 min and then pyrrolidine (2.7 mL, 33 mmol) was added slowly to the mixture. The mixture was heated to 45° C. for 6 hours and then the solvent was removed to dryness. After purification by column chromatography ($SiO_2$, using a mixture of $CH_2Cl_2$, MeOH, $NH_4OH$), the product was obtained as a clear oil (0.816 g, 66% yield).

Preparation of EVII (1R,2R)-2-amino-1-(4-methoxyphenyl)-3-(pyrrolidin-1-yl)propan-1-ol as the amine was prepared by the procedures described below:

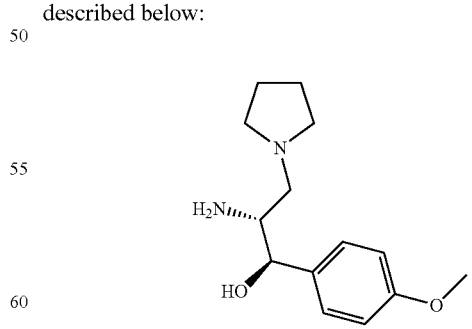

A mixture of benzyl (1R,2R)-1-hydroxy-1-(4-methoxyphenyl)-3-(pyrrolidin-1-yl)propan-2-ylcarbamate (0.10 g, 0.26 mmol) and Pd/C (5%, 21 mg) in EtOH (1 mL)/HCl (1 M, 50 μL) was degassed and hydrogen gas was added. The mixture was hydrogenated at atmospheric pressure for two hours.

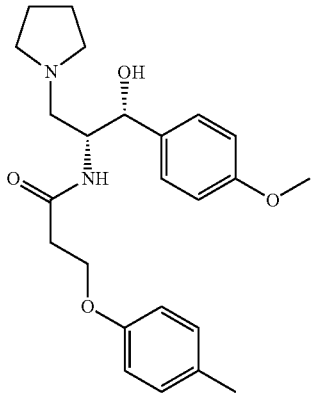 [SMILES: COc1ccc([C@@H](O)[C@@H](CN2CCCC2)NC(=O)CCOc2ccc(C)cc2)cc1]

Preparation of Compound 247

N-((1R,2R)-1-hydroxy-1-(4-methoxyphenyl)-3-(pyrrolidin-1-yl)propan-2-yl)-3-(p-tolyloxy)propanamide $^1$H NMR (CDCl$_3$, 400 mHz, ppm); 1.75 (br, 4H), 2.3 (s, 3H), 2.65 (br, 6H), 2.85 (m, 2H), 3.75 (s, 3H), 4.1 (m, 2H), 4.25 (m, 1H), 5.05 (sd, 1H), 6.5 (br, 1H), 6.8 (m, 4H), 7.1 (d, 2H), 7.2 (d, 2H). M/Z for C$_{24}$H$_{32}$N$_2$O$_4$ [M−H]$^−$=413.

Example 2E3

Preparation of Compound 251

N-((1R,2R)-1-hydroxy-1-(4-methoxyphenyl)-3-(pyrrolidin-1-yl)propan-2-yl)-2-(4-(trifluoromethyl)phenyl)acetamide

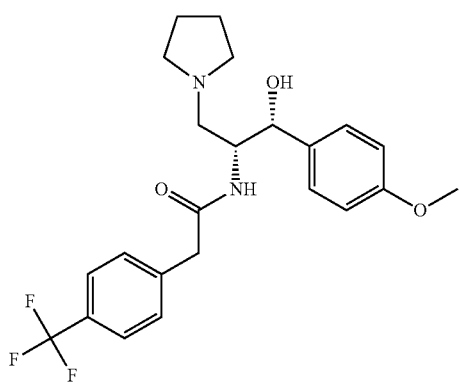 [SMILES: COc1ccc([C@@H](O)[C@@H](CN2CCCC2)NC(=O)Cc2ccc(C(F)(F)F)cc2)cc1]

$^1$H NMR (CDCl$_3$, 400 mHz, ppm); 1.75 (br, 4H), 2.55 (br, 4H), 2.85 (m, 2H), 3.5 (s, 2H), 3.8 (s, 3H), 4.2 (m, 1H), 5.05 (sd, 1H), 5.8 (d, 1H), 6.8 (d, 2H), 7.1 (d, 2H), 7.2 (d, 2H), 7.55 (d, 2H). M/Z for C$_{23}$H$_{27}$F$_3$N$_2$O$_3$ [M−H]$^−$=437.

Example 2E4

Preparation of Compound 5

N-((1R,2R)-1-(2,3-dihydrobenzo[β][1,4]dioxin-6-yl)-1-hydroxy-3-(pyrrolidin-1-yl)propan-2-yl)benzo[b]thiophene-2-carboxamide

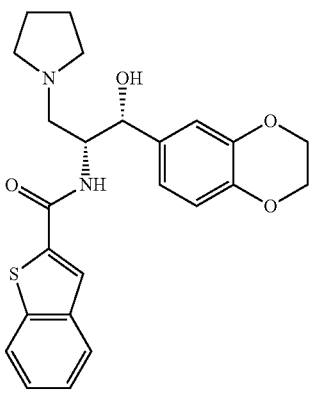 [SMILES: O=C(N[C@H](CN1CCCC1)[C@H](O)c1ccc2c(c1)OCCO2)c1cc2ccccc2s1]

$^1$H NMR (CDCl$_3$, 400 mHz, ppm); 1.8 (br, 4H), 2.7 (br, 4H), 3.0 (m, 2H), 4.25 (s, 4H), 4.45 (m, 1H), 5.05 (sd, 1H), 6.6 (br, 1H), 6.85 (s, 2H), 6.95 (s, 1H), 7.4 (m, 2H), 7.7 (s, 1H), 7.85 (m, 2H). M/Z for C$_{24}$H$_{26}$N$_2$O$_4$S [M−H]$^−$=439.

Example 2E5

Preparation of Compound 11

N-((1R,2R)-1-(2,3-dihydrobenzo[β][1,4]dioxin-6-yl)-1-hydroxy-3-(pyrrolidin-1-yl)propan-2-yl)-2-(phenylthio)acetamide

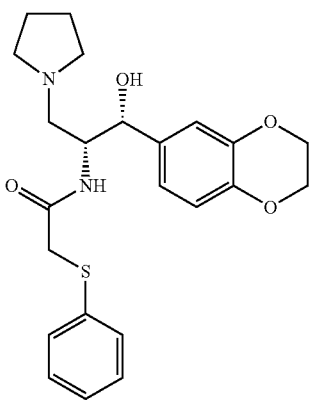 [SMILES: O=C(CSc1ccccc1)N[C@H](CN1CCCC1)[C@H](O)c1ccc2c(c1)OCCO2]

$^1$H NMR (CDCl$_3$, 400 mHz, ppm); 1.7 (br, 4H), 2.5 (br, 4H), 2.8 (br, 2H), 3.6 (q, 2H), 4.1.5 (m, 1H), 4.2 (s, 4H), 5.9 (sd, 1H), 6.7 (m, 2H), 6.8 (s, 1H), 7.2 (m, 7H). M/Z for C$_{23}$H$_{28}$N$_2$O$_4$S [M−H]$^−$=429.

Example 2E6

Preparation of Compound 12

N-((1R,2R)-1-(2,3-dihydrobenzo[β][1,4]dioxin-6-yl)-1-hydroxy-3-(pyrrolidin-1-yl)propan-2-yl)biphenyl-4-carboxamide

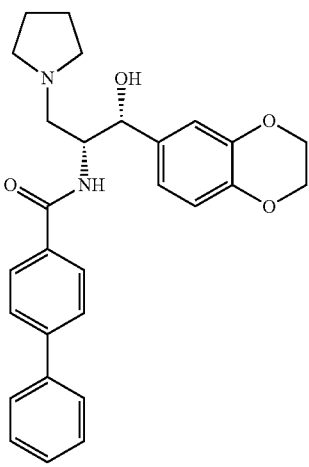 [SMILES: O=C(N[C@H](CN1CCCC1)[C@H](O)c1ccc2c(c1)OCCO2)c1ccc(-c2ccccc2)cc1]

$^1$H NMR (CDCl$_3$, 400 mHz, ppm); 1.8 (br, 4H), 2.7 (br, 4H), 3.0 (m, 2H), 4.25 (s, 4H), 4.4 (br, 1H), 5.05 (sd, 1H), 6.6 (sd, 1H), 6.85 (m, 2H), 6.95 (s, 1H), 7.45 (m, 3H), 7.6 (m, 4H), 7.75 (m, 2H). M/Z for C$_{28}$H$_{30}$N$_2$O$_4$ [M–H]$^-$=459.

Example 2E7

Preparation of Compound 19

N-((1R,2R)-1-(2,3-dihydrobenzo[β][1,4]dioxin-6-yl)-1-hydroxy-3-(pyrrolidin-1-yl)propan-2-yl)benzo[b]thiophene-5-carboxamide

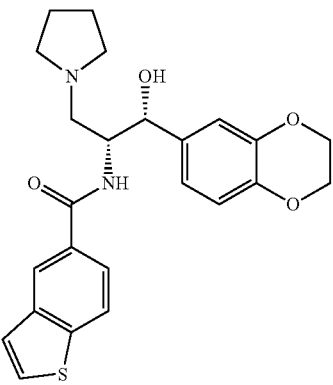 [SMILES: O=C(N[C@H](CN1CCCC1)[C@H](O)c1ccc2c(c1)OCCO2)c1ccc2sccc2c1]

$^1$H NMR (d$_6$-dmso, 400 mHz, ppm); 1.6 (br, 4H), 2.4 (br, 5H), 2.65 (m, 1H), 4.15 (s, 4H), 4.25 (m, 1H), 4.75 (sd, 1H), 5.6 (br, 1H), 6.7 (m, 3H), 7.5 (sd, 1H), 7.7 (sd, 1H), 7.8 (sd, 1H), 7.85 (sd, 1H), 8.0 (sd, 1H), 8.2 (s, 1H). M/Z for C$_{24}$H$_{26}$N$_2$O$_4$S [M–H]$^-$=439.

Example 2E8

Preparation of Compound 23

2-(biphenyl-4-yl)-N-((1R,2R)-1-(2,3-dihydrobenzo[β][1,4]dioxin-6-yl)-1-hydroxy-3-(pyrrolidin-1-yl)propan-2-yl)acetamide

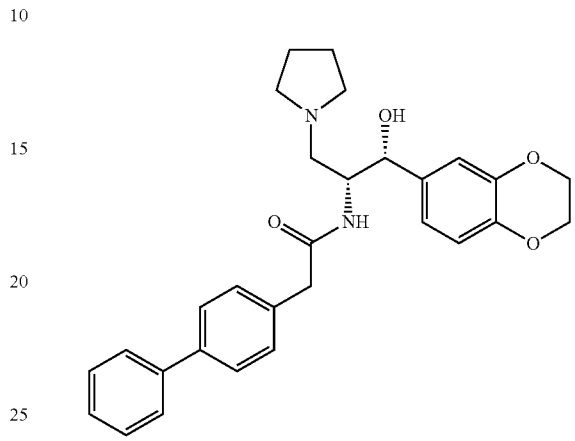

$^1$H NMR (CDCl$_3$, 400 mHz, ppm); 1.7 (br, 4H), 2.5 (br, 4H), 2.8 (d, 2H), 3.55 (s, 2H), 4.2 (m, 5H), 4.85 (sd, 1H), 5.95 (br, 1H), 6.6 (m, 1H), 6.75 (m, 2H), 7.2 (sd, 2H), 7.4 (m, 1H), 7.5 (st, 2H), 7.6 (m, 4H). M/Z for C$_{29}$H$_{32}$N$_2$O$_4$ [M–H]$^-$=473.

Example 2E9

Preparation of Compound 24

N-((1R,2R)-1-(2,3-dihydrobenzo[β][1,4]dioxin-6-yl)-1-hydroxy-3-(pyrrolidin-1-yl)propan-2-yl)-2-(4-phenoxyphenyl)acetamide

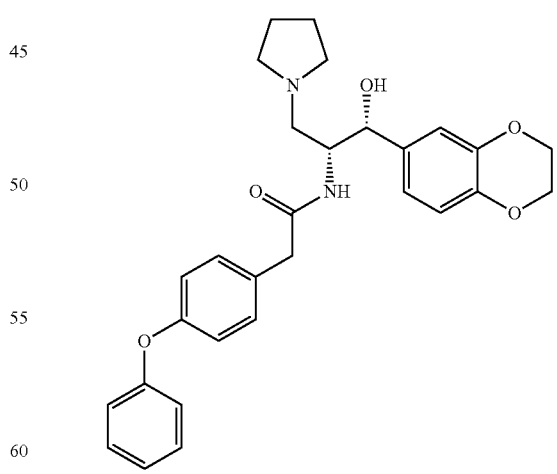

$^1$H NMR (CDCl$_3$, 400 mHz, ppm); 1.8 (br, 4H), 2.6 (br, 4H), 2.8 (sd, 2H), 3.45 (s, 2H), 4.15 (m, 1H), 4.25 (s, 4H), 4.85 (sd, 1H), 5.9 (br, 1H), 6.6 (m, 1H), 6.7 (s, 1H), 6.8 (m, 1H), 7.15 (m, 7H), 7.4 (m, 2H). M/Z for C$_{29}$H$_{32}$N$_2$O$_5$ [M–H]$^-$=489.

Example 2E10

Preparation of Compound 25

(S)—N-((1R,2R)-1-(2,3-dihydrobenzo[β][1,4]di-oxin-6-yl)-1-hydroxy-3-(pyrrolidin-1-yl)propan-2-yl)-2-hydroxy-3-phenylpropanamide

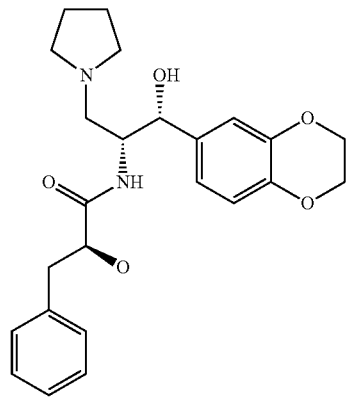 [SMILES: O=C(N[C@H](CN1CCCC1)[C@H](O)c1ccc2c(c1)OCCO2)[C@@H](O)Cc1ccccc1]

$^1$H NMR (CDCl$_3$, 400 mHz, ppm); 1.8 (br, 4H), 2.65 (br, 7H), 3.1 (dd, 2H), 4.2 (m, 6H), 4.8 (sd, 1H), 6.6 (m, 1H), 6.8 (m, 3H), 7.3 (m, 5H). M/Z for C$_{24}$H$_{30}$N$_2$O$_5$ [M−H]$^-$=427.

Example 2E11

Preparation of Compound 27

N-((1R,2R)-1-(2,3-dihydrobenzo[β][1,4]dioxin-6-yl)-1-hydroxy-3-(pyrrolidin-1-yl)propan-2-yl)-3-phenoxypropanamide

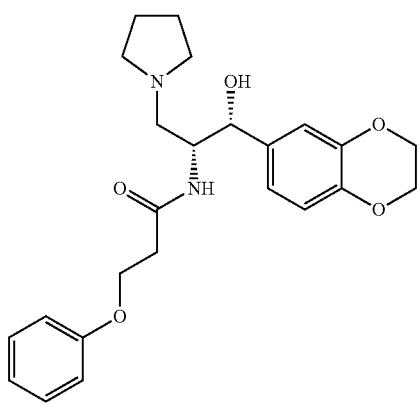 [SMILES: O=C(CCOc1ccccc1)N[C@H](CN1CCCC1)[C@H](O)c1ccc2c(c1)OCCO2]

$^1$H NMR (CDCl$_3$, 400 mHz, ppm); 1.8 (br, 4H), 2.7 (br, 6H), 2.9 (m, 2H), 4.2 (m, 7H), 4.95 (sd, 1H), 6.45 (m, 1H), 6.75 (s, 1H), 6.85 (m, 3H), 6.95 (t, 1H), 7.2 (m, 3H). M/Z for C$_{24}$H$_{30}$N$_2$O$_5$ [M−H]$^-$=427.

Example 2E12

Preparation of Compound 31

N-((1R,2R)-1-(2,3-dihydrobenzo[β][1,4]dioxin-6-yl)-1-hydroxy-3-pyrrolidin-1-yl)propan-2-yl)-2-oxo-2-phenylacetamide

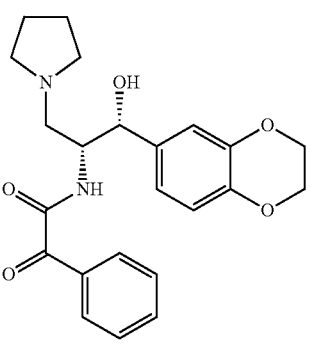 [SMILES: O=C(N[C@H](CN1CCCC1)[C@H](O)c1ccc2c(c1)OCCO2)C(=O)c1ccccc1]

$^1$H NMR (CDCl$_3$, 400 mHz, ppm); 1.8 (br, 4H), 2.8 (br, 4H), 3.0 (m, 2H), 4.2 (s, 4H), 4.3 (m, 1H), 5.05 (sd, 1H), 6.8 (s, 2H), 6.9 (s, 1H), 7.35 (m, 1H), 7.45 (t, 2H), 7.6 (t, 1H) 8.2 (d, 2H). M/Z for C$_{23}$H$_{26}$N$_2$O$_5$ [M−H]$^-$=411.

Example 2E13

Preparation of Compound 32

N-((1R,2R)-1-(2,3-dihydrobenzo[β][1,4]dioxin-6-yl)-1-hydroxy-3-(pyrrolidin-1-yl)propan-2-yl)-3-(phenylthio)propanamide

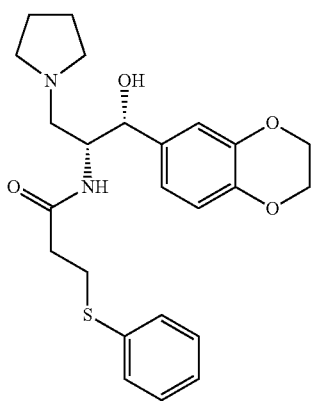 [SMILES: O=C(CCSc1ccccc1)N[C@H](CN1CCCC1)[C@H](O)c1ccc2c(c1)OCCO2]

$^1$H NMR (CDCl$_3$, 400 mHz, ppm); 1.8 (br, 4H), 2.4 (t, 2H), 2.7 (br, 4H), 2.8 (m, 2H), 3.1 (m, 2H), 4.2 (m, 5H), 4.9 (sd, 1H), 5.95 (br, 1H), 6.8 (m, 3H), 7.2 (m, 1H), 7.3 (m, 3H). M/Z for C$_{24}$H$_{30}$N$_2$O$_4$S [M−H]$^-$=443.

Example 2E14

Preparation of Compound 35

N-((1R,2R)-1-(2,3-dihydrobenzo[β][1,4]dioxin-6-yl)-1-hydroxy-3-(pyrrolidin-1-yl)propan-2-yl)-2-o-tolylacetamide

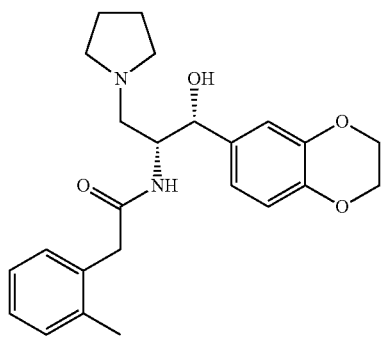 [SMILES: Cc1ccccc1CC(=O)N[C@H](CN1CCCC1)[C@H](O)c1ccc2c(c1)OCCO2]

$^1$H NMR (CDCl$_3$, 400 mHz, ppm); 1.7 (br, 4H), 2.1 (s, 3H), 2.5 (br, 4H), 2.75 (m, 2H), 3.5 (s, 2H), 4.1 (m, 1H), 4.25 (s, 4H), 4.8 (sd, 1H), 5.75 (br, 1H), 6.5 (d, 1H), 6.65 (s, 1H), 6.75 (d, 1H), 7.1 (d, 1H), 7.2 (m, 3H). M/Z for C$_{24}$H$_{30}$N$_2$O$_4$ [M−H]$^-$=411.

Example 2E15

Preparation of Compound 36

N-((1R,2R)-1-(2,3-dihydrobenzo[b][1,4]dioxin-6-yl)-1-hydroxy-3-(pyrrolidin-1-yl)propan-2-yl)-2-m-tolylacetamide

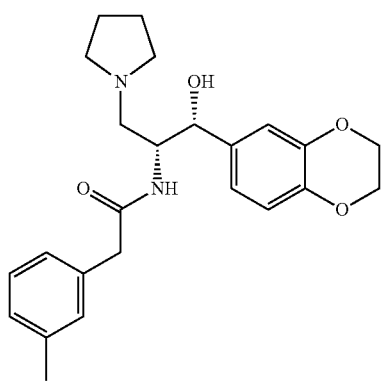 [SMILES: Cc1cccc(CC(=O)N[C@H](CN2CCCC2)[C@H](O)c2ccc3c(c2)OCCO3)c1]

$^1$H NMR (CDCl$_3$, 400 mHz, ppm); 1.7 (br, 4H), 2.35 (s, 3H), 2.5 (br, 4H), 2.75 (m, 2H), 3.45 (s, 2H), 4.1 (m, 1H), 4.25 (s, 4H), 4.85 (sd, 1H), 5.8 (br, 1H), 6.55 (d, 1H), 6.75 (m, 2H), 6.9 (d, 2H), 7.1 (sd, 1H), 7.2 (m, 1H). M/Z for C$_{24}$H$_{30}$N$_2$O$_4$ [M−H]$^-$=411.

Example 2E16

Preparation of Compound 39

2-(benzylthio)-N-((1R,2R)-1-(2,3-dihydrobenzo[β][1,4]dioxin-6-yl)-1-hydroxy-3-(pyrrolidin-1-yl)propan-2-yl)acetamide

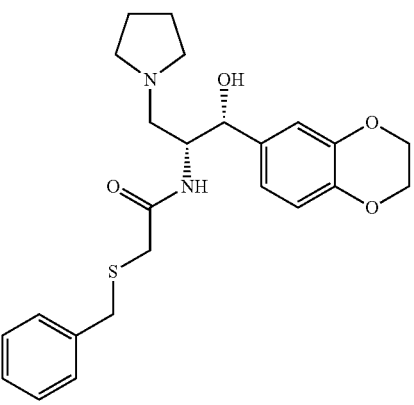 [SMILES: O=C(CSCc1ccccc1)N[C@H](CN1CCCC1)[C@H](O)c1ccc2c(c1)OCCO2]

$^1$H NMR (CDCl$_3$, 400 mHz, ppm); 1.8 (br, 4H), 2.7 (br, 4H), 2.9 (m, 2H), 3.0 (m, 2H), 3.3 (d, 1H), 3.55 (d, 1H), 4.2 (m, 5H), 5.05 (sd, 1H), 6.85 (s, 2H), 6.9 (s, 1H), 7.1 (sd, 2H), 7.3 (m, 3H). M/Z for C$_{24}$H$_{30}$N$_2$O$_4$S [M−H]$^-$=443.

Example 2E17

Preparation of Compound 47

N-((1R,2R)-1-(2,3-dihydrobenzo[β][1,4]dioxin-6-yl)-1-hydroxy-3-pyrrolidin-1-yl)propan-2-yl)-2-(4-(pyridin-3-yl)phenyl)acetamide

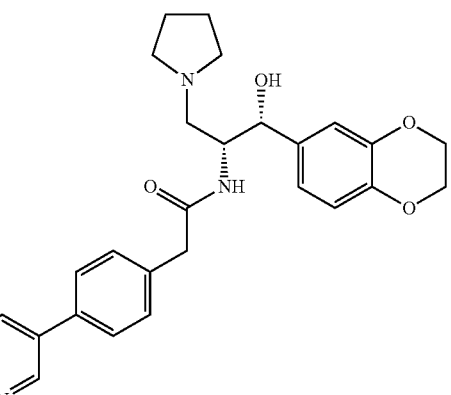

$^1$H NMR (CDCl$_3$, 400 mHz, ppm); 1.7 (br, 4H), 2.6 (br, 4H), 2.8 (sd, 2H), 3.55 (s, 2H), 4.15 (m, 1H), 4.2 (s, 4H), 4.85 (sd, 1H), 5.85 (br, 1H), 6.6 (d, 1H), 6.75 (m, 2H), 7.25 (d, 3H), 7.4 (m, 1H), 7.6 (sd, 2H), 7.9 (sd, 1H), 8.6 (sd, 1H), 8.85 (s, 1H). M/Z for C$_{28}$H$_{31}$N$_3$O$_4$ [M−H]$^-$=474.

Example 2E18

Preparation of Compound 48

2-(4'-chlorobiphenyl-4-yl)-N-((1R,2R)-1-(2,3-dihydrobenzo[β][1,4]dioxin-6-yl)-1-hydroxy-3-(pyrrolidin-1-yl)propan-2-yl)acetamide

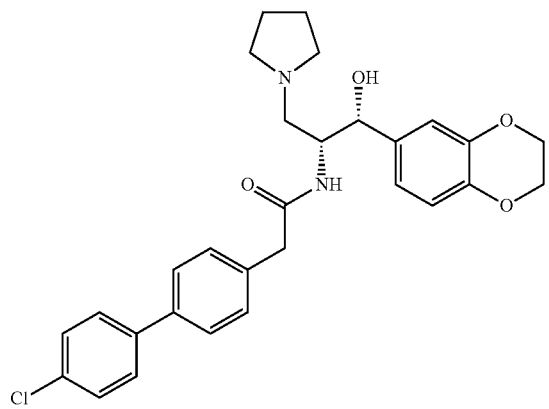 [SMILES: O=C(Cc1ccc(-c2ccc(Cl)cc2)cc1)N[C@H](CN1CCCC1)[C@H](O)c1ccc2c(c1)OCCO2]

$^1$H NMR (CDCl$_3$, 400 mHz, ppm); 1.75 (br, 4H), 2.55 (br, 4H), 2.8 (sd, 2H), 3.55 (s, 2H), 4.15 (m, 1H), 4.2 (s, 4H), 4.85 (sd, 1H), 5.8 (br, 1H), 6.6 (d, 1H), 6.75 (m, 2H), 7.2 (d, 2H), 7.4 (m, 2H), 7.55 (sd, 4H). M/Z for C$_{29}$H$_{31}$ClN$_2$O$_4$ [M−H]$^-$ = 508.

Example 2E19

Preparation of Compound 51

N-((1R,2R)-1-(2,3-dihydrobenzo[β][1,4]dioxin-6-yl)-1-hydroxy-3-(pyrrolidin-1-yl)propan-2-yl)-2-(3-(trifluoromethyl)phenyl)acetamide

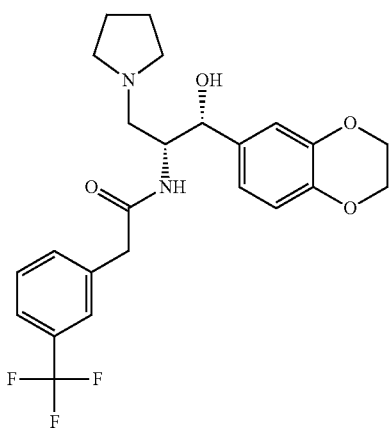 [SMILES: O=C(Cc1cccc(C(F)(F)F)c1)N[C@H](CN1CCCC1)[C@H](O)c1ccc2c(c1)OCCO2]

$^1$H NMR (CDCl$_3$, 400 mHz, ppm); 1.7 (br, 4H), 2.55 (br, 4H), 2.8 (sd, 2H), 3.55 (s, 2H), 4.15 (m, 1H), 4.25 (s, 4H), 4.85 (sd, 1H), 5.8 (br, 1H), 6.6 (d, 1H), 6.75 (m, 2H), 7.35 (d, 1H), 7.45 (m, 2H), 7.55 (sd, 1H). M/Z for C$_{24}$H$_{27}$F$_3$N$_2$O$_4$ [M−H]$^-$=465.

Example 2E20

Preparation of Compound 53

N-((1R,2R)-1-(2,3-dihydrobenzo[β][1,4]dioxin-6-yl)-1-hydroxy-3-(pyrrolidin-1-yl)propan-2-yl)-2-(3-fluorophenyl)acetamide

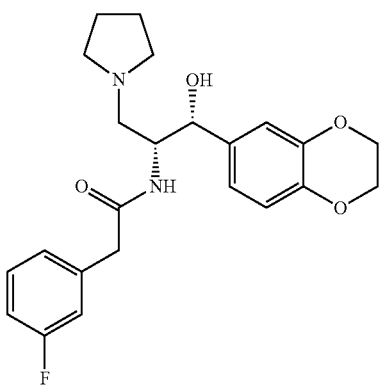 [SMILES: O=C(Cc1cccc(F)c1)N[C@H](CN1CCCC1)[C@H](O)c1ccc2c(c1)OCCO2]

$^1$H NMR (CDCl$_3$, 400 mHz, ppm); 1.7 (br, 4H), 2.55 (br, 4H), 2.8 (sd, 2H), 3.50 (s, 2H), 4.15 (m, 1H), 4.25 (s, 4H), 4.85 (sd, 1H), 5.8 (br, 1H), 6.6 (d, 1H), 6.75 (m, 1H), 6.8 (d, 1H), 6.85 (d, 1H), 6.9 (d, 1H), 7.0 (t, 1H), 7.3 (sq, 1H). M/Z for C$_{23}$H$_{27}$FN$_2$O$_4$ [M−H]$^-$=415.

Example 2E21

Preparation of Compound 54

N-((1R,2R)-1-(2,3-dihydrobenzo[β][1,4]dioxin-6-yl)-1-hydroxy-3-(pyrrolidin-1-yl)propan-2-yl)-3-(3-methoxyphenoxy)propanamide

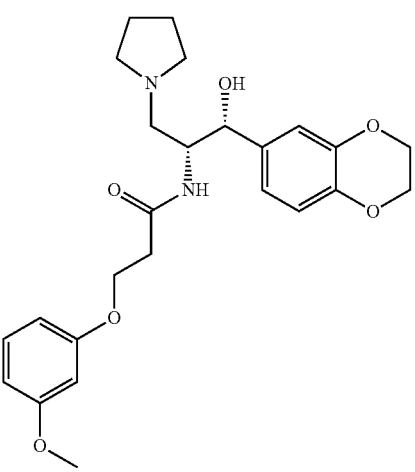 [SMILES: COc1cccc(OCCC(=O)N[C@H](CN2CCCC2)[C@H](O)c2ccc3c(c2)OCCO3)c1]

$^1$H NMR (CDCl$_3$, 400 mHz, ppm); 1.7 (br, 4H), 2.65 (br, 6H), 2.85 (m, 2H), 3.80 (s, 3H), 4.2 (m, 7H), 4.95 (sd, 1H), 6.45 (m, 4H), 6.75 (s, 2H), 6.85 (s, 1H), 7.2 (t, 1H). M/Z for C$_{25}$H$_{32}$N$_2$O$_6$ [M−H]$^-$=457.

Example 2E22

Preparation of Compound 55

3-(2,5-dichlorophenoxy)-N-((1R,2R)-1-(2,3-dihydrobenzo[β][1,4]dioxin-6-yl)-1-hydroxy-3-(pyrrolidin-1-yl)propan-2-yl)propanamide

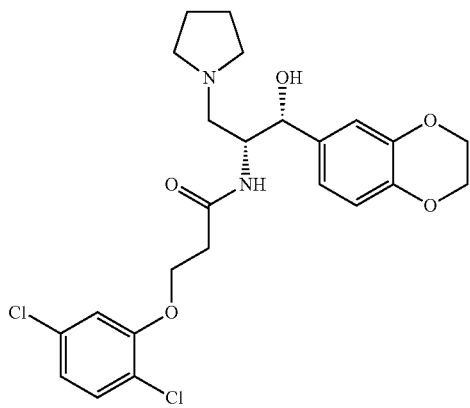 [SMILES: O=C(CCOc1cc(Cl)ccc1Cl)N[C@H](CN1CCCC1)[C@H](O)c1ccc2c(c1)OCCO2]

¹H NMR (CDCl₃, 400 mHz, ppm); 1.8 (br, 4H), 2.65 (br, 6H), 2.8 (m, 2H), 4.1 (m, 1H), 4.25 (m, 6H), 4.95 (sd, 1H), 6.3 (br, 1H), 6.75 (s, 2H), 6.8 (s, 1H), 6.9 (m, 2H), 7.25 (m, 1H). M/Z for $C_{24}H_{28}Cl_2N_2O_5$ [M−H]⁻=496.

Example 2E23

Preparation of Compound 57

3-(4-chlorophenoxy)-N-((1R,2R)-1-(2,3-dihydrobenzo[β][1,4]dioxin-6-yl)-1-hydroxy-3-(pyrrolidin-1-yl)propan-2-yl)propanamide

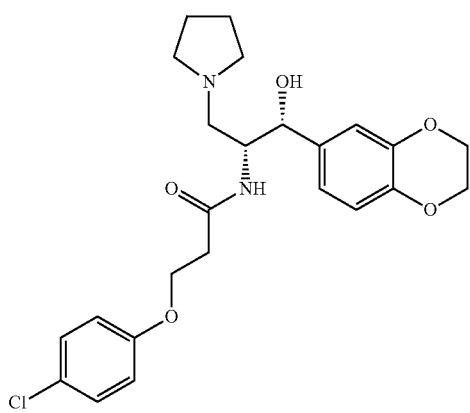 [SMILES: O=C(CCOc1ccc(Cl)cc1)N[C@H](CN1CCCC1)[C@H](O)c1ccc2c(c1)OCCO2]

¹H NMR (CDCl₃, 400 mHz, ppm); 1.75 (br, 4H), 2.65 (br, 6H), 2.8 (m, 2H), 4.2 (m, 7H), 4.95 (sd, 1H), 6.3 (br, 1H), 6.8 (m, 5H), 7.2 (m, 2H). M/Z for $C_{24}H_{29}ClN_2O_5$ [M−H]⁻=461.

Example 2E24

Preparation of Compound 58

N-((1R,2R)-1-(2,3-dihydrobenzo[β][1,4]dioxin-6-yl)-1-hydroxy-3-(pyrrolidin-1-yl)propan-2-yl)-3-(4-fluorophenoxy)propanamide

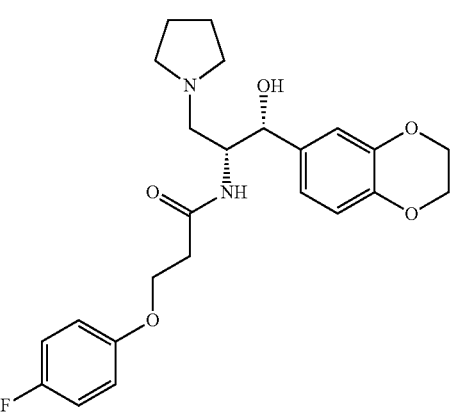 [SMILES: O=C(CCOc1ccc(F)cc1)N[C@H](CN1CCCC1)[C@H](O)c1ccc2c(c1)OCCO2]

¹H NMR (CDCl₃, 400 mHz, ppm); 1.75 (br, 4H), 2.65 (br, 6H), 2.8 (m, 2H), 4.2 (m, 7H), 4.95 (sd, 1H), 6.4 (br, 1H), 6.8 (m, 5H), 7.0 (m, 2H). M/Z for $C_{24}H_{29}FN_2O_5$ [M−H]⁻=445.

Example 2E25

Preparation of Compound 59

N-((1R,2R)-1-(2,3-dihydrobenzo[β][1,4]dioxin-6-yl)-1-hydroxy-3-(pyrrolidin-1-yl)propan-2-yl)-3-(p-tolyloxy)propanamide

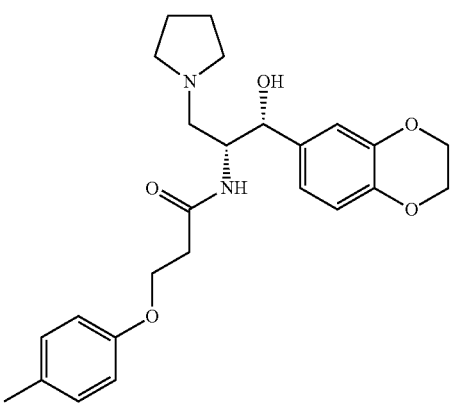 [SMILES: Cc1ccc(OCCC(=O)N[C@H](CN2CCCC2)[C@H](O)c2ccc3c(c2)OCCO3)cc1]

¹H NMR (CDCl₃, 400 mHz, ppm); 1.75 (br, 4H), 2.3 (s, 3H), 2.65 (br, 6H), 2.8 (m, 2H), 4.2 (m, 7H), 4.95 (sd, 1H), 6.45 (br, 1H), 6.75 (m, 4H), 6.85 (s, 1H), 7.1 (m, 2H). M/Z for $C_{25}H_{32}N_2O_5$ [M−H]⁻=441.

Example 2E26

Preparation of Compound 60

N-((1R,2R)-1-(2,3-dihydrobenzo[β][1,4]dioxin-6-yl)-1-hydroxy-3-(pyrrolidin-1-yl)propan-2-yl)-3-(2-fluorophenoxy)propanamide

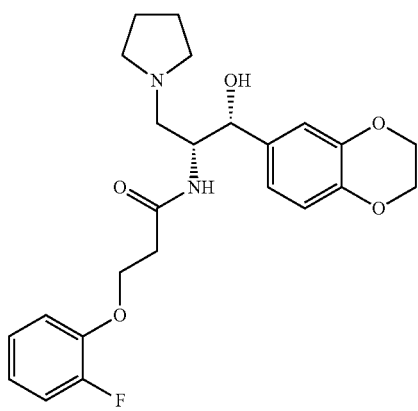 [SMILES: O=C(CCOc1ccccc1F)N[C@H](CN1CCCC1)[C@H](O)c1ccc2c(c1)OCCO2]

$^1$H NMR (CDCl$_3$, 400 mHz, ppm); 1.75 (br, 4H), 2.65 (br, 6H), 2.75 (m, 2H), 4.2 (m, 7H), 4.95 (sd, 1H), 6.35 (br, 1H), 6.7 (s, 2H), 6.85 (s, 1H), 6.95 (m, 2H), 7.05 (m, 2H). M/Z for C$_{24}$H$_{29}$FN$_2$O$_5$ [M−H]$^−$=445.

Example 2E27

Preparation of Compound 61

N-((1R,2R)-1-(2,3-dihydrobenzo[β][1,4]dioxin-6-yl)-1-hydroxy-3-(pyrrolidin-1-yl)propan-2-yl)-3-(4-methoxyphenoxy)propanamide

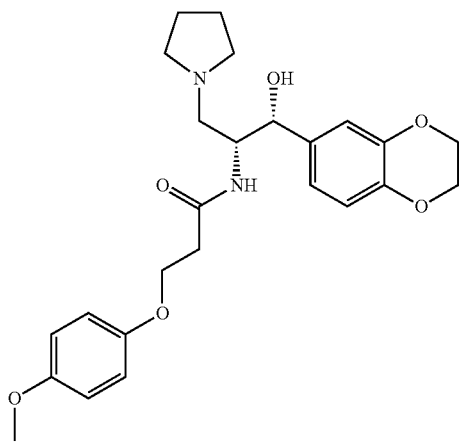 [SMILES: COc1ccc(OCCC(=O)N[C@H](CN2CCCC2)[C@H](O)c2ccc3c(c2)OCCO3)cc1]

$^1$H NMR (CDCl$_3$, 400 mHz, ppm); 1.75 (br, 4H), 2.65 (br, 6H), 2.75 (m, 2H), 3.8 (s, 3H), 4.1 (m, 2H), 4.2 (br, 5H), 4.95 (sd, 1H), 6.45 (br, 1H), 6.8 (m, 7H). M/Z for C$_{25}$H$_{32}$N$_2$O$_6$ [M−H]$^−$=457.

Example 2E28

Preparation of Compound 188

N-((1R,2R)-1-(2,3-dihydrobenzo[b][1,4]dioxin-6-yl)-1-hydroxy-3-(pyrrolidin-1-yl)propan-2-yl)-3-(4-ethylphenoxy)propanamide (2R,3R)-2,3-dihydroxysuccinate

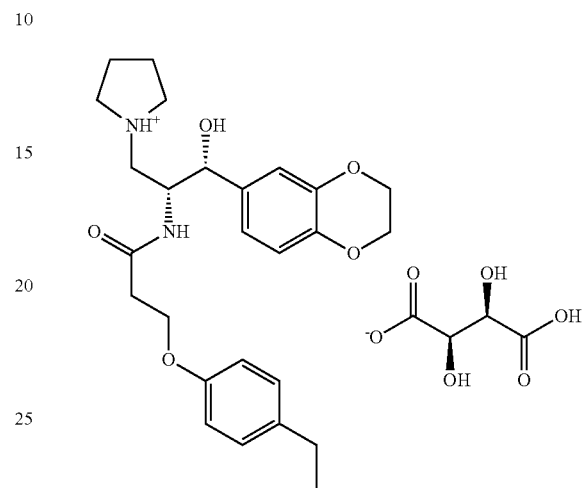

$^1$H NMR (D$_2$O, 400 mHz, ppm); 0.93 (t, 3H), 1.75 (br, 2H), 1.86 (br, 2H), 2.35 (q, 2H), 2.4 (br, 2H), 2.9 (br, 2H), 3.25 (m, 2H), 3.4 (br, 2H), 3.9 (br, 6H), 4.3 (br, 3H), 4.6 (br, 1H), 6.6 (m, 5H), 7.0 (d, 2H). M/Z for C$_{26}$H$_{34}$N$_2$O$_5$·C$_4$H$_6$O$_6$ [M−H]$^−$= 454.

Example 2E29

Preparation of Compound 189

N-((1R,2R)-1-(2,3-dihydrobenzo[b][1,4]dioxin-6-yl)-1-hydroxy-3-(pyrrolidin-1-yl)propan-2-yl)-3-(4-propionylphenoxy)propanamide (2R,3R)-2,3-dihydroxysuccinate

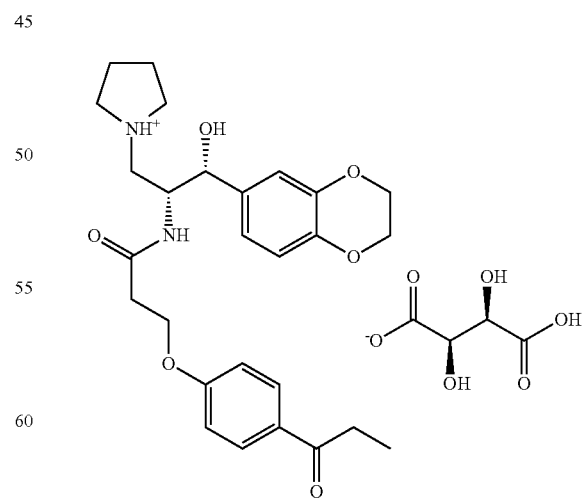

$^1$H NMR (D$_2$O, 400 mHz, ppm); 0.93 (t, 3H), 1.75 (br, 2H), 1.86 (br, 2H), 2.45 (br, 2H), 2.8 (q, 2H), 2.9 (br, 2H), 3.25 (m, 2H), 3.4 (br, 2H), 3.9 (br, 6H), 4.3 (br, 3H), 4.6 (br, 1H), 6.5

(d, 1H), 6.5 (d, 2H), 6.7 (d, 2H), 7.7 (d, 2H). M/Z for $C_{27}H_{34}N_2O_6 \cdot C_4H_6O_6$ [M–H]$^-$=483.

Example 2E30

Preparation of Compound 193

N-((1R,2R)-1-(2,3-dihydrobenzo[b][1,4]dioxin-6-yl)-1-hydroxy-3-(pyrrolidin-1-yl)propan-2-yl)-3-(4-(3-oxobutyl)phenoxy)propanamide (2R,3R)-2,3-dihydroxysuccinate

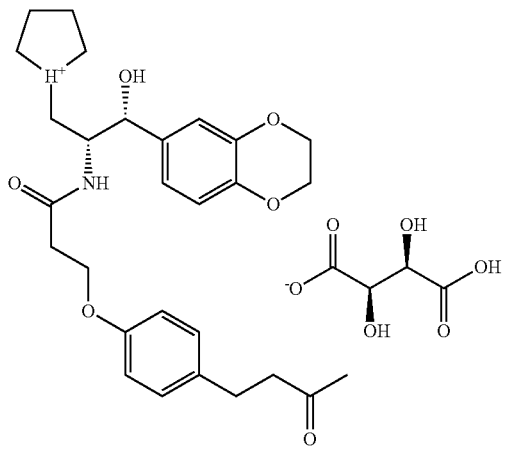

$^1$H NMR (D$_2$O, 400 mHz, ppm); 1.75 (br, 2H), 1.86 (br, 2H), 1.94 (s, 3H), 2.45 (br, 2H), 2.6 (m, 4H), 2.9 (br, 2H), 3.25 (m, 2H), 3.4 (br, 2H), 3.9 (br, 6H), 4.3 (br, 3H), 4.6 (br, 1H), 6.6 (m, 5H), 7.0 (d, 2H). M/Z for $C_{28}H_{36}N_2O_6 \cdot C_4H_6O_6$ [M–H]$^-$=497.

Example 2E31

Preparation of Compound 202

N-((1R,R)-1-(2,3-dihydrobenzo[β][1,4]dioxin-6-yl)-1-hydroxy-3-(pyrrolidin-1-yl)propan-2-yl)-3-(4-(2-methoxyethyl)phenoxy)propanamide (2R,R)-2,3-dihydroxysuccinate

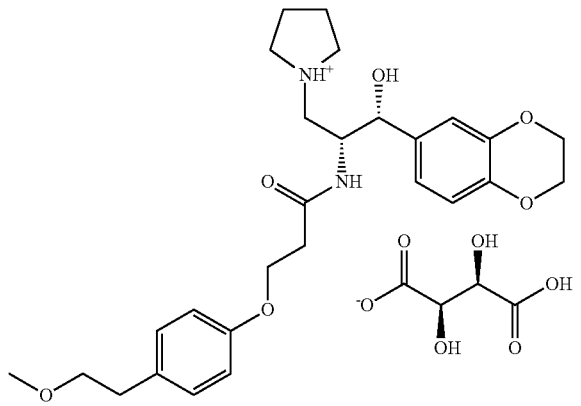

$^1$H NMR (D$_2$O, 400 mHz, ppm); 1.75 (br, 2H), 1.86 (br, 2H), 2.45 (br, 2H), 2.62 (t, 2H), 2.9 (br, 2H), 3.1 (s, 3H), 3.25 (m, 2H), 3.4 (br, 4H), 3.9 (br, 6H), 4.3 (br, 3H), 4.6 (br, 1H), 6.6 (m, 5H), 7.0 (d, 2H). M/Z for $C_{27}H_{36}N_2O_6 \cdot C_4H_6O_6$ [M–H]$^-$=485.

Example 2E32

Preparation of Compound 63

N-((1R,2R)-1-(2,3-dihydrobenzo[β][1,4]dioxin-6-yl)-1-hydroxy-3-(pyrrolidin-1-yl)propan-2-yl)-2-(3'-methoxybiphenyl-4-yl)acetamide

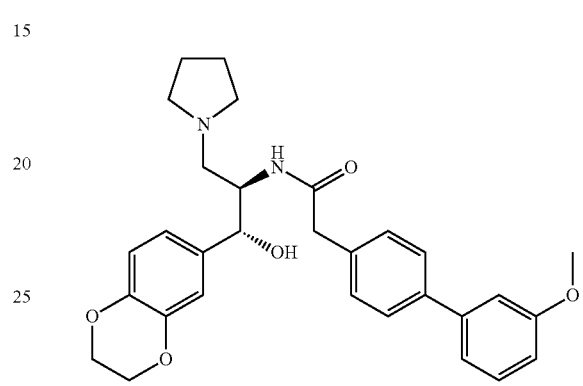

$^1$H NMR (CDCl$_3$, 400 mHz, ppm); 1.7 (br, 4H), 2.5 (br, 4H), 2.75 (m, 2H), 3.5 (br, 2H), 3.9 (sd, 3H), 4.2 (m, 5H), 4.95 (sd, 1H), 5.9 (br, 1H), 6.5-7.6 (m, 11H). M/Z for $C_{30}H_{34}N_2O_5$ [M–H]$^-$=503.

Example 2E33

Preparation of Compound 127

N-((1R,2R)-1-(2,3-dihydrobenzo[b][1,4]dioxin-6-yl)-1-hydroxy-3-(pyrrolidin-1-yl)propan-2-yl)-4-(4-ethoxyphenyl)-4-oxobutanamide

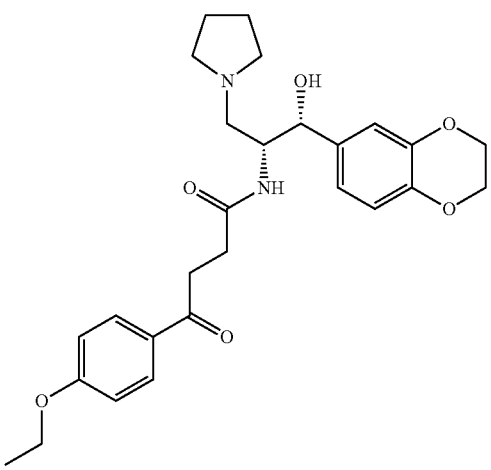 [SMILES: CCOc1ccc(C(=O)CCC(=O)N[C@H](CN2CCCC2)[C@H](O)c2ccc3c(c2)OCCO3)cc1]

$^1$H NMR (CDCl$_3$, 400 mHz, ppm); 1.4 (t, 3H), 1.8 (br, 4H), 2.7 (br, 6H), 3.2 (m, 2H), 4.05 (q, 2H), 4.2 (m, 2H), 4.25 (m, 5H), 4.95 (sd, 1H), 6.05 (br, 1H), 6.9 (m, 5H), 7.95 (d, 2H). M/Z for $C_{27}H_{34}N_2O_6$ [M−H]⁻=483.

Example 2E34

Preparation of Compound 154

N-((1R,2R)-1-(2,3-dihydrobenzo[b][1,4]dioxin-6-yl)-1-hydroxy-3-pyrrolidin-1-yl)propan-2-yl)-4-(4-methoxyphenyl)-4-oxobutanamide

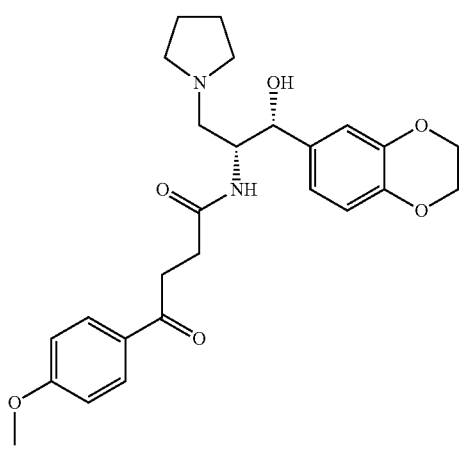 [SMILES: COc1ccc(C(=O)CCC(=O)N[C@H](CN2CCCC2)[C@H](O)c2ccc3c(c2)OCCO3)cc1]

¹H NMR (CDCl₃, 400 mHz, ppm); 1.8 (br, 4H), 2.7 (br, 6H), 3.2 (m, 1H), 3.45 (s, 3H), 3.9 (s, 3H), 4.2 (m, 5H), 4.95 (sd, 1H), 6.05 (br, 1H), 6.9 (m, 5H), 7.95 (d, 2H). M/Z for $C_{26}H_{32}N_2O_6$ [M−H]⁻=469.

Example 2E35

Preparation of Compound 181

N-((1R,2R)-1-(2,3-dihydrobenzo[b][1,4]dioxin-6-yl)-1-hydroxy-3-(pyrrolidin-1-yl)propan-2-yl)-6-(4-isopropoxyphenyl)-6-oxohexanamide

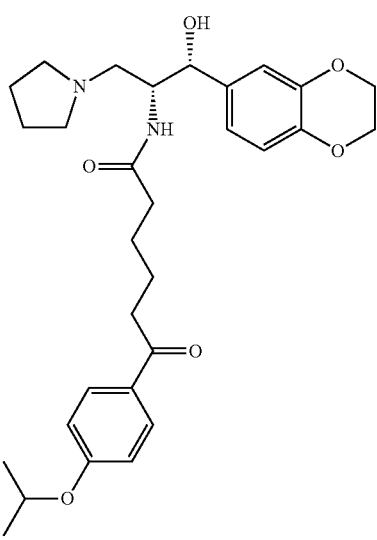 [SMILES: CC(C)Oc1ccc(C(=O)CCCCC(=O)N[C@H](CN2CCCC2)[C@H](O)c2ccc3c(c2)OCCO3)cc1]

¹H NMR (CDCl₃, 400 mHz, ppm); 1.4 (d, 6H), 1.8 (br, 8H), 2.15 (br, 2H), 2.8 (br, 10H), 4.25 (m, 5H), 4.65 (m, 1H), 4.95 (sd, 1H), 6.05 (br, 1H), 6.9 (m, 5H), 7.95 (d, 2H). M/Z for $C_{30}H_{40}N_2O_6$ [M−H]⁻=525.

Example 2E36

Preparation of Compound 191

N-((1R,2R)-1-(2,3-dihydrobenzo[β][1,4]dioxin-6-yl)-1-hydroxy-3-(pyrrolidin-1-yl)propan-2-yl)-5-(4-methoxyphenyl)-5-oxopentanamide (2R,3R)-2,3-dihydroxysuccinate

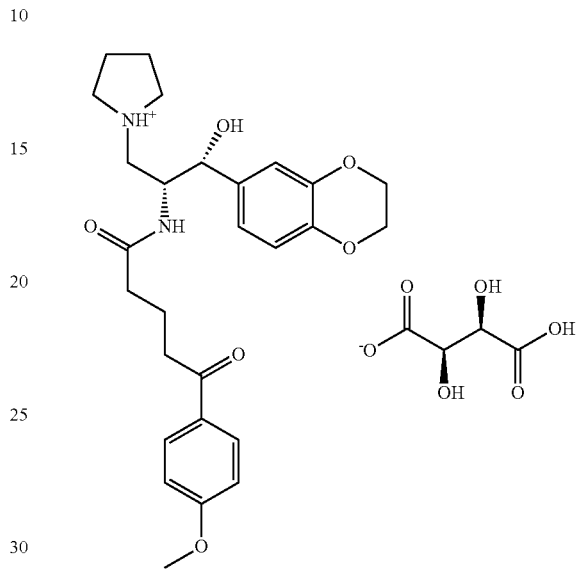

¹H NMR (D₂O, 400 mHz, ppm); 1.40 (br, 1H), 1.53 (br, 1H), 1.75 (br, 2H), 1.91 (br, 2H), 1.98 (m, 1H), 2.15 (m, 1H), 2.45 (m, 2H), 2.95 (m, 2H), 3.35 (dd, 2H), 3.4 (m, 2H), 3.68 (br, 5H), 3.77 (br, 2H), 4.3 (br, 3H), 4.68 (br, 1H), 6.47 (d, 1H), 6.65 (d, 2H), 6.85 (d, 2H), 7.63 (d, 2H). M/Z for $C_{27}H_{34}N_2O_6 \cdot C_4H_6O_6$ [M−H]=483.

Example 2E37

Preparation of Compound 265

N-((1R,2R)-1-(benzo[δ][1,3]dioxol-5-yl)-1-hydroxy-3-(pyrrolidin-1-yl)propan-2-yl)-5-(4-isopropoxyphenyl)-5-oxopentanamide (2S,3S)-2,3-dihydroxysuccinate

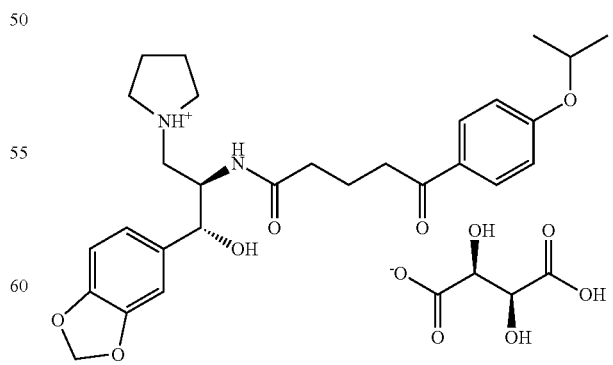

¹H NMR (400 MHz, CD₃OD) δ 1.30 (sd, 6H), 1.70-1.85 (m, 2H), 2.04 (br, 4H), 2.09-2.26 (m, 2H), 2.64-2.82 (m, 2H), 3.31-3.48 (m, 5H), 4.37 (s, 2H), 4.43 (br, 1H), 4.68 (m, 1H), 4.71 (sd, 1H), 5.76 (s, 2H), 6.66 (d, 1H), 6.82-6.95 (m, 4H), 7.84 (d, 2H); MS for $C_{28}H_{36}N_2O_6 \cdot C_4H_6O_6$: [M–H]⁻ 645.

Example 2E38

Preparation of Compound 267

N-((1R,2R)-1-(benzo[δ][1,3]-dioxol-5-yl)-1-hydroxy-3-(pyrrolidin-1-yl)propan-2-yl)-6-(4-methoxyphenyl)-6-oxohexanamide (2S,3S)-2,3-dihydroxysuccinate

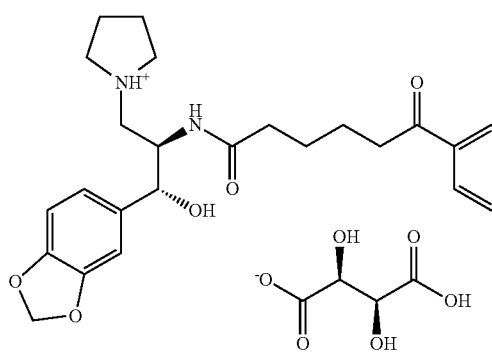

¹H NMR (400 MHz, CD₃OD) δ 1.49 (br, 4H), 2.03 (br, 4H), 2.89 (t, 2H), 3.33-3.46 (m, 6H), 3.84 (s, 3H), 4.37 (s, 2H), 4.43 (d, 1H), 4.76 (br, 1H), 5.81 (s, 2H), 6.68 (d, 1H), 6.81 (d, 1H), 6.88 (s, 1H), 6.96 (d, 2H), 7.92 (d, 2H); MS for $C_{27}H_{34}N_2O_6 \cdot C_4H_6O_6$: [M–H]⁻ 633.

Example 2E39

Preparation of Compound 268

N-((1R,2R)-1-(benzo[δ][1,3]dioxol-5-yl)-1-hydroxy-3-(pyrrolidin-1-yl)propan-2-yl)-7-(4-isopropoxyphenyl)-7-oxoheptanamide (2S,3S)-2,3-dihydroxysuccinate

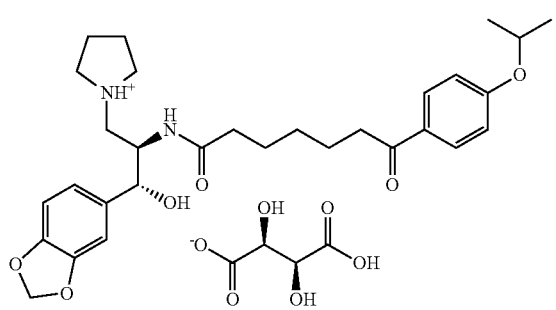

¹H NMR (400 MHz, CD₃OD) δ 1.15-1.18 (m, 2H), 1.30 (d, 6H), 1.40-1.45 (m, 2H), 1.57-1.65 (m, 2H), 2.03 (br, 4H), 2.12-2.17 (m, 2H), 2.88 (t, 2H), 3.33-3.48 (m, 5H), 4.38 (s, 2H), 4.42 (d, 1H), 4.67 (m, 1H), 4.78 (d, 2H), 5.83 (d, 2H), 6.71 (d, 1H), 6.82 (d, 1H), 6.89 (s, 1H), 6.92 (d, 2H), 7.90 (d, 2H); MS for $C_{30}H_{40}N_2O_6 \cdot C_4H_6O_6$: [M–H]⁻ 675.

Example 2E40

Preparation of Compound 197

N-((1R,2R)-1-(2,3-dihydrobenzo[β][1,4]dioxin-6-yl)-1-hydroxy-3-(pyrrolidin-1-yl)propan-2-yl)-4-(4-methoxyphenoxy)butanamide (2S,3S)-2,3-dihydroxysuccinate

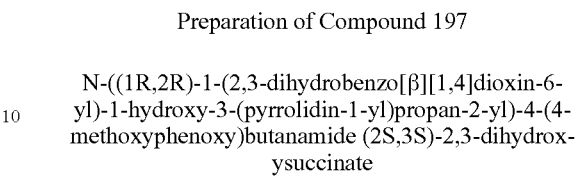
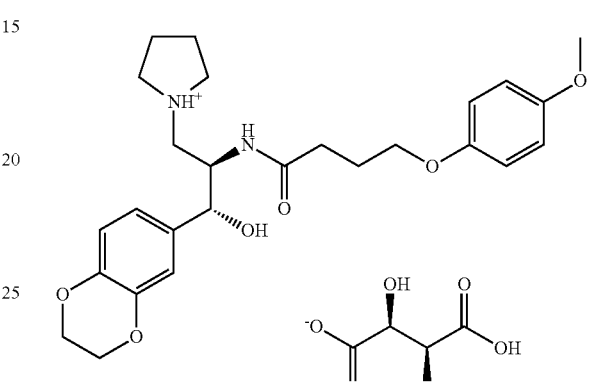

¹H NMR (400 MHz, CD₃OD) δ 1.78-1.91 (m, 2H), 2.00 (br, 4H), 2.32 (t, 2H), 3.33-3.47 (m, 6H), 3.69 (s, 3H), 3.72 (t, 2H), 4.11 (br, 4H), 4.37 (s, 2H), 4.41 (d, 1H), 4.72 (d, 1H), 6.69-6.86 (m, 7H); MS for $C_{26}H_{34}N_2O_6 \cdot C_4H_6O_6$: [M–H]⁻ 621.

Example 2E41

Preparation of Compound 187

N-((1R,2R)-1-(2,3-dihydrobenzo[β][1,4]dioxin-6-yl)-1-hydroxy-3-(pyrrolidin-1-yl)propan-2-yl)-3-(4-(3-methylbutanoyl)phenoxy)propanamide (2S,3S)-2,3-dihydroxysuccinate

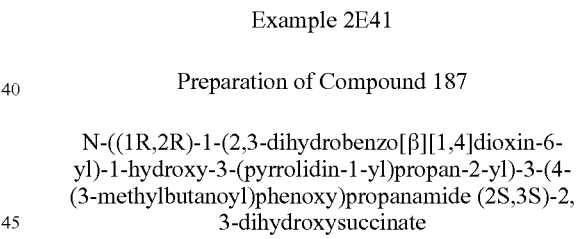
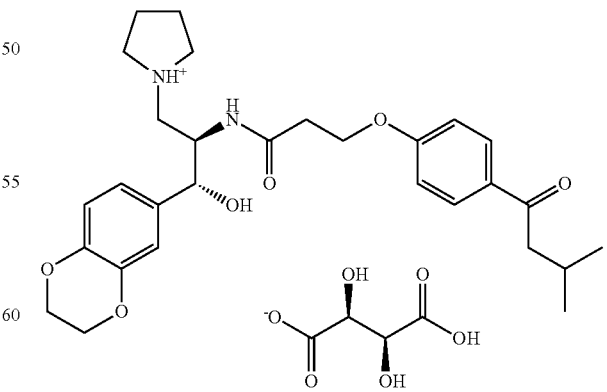

¹H NMR (400 MHz, CD₃OD) δ 0.95 (d, 6H), 2.00 (br, 4H), 2.17 (m, 2H), 2.66 (t, 2H), 2.78 (d, 2H), 3.34-3.44 (m, 5H), 4.12-4.17 (m, 6H), 4.40 (s, 2H), 4.45 (d, 1H), 4.73 (sd, 1H), 6.67 (d, 1H), 6.79 (d, 1H), 6.86 (s, 1H), 6.93 (d, 2H), 7.91 (d, 2H); MS for $C_{29}H_{38}N_2O_6 \cdot C_4H_6O_6$: [M–H]$^-$ 661.

Example 2E42

Preparation of Compound 83

2-(4-chlorophenoxy)-N-((1R,2R)-1-(2,3-dihydrobenzo[β][1,4]dioxin-6-yl)-1-hydroxy-3-(pyrrolidin-1-yl)propan-2-yl)acetamide

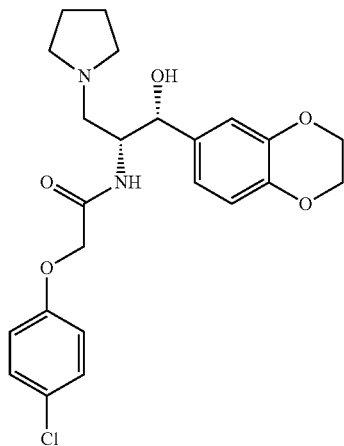 [SMILES: O=C(COc1ccc(Cl)cc1)N[C@H](CN1CCCC1)[C@H](O)c1ccc2c(c1)OCCO2]

$^1$H NMR (400 MHz, CDCl$_3$) δ 1.76 (br, 4H), 2.63 (br, 4H), 2.78 (dd, 1H), 2.89 (dd, 1H), 4.24 (s, 4H), 4.27 (br, 1H), 4.36 (q, 2H), 4.94 (d, 1H), 6.71 (d, 1H), 6.77-6.82 (m, 4H), 6.86 (d, 1H), 7.24 (s, 1H); MS for $C_{23}H_{27}ClN_2O_5$: [M–H]$^-$ 447.

Example 2E43

Preparation of Compound 87

2-(3,4-dichlorophenoxy)-N-((1R,2R)-1-(2,3-dihydrobenzo[β][1,4]dioxin-6-yl)-1-hydroxy-3-(pyrrolidin-1-yl)propan-2-yl)acetamide

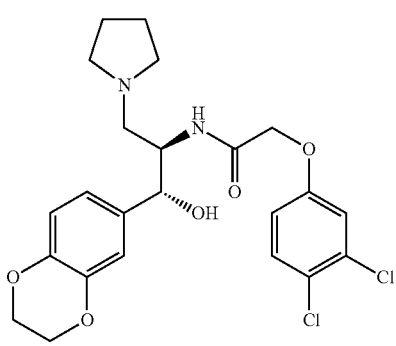 [SMILES: O=C(COc1ccc(Cl)c(Cl)c1)N[C@H](CN1CCCC1)[C@H](O)c1ccc2c(c1)OCCO2]

$^1$H NMR (400 MHz, CDCl$_3$) δ 1.78 (br, 4H), 2.67 (br, 4H), 2.79 (dd, 1H), 2.92 (dd, 1H), 4.25 (br, s, 5H), 4.35 (q, 2H), 4.95 (d, 1H), 6.71-6.84 (m, 5H), 7.01 (d, 1H), 7.34 (d, 1H); MS for $C_{23}H_{26}Cl_2N_2O_5$: [M–H]$^-$ 482.

Example 2E44

Preparation of Compound 86

N-((1R,2R)-1-(2,3-dihydrobenzo[b][1,4]dioxin-6-yl)-1-hydroxy-3-(pyrrolidin-1-yl)propan-2-yl)-2-(3-phenoxyphenyl)acetamide

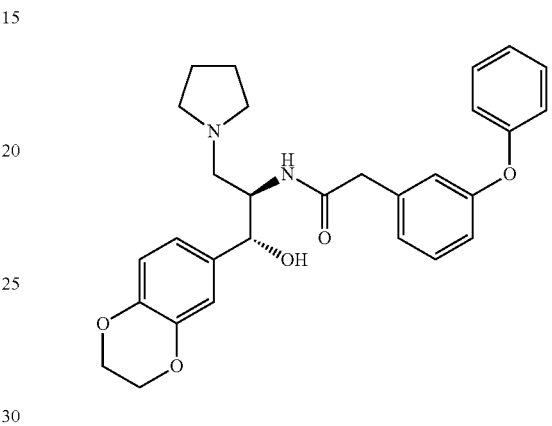

$^1$H NMR (400 MHz, CDCl$_3$) δ 1.72 (br, 4H), 2.57 (br, 4H), 2.75-2.80 (m, 2H), 3.45 (s, 2H), 4.11-4.13 (m, 1H), 4.23 (s, 4H), 4.84 (d, 1H), 5.86 (d, 1H), 6.55 (dd, 1H), 6.71 (d, 1H), 6.74 (d, 1H), 6.80 (br, 1H), 6.85 (dd, 1H), 6.92 (dd, 1H), 6.98 (d, 1H), 7.14 (t, 1H), 7.28-7.36 (m, 2H); MS for $C_{29}H_{32}N_2O_5$: [M–H]$^-$ 489.

Example 2E45

Preparation of Compound 280

2-(3,4-difluorophenyl)-N-((1R,2R)-1-(2,3-dihydrobenzo[β][1,4]dioxin-6-yl)-1-hydroxy-3-(pyrrolidin-1-yl)propan-2-yl)acetamide

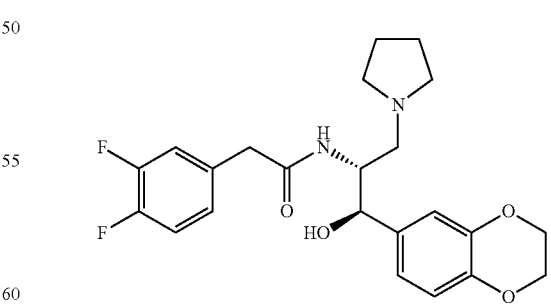

$^1$H NMR (400 MHz, CDCl$_3$) δ 1.80 (br, 4H, 2.68 (br, 4H), 2.84 (d, 2H), 3.45 (s, 2H), 4.17 (m, 1H), 4.25 (s, 4H), 4.88 (d, 1H), 5.88 (d, 1H), 6.65 (d, 1H), 6.79 (d, 1H), 6.95 (m, 1H), 6.95 (t, 1H), 7.13 (q, 1H); MS for $C_{23}H_{26}F_2N_2O_4$: [M–H]$^-$ 434.

Example 2E46

Preparation of Compound 103

N-((1R,2R)-1-(2,3-dihydrobenzo[β][1,4]dioxin-6-yl)-1-hydroxy-3-(pyrrolidin-1-yl)propan-2-yl)-2-(4-(trifluoromethoxy)phenyl)acetamide

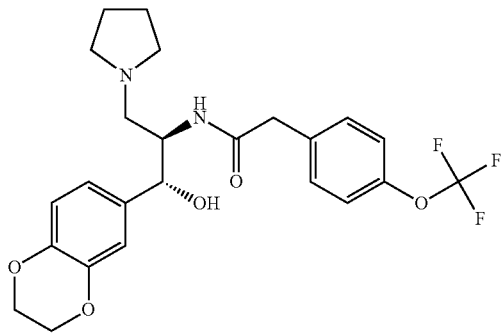 [SMILES: O=C(Cc1ccc(OC(F)(F)F)cc1)N[C@H](CN1CCCC1)[C@H](O)c1ccc2c(c1)OCCO2]

$^1$H NMR (400 MHz, CDCl$_3$) δ 1.65 (br, 4H), 2.48 (br, 4H), 2.69 (d, 2H), 3.40 (s, 2H), 4.08 (m, 1H), 4.17 (s, 4H), 4.80 (s, 1H), 5.84 (t, 1H), 6.55 (d, 1H), 6.66 (s, 1H), 6.70 (d, 1H), 7.10 (t, 3H); MS for C$_{24}$H$_{27}$F$_3$N$_2$O$_5$: [M–H]$^-$ 481.

Example 2E47

Preparation of Compound 90

N-((1R,2R)-1-(2,3-dihydrobenzo[β][1,4]dioxin-6-yl)-1-hydroxy-3-(pyrrolidin-1-yl)propan-2-yl)-5-(thiophen-2-yl)isoxazole-3-carboxamide

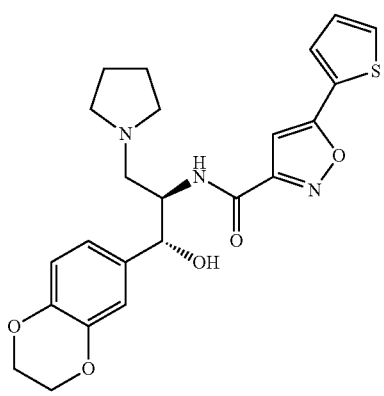 [SMILES: O=C(N[C@H](CN1CCCC1)[C@H](O)c1ccc2c(c1)OCCO2)c1cc(-c2cccs2)on1]

$^1$H NMR (400 MHz, CDCl$_3$) δ 1.82 (br, 4H), 2.73-2.81 (m, 4H), 2.89-2.93 (m, 1H), 3.02-3.07 (m, 1H), 4.23 (s, 4H), 4.41 (br, 1H), 5.07 (s, 1H), 5.30 (d, 1H), 6.74 (s, 1H), 6.83 (t, 2H), 6.90 (s, 1H), 7.12-7.14 (m, 2H), 7.47 (d, 1H), 7.52 (d, 1H); MS for C$_{23}$H$_{25}$N$_3$O$_5$S: [M–H]$^-$ 456.

Example 2E48

Preparation of Compound 92

3-(3-chloro-4-methoxyphenyl)-N-((1R,2R)-1-(2,3-dihydrobenzo[β][1,4]dioxin-6-yl)-1-hydroxy-3-(pyrrolidin-1-yl)propan-2-yl)propanamide

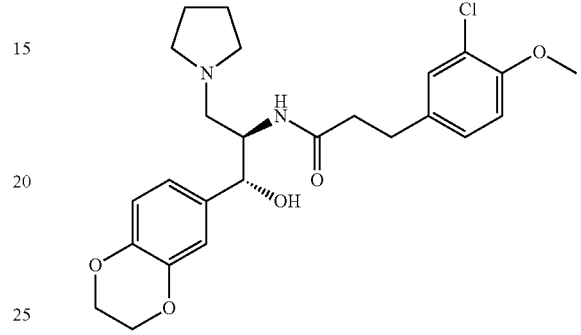

$^1$H NMR (400 MHz, CDCl$_3$) δ 1.77 (br, 4H), 2.38 (t, 2H), 2.60 (br, 4H), 2.8 (m, 4H), 3.86 (s, 3H), 4.20 (br, 1H), 4.24 (s, 4H), 4.87 (s, 1H), 5.80 (d, 1H), 6.66 (d, 1H), 6.8 (m, 3H), 7.00 (d, 1H), 7.18 (s, 1H); MS for C$_{25}$H$_{31}$ClN$_2$O$_5$: [M–H]$^-$ 475.

Example 2E49

Preparation of Compound 96

N-((1R,2R)-1-(2,3-dihydrobenzo[β][1,4]dioxin-6-yl)-1-hydroxy-3-(pyrrolidin-1-yl)propan-2-yl)-3-(4-(trifluoromethyl)phenyl)propanamide

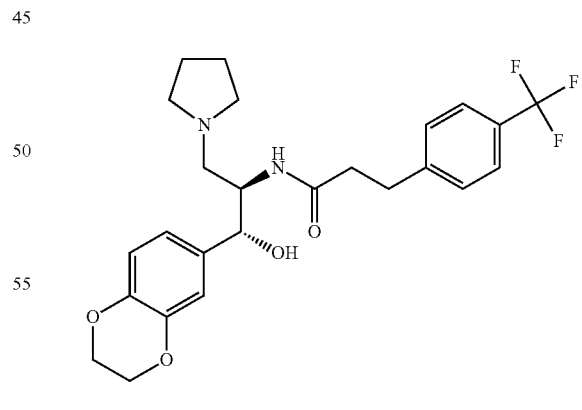

$^1$H NMR (400 MHz, CDCl$_3$) δ 1.73 (br, 4H), 2.4 (m, 2H), 2.53 (m, 4H), 2.7 (m, 2H), 2.90-2.97 (m, 2H), 4.17 (br, 1H), 4.23 (s, 4H), 4.89 (s, 1H), 5.83 (br, 1H), 6.68 (d, 1H), 6.79 (d, 2H), 7.24 (d, 2H), 7.50 (d, 2H); MS for C$_{25}$H$_{29}$F$_3$N$_2$O$_5$: [M–H]$^-$ 479.

Example 2E50

Preparation of Compound 101

4-(benzo[d]thiazol-2-yl)-N-((1R,2R)-1-(2,3-dihydrobenzo[β][1,4]dioxin-6-yl)-1-hydroxy-3-(pyrrolidin-1-yl)propan-2-yl)butanamide

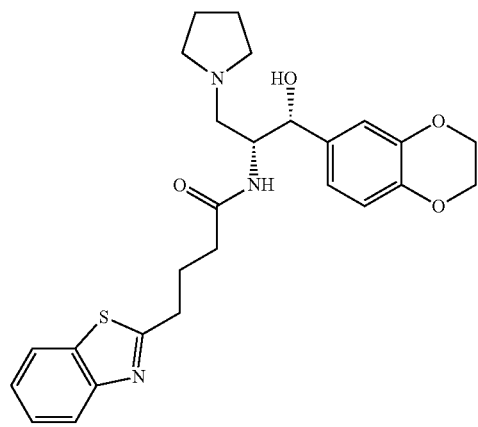 [SMILES: O=C(CCCc1nc2ccccc2s1)N[C@H](CN1CCCC1)[C@H](O)c1ccc2c(c1)OCCO2]

$^1$H NMR (400 MHz, CDCl$_3$) δ 1.77 (br, 4H), 2.10-2.15 (m, 2H), 2.24-2.27 (m, 2H), 2.64-2.67 (m, 4H), 2.79-2.83 (m, 2H), 3.02 (t, 2H), 4.18 (s, 4H), 4.26 (br, 1H), 4.92 (d, 1H), 6.12 (br, 1H), 6.75-6.81 (m, 2H), 6.86 (s, 1H), 7.37 (t, 1H), 7.45 (t, 1H), 7.85 (d, 1H), 7.92 (d, 1H); MS for C$_{26}$H$_{31}$N$_3$O$_4$S: [M−H]$^-$ 482.

Example 2E51

Preparation of Compound 102

N-((1R,2R)-1-(2,3-dihydrobenzo[β][1,4]dioxin-6-yl)-1-hydroxy-3-(pyrrolidin-1-yl)propan-2-yl)-6-(2,3-dihydrobenzo[β][1,4]dioxine-6-sulfonamido)hexanamide

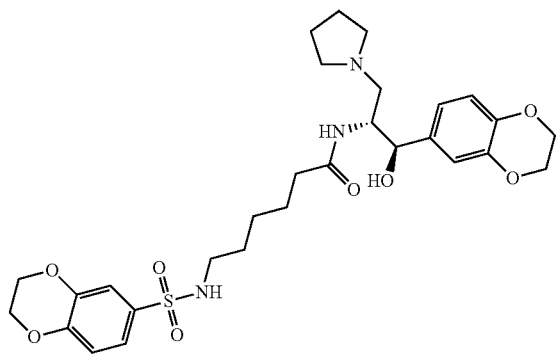 [SMILES: O=C(CCCCCNS(=O)(=O)c1ccc2c(c1)OCCO2)N[C@H](CN1CCCC1)[C@H](O)c1ccc2c(c1)OCCO2]

$^1$H NMR (400 MHz, CDCl$_3$) δ 1.15-1.20 (m, 2H), 1.38-1.50 (m, 4H), 1.77 (br, 4H), 2.08 (q, 2H), 2.63-2.66 (m, 4H), 2.79 (d, 2H), 2.87 (t, 2H), 4.2 (m, 9H), 4.91 (br, 1H), 5.93 (br, 1H), 6.77 (q, 2H), 6.84 (s, 1H), 6.93 (d, 1H), 7.31 (d, 1H), 7.37 (s, 1H); MS for C$_{29}$H$_{39}$N$_3$O$_8$S: [M−H]$^-$ 590.

Example 2E52

Preparation of Compound 104

N-(5-((1R,2R)-1-(2,3-dihydrobenzo[β][1,4]dioxin-6-yl)-1-hydroxy-3-(pyrrolidin-1-yl)propan-2-ylamino)-5-oxopentyl)benzamide

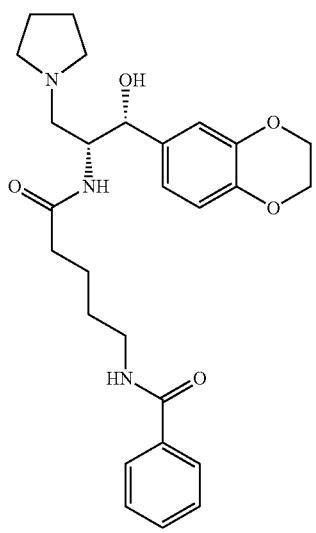 [SMILES: O=C(CCCCNC(=O)c1ccccc1)N[C@H](CN1CCCC1)[C@H](O)c1ccc2c(c1)OCCO2]

$^1$H NMR (400 MHz, CDCl$_3$) δ 1.47-1.52 (m, 2H), 1.59-1.69 (m, 2H), 1.77 (br, 4H), 2.15-2.21 (m, 2H), 2.62-2.65 (m, 4H), 2.81 (br, 2H), 3.30-3.42 (m, 2H), 4.19-4.23 (m, 5H), 4.94 (br, 1H), 5.98 (br, 1H), 6.76 (br, 1H), 6.78-6.86 (m, 3H), 7.40-7.50 (m, 3H), 7.80 (d, 2H); MS for C$_{27}$H$_{35}$N$_3$O$_5$: [M−H]$^-$ 482.

Example 2E53

Preparation of Compound 281

N1-((1R,2R)-1-(2,3-dihydrobenzo[β][1,4]dioxin-6-yl)-1-hydroxy-3-(pyrrolidin-1-yl)propan-2-yl)-N5-(thiazol-2-yl)glutaramide

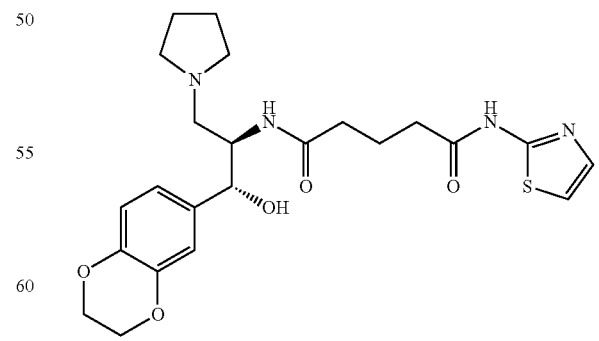

$^1$H NMR (400 MHz, CDCl$_3$) δ 1.74 (br, 4H), 1.97-2.03 (m, 2H), 2.20-2.26 (m, 2H), 2.40-2.45 (m, 2H), 2.64-2.68 (m, 5H), 2.88 (m, 1H), 4.20 (s, 4H), 4.26-4.29 (m, 1H), 4.83 (d, 1H), 6.12 (br, 1H), 6.74-6.79 (m, 2H), 6.85 (s, 1H), 6.95 (d, 1H), 7.41 (d, 1H); MS for C$_{23}$H$_{30}$N$_4$O$_5$S: [M−H]$^-$ 475.

Example 2E54

Preparation of Compound 282

N-((1R,2R)-1-(2,3-dihydrobenzo[β][1,4]dioxin-6-yl)-1-hydroxy-3-(pyrrolidin-1-yl)propan-2-yl)-5-(3,4-dimethoxyphenyl)-5-oxopentanamide

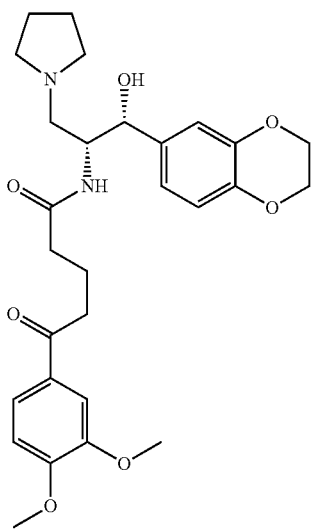 [SMILES: COc1ccc(C(=O)CCCC(=O)N[C@H](CN2CCCC2)[C@H](O)c2ccc3c(c2)OCCO3)cc1OC]

$^1$H NMR (400 MHz, CDCl$_3$) δ 1.76 (br, 4H), 1.92-2.00 (m, 2H), 2.21-2.26 (m, 2H), 2.60-2.65 (m, 4H), 2.70-2.95 (m, 4H), 3.93 (d, 6H), 4.17-4.23 (m, 5H), 4.90 (d, 1H), 5.96 (br, 1H), 6.75-6.79 (m, 2H), 6.85 (s, 1H), 6.87 (d, 1H), 7.50 (s, 1H), 7.55 (d, 1H); MS for C$_{28}$H$_{36}$N$_2$O$_7$: [M−H]$^−$ 513.

Example 2E55

Preparation of Compound 283

N-((1R,2R)-1-(2,3-dihydrobenzo[b][1,4]dioxin-6-yl)-1-hydroxy-3-(pyrrolidin-1-yl)propan-2-yl)-5-oxo-5-p-tolylpentanamide

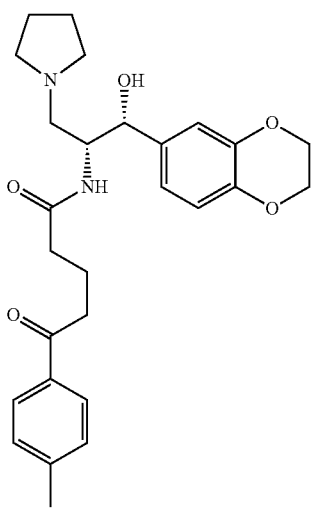 [SMILES: Cc1ccc(C(=O)CCCC(=O)N[C@H](CN2CCCC2)[C@H](O)c2ccc3c(c2)OCCO3)cc1]

$^1$H NMR (400 MHz, CDCl$_3$) δ 1.77 (br, 4H), 1.96-2.02 (m, 2H), 2.21-2.26 (m, 2H), 2.40 (s, 3H), 2.63-2.80 (m, 4H), 2.82-2.95 (m, 4H), 4.18-4.23 (m, 5H), 4.91 (d, 1H), 5.94 (br, 1H), 6.74-6.77 (m, 2H), 6.85 (s, 1H), 7.26 (d, 2H), 7.81 (d, 2H); MS for C$_{27}$H$_{34}$N$_2$O$_5$: [M−H]$^−$ 467.

Example 2E56

Preparation of Compound 113

N-((1R,2R)-1-(2,3-dihydrobenzo[β][1,4]dioxin-6-yl)-1-hydroxy-3-pyrrolidin-1-yl)propan-2-yl)-5-oxo-5-phenylpentanamide

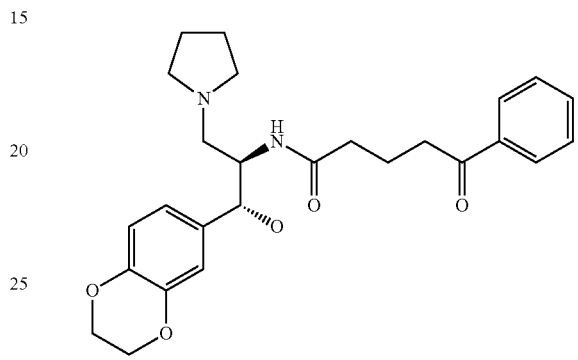

$^1$H NMR (400 MHz, CDCl$_3$) δ 1.76 (br, 4H), 1.95-2.01 (m, 2H), 2.22-2.25 (m, 2H), 2.62-2.63 (m, 4H), 2.78-2.95 (m, 4H), 4.17-4.22 (m, 5H), 4.91 (sd, 1H), 5.99 (br, 1H), 6.77 (st, 2H), 6.85 (s, 1H), 7.44-7.58 (m, 3H), 7.92 (d, 2H); MS for C$_{26}$H$_{32}$N$_2$O$_5$: [M−H]$^−$ 453.

Example 2E57

Preparation of Compound 284

N-((1R,2R)-1-(2,3-dihydrobenzo[β][1,4]dioxin-6-yl)-1-hydroxy-3-(pyrrolidin-1-yl)propan-2-yl)-5-(4-isopropoxyphenyl)-5-oxopentanamide

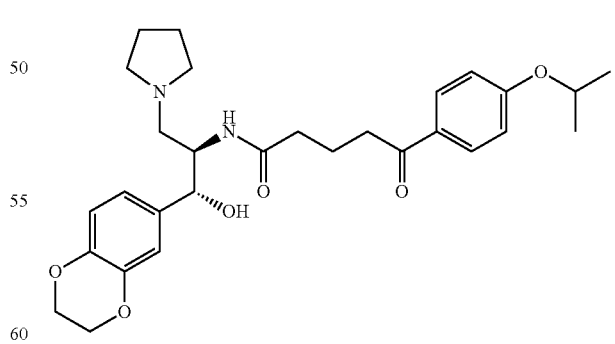

$^1$H NMR (400 MHz, CDCl$_3$) δ 1.36 (d, 6H), 1.75 (br, 4H), 1.90-2.02 (m, 2H), 2.20-2.25 (m, 2H), 2.60-2.66 (m, 4H), 2.70-2.86 (m, 4H), 4.17 (s, 4H), 4.22 (br, 1H), 4.62-4.65 (m, 1H), 4.89 (sd, 1H), 6.07 (d, 1H), 6.77 (s, 2H), 6.85 (s, 1H), 6.87 (d, 2H), 7.86 (d, 2H); MS for C$_{29}$H$_{38}$N$_2$O$_6$: [M−H]$^−$ 511.

Example 2E58

Preparation of Compound 140

N-((1R,2R)-1-(2,3-dihydrobenzo[β][1,4]dioxin-6-yl)-1-hydroxy-3-(pyrrolidin-1-yl)propan-2-yl)-6-(4-methoxy-3,5-dimethylphenyl)-6-oxohexanamide

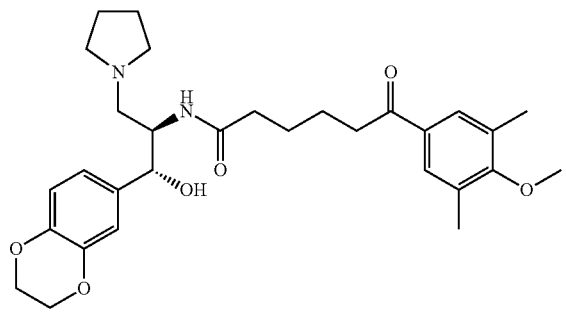 [SMILES: COc1c(C)cc(C(=O)CCCCC(=O)N[C@H](CN2CCCC2)[C@H](O)c2ccc3c(c2)OCCO3)cc1C]

$^1$H NMR (400 MHz, CDCl$_3$) δ 1.61-1.63 (m, 4H), 1.77 (br, 4H), 2.16 (t, 2H), 2.32 (s, 6H), 2.61-2.67 (m, 4H), 2.74-2.89 (m, 2H), 2.91 (t, 2H), 3.75 (s, 3H), 4.21 (br, 5H), 4.90 (sd, 1H), 5.93 (br, 1H), 6.75-6.82 (m, 2H), 6.85 (sd, 1H), 7.61 (s, 2H); MS for C$_{30}$H$_{40}$N$_2$O$_6$: [M–H]$^-$ 525.

Example 2E59

Preparation of Compound 141

N-((1R,2R)-1-(2,3-dihydrobenzo[β][1,4]dioxin-6-yl)-1-hydroxy-3-(pyrrolidin-1-yl)propan-2-yl)-6-(4-methoxyphenyl)-6-oxohexanamide

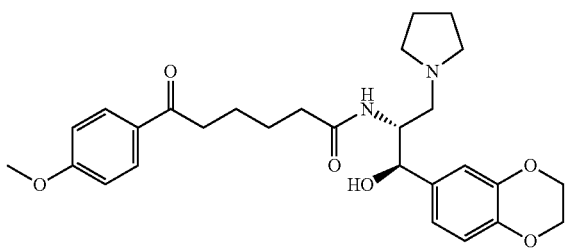 [SMILES: COc1ccc(C(=O)CCCCC(=O)N[C@H](CN2CCCC2)[C@H](O)c2ccc3c(c2)OCCO3)cc1]

$^1$H NMR (400 MHz, CDCl$_3$) δ 1.62-1.64 (m, 4H), 1.76 (br, 4H), 2.17 (t, 2H), 2.61-2.65 (m, 4H), 2.72-2.79 (m, 2H), 2.89 (t, 2H), 3.86 (s, 3H), 4.20 (br, 5H), 4.89 (d, 1H), 6.01 (br, 1H), 6.77 (q, 2H), 6.85 (s, 1H), 6.91 (d, 2H), 7.90 (d, 2H); MS for C$_{28}$H$_{36}$N$_2$O$_6$: [M–H]$^-$ 497.

Example 2E60

Preparation of Compound 155

6-(4-tert-butylphenyl)-N-((1R,2R)-1-(2,3-dihydrobenzo[β][1,4]dioxin-6-yl)-1-hydroxy-3-(pyrrolidin-1-yl)propan-2-yl)-6-oxohexanamide

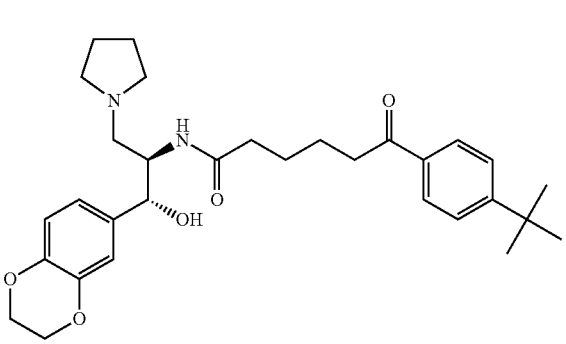 [SMILES: CC(C)(C)c1ccc(C(=O)CCCCC(=O)N[C@H](CN2CCCC2)[C@H](O)c2ccc3c(c2)OCCO3)cc1]

$^1$H NMR (400 MHz, CDCl$_3$) δ 1.34 (s, 9H), 1.63-1.65 (m, 4H), 1.77 (br, 2.17 (t, 2H), 2.64-2.66 (br, 4H), 2.75 (dd, 1H), 2.2.81 (dd, 1H), 2.91 (t, 2H), 4.20 (br, 5H), 4.90 (d, 1H), 6.02 (br, 1H), 6.77-6.82 (q, 2H), 6.85 (d, 1H), 7.46 (d, 2H), 7.86 (d, 2H); MS for C$_{31}$H$_{42}$N$_2$O$_5$: [M–H]$^-$ 523.

Example 2E61

Preparation of Compound 156

N-((1R,2R)-1-(2,3-dihydrobenzo[β][1,4]dioxin-6-yl)-1-hydroxy-3-(pyrrolidin-1-yl)propan-2-yl)-7-(4-methoxyphenyl)-7-oxoheptanamide

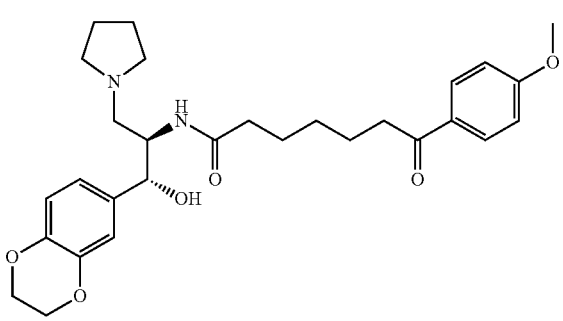 [SMILES: COc1ccc(C(=O)CCCCCC(=O)N[C@H](CN2CCCC2)[C@H](O)c2ccc3c(c2)OCCO3)cc1]

$^1$H NMR (400 MHz, CDCl$_3$) δ 1.25-1.30 (m, 2H), 1.55-1.70 (m, 4H), 1.77 (br, 4H), 2.13 (t, 2H), 2.61-2.66 (m, 4H), 2.74-2.82 (m, 2H), 2.88 (t, 2H), 3.86 (s, 3H), 4.20 (br, 5H), 4.90 (d, 1H), 5.93 (br, 1H), 6.78 (q, 2H), 6.85 (s, 1H), 6.91 (d, 2H), 7.92 (d, 2H); MS for C$_{29}$H$_{38}$N$_2$O$_6$: [M–H]$^-$ 511.

Example 2E62

Preparation of Compound 144

N-((1R,2R)-1-(2,3-dihydrobenzo[β][1,4]dioxin-6-yl)-1-hydroxy-3-(pyrrolidin-1-yl)propan-2-yl)-8-(4-methoxyphenyl)-8-oxooctanamide

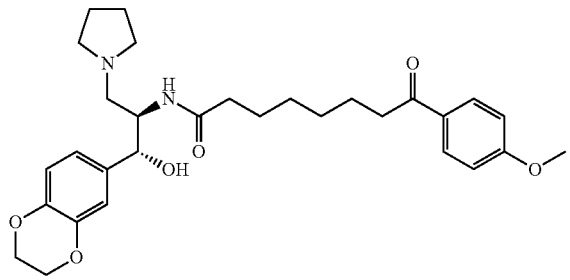 [SMILES: COc1ccc(C(=O)CCCCCCC(=O)N[C@H](CN2CCCC2)[C@H](O)c2ccc3c(c2)OCCO3)cc1]

$^1$H NMR (400 MHz, CDCl$_3$) δ 1.25-1.33 (m, 4H), 1.54 (m, 2H), 1.68 (t, 2H), 1.78 (br, 4H), 2.11 (br, 2H), 2.65 (br, 4H), 2.76-2.11 (m, 4H), 3.86 (s, 3H), 4.21 (br, 5H), 4.90 (br, 1H), 6.02 (d, 1H), 6.78-6.84 (m, 3H), 6.91 (d, 2H), 7.92 (d, 2H); MS for C$_{30}$H$_{40}$N$_2$O$_6$: [M−H]$^-$ 525.

Example 2E63

Preparation of Compound 159

7-(4-chlorophenyl)-N-((1R,2R)-1-(2,3-dihydrobenzo[β][1,4]dioxin-6-yl)-1-hydroxy-3-(pyrrolidin-1-yl)propan-2-yl)-7-oxoheptanamide

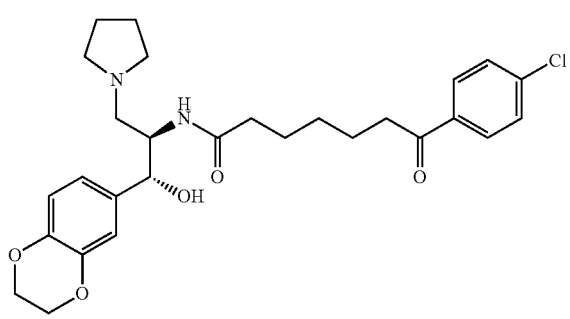 [SMILES: O=C(CCCCCC(=O)c1ccc(Cl)cc1)N[C@H](CN1CCCC1)[C@H](O)c1ccc2c(c1)OCCO2]

$^1$H NMR (400 MHz, CDCl$_3$) δ 1.26-1.37 (m, 2H), 1.57 (m, 2H), 1.68 (m, 2H), 1.77 (br, 4H), 2.13 (t, 2H), 2.62-2.65 (m, 4H), 2.76-2.82 (m, 2H), 2.90 (t, 2H), 4.20 (br, 5H), 4.90 (d, 1H), 5.93 (d, 1H), 6.78 (q, 2H), 6.85 (s, 1H), 7.42 (d, 2H), 7.87 (d, 2H); MS for C$_{28}$H$_{35}$ClN$_2$O$_5$: [M−H]$^-$ 515.

Example 2E64

Preparation of Compound 160

7-(4-tert-butylphenyl)-N-((1R,2R)-1-(2,3-dihydrobenzo[β][1,4]dioxin-6-yl)-1-hydroxy-3-(pyrrolidin-1-yl)propan-2-yl)-7-oxoheptanamide

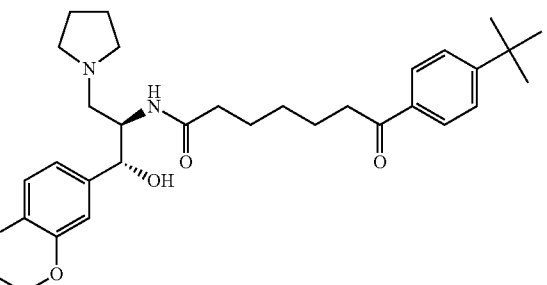

$^1$H NMR (400 MHz, CDCl$_3$) δ 1.27-1.34 (m, 11H), 1.56-1.71 (m, 4H), 1.77 (br, 4H), 2.13 (t, 2H), 2.63-2.66 (m, 4H), 2.76-2.819 (m, 2H), 2.91 (t, 2H), 4.20 (br, 5H), 4.90 (sd, 1H), 5.90 (d, 1H), 6.81 (q, 2H), 6.85 (s, 1H), 7.46 (d, 2H), 7.88 (d, 2H); MS for C$_{32}$H$_{44}$N$_2$O$_5$: [M−H]$^-$ 537.

Example 2E65

Preparation of Compound 168

N-((1R,2R)-1-(2,3-dihydrobenzo[b][1,4]dioxin-6-yl)-1-hydroxy-3-(pyrrolidin-1-yl)propan-2-yl)-7-(4-methoxyphenyl)-7-oxoheptanamide (2S,3S)-2,3-dihydroxysuccinate

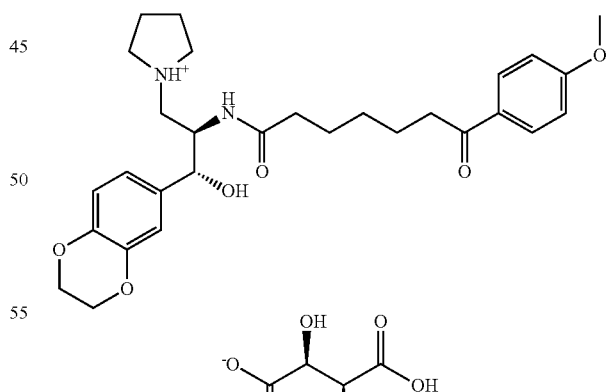

$^1$H NMR (400 MHz, CD$_3$OD) δ 1.15-1.19 (m, 2H), 1.40-1.47 (m, 2H), 1.60 (m, 2H), 2.02 (br, 4H), 2.09-2.21 (m, 2H), 2.90 (t, 2H), 3.35-3.49 (m, 5H), 3.83 (s, 3H), 4.12 (br, 4H), 4.38 (s, 2H), 4.43 (m, 1H), 4.74 (sd, 1H), 6.71 (d, 1H), 6.79 (dq, 1H), 6.86 (sd, 1H), 6.96 (d, 2H), 7.92 (d, 2H); MS for C$_{29}$H$_{38}$N$_2$O$_6$·C$_4$H$_6$O$_6$: [M−H]$^-$ 661.

Example 2E66

Preparation of Compound 162

N-((1R,2R)-1-(2,3-dihydrobenzo[β][1,4]dioxin-6-yl)-1-hydroxy-3-(pyrrolidin-1-yl)propan-2-yl)-4-(4-isopropoxyphenyl)-4-oxobutanamide

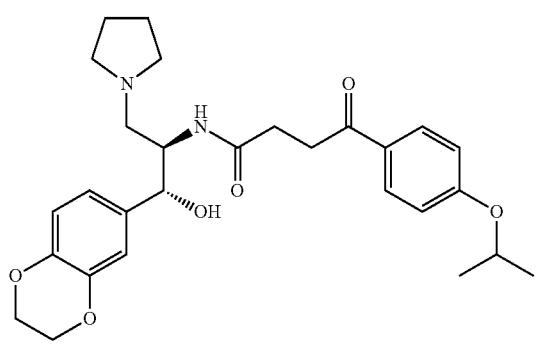 [SMILES: CC(C)Oc1ccc(C(=O)CCC(=O)N[C@H](CN2CCCC2)[C@H](O)c2ccc3c(c2)OCCO3)cc1]

$^1$H NMR (400 MHz, CDCl$_3$) δ 1.35 (d, 6H), 1.77 (br, 4H), 2.52-2.56 (m, 2H), 2.64-2.83 (m, 6H), 3.09-3.36 (m, 2H), 4.22 (br, 5H), 4.63-4.66 (m, 1H), 4.89 (sd, 1H), 6.13 (d, 1H), 6.78 (s, 2H), 6.88 (t, 3H), 7.90 (d, 2H); MS for C$_{28}$H$_{36}$N$_2$O$_6$: [M–H]$^-$ 497.

Example 2E67

Preparation of Compound 176

N-((1R,2R)-1-(2,3-dihydrobenzo[β][1,4]dioxin-6-yl)-1-hydroxy-3-(pyrrolidin-1-yl)propan-2-yl)-4-oxo-4-(4-(trifluoromethyl)phenyl)butanamide (2S,3S)-2,3-dihydroxysuccinate

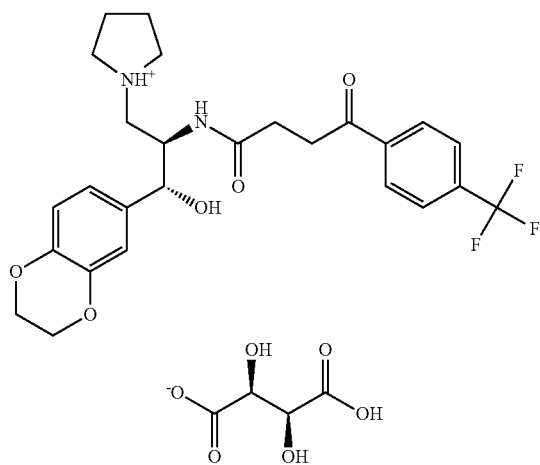

$^1$H NMR (400 MHz, CD$_3$OD) δ 2.08 (br, 4H), 2.54-2.72 (m, 2H), 3.24-3.48 (m, 6H), 4.19 (s, 4H), 4.29 (m, 4H), 4.74 (sd, 1H), 6.76 (d, 1H), 6.86 (d, 1H), 6.92 (s, 1H), 7.81 (d, 2H), 8.13 (d, 2H); MS for C$_{26}$H$_{29}$F$_3$N$_2$O$_5$·C$_4$H$_6$O$_6$: [M–H]$^-$ 657.

Example 2E68

Preparation of Compound 65 (Genz-528152-1)

2-(3'-chlorobiphenyl-4-yl)-N-((1R,2R)-1-(2,3-dihydrobenzo[β][1,4]dioxin-6-yl)-1-hydroxy-3-(pyrrolidin-1-yl)propan-2-yl)acetamide

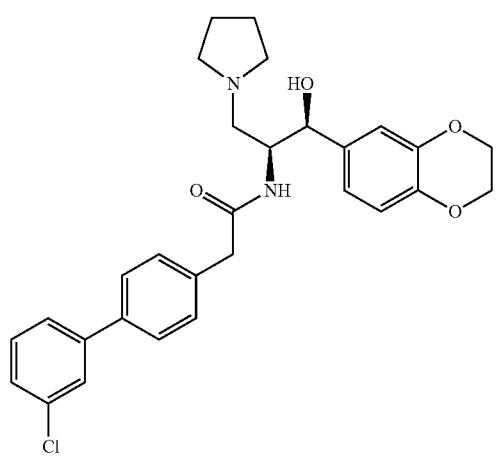 [SMILES: O=C(Cc1ccc(-c2cccc(Cl)c2)cc1)N[C@@H](CN1CCCC1)[C@@H](O)c1ccc2c(c1)OCCO2]

$^1$H NMR (400 MHz, CDCl$_3$) δ 1.70 (br, 4H), 2.54 (br, 4H), 2.72-2.81 (m, 2H), 3.53 (s, 2H), 4.12-4.23 (m, 5H), 4.85 (d, 1H), 5.82 (d, 1H), 6.58 (dd, 1H), 6.70 (sd, 1H), 6.73 (d, 1H), 7.19 (d, 1H), 7.32-7.34 (m, 1H), 7.38 (t, 1H), 7.46-7.49 (m, 1H), 7.52 (d, 2H), 7.59 (d, 1H); C$_{29}$H$_{31}$ClN$_2$O$_4$: [M–H]$^-$ 507.

Example 2E69

Preparation of Compound 262

N-[2-Hydroxy-2-(4-methoxy-phenyl)-1-pyrrolidin-1-ylmethyl-ethyl]-3-(4-methoxy-phenoxy)-propionamide

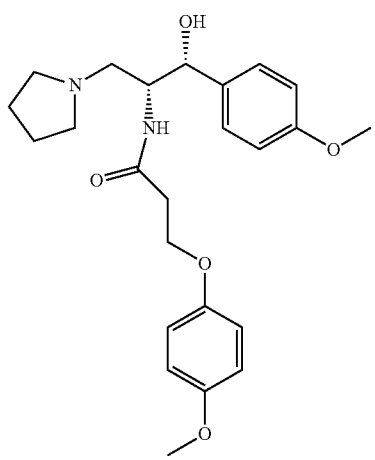 [SMILES: COc1ccc(OCCC(=O)N[C@H](CN2CCCC2)[C@H](O)c2ccc(OC)cc2)cc1]

$^1$H NMR (CDCl$_3$ 400 mHz, ppm); 1.75 (m, 4H), 2.55 (m, 2H), 2.65 (m, 4H), 2.85 (m, 2H), 3.8 (s, 6H), 4.1 (m, 2H), 4.25 (m, 1H), 5.0 (d, 1H), 6.5 (br. d, 1H), 6.8 (m, 4H), 7.25 (m, 4H). M/Z for C$_{24}$H$_{32}$N$_2$O$_5$ [M–H]$^+$ 429.

Example 2E70

Preparation of Compound 270

5-(4-Isopropoxy-phenyl)-5-oxo-pentanoic acid [2-hydroxy-2-(4-methoxy-phenyl)-1-pyrrolidin-1-ylmethyl-ethyl]amide

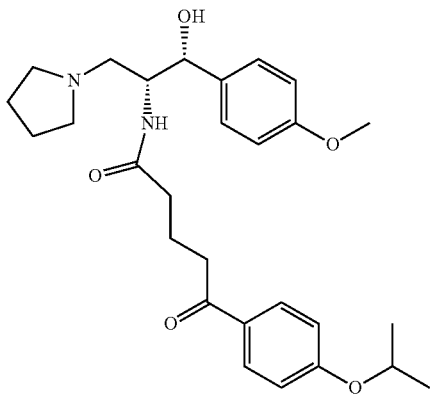 [SMILES: COc1ccc([C@@H](O)[C@@H](CN2CCCC2)NC(=O)CCCC(=O)c2ccc(OC(C)C)cc2)cc1]

$^1$H NMR (CDCl$_3$ 400 mHz, ppm); 1.4 (d, 6H), 1.8 (m, 4H), 2.0 (m, 2H), 2.2 (m, 2H), 2.6 (m, 4H), 2.8 (m, 4H), 3.75 (s, 3H), 4.25 (m, 1H), 4.65 (m, 1H), 5.0 (d, 1H), 5.95 (br. d, 1H), 6.85 (m, 4H), 7.25 (m, 2H), 7.9 (m, 2H). M/Z for C$_{24}$H$_{32}$N$_2$O$_5$ [M−H]$^+$ 483.3.

Example 2E71

Preparation of Compound 285

7-(4-Methoxy-phenyl)-7-oxo-heptanoic acid [2-hydroxy-2-(4-methoxy-phenyl)-1-pyrrolidin-1-ylmethyl-ethyl]-amide

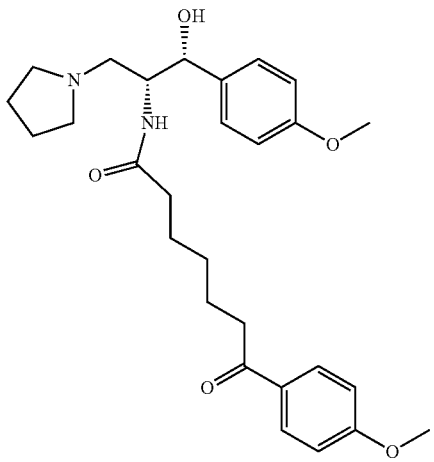 [SMILES: COc1ccc(C(=O)CCCCCC(=O)N[C@H](CN2CCCC2)[C@H](O)c2ccc(OC)cc2)cc1]

$^1$H NMR (CDCl$_3$ 400 mHz, ppm); 1.25 (m, 2H), 1.6 (m, 4H), 1.8 (m, 4H), 2.15 (m, 2H), 2.65 (m, 4H), 2.85 (m, 4H), 3.75 (s, 3H), 3.9 (s, 3H), 4.2 (m, 1H), 5.0 (d, 1H), 5.9 (br. d, 1H), 6.85 (d, 2H), 6.95 (d, 2H), 7.2 (d, 2H), 7.95 (d, 2H). M/Z for C$_{24}$H$_{32}$N$_2$O$_5$ [M−H]$^+$ 483.3

Example 2E72

Preparation of Compound 262

N-[2-Hydroxy-2-(4-methoxy-phenyl)-1-pyrrolidin-1-ylmethyl-ethyl]-3-(4-methoxy-phenoxy)-propionamide

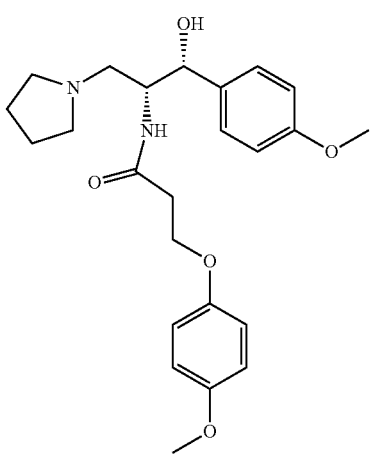 [SMILES: COc1ccc(OCCC(=O)N[C@H](CN2CCCC2)[C@H](O)c2ccc(OC)cc2)cc1]

$^1$H NMR (CDCl$_3$ 400 mHz, ppm); 1.75 (m, 4H), 2.55 (m, 2H), 2.65 (m, 4H), 2.85 (m, 2H), 3.8 (s, 6H), 4.1 (m, 2H), 4.25 (m, 1H), 5.0 (d, 1H), 6.5 (br. d, 1H), 6.8 (m, 4H), 7.25 (m, 4H). M/Z for C$_{24}$H$_{32}$N$_2$O$_5$ [M−H]$^+$ 429.

Example 2E73

Preparation of Compound 270

5-(4-Isopropoxy-phenyl)-5-oxo-pentanoic acid [2-hydroxy-2-(4-methoxy-phenyl)-1-pyrrolidin-1-lymethyl-ethyl]amide

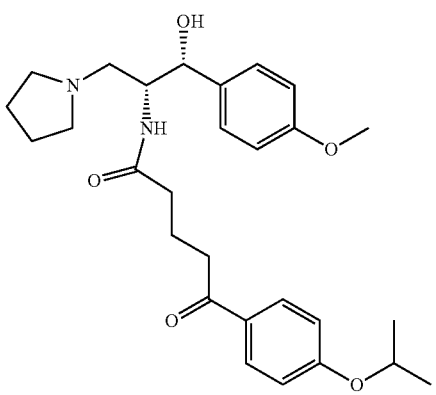 [SMILES: COc1ccc([C@@H](O)[C@@H](CN2CCCC2)NC(=O)CCCC(=O)c2ccc(OC(C)C)cc2)cc1]

$^1$H NMR (CDCl$_3$ 400 mHz, ppm); 1.4 (d, 6H), 1.8 (m, 4H), 2.0 (m, 2H), 2.2 (m, 2H), 2.6 (m, 4H), 2.8 (m, 4H), 3.75 (s, 3H), 4.25 (m, 1H), 4.65 (m, 1H), 5.0 (d, 1H), 5.95 (br. d, 1H), 6.85 (m, 4H), 7.25 (m, 2H), 7.9 (m, 2H). M/Z for C$_{24}$H$_{32}$N$_2$O$_5$ [M−H]$^+$ 483.3.

Example 2E74

Preparation of Compound 305

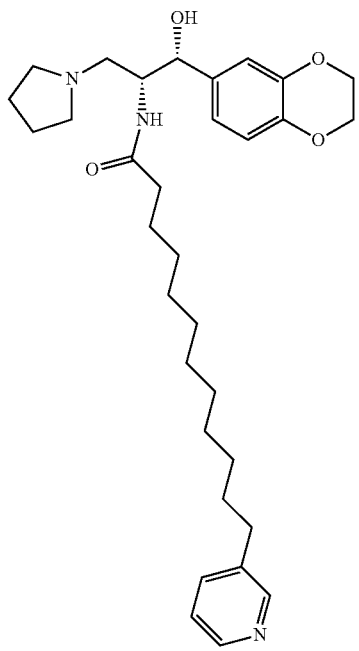 [SMILES: O=C(CCCCCCCCCCCc1cccnc1)N[C@H](CN1CCCC1)[C@H](O)c1ccc2c(c1)OCCO2]

¹H NMR (CDCl₃ 400 mHz, ppm); 1.25 (m, 14H), 1.6 (m, 4H), 1.8 (m, 4H), 2.1 (t, 2H), 2.6 (t, 2H), 2.8 (m, 6H), 4.2 (m, 5H), 4.9 (d, 1H), 6.0 (br d, 1H), 6.8 (m, 3H), 7.2 (m, 1H), 7.5 (m, 1H), 8.4 (m, 2H). M/Z for $C_{24}H_{32}N_2O_5$ [M–H]⁺ 538.

Example 2E75

Preparation of Compound 320

Octanoic acid [2-hydroxy-2(4-methoxy-phenyl)-1-Pyrrolidin1-ylmethyl-ethyl]-amide

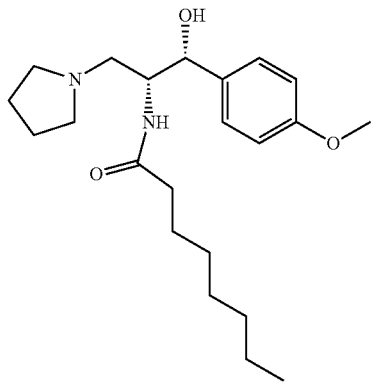 [SMILES: CCCCCCCC(=O)N[C@H](CN1CCCC1)[C@H](O)c1ccc(OC)cc1]

¹H NMR (CDCl₃ 400 mHz, ppm); 0.9 (t, 3H), 1.2 (m, 8H), 1.5 (m, 2H), 1.8 (m, 4H), 2.1 (t, 2H), 2.65 (m, 4H), 2.8 (d, 2H), 3.8 (s, 3H), 4.2 (m, 1H), 4.95 (d, 1H), 5.9 (br d, 1H), 6.9 (2s, 2H), 7.25 (m, 2H). M/Z for $C_{22}H_{36}N_2O_3$ [M–H]⁺ 377.4.

Example 2E76

Preparation of Cyclic Amide Analogs

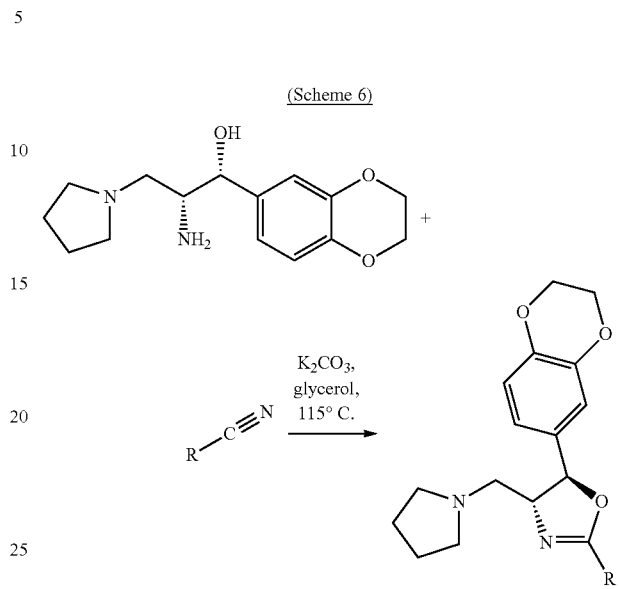

Cyclic amide analogs were prepared according to Scheme 6. 2-Amino-1-(2,3-dihydro-benzo[1,4]dioxin-6-yl)-3-pyrrolidin-1-yl-propan-1-ol was prepared according to the preparation of intermediate 4 of U.S. Pat. No. 6,855,830 B2. This amine was coupled with various nitriles in potassium carbonate and glycerol, under an atmosphere of nitrogen, for example, at 115° C. for 18 hours. Compound 323 characterized by the following structural formula was prepared by following Scheme 6. Compound 323 was purified by column chromatography using a mixture of methanol and methylene chloride.

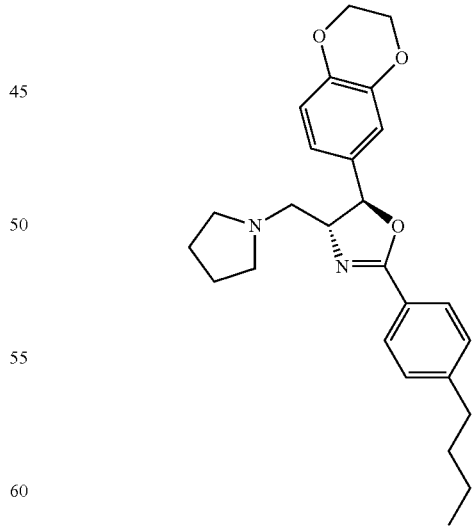

¹H NMR (CDCl₃ 400 mHz, ppm); 0.95 (t, 3H), 1.35 (m, 2H), 1.6 (m, 2H), 1.8 (m, 4H), 2.7 (m, 6H), 2.8 (m, 2H), 4.2 (m, 5H), 5.4 (d, 1H), 6.85 (m, 3H), 7.2 (m, 2H), 7.9 (d, 2H). M/Z for $C_{24}H_{32}N_2O_5$ [M–H]⁺ 421.54.

Example 2E77

Preparation of N-((1R,2R)-1-(2,3-dihydrobenzo[b][1,4]dioxin-6-yl)-1-hydroxy-3-(pyrrolidin-1-yl)propan-2-yl)-5-(4-(2-methoxyethoxy)phenyl)-5-oxopentanamide

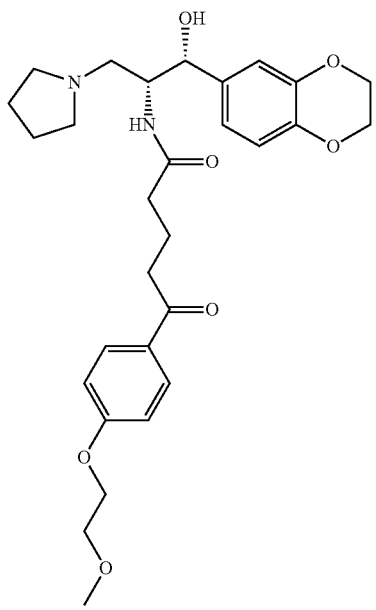 [SMILES: COCCOc1ccc(C(=O)CCCC(=O)N[C@H](CN2CCCC2)[C@H](O)c2ccc3c(c2)OCCO3)cc1]

¹H NMR (CDCl₃, 400 mHz, ppm): 1.25 (t, 3H), 1.8 (br, 4H), 1.95 (m, 2H), 2.05 (t, 3H), 2.25 (m, 2H), 3.65 (m, 4H), 2.90 (m, 4H), 3.4 (s, 4H), 3.8 (m, 2H), 4.15 (m, 9H), 4.95 (br, 1H), 5.95 (br, 1H), 6.88-6.95 (m, 5H), 7.9 (m, 2H). M/Z for $C_{29}H_{38}N_2O_7$ [M+H]=527.

Example 2E78

Preparation of N-((1R,2R)-1-(4-chlorophenyl)-1-hydroxy-3-(pyrrolidin-1-yl)propan-2-yl)-3-(4-methoxyphenoxy)propanamide

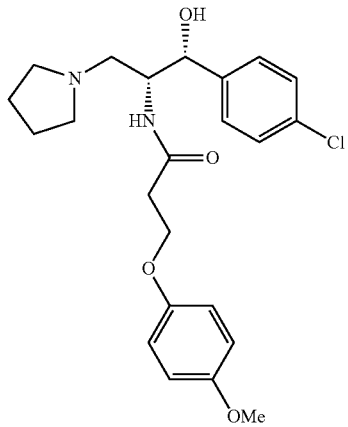 [SMILES: COc1ccc(OCCC(=O)N[C@H](CN2CCCC2)[C@H](O)c2ccc(Cl)cc2)cc1]

¹H NMR (CDCl₃, 400 mHz, ppm): 1.76 (br, 4H), 2.52-2.57 (sq, 2H), 2.60-2.73 (br, 4H), 2.88-2.96 (st, 2H), 3.8 (s, 3H), 3.96-4.0 (m, 1H), 4.06-4.11 (1H), 4.21-4.24 (m, 1H), 5.07 (d, 1H), 6.57 (bd, 1H), 6.77-6.87 (sq, 4H), 7.20-7.27 (sd, 6H). M/Z for $C_{23}H_{29}ClN_2O_4$ [M+H]=433.

Example 2E79

Preparation of N-((1R,2R)-1-(4-chlorophenyl)-1-hydroxy-3-(pyrrolidin-1-yl)propan-2-yl)-6-(4-methoxyphenyl)-6-oxohexanamide

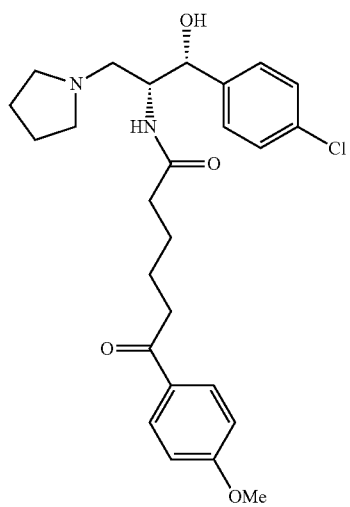 [SMILES: COc1ccc(C(=O)CCCCC(=O)N[C@H](CN2CCCC2)[C@H](O)c2ccc(Cl)cc2)cc1]

¹H NMR (CDCl₃, 400 mHz, ppm): 1.54-1.62 (br, 4H), 1.79 (br, 4H), 2.14 (t, 2H), 2.63-2.69 (br, 4H), 2.83-2.89 (m, 4H), 3.88 (s, 3H), 4.24 (br, 1H), 5.03 (d, 1H), 5.93 (d, 1H), 6.93 (d, 2H), 7.26-7.32 (m, 4H), 7.93 (d, 2H). M/Z for $C_{26}H_{33}ClN_2O_4$ [M+H]=473.

Example 2E80

Preparation of N-((1R,2R)-1-hydroxy-1-(4-methoxy-3-methylphenyl)-3-(pyrrolidin-1-yl)propan-2-yl)-6-(4-methoxyphenyl)-6-oxohexanamide

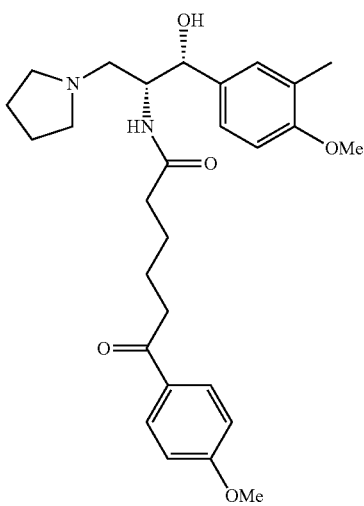 [SMILES: COc1ccc(C(=O)CCCCC(=O)N[C@H](CN2CCCC2)[C@H](O)c2ccc(OC)c(C)c2)cc1]

¹H NMR (CDCl₃, 400 mHz, ppm): 1.77 (br, 4H), 1.91-2.0 (m, 2H), 2.18 (s, 3H), 2.2-2.25 (m, 2H), 2.62-2.69 (m, 4H), 2.77-2.89 (m, 4H), 3.75 (s, 3H), 3.88 (s, 3H), 4.23 (m, 1H), 4.96 (sd, 1H), 5.93 (br, 1H), 6.75 (br, 1H), 6.94 (d, 2H), 7.1 (br, 2H), 7.88 (m, 2H). M/Z for $C_{28}H_{38}N_2O_5$ [M+H]=483.

Example 2E81

Preparation of N-((1R,2R)-1-hydroxy-1-(4-methoxy-3-methylphenyl)-3-(pyrrolidin-1-yl)propan-2-yl)-2-(4-(trifluoromethoxy)phenyl)acetamide

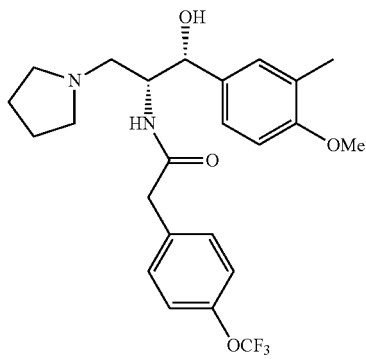 [SMILES: COc1ccc([C@@H](O)[C@@H](CN2CCCC2)NC(=O)Cc2ccc(OC(F)(F)F)cc2)cc1C]

$^1$H NMR (CDCl$_3$, 400 mHz, ppm): 1.73 (br, 4H), 2.20 (s, 3H), 2.55 (br, 4H), 2.81 (st, 2H), 3.46 (s, 2H), 3.82 (s, 3H), 4.15 (m, 1H), 4.92 (sd, 1H), 5.85 (br, 1H), 672 (d, 1H), 6.95 (sd, 1H), 7.00 (br, 1H), 7.2 (m, 4H). M/Z for $C_{24}H_{29}F_3N_2O_4$ [M+H]=467.

Example 2E82

Preparation of N-((1R,2R)-1-hydroxy-3-(pyrrolidin-1-yl)-1-(2,2,3,3-tetrafluoro-2,3-dihydrobenzo[b][1,4]dioxin-6-yl)propan-2-yl)octanamide

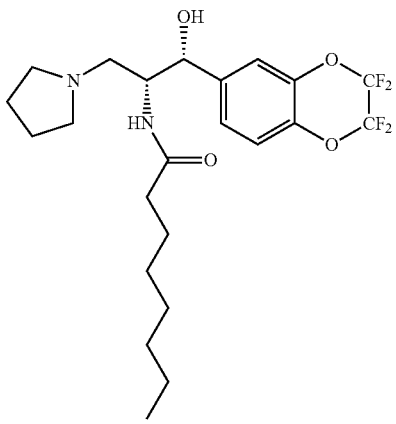 [SMILES: CCCCCCCC(=O)N[C@H](CN1CCCC1)[C@H](O)c1ccc2c(c1)OC(F)(F)C(F)(F)O2]

$^1$H NMR (CDCl$_3$, 400 mHz, ppm): 0.9 (t, 3H), 1.2 (m, 11H), 1.5 (bm, 8H), 1.8 (br, 4H), 2.1 (m, 2H), 2.65 (m, 4H), 2.90 (m, 2H), 4.2 (m, 1H), 5.05 (d, 1H), 5.85 (br, 1H), 7.2 (m, 3H). M/Z for $C_{23}H_{32}F_4N_2O_4$ [M+H]=477.

Example 2E83

Preparation of N-((1R,2R)-1-(2,2-difluorobenzo[d][1,3]dioxol-5-yl)-1-hydroxy-3-(pyrrolidin-1-yl)propan-2-yl)-2-(4-(trifluoromethoxy)phenyl)acetamide

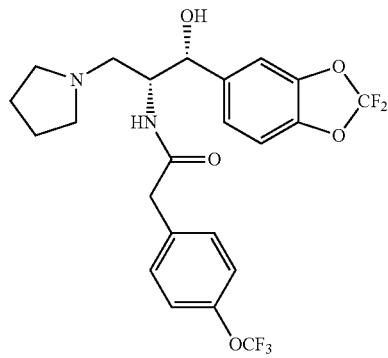 [SMILES: O=C(Cc1ccc(OC(F)(F)F)cc1)N[C@H](CN1CCCC1)[C@H](O)c1ccc2c(c1)OC(F)(F)O2]

$^1$H NMR (CDCl$_3$, 400 mHz, ppm): 1.75 (br, 4H), 2.55 (br, 4H), 2.85 (m, 2H), 3.45 (s, 2H), 4.1 (m, 1H), 5.0 (d, 1H), 5.85 (br, 1H), 6.8-6.95 (3H), 7.1-7.20 (4H). M/Z for $C_{23}H_{23}F_5N_2O_5$ [M+H]=503.

Example 2E84

Preparation of N-((1R,2R)-1-hydroxy-1-(4-(2-phenoxyethoxy)phenyl)-3-(pyrrolidin-1-yl)propan-2-yl)-6-(4-methoxyphenyl)-6-oxohexanamide

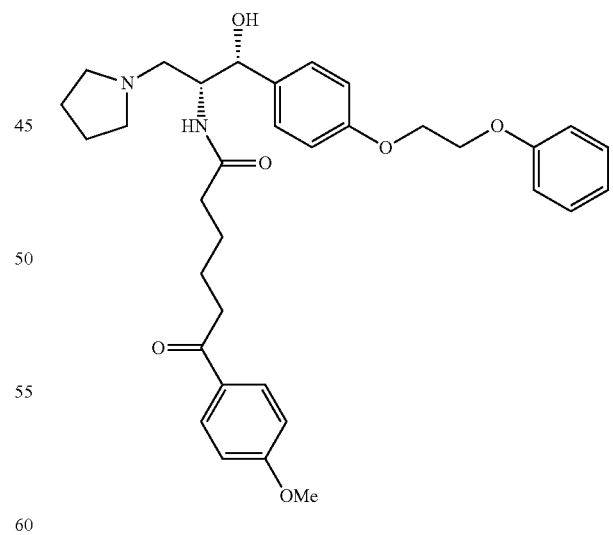

$^1$H NMR (CDCl$_3$, 400 mHz, ppm): 1.6 (m, 4H), 1.8 (m, 4H), 2.15 (t, 2H), 2.7 (m, 4H), 2.85 (m, 4H), 3.8 (s, 3H), 4.25 (m, 1H), 4.3 (s, 3H), 5.0 (d, 1H), 5.95 (br, 1H), 6.9 (m, 7H), 7.2 (m, 4H), 7.95 (m, 2H). M/Z for $C_{34}H_{42}N_2O_6$ [M+H]=575.

Example 2E85

Preparation of N-((1R,2R)-1-(4-(cyclobutylmethoxy)phenyl)-1-hydroxy-3-(pyrrolidin-1-yl)propan-2-yl)-6-(4-methoxyphenyl)-6-oxohexanamide

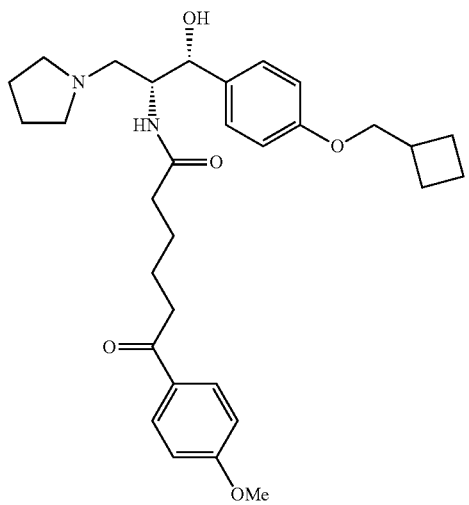 [SMILES: COc1ccc(C(=O)CCCCC(=O)N[C@H](CN2CCCC2)[C@H](O)c2ccc(OCC3CCC3)cc2)cc1]

$^1$H NMR (CDCl$_3$, 400 mHz, ppm): 1.6 (br, 4H), 1.9 (m, 9H), 2.05 (m, 5H), 2.75-3.0 (m, 9H), 3.8 (m, 5H), 4.3 (m, 1H), 5.0 (m, 1H), 6.2 (br, 1H), 6.9 (m, 4H), 7.25 (m, 2H), 7.9 (m, 2H). M/Z for C$_{31}$H$_{42}$N$_2$O$_5$ [M+H]=523.

Example 2E86

Preparation of N-((1R,2R)-1-(4-(4-fluorobutoxy)phenyl)-1-hydroxy-3-(pyrrolidin-1-yl)propan-2-yl)-6-(4-methoxyphenyl)-6-oxohexanamide

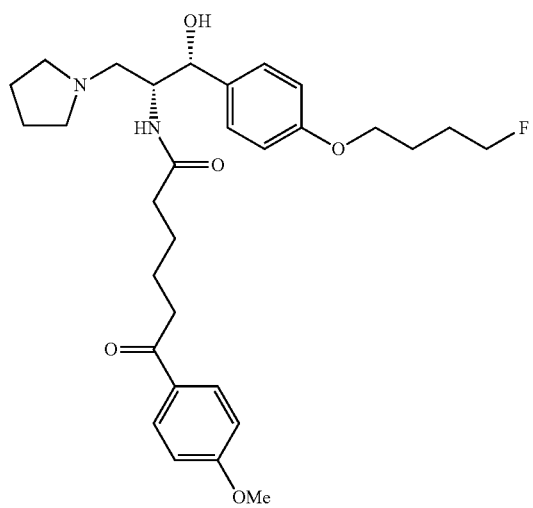 [SMILES: COc1ccc(C(=O)CCCCC(=O)N[C@H](CN2CCCC2)[C@H](O)c2ccc(OCCCCF)cc2)cc1]

$^1$H NMR (CDCl$_3$, 400 mHz, ppm): 1.6 (m, 8H), 1.8 (m, 10H), 2.15 (t, 2H), 2.65 (m, 4H), 2.8 (d, 2H), 2.9 (m, 5H), 2.95 (s, 3H), 4.0 (t, 2H), 4.15 (m, 1H), 4.45 (t, 1H), 4.55 (t, 1H), 4.95 (br, 2H), 5.9 (br, 1H), 6.90 (m, 4H), 7.20 (m, 2H), 7.95 (m, 2H), 8.05 (br, 1H). M/Z for C$_{30}$H$_{41}$FN$_2$O$_5$ [M+H]=529.

Example 2E87

Preparation of N-((1R,2R)-1-hydroxy-3-(pyrrolidin-1-yl)-1-(4-(3-(p-tolyloxy)propoxy)phenyl)propan-2-yl)-6-(4-methoxyphenyl)-6-oxohexanamide

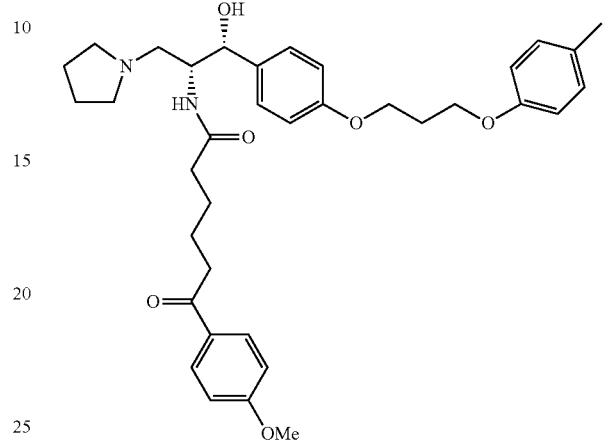

$^1$H NMR (CDCl$_3$, 400 mHz, ppm): 1.65 (m, 4H), 1.8 (m, 4H), 2.15 (t, 2H), 2.25 (t, 2H), 2.3 (s, 3H), 2.65 (m, 4H), 2.8 (m, 2H), 2.9 (t, 2H), 3.85 (s, 3H), 4.15 (m, 4H), 4.25 (m, 1H), 4.95 (br, 1H), 6.85 (br, 1H), 6.8-6.95 (m, 6H), 7.05 (m, 2H), 7.2 (m, 2H), 7.95 (2H). M/Z for C$_{36}$H$_{46}$N$_2$O$_6$ [M+H]=603.

Example 2E88

Preparation of N-((1R,2R)-1-(4-butoxyphenyl)-1-hydroxy-3-(pyrrolidin-1-yl)propan-2-yl)-6-(4-methoxyphenyl)-6-oxohexanamide

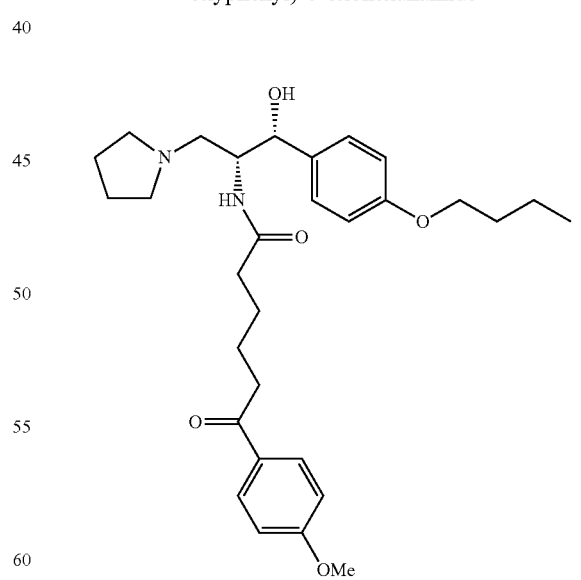

$^1$H NMR (CDCl$_3$, 400 mHz, ppm): 1.0 (t, 3H), 1.5 (m, 2H), 1.65 (m, 4H), 1.8 (m, 6H), 2.15 (t, 2H), 2.65 (m, 4H), 2.8 (m, 2H), 2.9 (t, 2H), 3.85 (s, 3H), 3.9 (t, 2H), 4.15 (m, 1H), 4.95 (br, 1H), 5.90 (br, 1H), 6.8-6.95 (m, 4H), 7.2 (br, 2H), 7.90 (br, 2H). M/Z for C$_{30}$H$_{42}$N$_2$O$_5$ [M+H]=511.

Example 2E89

Preparation of N-((1R,2R)-1-(4-(hexyloxy)phenyl)-1-hydroxy-3-(pyrrolidin-1-yl)propan-2-yl)-5-(4-(2-methoxyethoxy)phenyl)-5-oxopentanamide

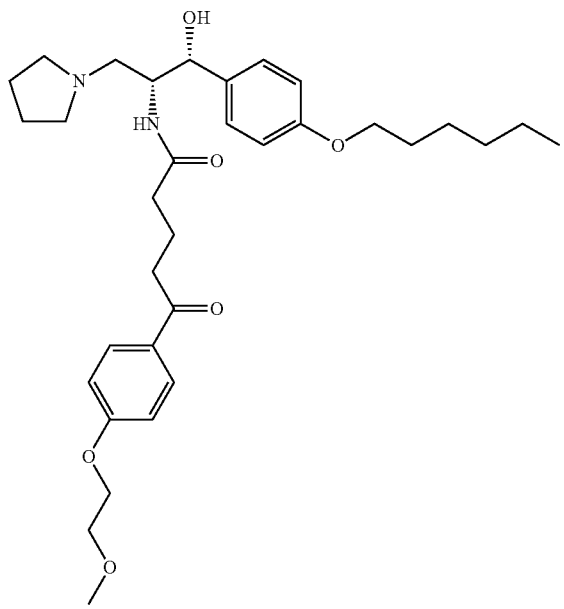 [SMILES: CCCCCCOc1ccc([C@@H](O)[C@@H](CN2CCCC2)NC(=O)CCCC(=O)c2ccc(OCCOC)cc2)cc1]

¹H NMR (CDCl₃, 400 mHz, ppm): 0.95 (t, 3H), 1.35 (m, 4H), 1.45 (m, 2H), 1.7 (m, 6H), 1.95 (m, 2H), 2.20 (m, 2H), 2.65 (m, 4H), 2.85 (m, 4H), 3.45 (s, 3H), 3.75 (m, 2H), 3.90 (t, 2H), 4.15 (m, 2H), 4.25 (m, 1H), 4.95 (m, 1H), 6.0 (br, 1H), 6.8 (m, 2H), 6.9 (m, 2H), 7.2 (m, 2H), 7.90 (m, 2H). M/Z for $C_{33}H_{48}N_2O_6$ [M+H]=569.

Example 2E90

Preparation of N-((1R,2R)-1-(4-(hexyloxy)phenyl)-1-hydroxy-3-((S)-3-hydroxypyrrolidin-1-yl)propan-2-yl)-3-(4-methoxyphenoxy)propanamide

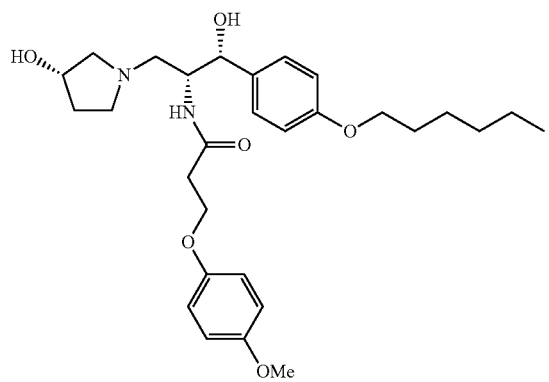 [SMILES: CCCCCCOc1ccc([C@@H](O)[C@@H](CN2CC[C@H](O)C2)NC(=O)CCOc2ccc(OC)cc2)cc1]

¹H NMR (CDCl₃, 400 mHz, ppm): 0.95 (t, 3H), 1.35 (m, 4H), 1.45 (m, 2H), 1.75 (m, 3H), 2.1 (m, 1H), 2.4 (m, 1H), 2.55 (t, 2H), 2.75 (m, 3H), 2.85 (m, 1H), 3.0 (m, 1H), 3.75 (s, 3H), 3.90 (t, 2H), 4.05 (m, 2H), 4.1 (m, 1H), 4.15 (m, 1H), 5.0 (br, 1H), 6.6 (br, 1H), 6.8 (m, 6H), 7.2 (m, 2H). M/Z for $C_{29}H_{42}N_2O_6$ [M+H]=515.

Example 2E91

Preparation of 2-(4'-chlorobiphenyl-4-yl)-N-((1R,2R)-3-((R)-3-fluoropyrrolidin-1-yl)-1-hydroxy-1-(4-isopropoxyphenyl)propan-2-yl)acetamide

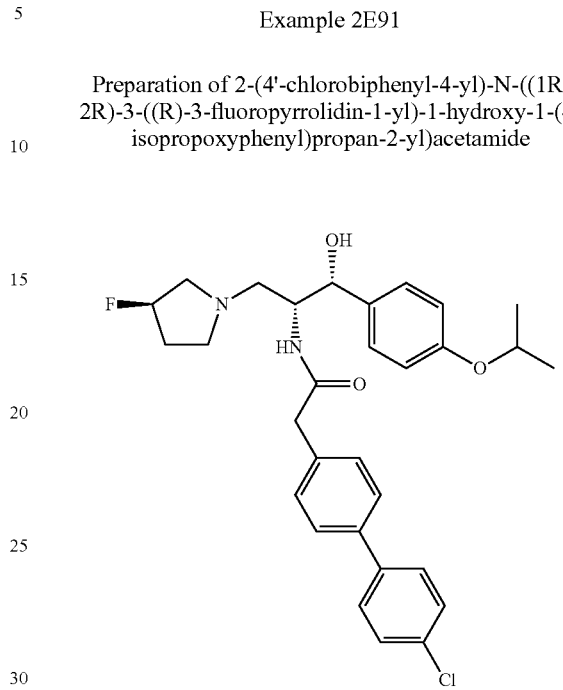

¹H NMR (CDCl₃, 400 mHz, ppm): 1.15 (m, 6H), 2.10 (m, 2H), 2.4 (q, 1H), 2.5-2.75 (m, 4H), 2.95 (m, 2H), 3.55 (d, 2H), 4.15 (m, 1H), 4.45 (m, 1H), 4.85 (br, 1H), 5.10 (m, 1H), 5.9 (br, 1H), 6.75 (m, 2H), 7.05 (br, 2H), 7.20 (m, 2H), 7.4 (m, 2H), 7.5 (m, 4H). M/Z for $C_{30}H_{34}ClFN_2O_3$ [M+H]=528.

Example 2E92

Preparation of N-((1R,2R)-1-hydroxy-3-((S)-3-hydroxypyrrolidin-1-yl)-1-(4-isopropoxyphenyl)propan-2-yl)-3-(4-methoxyphenoxy)propanamide

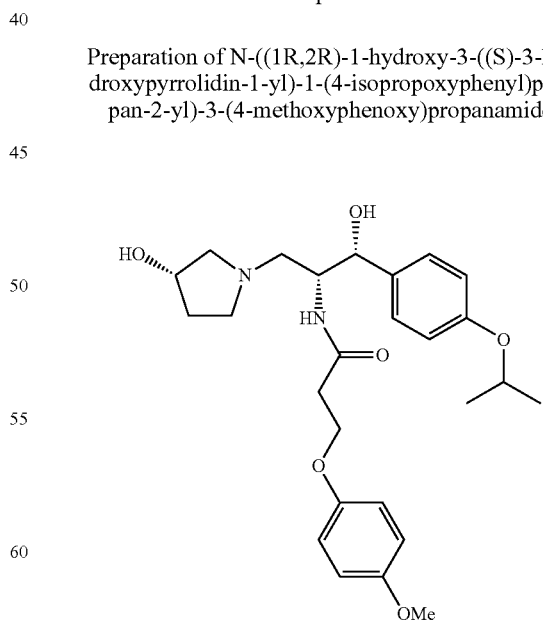

¹H NMR (CDCl₃, 400 mHz, ppm): 1.35 (d, 6H), 1.7 (m, 1H), 2.1 (m, 1H), 2.45 (m, 1H), 2.55 (t, 2H), 2.7-2.9 (m, 4H), 3.0 (m, 1H), 3.8 (s, 3H), 4.05 (m, 1H), 4.15 (m, 1H), 4.20 (m, 1H), 4.35 (m, 1H), 4.5 (m, 1H), 4.95 (d, 1H), 6.55 (br, 1H), 6.75-6.85 (m, 6H), 7.2 (m, 2H). M/Z for $C_{26}H_{36}N_2O_6$ [M+H]=473.

Example 2E93

Preparation of N-((1R,2R)-1-(4-(4-fluorobutoxy)phenyl)-1-hydroxy-3-((R)-3-hydroxypyrrolidin-1-yl)propan-2-yl)-5-(4-methoxyphenyl)-5-oxopentanamide

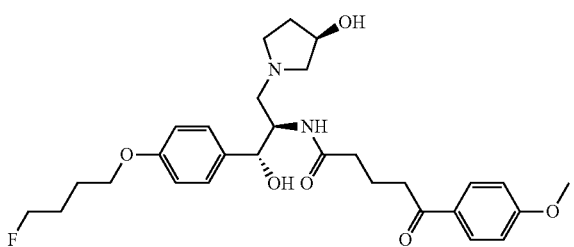 [SMILES: COc1ccc(C(=O)CCCC(=O)N[C@H](CN2CC[C@@H](O)C2)[C@H](O)c2ccc(OCCCCF)cc2)cc1]

$^1$H NMR (400 MHz, CDCl$_3$) δ=1.7-2.2 (m, 12H), 2.4 (dd, 1H), 2.65-2.9 (m, 6H), 3.0 (dd, 1H), 3.90 (s, 3H), 3.91 (dd, 2H), 4.1-4.22 (m, 1H), 4.3-4.4 (m, 1H), 4.4 (dd, 1H), 4.6 (dd, 1H), 4.91 (d, 1H), 6.19 (d, 1H), 6.83 (d, 2H), 6.92 (d, 2H), 7.22 (d, 2H), 7.9 (d, 2H); MS for $C_{29}H_{39}FN_2O_6$ m/z 531 [M+H].

Example 2E94

Preparation of N-((1R,2R)-1-(4-(4-fluorobutoxy)phenyl)-1-hydroxy-3-((R)-3-hydroxypyrrolidin-1-yl)propan-2-yl)-8-methoxyoctanamide

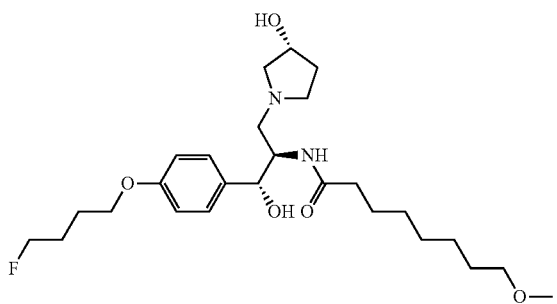 [SMILES: COCCCCCCCC(=O)N[C@H](CN1CC[C@@H](O)C1)[C@H](O)c1ccc(OCCCCF)cc1]

$^1$H NMR (400 MHz, CDCl$_3$) δ=1.2-1.34 (m, 6H), 1.45-1.6 (m, 4H), 1.7-1.8 (m, 1H), 1.86-1.95 (m, 4H), 2.0-2.2 (m, 4), 2.4-2.5 (m, 2H), 2.7-2.8 (m, 4H), 2.98 (dd, 1H), 3.3 (s, 3H), 3.53 (dd, 1H), 4.0 (dd, 2H), 4.1-4.2 (m, 1H), 4.3-4.4 (m, 1H), 4.5 (dd, 1H), 4.58 (dd, 1H), 4.9 (d, 1H), 5.9 (d, 1H), 6.85 (d, 2H), 7.22 (d, 2H); MS for $C_{26}H_{43}FN_2O_5$ m/z 483 [M+H]

Example 2E95

Preparation of N-((1R,2R)-1-(4-(4-fluorobutoxy)phenyl)-1-hydroxy-3-((R)-3-hydroxypyrrolidin-1-yl)propan-2-yl)-4-(4-methoxyphenoxy)butanamide

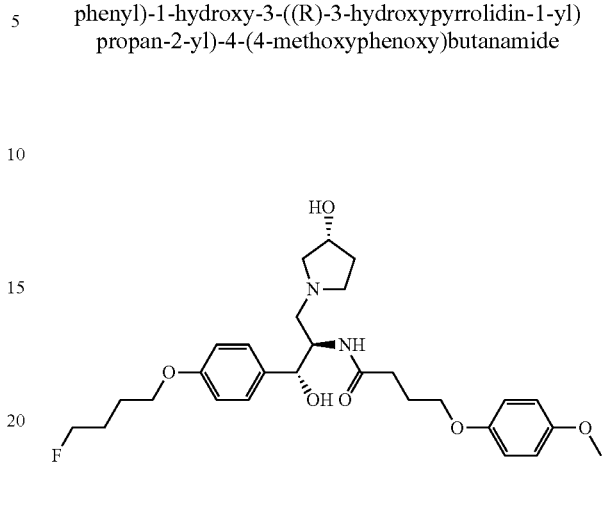

$^1$H NMR (400 MHz, CDCl$_3$) δ=1.6-2.2 (m, 9H), 2.3-2.5 (m, 4H), 2.6-2.8 (m, 5), 2.9 (dd, 1H), 3.7 (s, 3H), 3.85 (dd, 2H), 3.95 (dd, 2H), 4.2-4.3 (m, 2H), 4.5 (dd, 1H), 4.6 (dd, 1H), 4.9 (d, 1H), 6.0 (d, 1H), 6.7-7 (m, 6H), 7.1-7.2 (d, 2H); MS for $C_{28}H_{39}FN_2O_6$ m/z 519 [M+H].

Example 2E96

Preparation of N-((1R,2R)-1-(4-(4-fluorobutoxy)phenyl)-1-hydroxy-3-((R)-3-hydroxypyrrolidin-1-yl)propan-2-yl)-3-(4-methoxyphenoxy)propanamide

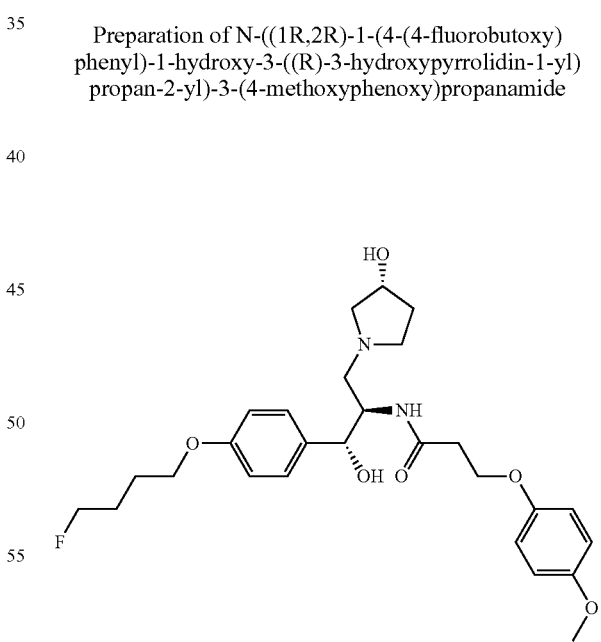

$^1$H NMR (400 MHz, CDCl$_3$) δ=1.6-1.7 (m, 1H), 1.8-2 (m, 4H), 2.1-2.2 (m, 1), 2.4-2.5 (m, 1H), 2.6 (t, 2H), 2.7-2.85 (m, 4H), 3.0 (dd, 1H), 3.7 (s, 3H), 4.0 (t, 2H), 4.1-4.3 (m, 4H), 4.5 (dd, 1H), 4.6 (dd, 1H), 4.98 (d, 1H), 6.6 (d, 1H), 6.7-6.9 (m, 6H), 7.1-7.22 (d, 2H); MS for $C_{27}H_{37}FN_2O_6$ m/z 505 [M+H].

Example 2E97

Preparation of N-((1R,2R)-1-(4-(4-fluorobutoxy)phenyl)-1-hydroxy-3-((R)-3-hydroxypyrrolidin-1-yl)propan-2-yl)-7-(4-methoxyphenyl)-7-oxoheptanamide

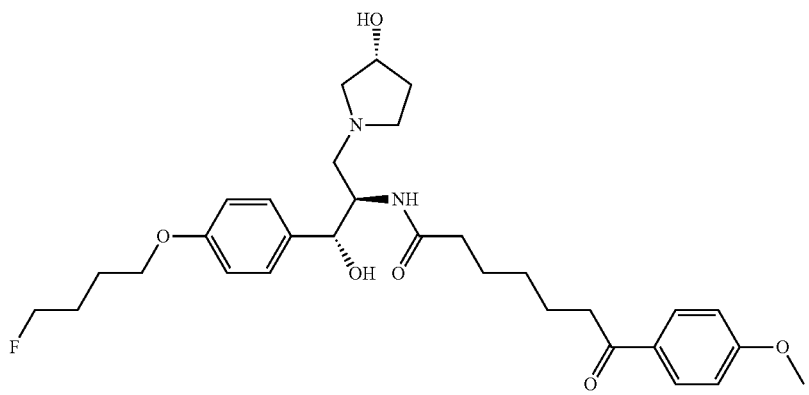 [SMILES: COc1ccc(C(=O)CCCCCC(=O)N[C@H](CN2CC[C@@H](O)C2)[C@H](O)c2ccc(OCCCCF)cc2)cc1]

$^1$H NMR (400 MHz, CDCl$_3$) δ=1.1-1.4 (m, 3H), 1.5-2.0 (m, 12H), 2.1-2.2 (dd, 4H), 2.4-2.90 (m, 10H), 3.0 (dd, 1H), 3.75 (s, 3H), 3.9 (dd, 2H), 4.1-4.2 (m, 1H), 4.3-4.4.5 (m, 2H), 4.57 (dd, 1H), 4.9 (d, 1H), 5.9 (d, 1H), 6.8 (d, 2H), 6.9 (d, 2H), 7.2 (d, 2H), 7.9 (d, 2H); MS for C$_{31}$H$_{43}$FN$_2$O$_6$ m/z 559 [M+H].

Example 2E98

Preparation of N-((1R,2R)-1-(4-(4-fluorobutoxy)phenyl)-1-hydroxy-3-((R)-3-hydroxypyrrolidin-1-yl)propan-2-yl)-6-(4-methoxyphenyl)-6-oxohexanamide

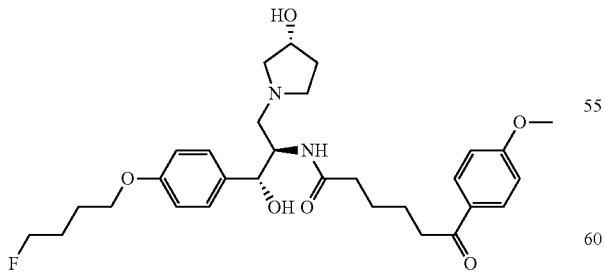

$^1$H NMR (400 MHz, CD$_3$OD) δ=1.4-1.6 (m, 4H), 1.6-1.8 (m, 5H), 2.0-2.2 (m, 1H), 2.2-2.3 (m, 2H), 2.4-2.6 (m, 3H), 2.7-3.0 (m, 5H), 3.8 (s, 3H), 3.9 (dd, 1H), 4.1-4.25 (m, 1H), 4.3-4.38 (m, 1H), 4.4 (dd, 1H), 4.5 (dd, 1H), 6.8 (d, 2H), 7.1 (d, 2H), 7.2 (d, 2H), 8 (d, 2H); MS for C$_{30}$R$_{41}$FN$_2$O$_6$ m/z 545 [M+H]

Example 2E99

Preparation of N-((1S,2R)-1-(5-chlorothiophen-2-yl)-1-hydroxy-3-(pyrrolidin-1-yl)propan-2-yl)-3-(4-methoxyphenoxy)propanamide

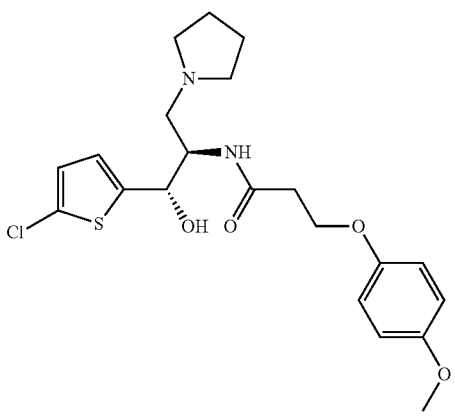 [SMILES: COc1ccc(OCCC(=O)N[C@H](CN2CCCC2)[C@H](O)c2ccc(Cl)s2)cc1]

$^1$H NMR (400 MHz, CDCl$_3$) δ=1.7 (broad s, 4H), 2.5-2.7 (m, 7H), 2.8 (dd, 1H), 2.94 (dd, 1H), 3.77 (s, 3H), 4.1-4.2 (m, 2H), 4.3-4.35 (m, 1H), 5.18 (d, 1H), 6.55 (d, 1H), 6.66 (d, 1H), 6.67 (d, 1H), 6.7-6.9 (m, 4H); MS for C$_{21}$H$_{27}$ClN$_2$O$_4$S m/z 439 [M+H].

Example 2E100

Preparation of N-((1S,2R)-1-hydroxy-1-(3-methylthiophen-2-yl)-3-(pyrrolidin-1-yl)propan-2-yl)-3-(4-methoxyphenoxy)propanamide 2,2,2-trifluoroacetate

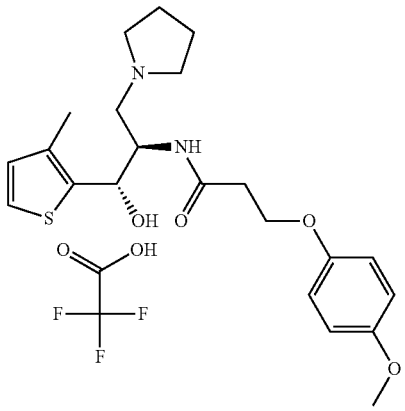

$^1$H NMR (400 MHz, CD$_3$OD) δ=1.8-2.2 (m, 4H), 2.24 (s, 3H), 2.5-2.8 (m, 2H), 3.0-3.2 (m, 2H), 3.5 (dd, 2H), 3.7 (s, 3H), 3.6-3.8 (m, 2H), 4.0-4.2 (m, 2H), 4.5 (dd, 1H), 5.2 (s, 1H), 6.8 (d, 1H), 6.84 (broad s, 4H), 7.2 (d, 1H); MS for C$_{22}$H$_{30}$N$_2$O$_4$S m/z 419 [M+H].

Example 2E101

Preparation of Compound 257

N-((1R,2R)-1-(2,3-dihydrobenzo[β][1,4]dioxin-6-yl)-1-hydroxy-3-morpholinopropan-2-yl)-3-(4-methoxyphenoxy)propanamide

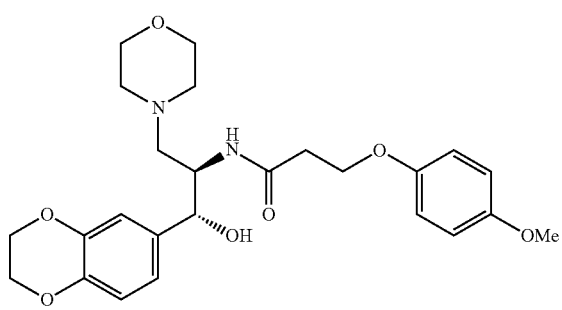 [SMILES: COc1ccc(OCCC(=O)N[C@H](CN2CCOCC2)[C@H](O)c2ccc3c(c2)OCCO3)cc1]

$^1$H NMR (400 MHz, CDCl$_3$) δ=2.4-2.6 (m, 7H), 2.7 (dd, 1H), 3.5-3.7 (m, 4H), 3.8 (s, 3H), 4-4.2 (m, 2H), 4.2 (s, 4H), 4.2-4.3 (m, 1H), 4.9 (d, 1H), 6.5 (d, 1H), 6.7-6.9 (m, 7H); MS for C$_{25}$H$_{32}$N$_2$O$_7$ m/z 473.1 [M+H].

Example 2E102

Preparation of Compound 261

N-((1R,2R)-1-(2,3-dihydrobenzo[β][1,4]dioxin-6-yl)-1-hydroxy-3-(piperidin-1-yl)propan-2-yl)-3-(4-methoxyphenoxy)propanamide

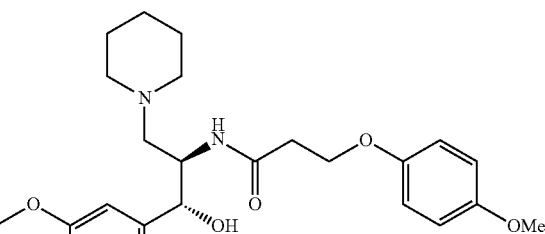

$^1$H NMR (400 MHz, CDCl$_3$) δ=1.4 (br, 2H), 1.6 (br, 4H), 2.2-2.8 (m, 6H), 3.8 (s, 3H), 4.0-4.2 (m, 2H), 4.2 (s, 4H), 4.2-4.3 (m, 1H), 4.9 (s, 1H), 6.4 (d, 1H), 6.7-6.9 (m, 7H); MS for C$_{25}$H$_{34}$N$_2$O$_6$ m/z 471.1 [M+H].

Example 2B1

Preparation of Compound 6

1-benzyl-3-((1R,2R)-1-(2,3-dihydrobenzo[β][1,4]dioxin-6-yl)-1-hydroxy-3-(pyrrolidin-1-yl)propan-2-yl)urea

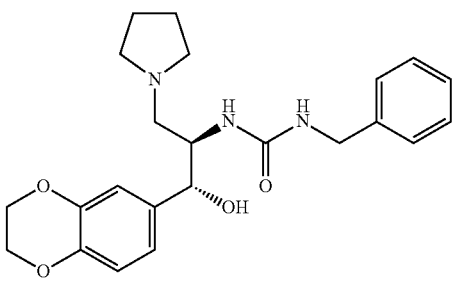 [SMILES: O=C(NCc1ccccc1)N[C@H](CN1CCCC1)[C@H](O)c1ccc2c(c1)OCCO2]

$^1$H NMR (400 MHz, CDCl$_3$) δ=1.7 (s, 4H), 2.4-2.6 (m, 5H), 2.6-2.7 (dd, 1H), 4.0 (m, 1H), 4.2 (s, 4H), 4.3 (m, 2H), 4.8 (d, 1H), 4.86 (d, 1H), 5.0 (br, 1H), 6.6-6.9 (m, 3H), 7.2-7.4 (m, 5H); MS for C$_{23}$H$_{29}$N$_3$O$_4$ m/z 412.2 [M+H].

Example 2B2

Preparation of Compound 17

1-((1R,2R)-1-(2,3-dihydrobenzo[β][1,4]dioxin-6-yl)-1-hydroxy-3-(pyrrolidin-1-yl)propan-2-yl)-3-(4-fluorobenzyl)urea

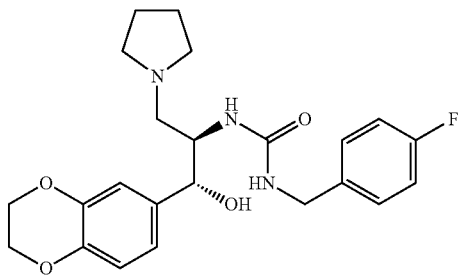 [SMILES: O=C(NCc1ccc(F)cc1)N[C@H](CN1CCCC1)[C@H](O)c1ccc2c(c1)OCCO2]

$^1$H NMR (400 MHz, CDCl$_3$) δ=1.6 (s, 4H), 2.4-2.6 (m, 6H), 3.9 (m, 1H), 4.0-4.1 (m, 2H), 4.13 (s, 4H), 4.7 (d, 1H), 5.4 (d, 1H), 6.6-7.1 (m, 7H); MS for C$_{23}$H$_{28}$FN$_3$O$_4$ m/z 430.2 [M+H].

Example 2B3

Preparation of Compound 40

1-(4-bromobenzyl)-3-((1R,2R)-1-(2,3-dihydrobenzo[β][1,4]dioxin-6-yl)-1-hydroxy-3-(pyrrolidin-1-yl)propan-2-yl)urea

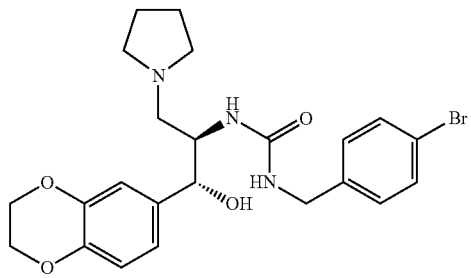 [SMILES: O=C(NCc1ccc(Br)cc1)N[C@H](CN1CCCC1)[C@H](O)c1ccc2c(c1)OCCO2]

$^1$H NMR (400 MHz, CDCl$_3$) δ=1.7 (s, 4H), 2.4-2.8 (m, 6H), 4.0 (m, 1H), 4.1-4.2 (m, 2H), 4.2 (s, 4H), 4.8 (d, 1H), 5.3 (d, 1H), 5.6-5.8 (br, 1H), 6.8-7.0 (m, 3H), 7.0 (d, 2H), 7.4 (d, 2H); MS for C$_{23}$H$_{28}$BrN$_3$O$_4$ m/z 490 [M], 491 [M+H], 492 [M+2].

Example 2B4

Preparation of Compound 41

1-((1R,2R)-1-(2,3-dihydrobenzo[β][1,4]dioxin-6-yl)-1-hydroxy-3-(pyrrolidin-1-yl)propan-2-yl)-3-(4-methoxybenzyl)urea

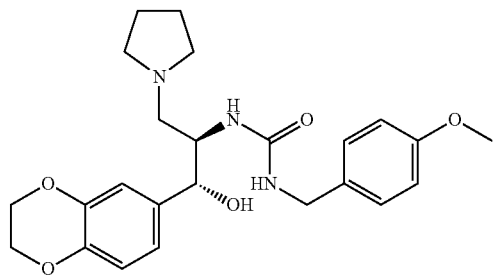 [SMILES: COc1ccc(CNC(=O)N[C@H](CN2CCCC2)[C@H](O)c2ccc3c(c2)OCCO3)cc1]

$^1$H NMR (400 MHz, CDCl$_3$) δ=1.6 (s, 4H), 2.4-2.6 (m, 6H), 3.7 (s, 3H), 3.9 (m, 1H), 4.1 (d, 2H), 4.2 (s, 4H), 4.7 (d, 1H), 5.2 (d, 1H), 5.5-5.7 (br, 1H), 6.6-6.8 (m, 5H), 7.1 (d, 2H); MS for C$_{24}$H$_{31}$N$_3$O$_5$ m/z 442.2 [M+H].

Example 2B5

Preparation of Compound 80

1-((1R,2R)-1-(2,3-dihydrobenzo[β][1,4]dioxin-6-yl)-1-hydroxy-3-(pyrrolidin-1-yl)propan-2-yl)-3-(3-methoxybenzyl)urea

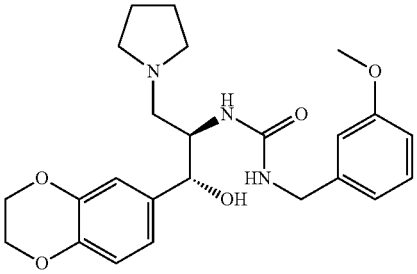 [SMILES: COc1cccc(CNC(=O)N[C@H](CN2CCCC2)[C@H](O)c2ccc3c(c2)OCCO3)c1]

$^1$H NMR (400 MHz, CDCl$_3$) δ=1.7 (s, 4H), 2.4-2.6 (m, 6H), 3.8 (s, 3H), 4.0 (m, 1H), 4.1-4.2 (s, 6H), 4.8 (d, 1H), 5.1 (d, 1H), 5.2-5.4 (br, 1H), 6.6-6.8 (m, 6H), 7.2 (dd, 1H); MS for C$_{24}$H$_{31}$N$_3$O$_5$ m/z 442.2 [M+H].

Example 2B6

Preparation of Compound 42

1-((1R,2R)-1-(2,3-dihydrobenzo[β][1,4]dioxin-6-yl)-1-hydroxy-3-(pyrrolidin-1-yl)propan-2-yl)-3-(4-methylbenzyl)urea

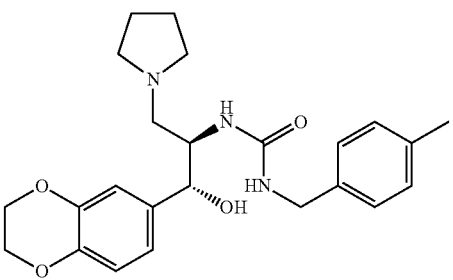 [SMILES: Cc1ccc(CNC(=O)N[C@H](CN2CCCC2)[C@H](O)c2ccc3c(c2)OCCO3)cc1]

$^1$H NMR (400 MHz, CDCl$_3$) δ=1.6 (s, 4H), 2.3 (s, 3H), 2.4-2.6 (m, 6H), 4.0 (m, 1H), 4.2 (d, 2H), 4.21 (s, 4H), 4.7 (d, 1H), 5.2 (d, 1H), 5.4-5.6 (br, 1H), 6.7-7.1 (m, 7H); MS (for C$_{24}$H$_{31}$N$_3$O$_4$ m/z 426.2 [M+H].

Example 2B7

Preparation of Compound 43

1-(4-chlorobenzyl)-3-(1R,2R)-1-(2,3-dihydrobenzo[β][1,4]dioxin-6-yl)-1-hydroxy-3-(pyrrolidin-1-yl)propan-2-yl)urea

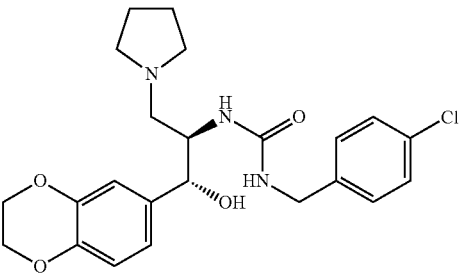 [SMILES: O=C(NCc1ccc(Cl)cc1)N[C@H](CN1CCCC1)[C@H](O)c1ccc2c(c1)OCCO2]

$^1$H NMR (400 MHz, CDCl$_3$) δ=1.7 (s, 4H), 2.5-2.7 (m, 6H), 4.0 (m, 1H), 4.2 (s, 6H), 4.8 (d, 1H), 5.2 (d, 1H), 5.4-5.5

(br, 1H), 6.7-6.9 (m, 3H), 7.1 (d, 2H), 7.3 (d, 2H); MS for $C_{23}H_{28}N_3ClO_4$ m/z 446 [M+H], 447.5 [M+2].

Example 2B8

Preparation of Compound 10

1-((1R,2R)-1-(2,3-dihydrobenzo[β][1,4]dioxin-6-yl)-1-hydroxy-3-(pyrrolidin-1-yl)propan-2-yl)-3-((S)-1-phenylethyl)urea

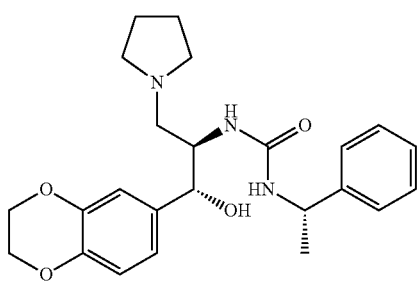 [SMILES: C[C@H](NC(=O)N[C@H](CN1CCCC1)[C@H](O)c1ccc2c(c1)OCCO2)c1ccccc1]

$^1$H NMR (400 MHz, CDCl$_3$) δ=1.4 (d, 3H), 1.6 (s, 4H), 2.2-2.5 (m, 4H), 2.5 (dd, 1H), 2.6 (dd, 1H), 3.9 (m, 1H), 4.2 (s, 4H), 4.5 (m, 1H), 4.8 (d, 1H), 5.0 (d, 1H), 5.1-5.3 (br, 1H), 6.6-6.9 (m, 3H), 7.2-7.4 (m, 5H); MS for $C_{24}H_{31}N_3O_4$ m/z 426.2 [M+H].

Example 2B9

Preparation of Compound 286

1-((1R,2R)-1-(2,3-dihydrobenzo[β][1,4]dioxin-6-yl)-1-hydroxy-3-(pyrrolidin-1-yl)propan-2-yl)-3-(®1-phenylethyl)urea

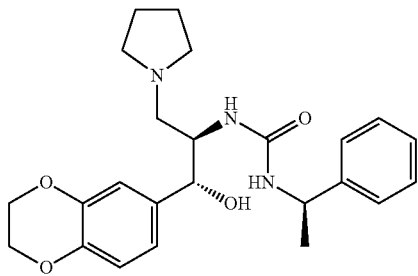 [SMILES: C[C@@H](NC(=O)N[C@H](CN1CCCC1)[C@H](O)c1ccc2c(c1)OCCO2)c1ccccc1]

$^1$H NMR (400 MHz, CDCl$_3$) δ=1.3 (d, 3H), 1.7 (s, 4H), 2.2-2.6 (m, 6H), 3.9 (m, 1H), 4.2 (s, 4H), 4.6-4.7 (m, 2H), 5.3 (d, 1H), 5.6-5.7 (br, 1H), 6.6 (d, 1H), 6.7 (d, 1H), 6.8 (s, 1H), 7.2-7.4 (m, 5H); MS for $C_{24}H_{31}N_3O_4$ m/z 426.0 [M+H].

Example 2B10

Preparation of Compound 69

1-((1R,2R)-1-(2,3-dihydrobenzo[β][1,4]dioxin-6-yl)-1-hydroxy-3-(pyrrolidin-1-yl)propan-2-yl)-3-(naphthalen-2-yl)urea

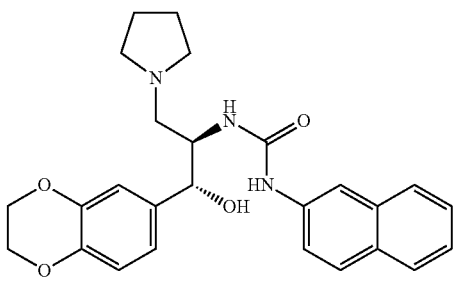 [SMILES: O=C(Nc1ccc2ccccc2c1)N[C@H](CN1CCCC1)[C@H](O)c1ccc2c(c1)OCCO2]

$^1$H NMR (400 MHz, CDCl$_3$) δ=1.6 (s, 4H), 2.4-2.8 (m, 6H), 4.1 (s, 5H), 4.8 (s, 1H), 6.0 (d, 1H), 6.7 (s, 2H), 6.9 (s, 1H), 7.1-7.8 (m, 7H); MS for $C_{26}H_{29}N_3O_4$ m/z 448.1 [M+H].

Example 2B11

Preparation of Compound 288

1-((1R,2R)-1-(2,3-dihydrobenzo[β][1,4]dioxin-6-yl)-1-hydroxy-3-(pyrrolidin-1-yl)propan-2-yl)-3-(naphthalen-1-yl)urea

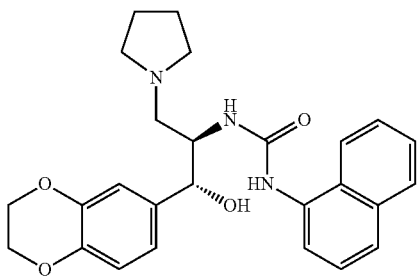 [SMILES: O=C(Nc1cccc2ccccc12)N[C@H](CN1CCCC1)[C@H](O)c1ccc2c(c1)OCCO2]

$^1$H NMR (400 MHz, CDCl$_3$) δ=1.6 (s, 4H), 2.4 (s, 4H), 2.6 (d, 2H), 4.1 (m, 1H), 4.2 (s, 4H), 4.8 (d, 1H), 5.4 (d, 1H), 6.5 (d, 1H), 6.6 (d, 1H), 6.7 (s, 1H), 7.2-7.6 (m, 3H), 7.7 (d, 1H), 7.8 (d, 1H), 8.0 (d, 1H); MS for $C_{26}H_{29}N_3O_4$ m/z 448.1 [M+H].

Example 2B12

Preparation of Compound 71

1-((1R,2R)-1-(2,3-dihydrobenzo[β][1,4]dioxin-6-yl)-1-hydroxy-3-(pyrrolidin-1-yl)propan-2-yl)-3-((S)-1-(naphthalen-1-yl)ethyl)urea

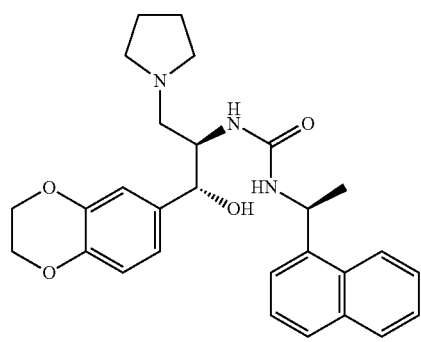 [SMILES: C[C@H](NC(=O)N[C@H](CN1CCCC1)[C@H](O)c1ccc2c(c1)OCCO2)c1cccc2ccccc12]

$^1$H NMR (400 MHz, CDCl$_3$) δ=1.4 (s, 4H), 1.5 (d, 3H), 2.3 (s, 4H), 2.4 (dd, 1H), 2.6 (dd, 1H), 3.9 (br, 1H), 4.2 (s, 4H), 4.7 (s, 1H), 5.0 (d, 1H), 5.3 (br, 1H), 5.5 (br, 1H), 6.6 (m, 3H), 7.4-7.6 (m, 4H), 7.7 (d, 1H), 7.8 (d, 1H), 8.1 (d, 1H); MS for C$_{28}$H$_{33}$N$_3$O$_4$ m/z 476.2 [M+H].

Example 2B13

Preparation of Compound 70

1-(biphenyl-4-yl)-3-((1R,2R)-1-(2,3-dihydrobenzo[β][1,4]dioxin-6-yl)-1-hydroxy-3-(pyrrolidin-1-yl)propan-2-yl)urea

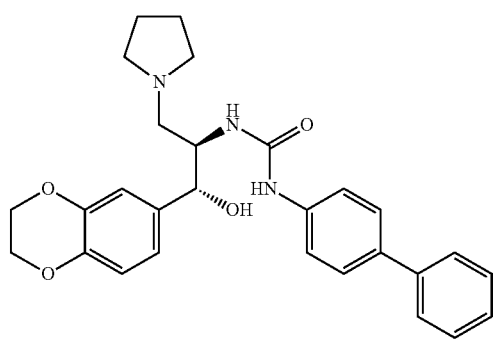 [SMILES: O=C(Nc1ccc(-c2ccccc2)cc1)N[C@H](CN1CCCC1)[C@H](O)c1ccc2c(c1)OCCO2]

$^1$H NMR (400 MHz, CDCl$_3$) δ=1.7 (s, 4H), 2.6-2.8 (m, 6H), 4.1 (br, 1H), 4.2 (s, 4H), 4.9 (br, 1H), 5.9 (d, 1H), 6.8 (s, 2H), 6.9 (s, 1H), 7.2-7.6 (m, 9H); for C$_{28}$H$_{31}$N$_3$O$_4$ m/z 474.1 [M+H].

Example 2B14

Preparation of Compound 81

1-((1R,2R)-1-(2,3-dihydrobenzo[β][1,4]dioxin-6-yl)-1-hydroxy-3-(pyrrolidin-1-yl)propan-2-yl)-3-(4-(trifluoromethyl)phenyl)urea

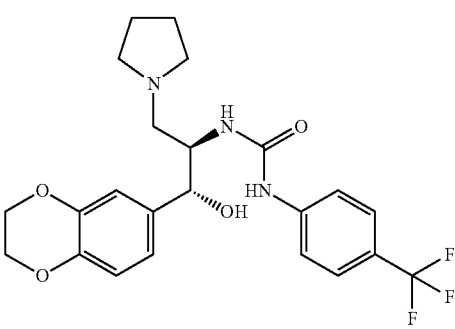 [SMILES: O=C(Nc1ccc(C(F)(F)F)cc1)N[C@H](CN1CCCC1)[C@H](O)c1ccc2c(c1)OCCO2]

$^1$H NMR (400 MHz, CDCl$_3$) δ=1.7 (s, 4H), 2.4-2.7 (m, 6H), 4.0 (br, 1H), 4.2 (s, 4H), 4.8 (br, 1H), 5.9 (br, 1H), 6.8 (s, 2H), 6.9 (s, 1H), 7.3 (d, 2H), 7.5 (d, 2H); MS for C$_{23}$H$_{26}$F$_3$N$_3$O$_4$ m/z 465.97 [M+H].

Example 2B15

Preparation of Compound 68

1-((1R,2R)-1-(2,3-dihydrobenzo[β][1,4]dioxin-6-yl)-1-hydroxy-3-(pyrrolidin-1-yl)propan-2-yl)-3-(3-(trifluoromethyl)phenyl)urea

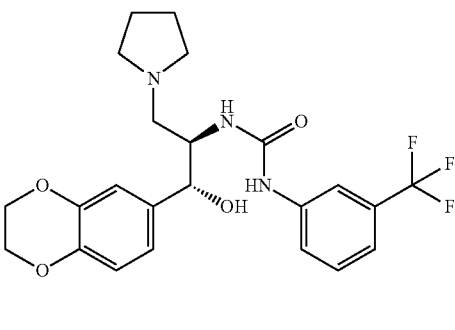 [SMILES: O=C(Nc1cccc(C(F)(F)F)c1)N[C@H](CN1CCCC1)[C@H](O)c1ccc2c(c1)OCCO2]

$^1$H NMR (400 MHz, CDCl$_3$) δ=1.7 (s, 4H), 2.5-2.9 (m, 6H), 4.0 (br, 1H), 4.2 (s, 4H), 4.8 (br, 1H), 5.9 (br, 1H), 6.8 (s, 2H), 6.9 (s, 1H), 7.2-7.6 (m, 4H); MS for C$_{23}$H$_{26}$F$_3$N$_3$O$_4$ m/z 466.0 [M+H].

Example 2B16

Preparation of Compound 82

1-((1R,2R)-1-(2,3-dihydrobenzo[β][1,4]dioxin-6-yl)-1-hydroxy-3-(pyrrolidin-1-yl)propan-2-yl)-3-(4-(trifluoromethoxy)phenyl)urea

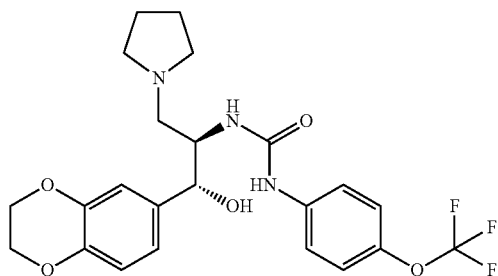 [SMILES: O=C(Nc1ccc(OC(F)(F)F)cc1)N[C@H](CN1CCCC1)[C@H](O)c1ccc2c(c1)OCCO2]

$^1$H NMR (400 MHz, CDCl$_3$) δ=1.7 (s, 4H), 2.4-2.7 (m, 6H), 4.0 (br, 1H), 4.2 (s, 4H), 4.8 (br, 1H), 5.9 (br, 1H), 6.8 (s, 2H), 6.9 (s, 1H), 7.0 (d, 2H), 7.2 (d, 2H); MS for C$_{23}$H$_{26}$F$_3$N$_3$O$_5$ m/z 481.5 [M], 482.5 [M+H].

Example 2B17

Preparation of Compound 133

1-((1R,2R)-1-(2,3-dihydrobenzo[β][1,4]dioxin-6-yl)-1-hydroxy-3-(pyrrolidin-1-yl)propan-2-yl)-3-(4-(2-methylthiazol-4-yl)phenyl)urea

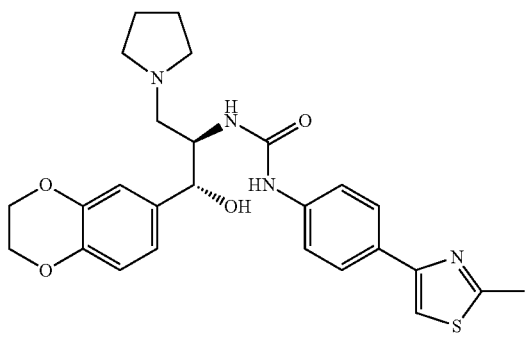 [SMILES: Cc1nc(-c2ccc(NC(=O)N[C@H](CN3CCCC3)[C@H](O)c3ccc4c(c3)OCCO4)cc2)cs1]

$^1$H NMR (400 MHz, CDCl$_3$) δ=1.7 (s, 4H), 2.4-2.7 (m, 6H), 2.7 (s, 3H), 4.1 (br, 1H), 4.2 (s, 4H), 4.8 (br, 1H), 5.9 (d, 1H), 6.8 (s, 2H), 6.9 (s, 1H), 7.2 (s, 1H), 7.3 (d, 2H), 7.7 (d, 2H); MS for C$_{26}$H$_{30}$N$_4$O$_4$S m/z 494.9 [M+H].

Example 2B18

Preparation of Compound 7

1-((1R,2R)-1-(2,3-dihydrobenzo[β][1,4]dioxin-6-yl)-1-hydroxy-3-(pyrrolidin-1-yl)propan-2-yl)-3-dodecylurea

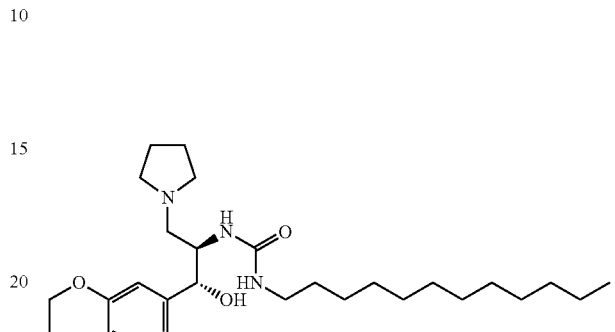

$^1$H NMR (400 MHz, CDCl$_3$) δ=0.9 (t, 3H), 1.3 (br, 18H), 1.4 (m, 2H), 1.8 (s, 4H), 2.5-2.7 (m, 6H), 3.1 (q, 2H), 4.0 (m, 1H), 4.3 (s, 4H), 4.4 (br, 1H), 4.76 (d, 1H), 4.8 (d, 1H), 6.7-6.8 (dd, 2H), 6.9 (s, 1H); MS for C$_{28}$H$_{47}$N$_3$O$_4$ m/z 489.7 [M+H], 490.9 [M+2].

Example 2B19

Preparation of Compound 287

1-((1R,2R)-1-(2,3-dihydrobenzo[β][1,4]dioxin-6-yl)-1-hydroxy-3-(pyrrolidin-1-yl)propan-2-yl)-3-(2-(thiophen-2-yl)ethyl)urea

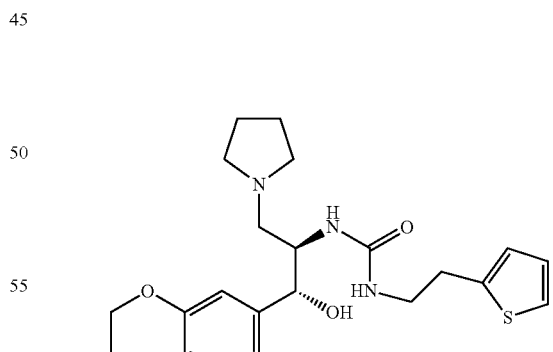

$^1$H NMR (400 MHz, CDCl$_3$) δ=1.7 (s, 4H), 2.5-2.7 (m, 6H), 3.0 (t, 2H), 3.8 (q, 2H), 4.0 (m, 1H), 4.2 (s, 4H), 4.8 (d, 2H), 4.9 (d, 1H), 6.7-6.8 (m, 3H), 6.9 (d, 1H), 6.9 (dd-1H), 7.1 (d, 1H); MS for C$_{22}$H$_{29}$N$_3$O4S m/z 432.1 [M+H].

Example 2B20

Preparation of 1-((1R,2R)-1-(4-(4-fluorobutoxy)phenyl)-1-hydroxy-3-((R)-3-hydroxypyrrolidin-1-yl)propan-2-yl)-3-(4-methoxybenzyl)urea 2,2,2-trifluoroacetate

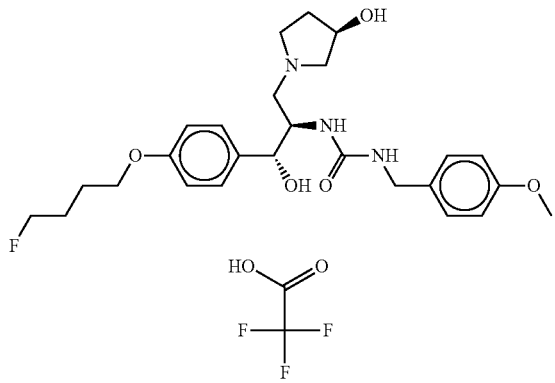

$^1$H NMR (400 MHz, CD$_3$OD) δ=1.8-2.2 (m, 6H), 3.2-3.3 (dd, 2H), 3.4-3.7 (m, 3H), 3.8 (s, 3H), 3.82-4.1 (m, 4H), 4.3 (dd, 2H), 4.4 (dd, 1H), 4.5 (dd, 2H), 4.8 (dd, 1H), 6.8 (d, 2H), 6.9 (d, 2H), 7 (m, 2H), 7.3 (d, 2H); MS for C$_{26}$H$_{36}$FN$_3$O$_5$ m/z 491 [M+H].

Example 2B21

Preparation of 1-(4-chlorobenzyl)-3-((1R,2R)-1-(4-(4-fluorobutoxy)phenyl)-1-hydroxy-3-((R)-3-hydroxypyrrolidin-1-yl)propan-2-yl)urea

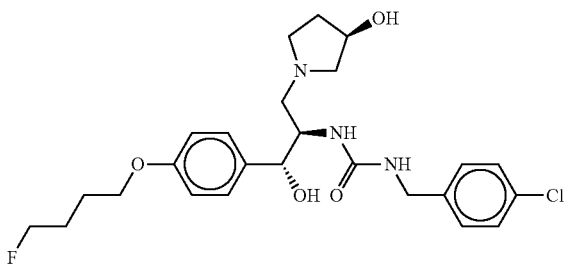

$^1$H NMR (400 MHz, CDCl$_3$) δ=1.6-1.8 (m, 3H), 1.8-2 (m, 5H), 2-2.2 (m, 2H), 2.2-2.3 (m, 2H), 2.8-2.4 (m, 5H), 2.9 (m, 1H), 3.9-4.0 (m, 3), 4.1-4.4 (m, 3H), 4.5 (t, 1H), 4.6-4.7 (m, 1H), 4.75 (d, 1H), 6.8 (d, 2H), 7.1 (d, 2H), 7.15-7.3 (m, 4H); MS for C$_{25}$H$_{33}$ClFN$_3$O$_4$ m/z 494 [M+H].

Example 3

GM3 Elisa Assay

B16-FO cells from ATCC (American Tissue Culture Collection) were grown in DMEM media (ATCC) with 10% Fetal Bovine Serum (Hyclone) and Pen/Step/Glutamine (Biowhittaker). 4000 cells per well were plated on collagen coated plates (BD) and allowed to attach for 6 hours in an incubator (37 degrees, 5% CO2). After 6 hours the compounds and controls were added to the wells, the plates mixed and returned to the incubator for 2 days. Day of assay the cells were fixed for 20 minutes with 1% formaldehyde and then washed with Tris Buffered Saline (TBS) 3 times, 150 μl of TBS was left in the wells and 50 μl of goat serum (Invitrogen) was added, the plates mixed and incubated for 1 hour at room temperature. The plates were flicked and the cells incubated with the monoclonal Antibody to GM3 (NeuAc) (Cosmo) for 45 minutes as room temperature. The plates were then washed 3 times with TBS, leaving 150 μl of TBS in the wells and Peroxidase AffinPure F (ab') 2 frag Gt Anti-mouse IgM, μ Chain Specific (Jackson Immuno Research) was added in 500, the plates mixed and incubated for 45 minutes at room temperature. The plates were washed 3 times with TBS, flicked and blotted and 100 μl of Quantablu (Pierce) was added to the wells and incubated for 1 hour then read on a Fluorometer at Ex 325 and Em 420. The data was then analyzed using standard programs.

The results of the GM3 Elisa assay are summarized in Tables 1 and 2. In Tables 1 and 2, IC50 values are indicated as "A," "B," "C," "D," and "E" for those of less than or equal to 0.1 μm; those of greater than 0.1 μm, and less than or equal to 1 μm; those of greater than 1 μm, and less than or equal to 3 μm; those of greater than 3 μm, and less than or equal to 10 μm; those of greater than 10 μm, respectively. As shown in Tables 1, 2 and 3, numerous compounds of the invention were shown to be inhibitors of GM3.

TABLE 1

| IC 50 Values from GM3 Elisa Assay | | |
|---|---|---|
| Z—R* | Compound | IC50_uM_Mean |
| 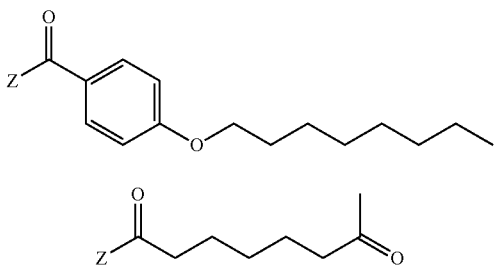 | 1 | B |
| | 2 | C |

TABLE 1-continued
IC 50 Values from GM3 Elisa Assay
| Z—R* | Compound | IC50_uM_Mean |
|---|---|---|
| 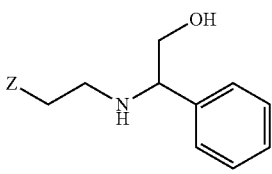 | 3 | C |
| 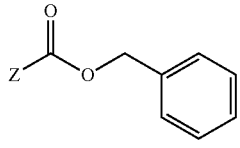 | 4 | B |
| 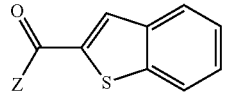 | 5 | B |
| 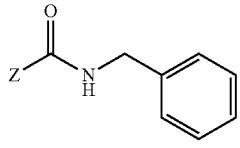 | 6 | B |
| 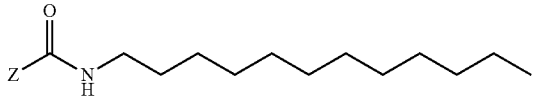 | 7 | A |
| 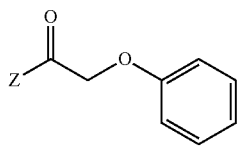 | 8 | B |
| 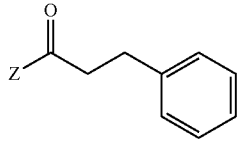 | 9 | B |
| 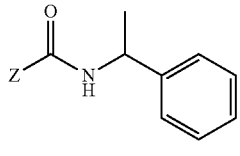 | 10 | B |
| 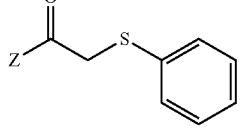 | 11 | A |

TABLE 1-continued
IC 50 Values from GM3 Elisa Assay
| Z—R* | Compound | IC50_uM_Mean |
|---|---|---|
| 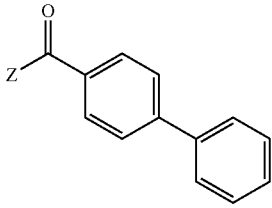 | 12 | B |
| 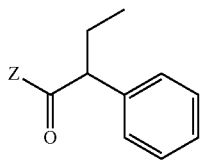 | 13 | B |
| 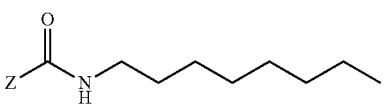 | 14 | B |
| 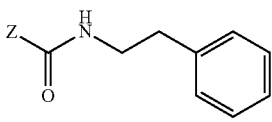 | 15 | B |
| 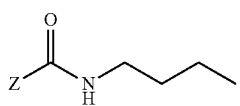 | 16 | D |
| 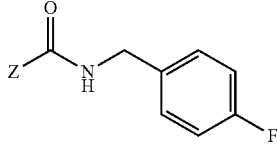 | 17 | A |
| 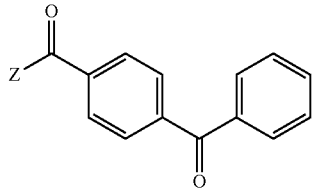 | 18 | B |
| 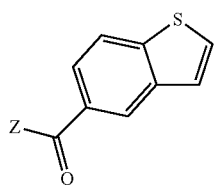 | 19 | B |
| 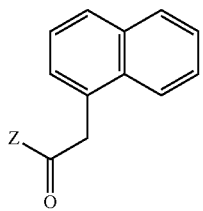 | 20 | B |

TABLE 1-continued
IC 50 Values from GM3 Elisa Assay
| Z—R* | Compound | IC50_uM_Mean |
|---|---|---|
| 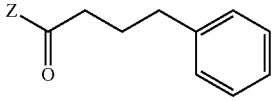 | 21 | A |
| 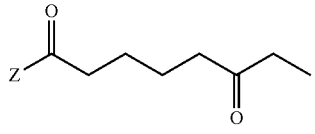 | 22 | C |
| 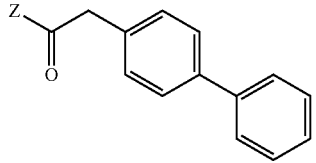 | 23 | A |
| 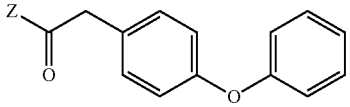 | 24 | B |
| 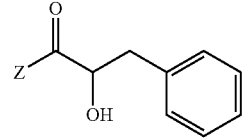 | 25 | B |
| 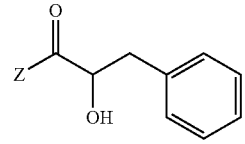 | 26 | B |
| 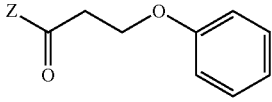 | 27 | A |
| 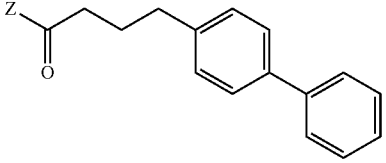 | 28 | A |
| 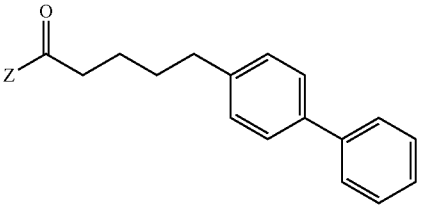 | 29 | A |
| 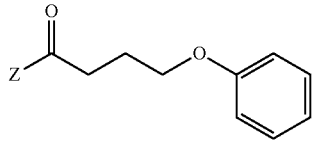 | 30 | B |

TABLE 1-continued
IC 50 Values from GM3 Elisa Assay
| Z—R* | Compound | IC50_uM_Mean |
|---|---|---|
| 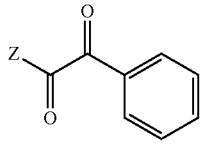 | 31 | B |
| 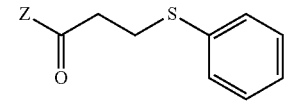 | 32 | A |
| 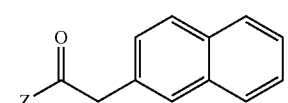 | 33 | A |
| 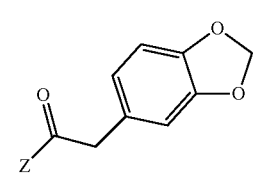 | 34 | C |
| 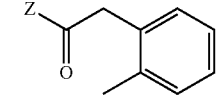 | 35 | C |
| 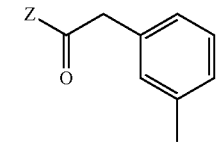 | 36 | B |
| 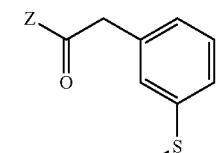 | 37 | B |
| 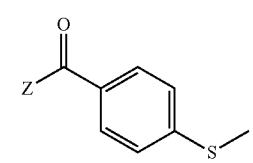 | 38 | B |
| 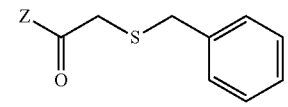 | 39 | A |
| 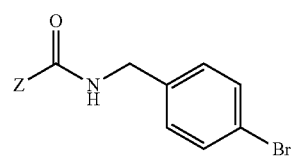 | 40 | A |

TABLE 1-continued
IC 50 Values from GM3 Elisa Assay
| Z—R* | Compound | IC50_uM_Mean |
|---|---|---|
| 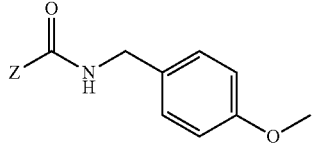 | 41 | A |
| 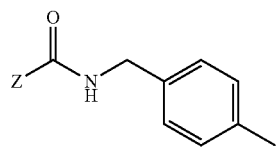 | 42 | A |
| 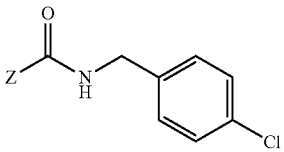 | 43 | A |
| 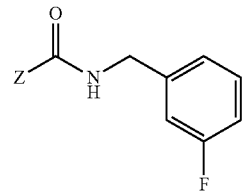 | 44 | B |
| 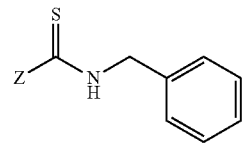 | 45 | B |
| 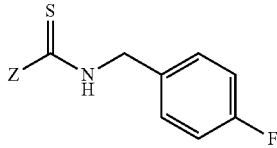 | 46 | B |
| 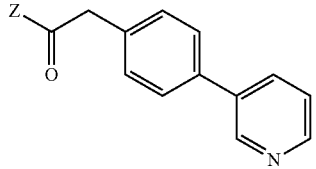 | 47 | B |
| 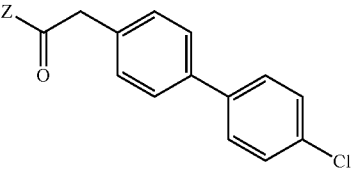 | 48 | A |

TABLE 1-continued
IC 50 Values from GM3 Elisa Assay
| Z—R* | Compound | IC50_uM_Mean |
|---|---|---|
| 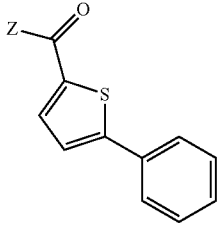 | 49 | A |
| 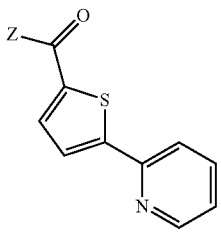 | 50 | B |
| 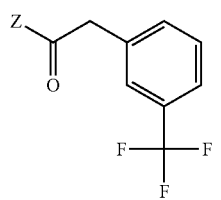 | 51 | B |
| 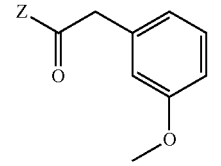 | 52 | B |
| 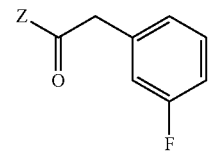 | 53 | C |
| 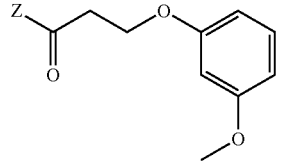 | 54 | A |
| 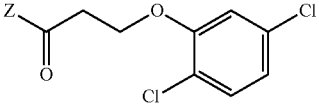 | 55 | A |
| 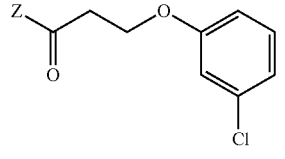 | 56 | A |

TABLE 1-continued
IC 50 Values from GM3 Elisa Assay
| Z—R* | Compound | IC50_uM_Mean |
|---|---|---|
| 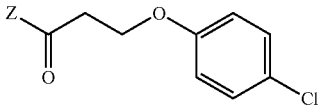 | 57 | A |
| 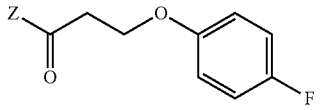 | 58 | B |
| 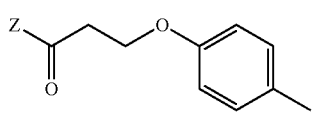 | 59 | A |
| 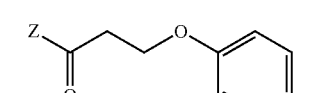 | 60 | A |
| 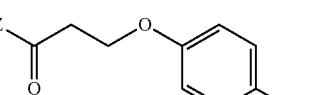 | 61 | A |
| 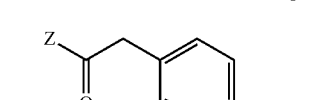 | 62 | B |
| 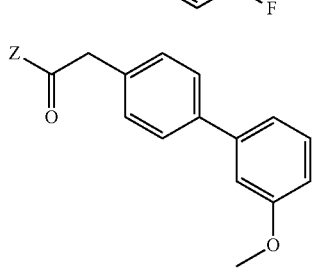 | 63 | A |
| 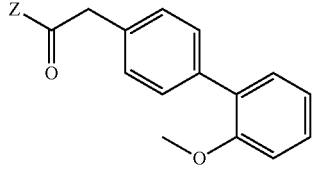 | 64 | A |
| 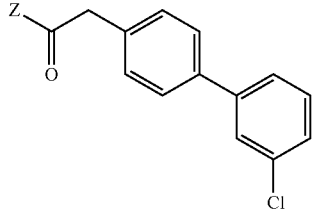 | 65 | A |
| 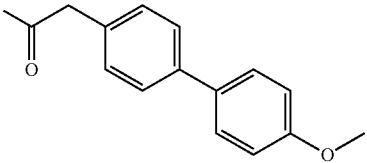 | 66 | A |

TABLE 1-continued
IC 50 Values from GM3 Elisa Assay
| Z—R* | Compound | IC50_uM_Mean |
|---|---|---|
| 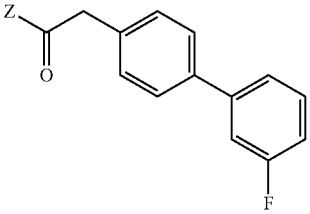 | 67 | A |
| 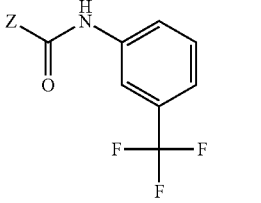 | 68 | B |
| 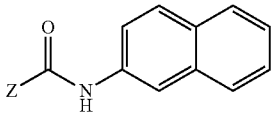 | 69 | B |
| 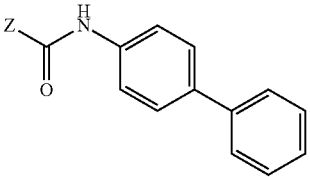 | 70 | A |
| 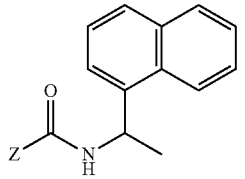 | 71 | B |
| 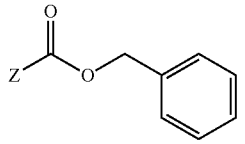 | 72 | B |
| 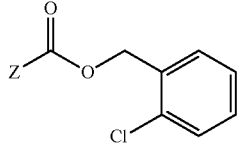 | 73 | A |
| 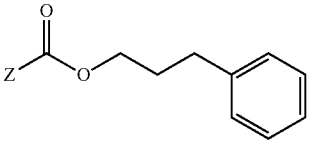 | 74 | B |
| 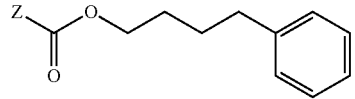 | 75 | B |

TABLE 1-continued
IC 50 Values from GM3 Elisa Assay
| Z—R* | Compound | IC50_uM_Mean |
|---|---|---|
| 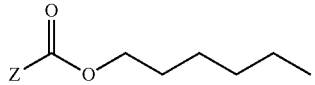 | 76 | B |
|  | 77 | A |
| 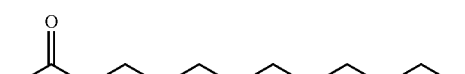 | 78 | B |
| 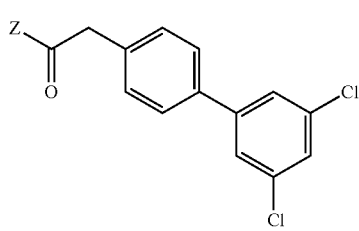 | 79 | A |
| 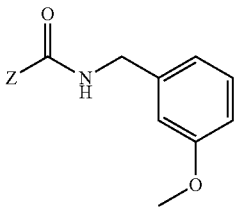 | 80 | B |
| 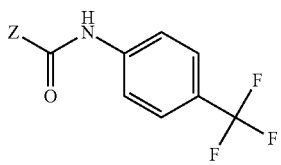 | 81 | B |
| 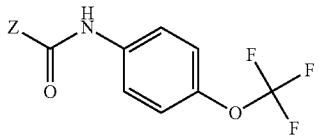 | 82 | A |
| 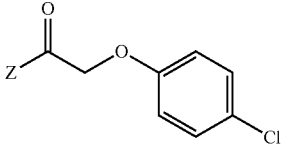 | 83 | A |
| 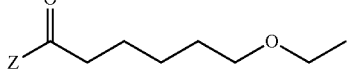 | 84 | C |
| 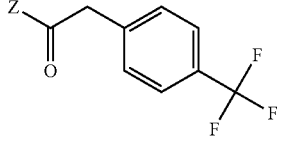 | 85 | A |

TABLE 1-continued
| IC 50 Values from GM3 Elisa Assay | | |
|---|---|---|
| Z—R* | Compound | IC50_uM_Mean |
| 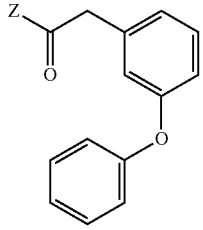 | 86 | A |
| 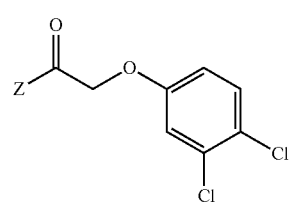 | 87 | A |
| 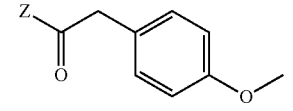 | 88 | B |
| 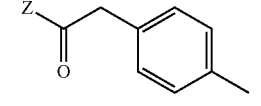 | 89 | B |
| 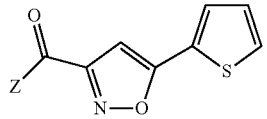 | 90 | B |
| 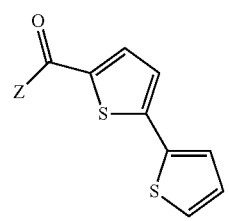 | 91 | B |
| 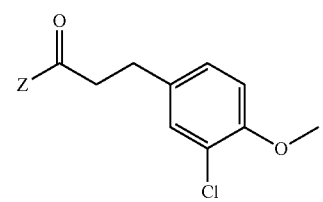 | 92 | A |
| 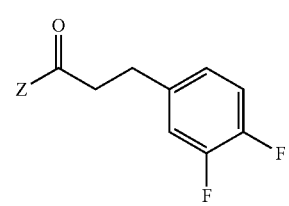 | 93 | A |
| 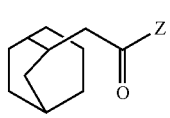 | 94 | C |

TABLE 1-continued
IC 50 Values from GM3 Elisa Assay
| Z—R* | Compound | IC50_uM_Mean |
|---|---|---|
| 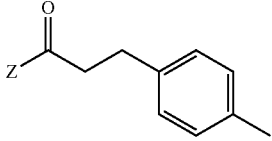 | 95 | A |
| 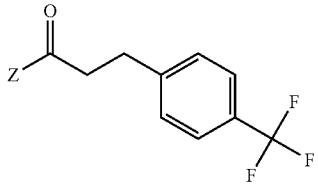 | 96 | A |
| 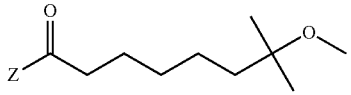 | 97 | B |
| 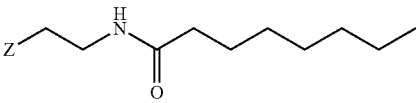 | 98 | D |
| 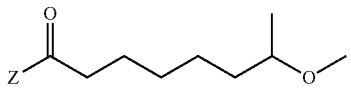 | 99 | B |
| 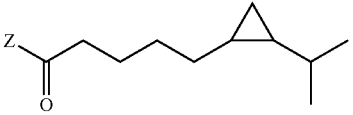 | 100 | A |
| 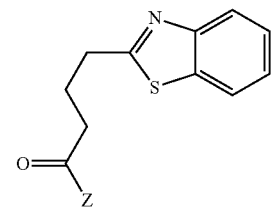 | 101 | A |
| 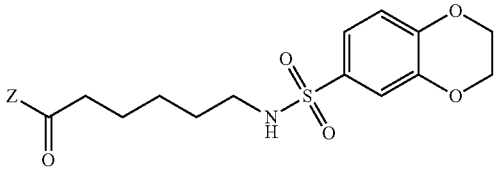 | 102 | C |
| 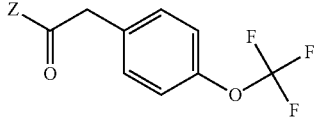 | 103 | A |
| 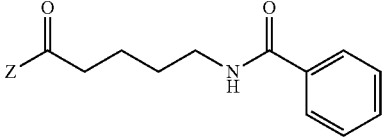 | 104 | B |

TABLE 1-continued
IC 50 Values from GM3 Elisa Assay
| Z—R* | Compound | IC50_uM_Mean |
|---|---|---|
| 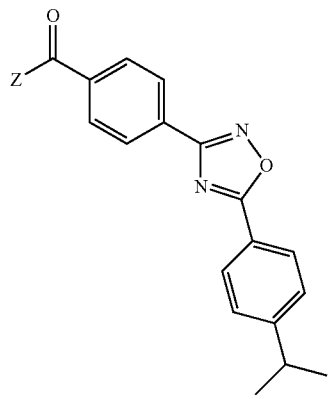 | 105 | B |
| 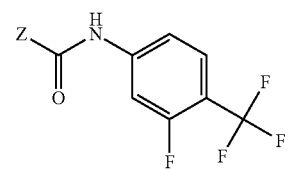 | 106 | B |
| 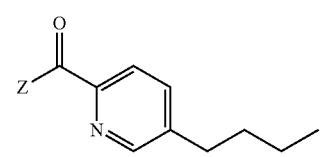 | 107 | D |
| 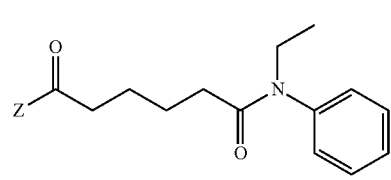 | 108 | B |
| 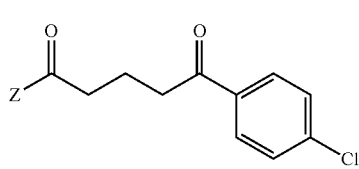 | 109 | A |
| 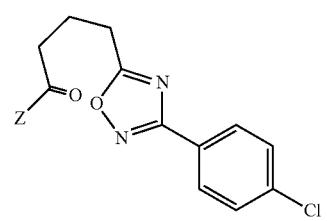 | 110 | A |
| 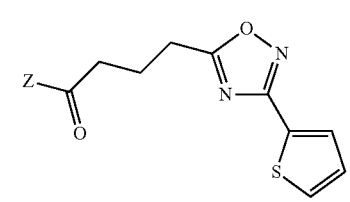 | 111 | B |

TABLE 1-continued

IC 50 Values from GM3 Elisa Assay

| Z—R* | Compound | IC50_uM_Mean |
|---|---|---|
| (structure) | 112 | B |
| (structure) | 113 | B |
| (structure) | 114 | B |
| (structure) | 115 | A |
| (structure) | 116 | B |
| (structure) | 117 | B |
| (structure) | 118 | B |

TABLE 1-continued
IC 50 Values from GM3 Elisa Assay
| Z—R* | Compound | IC50_uM_Mean |
|---|---|---|
| 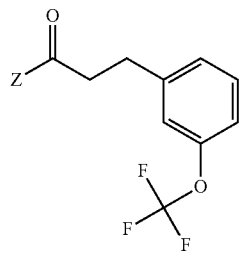 | 119 | A |
| 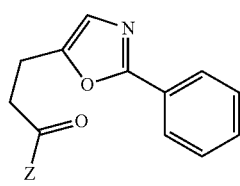 | 120 | B |
| 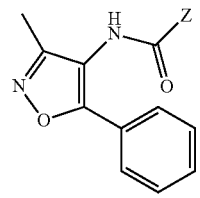 | 121 | D |
| 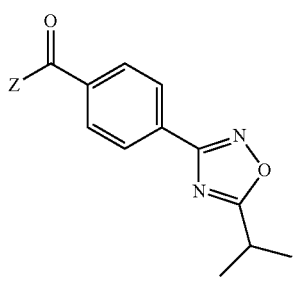 | 122 | D |
| 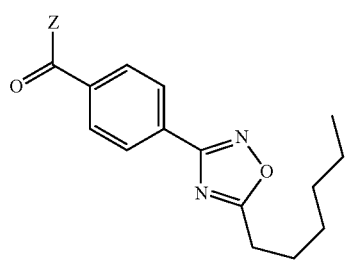 | 123 | C |
| 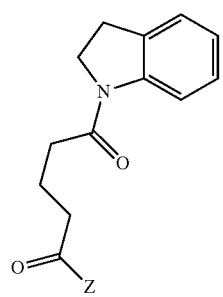 | 124 | C |

TABLE 1-continued
IC 50 Values from GM3 Elisa Assay
| Z—R* | Compound | IC50_uM_Mean |
|---|---|---|
| 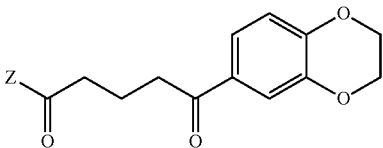 | 125 | B |
| 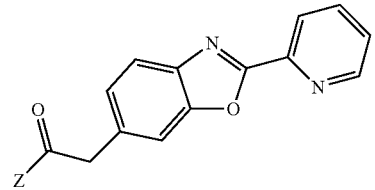 | 126 | D |
| 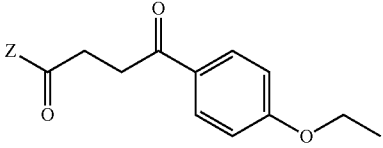 | 127 | B |
| 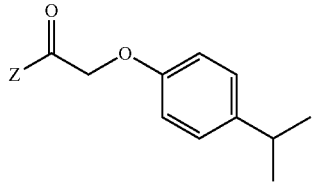 | 128 | C |
| 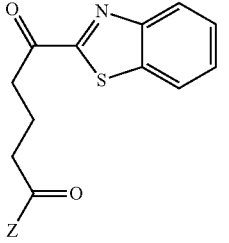 | 129 | B |
| 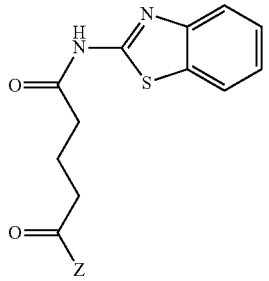 | 130 | C |
| 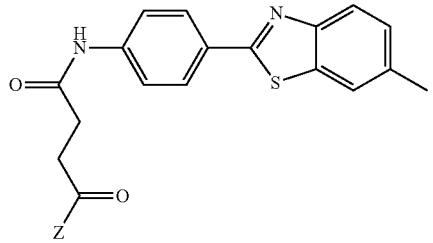 | 131 | A |

TABLE 1-continued

IC 50 Values from GM3 Elisa Assay

| Z—R* | Compound | IC50_uM_Mean |
|---|---|---|
| (structure) | 132 | D |
| (structure) | 133 | D |
| (structure) | 134 | C |
| (structure) | 135 | C |
| (structure) | 136 | A |
| (structure) | 137 | A |
| (structure) | 138 | A |

TABLE 1-continued

IC 50 Values from GM3 Elisa Assay

| Z—R* | Compound | IC50_uM_Mean |
|---|---|---|
| (structure) | 139 | A |
| (structure) | 140 | A |
| (structure) | 141 | A |
| (structure) | 142 | A |
| (structure) | 143 | A |
| (structure) | 144 | A |
| (structure) | 145 | B |

TABLE 1-continued

IC 50 Values from GM3 Elisa Assay

| Z—R* | Compound | IC50_uM_Mean |
|---|---|---|
| (3-((3,5-dimethylisoxazol-4-yl)methoxy)benzoyl structure) | 146 | B |
| (2-oxo-ethyl-(2-phenylthiazol-4-yl) structure) | 147 | B |
| (7-(benzyloxy)-7-methyloctanoyl structure) | 148 | A |
| (2-oxo-ethyl-(2-(p-tolyl)thiazol-4-yl) structure) | 149 | B |
| (2-methyl-4-(p-tolyl)thiazol-5-yl acetyl structure) | 150 | C |
| (5-(4-isopropylphenyl)-5-oxopentanoyl structure) | 151 | B |
| (5-(4-ethylphenyl)-5-oxopentanoyl structure) | 152 | A |

TABLE 1-continued

IC 50 Values from GM3 Elisa Assay

| Z—R* | Compound | IC50_uM_Mean |
|---|---|---|
| Z-C(O)-CH2CH2CH2CH2-C(O)-C6H4-4-iPr | 153 | B |
| Z-C(O)-CH2CH2-C(O)-C6H4-4-OMe | 154 | B |
| Z-C(O)-CH2CH2CH2CH2-C(O)-C6H4-4-tBu | 155 | B |
| Z-C(O)-CH2CH2CH2CH2CH2-C(O)-C6H4-4-OMe | 156 | A |
| Z-C(O)-CH2CH2CH2CH2CH2-C(O)-C6H4-4-OiPr | 157 | A |
| Z-C(O)-CH2CH2CH2CH2CH2-C(O)-(3,5-diMe-4-OMe-C6H2) | 158 | A |
| Z-C(O)-CH2CH2CH2CH2CH2-C(O)-C6H4-4-Cl | 159 | A |
| Z-C(O)-CH2CH2CH2CH2-C(O)-C6H4-4-tBu | 160 | B |

TABLE 1-continued
IC 50 Values from GM3 Elisa Assay
| Z—R* | Compound | IC50_uM_Mean |
|---|---|---|
| 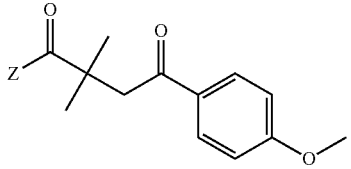 | 161 | B |
| 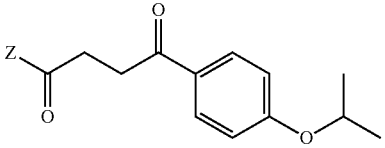 | 162 | A |
| 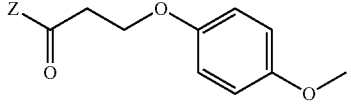 | 163 | A |
| 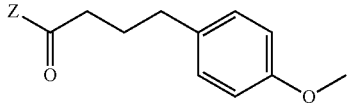 | 164 | A |
| 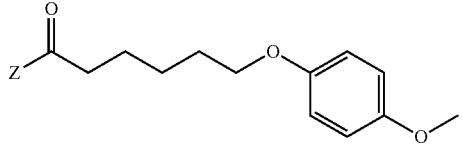 | 165 | A |
| 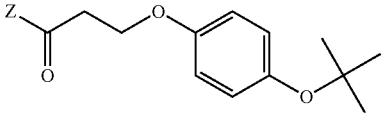 | 166 | A |
| 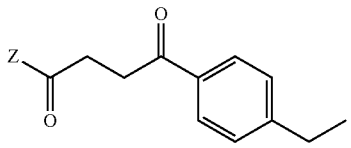 | 167 | A |
| 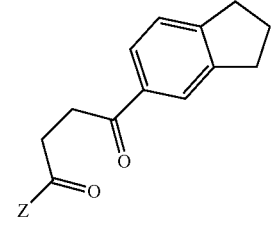 | 168 | A |
| 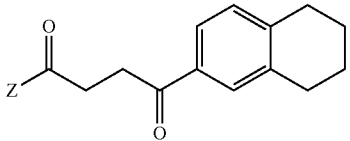 | 169 | A |

TABLE 1-continued
IC 50 Values from GM3 Elisa Assay
| Z—R* | Compound | IC50_uM_Mean |
|---|---|---|
| 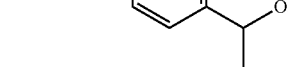 | 170 | B |
| 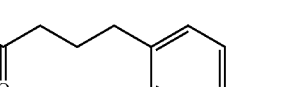 | 171 | C |
| 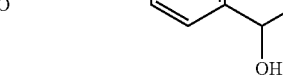 | 172 | B |
| 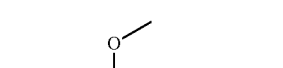 | 173 | A |
| 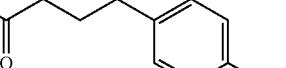 | 174 | A |
| 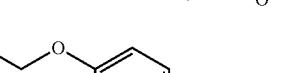 | 175 | A |
| 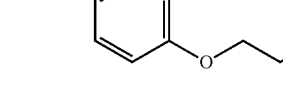 | 176 | A |
|  | 177 | B |
| 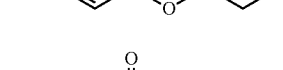 | 178 | A |

TABLE 1-continued
IC 50 Values from GM3 Elisa Assay
| Z—R* | Compound | IC50_uM_Mean |
|---|---|---|
| 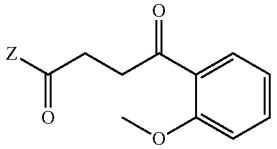 | 179 | A |
| 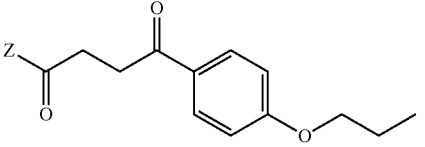 | 180 | B |
| 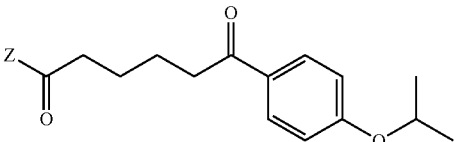 | 181 | A |
| 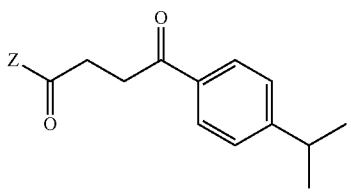 | 182 | B |
| 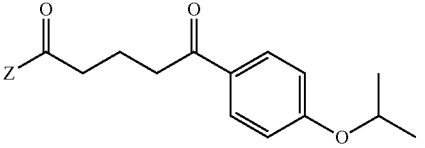 | 183 | A |
| 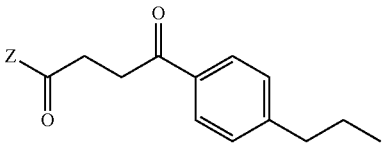 | 184 | B |
| 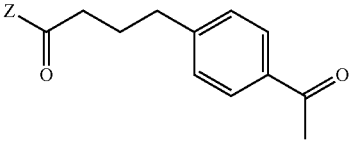 | 185 | B |
| 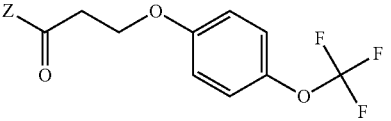 | 186 | A |
| 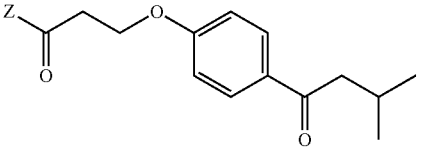 | 187 | B |

TABLE 1-continued
IC 50 Values from GM3 Elisa Assay
| Z—R* | Compound | IC50_uM_Mean |
|---|---|---|
| 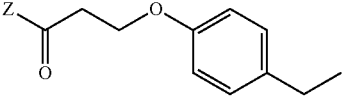 | 188 | B |
| 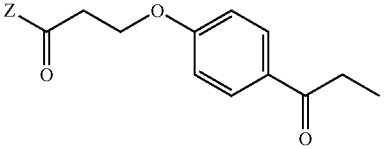 | 189 | B |
| 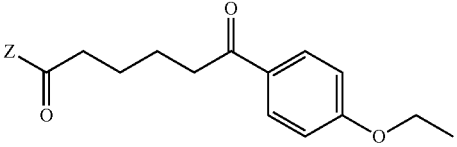 | 190 | A |
| 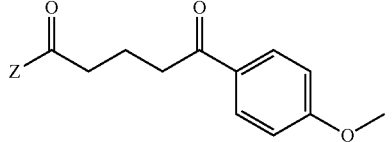 | 191 | A |
| 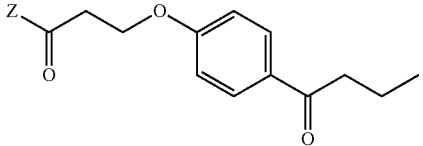 | 192 | B |
| 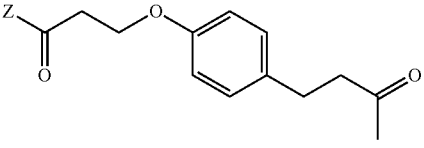 | 193 | B |
| 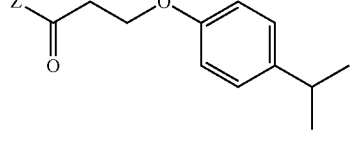 | 194 | B |
| 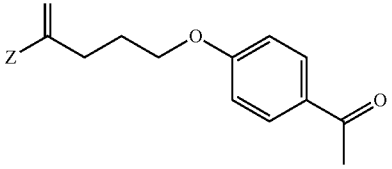 | 195 | B |
| 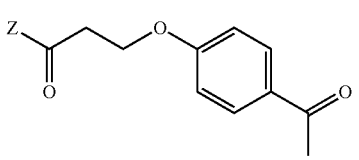 | 196 | C |

TABLE 1-continued

IC 50 Values from GM3 Elisa Assay

| Z—R* | Compound | IC50_uM_Mean |
|---|---|---|
| (structure) | 197 | A |
| (structure) | 198 | B |
| (structure) | 199 | A |
| (structure) | 200 | B |
| (structure) | 201 | C |
| (structure) | 202 | B |
| (structure) | 203 | A |
| (structure) | 204 | B |
| (structure) | 205 | A |

TABLE 1-continued

IC 50 Values from GM3 Elisa Assay

| Z—R* | Compound | IC50_uM_Mean |
|---|---|---|
| (structure) | 206 | B |
| (structure) | 207 | A |
| (structure) | 208 | B |
| (structure) | 209 | A |
| (structure) | 210 | B |
| (structure) | 211 | B |
| (structure) | 212 | D |
| (structure) | 213 | B |
| (structure) | 214 | D |
| (structure) | 215 | B |

TABLE 1-continued

IC 50 Values from GM3 Elisa Assay

| Z—R* | Compound | IC50_uM_Mean |
|---|---|---|
| (Z-C(=O)-O-(CH2)4-C6H4-OCH3, para-methoxyphenylbutyl carbonate) | 216 | A |
| (Z-C(=O)-O-(CH2)3-C6H4-OCH3, para-methoxyphenylpropyl carbonate) | 217 | A |
| (Z-C(=O)-(CH2)3-C(=O)-2-pyridyl) | 218 | D |
| (Z-C(=O)-(CH2)3-C(=O)-3-pyridyl) | 219 | D |
| (Z-C(=O)-(CH2)3-C(=O)-cyclohexyl) | 220 | B |
| (Z-C(=O)-(CH2)3-C(=O)-2-naphthyl) | 221 | A |
| (Z-C(=O)-(CH2)3-C(=O)-2-naphthyl) | 222 | A |
| (Z-C(=O)-O-(CH2)3-cyclohexyl) | 223 | A |
| (Z-C(=O)-O-(CH2)4-cyclohexyl) | 224 | B |
| (Z-C(=O)-O-(CH2)5-O-CH2-C6H5) | 225 | A |

TABLE 1-continued

IC 50 Values from GM3 Elisa Assay

| Z—R* | Compound | IC50_uM_Mean |
|---|---|---|
| (structure) | 226 | D |
| (structure) | 227 | C |
| (structure) | 228 | B |
| (structure) | 229 | E |
| (structure) | 230 | B |
| (structure) | 231 | A |
| (structure) | 232 | C |
| (structure) | 233 | C |

TABLE 1-continued

IC 50 Values from GM3 Elisa Assay

| Z—R* | Compound | IC50_uM_Mean |
|---|---|---|
| (cyclobutyl ketone with pentanoyl Z-carbonyl chain) | 234 | B |
| (Z-CO-CH2CH2-O-2-chloro-4-methoxyphenyl) | 235 | B |
| (Z-CO-(CH2)4-NH-CO-C6H4-O-iPr) | 236 | A |
| (Z-CO-CH2CH2-CO-NH-cyclohexyl) | 237 | A |
| (Z-CO-CH2CH2-CO-CH2CH2-CO-C6H4-OMe) | 238 | A |
| (Z-CO-(CH2)4-NH-CO-CF3) | 239 | D |
| (Z-CO-NH-CH2CH2-C6H4-OMe) | 240 | C |
| (Z-CO-(CH2)3-NH-CO-NH-cyclohexyl) | 241 | A |
| (Z-CO-(CH2)6-OH) | 291 | C |
| (Z-octyl) | 292 | C |

TABLE 1-continued
IC 50 Values from GM3 Elisa Assay
| Z—R* | Compound | IC50_uM_Mean |
|---|---|---|
| 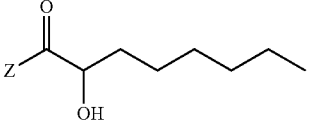 | 293 | B |
| 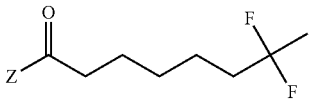 | 294 | B |
| 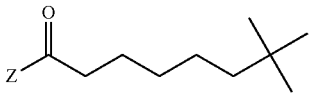 | 295 | A |
| 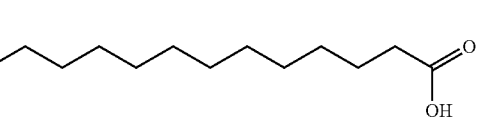 | 296 | B |
| 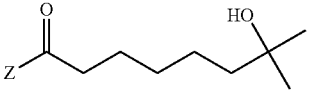 | 297 | C |
| 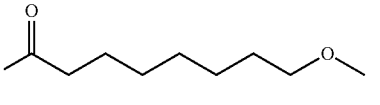 | 298 | B |
| 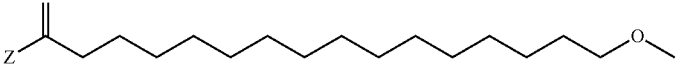 | 299 | A |
| 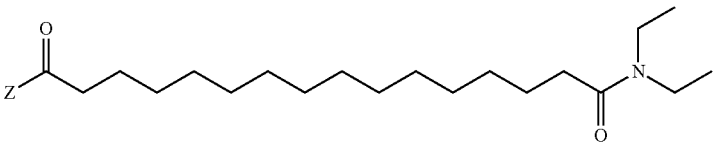 | 300 | A |
| 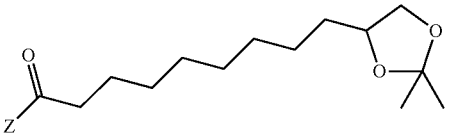 | 301 | A |
| 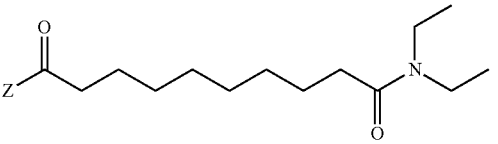 | 302 | A |
| 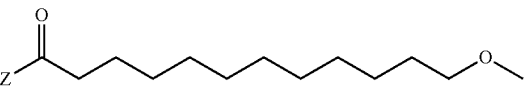 | 303 | A |
| 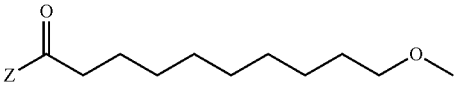 | 304 | A |

TABLE 1-continued
IC 50 Values from GM3 Elisa Assay
| Z—R* | Compound | IC50_uM_Mean |
|---|---|---|
| 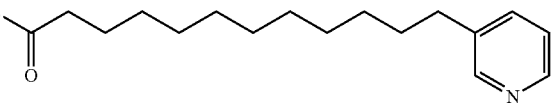 | 305 | A |
| 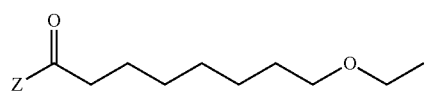 | 306 | B |
| 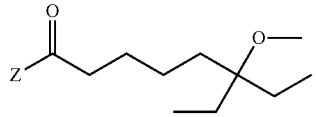 | 307 | A |
| 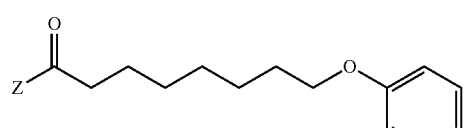 | 308 | A |
Z—R* = 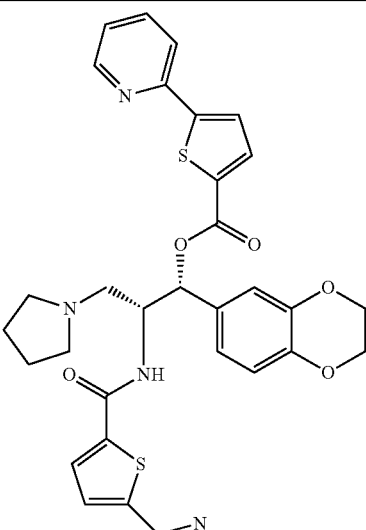
TABLE 2
IC 50 Values from GM3 Elisa Assay
| Structure | Compound | IC50_uM_Mean |
|---|---|---|
| 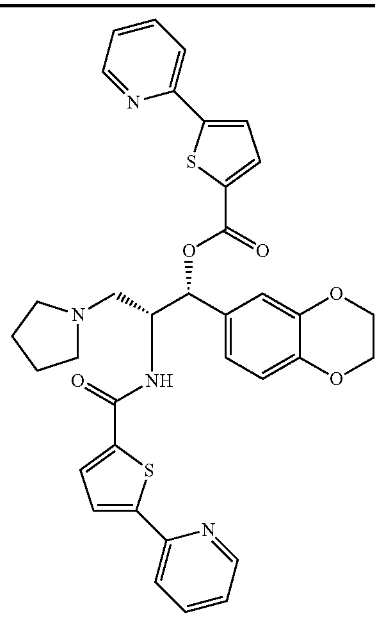 | 242 | D |

TABLE 2-continued

IC 50 Values from GM3 Elisa Assay

| Structure | Compound | IC50_uM_Mean |
|---|---|---|
| 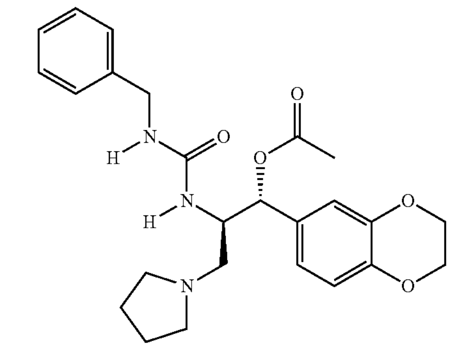 [SMILES: CC(=O)O[C@H](c1ccc2c(c1)OCCO2)[C@@H](CN1CCCC1)NC(=O)NCc1ccccc1] | 243 | A |
| 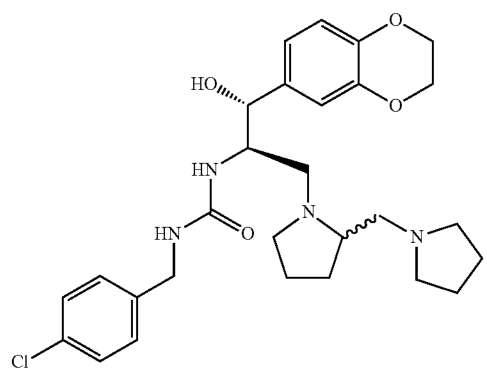 [SMILES: O=C(NCc1ccc(Cl)cc1)N[C@H](CN1CCCC1CN1CCCC1)[C@H](O)c1ccc2c(c1)OCCO2] | 244 | A |
| 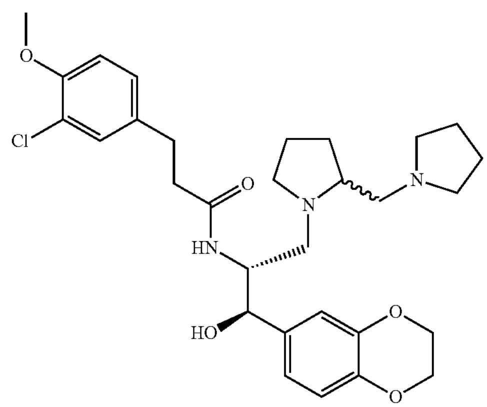 [SMILES: COc1ccc(CCC(=O)N[C@H](CN2CCCC2CN2CCCC2)[C@H](O)c2ccc3c(c2)OCCO3)cc1Cl] | 245 | D |
| 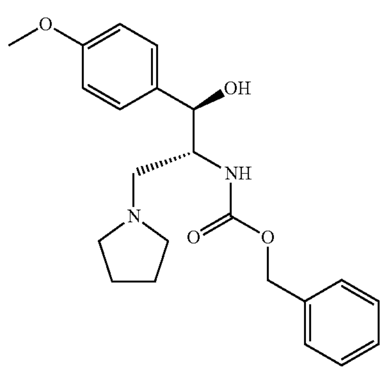 [SMILES: COc1ccc([C@@H](O)[C@@H](CN2CCCC2)NC(=O)OCc2ccccc2)cc1] | 246 | C |

TABLE 2-continued

IC 50 Values from GM3 Elisa Assay

| Structure | Compound | IC50_uM_Mean |
|---|---|---|
| 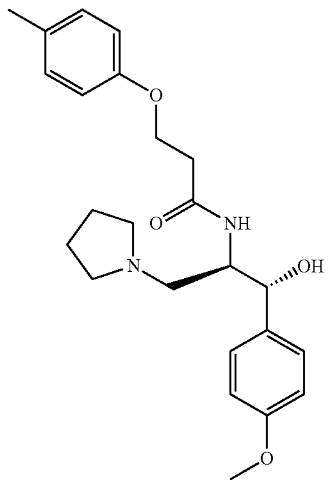 [SMILES: COc1ccc([C@@H](O)[C@@H](CN2CCCC2)NC(=O)CCOc2ccc(C)cc2)cc1] | 247 | A |
| 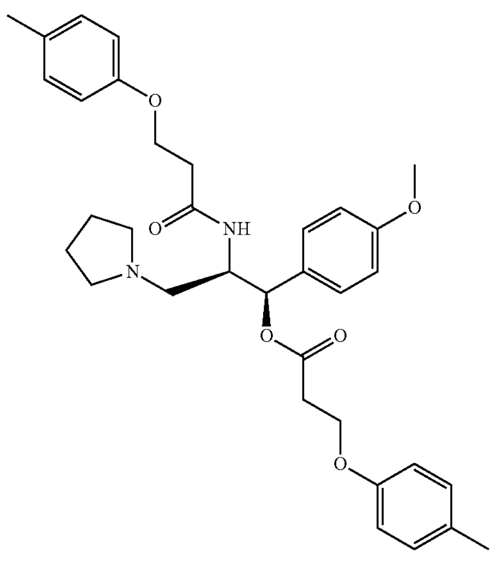 | 248 | B |
| 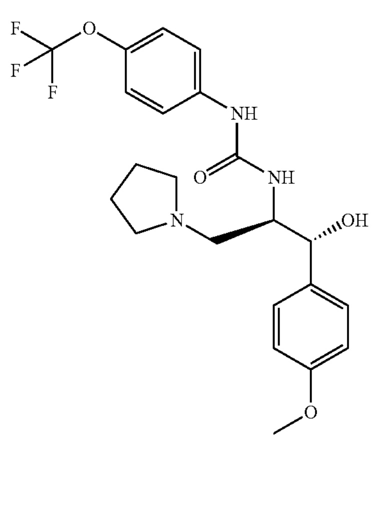 [SMILES: COc1ccc([C@@H](O)[C@@H](CN2CCCC2)NC(=O)Nc2ccc(OC(F)(F)F)cc2)cc1] | 249 | C |

TABLE 2-continued
IC 50 Values from GM3 Elisa Assay
| Structure | Compound | IC50_uM_Mean |
|---|---|---|
| 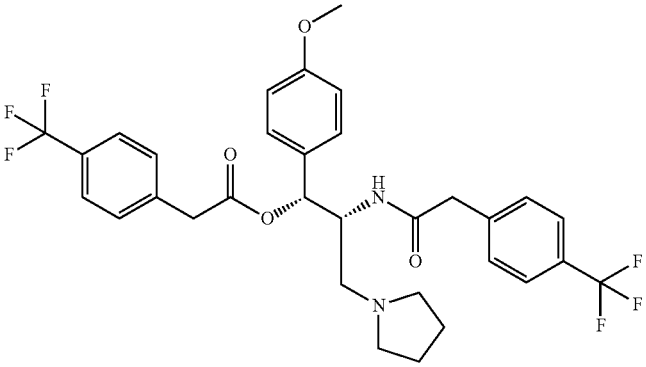 [SMILES: COc1ccc([C@@H](OC(=O)Cc2ccc(C(F)(F)F)cc2)[C@@H](CN2CCCC2)NC(=O)Cc2ccc(C(F)(F)F)cc2)cc1] | 250 | B |
| 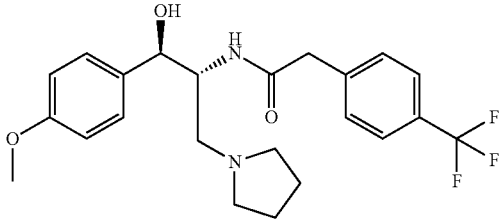 [SMILES: COc1ccc([C@@H](O)[C@@H](CN2CCCC2)NC(=O)Cc2ccc(C(F)(F)F)cc2)cc1] | 251 | B |
| 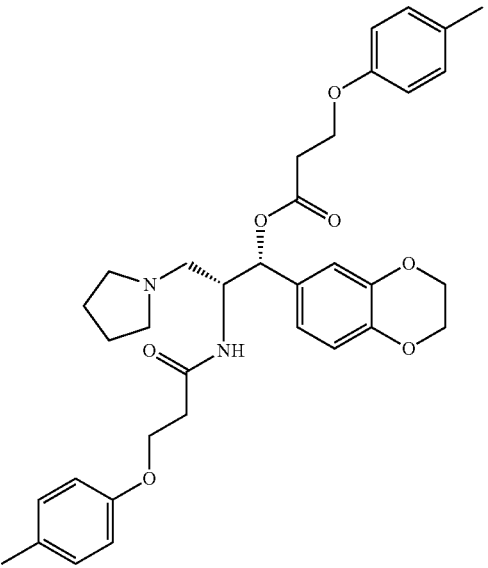 | 252 | B |

TABLE 2-continued
IC 50 Values from GM3 Elisa Assay
| Structure | Compound | IC50_uM_Mean |
|---|---|---|
| 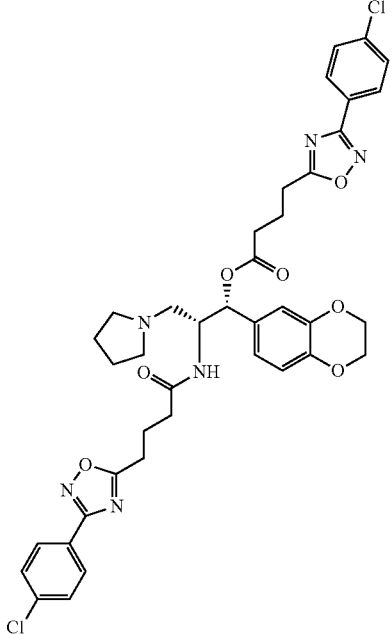 [SMILES: O=C(CCCc1nc(-c2ccc(Cl)cc2)no1)N[C@H](CN1CCCC1)[C@H](OC(=O)CCCc1nc(-c2ccc(Cl)cc2)no1)c1ccc2c(c1)OCCO2] | 253 | B |
| 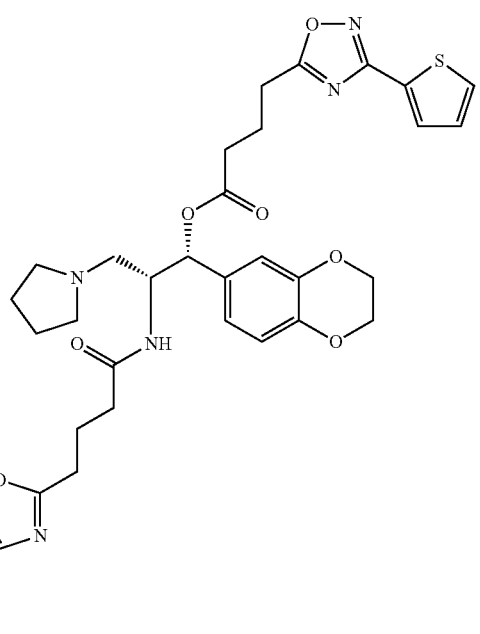 | 254 | B |

TABLE 2-continued

IC 50 Values from GM3 Elisa Assay

| Structure | Compound | IC50_uM_Mean |
|---|---|---|
| 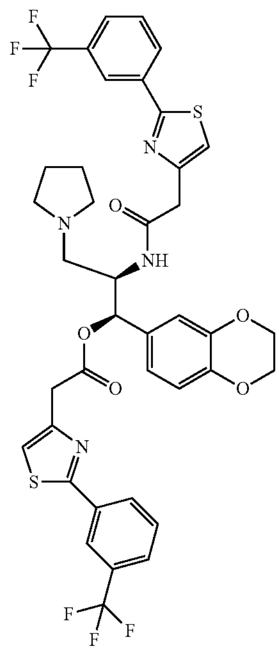 [SMILES: O=C(Cc1csc(-c2cccc(C(F)(F)F)c2)n1)N[C@H](CN1CCCC1)[C@H](OC(=O)Cc1csc(-c2cccc(C(F)(F)F)c2)n1)c1ccc2c(c1)OCCO2] | 255 | C |
| 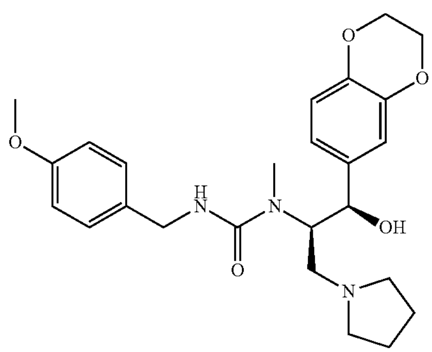 [SMILES: COc1ccc(CNC(=O)N(C)[C@H](CN2CCCC2)[C@H](O)c2ccc3c(c2)OCCO3)cc1] | 256 | B |
| 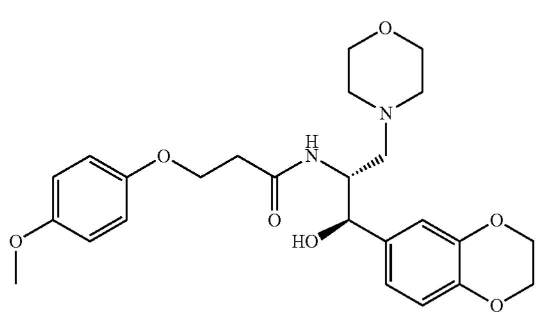 [SMILES: COc1ccc(OCCC(=O)N[C@H](CN2CCOCC2)[C@H](O)c2ccc3c(c2)OCCO3)cc1] | 257 | D |

TABLE 2-continued

IC 50 Values from GM3 Elisa Assay

| Structure | Compound | IC50_uM_Mean |
|---|---|---|
| 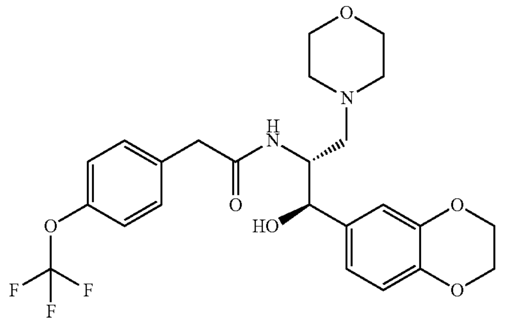 [SMILES: O=C(Cc1ccc(OC(F)(F)F)cc1)N[C@H](CN1CCOCC1)[C@H](O)c1ccc2c(c1)OCCO2] | 258 | D |
| 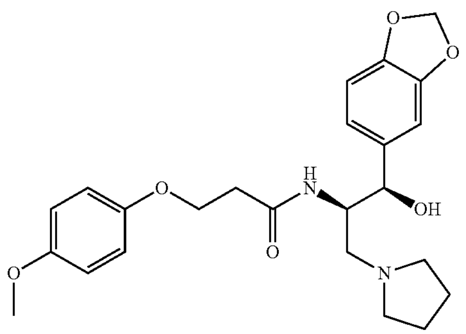 [SMILES: COc1ccc(OCCC(=O)N[C@H](CN2CCCC2)[C@H](O)c2ccc3c(c2)OCO3)cc1] | 259 | A |
| 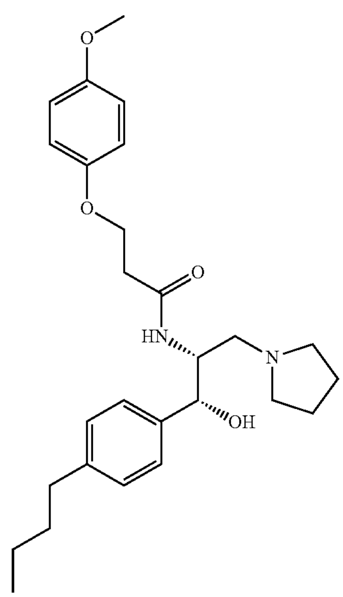 [SMILES: CCCCc1ccc([C@@H](O)[C@@H](CN2CCCC2)NC(=O)CCOc2ccc(OC)cc2)cc1] | 260 | A |
| 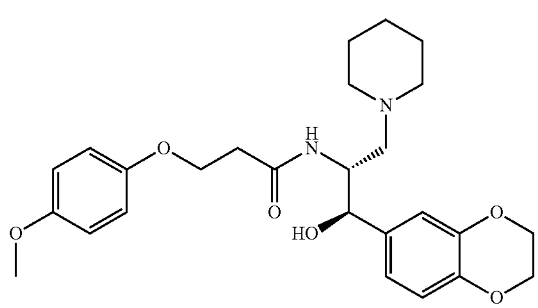 [SMILES: COc1ccc(OCCC(=O)N[C@H](CN2CCCCC2)[C@H](O)c2ccc3c(c2)OCCO3)cc1] | 261 | B |

TABLE 2-continued

IC 50 Values from GM3 Elisa Assay

| Structure | Compound | IC50_uM_Mean |
|---|---|---|
| 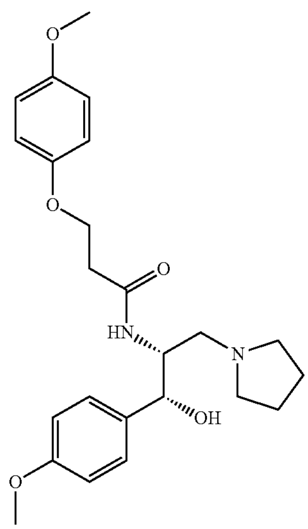 [SMILES: COc1ccc(OCCC(=O)N[C@H](CN2CCCC2)[C@H](O)c2ccc(OC)cc2)cc1] | 262 | A |
| 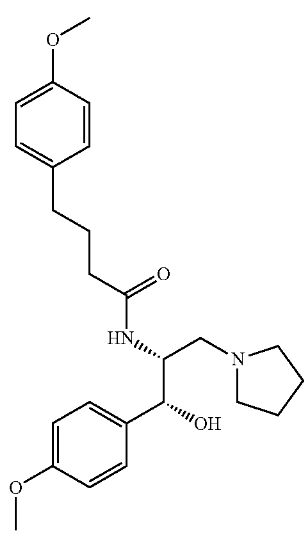 [SMILES: COc1ccc(CCCC(=O)N[C@H](CN2CCCC2)[C@H](O)c2ccc(OC)cc2)cc1] | 263 | B |
| 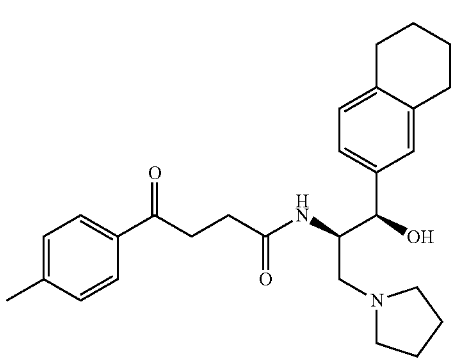 [SMILES: Cc1ccc(C(=O)CCC(=O)N[C@H](CN2CCCC2)[C@H](O)c2ccc3c(c2)CCCC3)cc1] | 264 | A |

TABLE 2-continued

IC 50 Values from GM3 Elisa Assay

| Structure | Compound | IC50_uM_Mean |
|---|---|---|
| 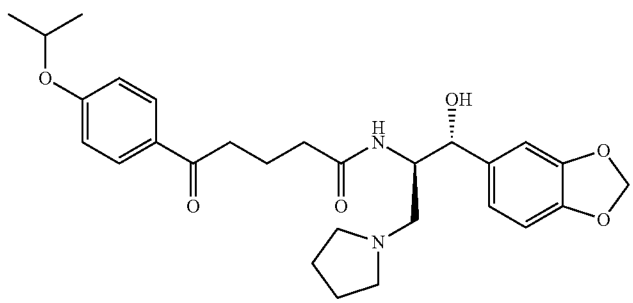 [SMILES: CC(C)Oc1ccc(C(=O)CCCC(=O)N[C@H](CN2CCCC2)[C@H](O)c2ccc3c(c2)OCO3)cc1] | 265 | A |
| 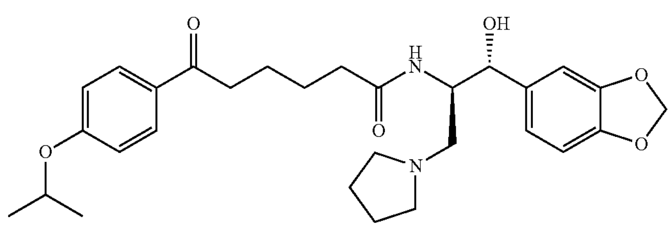 [SMILES: CC(C)Oc1ccc(C(=O)CCCCC(=O)N[C@H](CN2CCCC2)[C@H](O)c2ccc3c(c2)OCO3)cc1] | 266 | A |
| 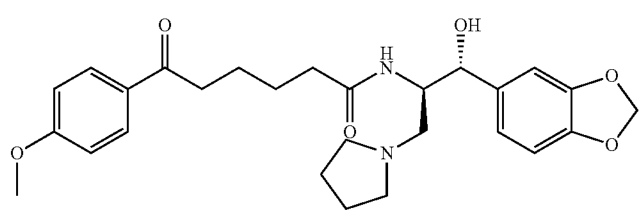 [SMILES: COc1ccc(C(=O)CCCCC(=O)N[C@H](CN2CCCC2)[C@H](O)c2ccc3c(c2)OCO3)cc1] | 267 | A |
| 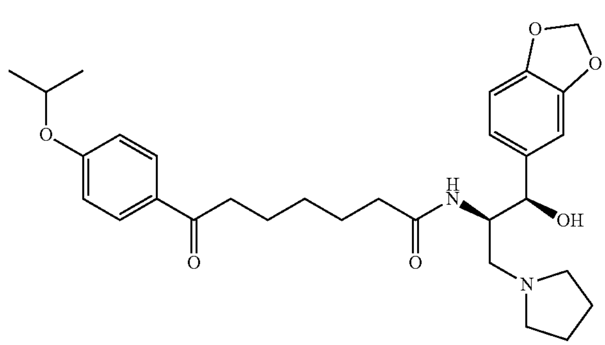 [SMILES: CC(C)Oc1ccc(C(=O)CCCCCC(=O)N[C@H](CN2CCCC2)[C@H](O)c2ccc3c(c2)OCO3)cc1] | 268 | A |

TABLE 2-continued
IC 50 Values from GM3 Elisa Assay
| Structure | Compound | IC50_uM_Mean |
|---|---|---|
| 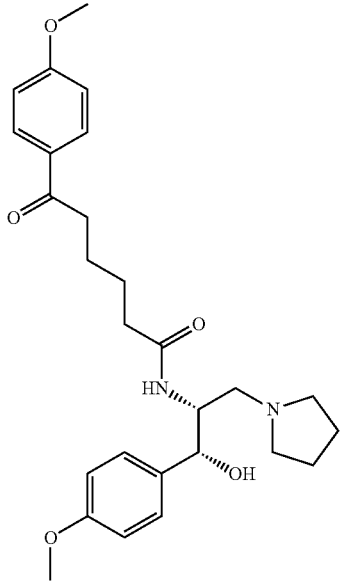 [SMILES: COc1ccc(C(=O)CCCCC(=O)N[C@H](CN2CCCC2)[C@H](O)c2ccc(OC)cc2)cc1] | 269 | A |
| 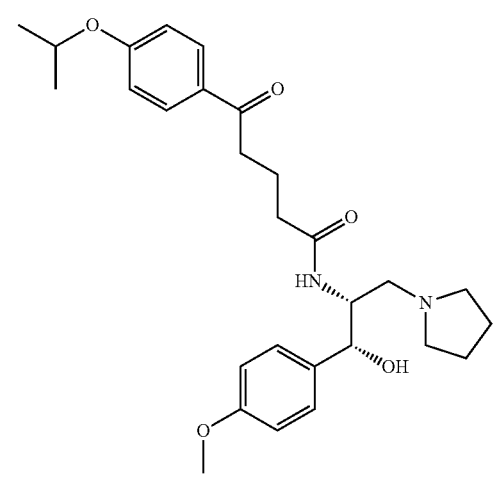 [SMILES: COc1ccc([C@@H](O)[C@@H](CN2CCCC2)NC(=O)CCCC(=O)c2ccc(OC(C)C)cc2)cc1] | 270 | A |
| 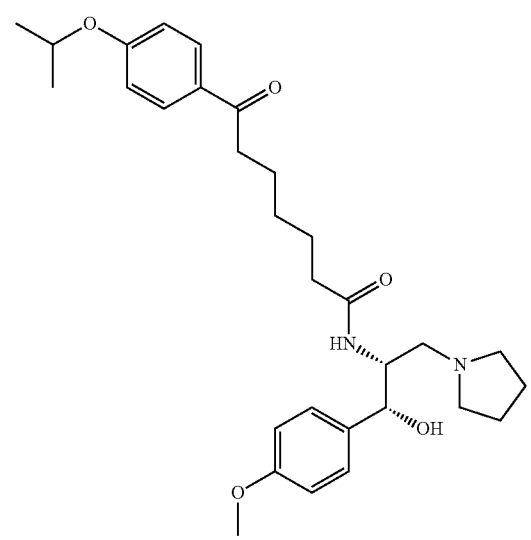 [SMILES: COc1ccc([C@@H](O)[C@@H](CN2CCCC2)NC(=O)CCCCCC(=O)c2ccc(OC(C)C)cc2)cc1] | 271 | A |

TABLE 2-continued

IC 50 Values from GM3 Elisa Assay

| Structure | Compound | IC50_uM_Mean |
|---|---|---|
| 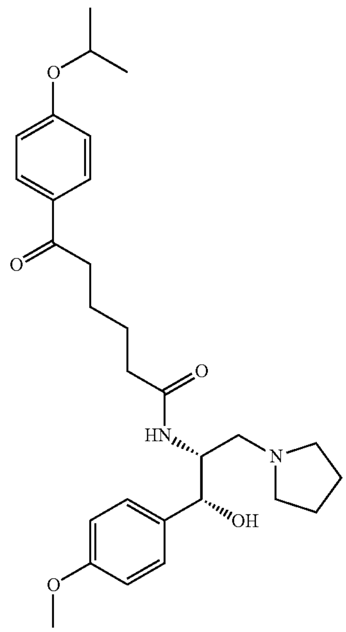 [SMILES: COc1ccc([C@@H](O)[C@@H](CN2CCCC2)NC(=O)CCCCC(=O)c2ccc(OC(C)C)cc2)cc1] | 272 | A |
| 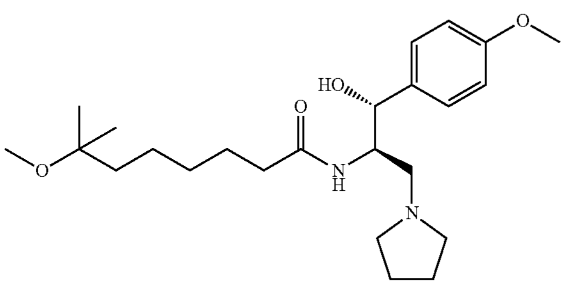 | 273 | B |
| 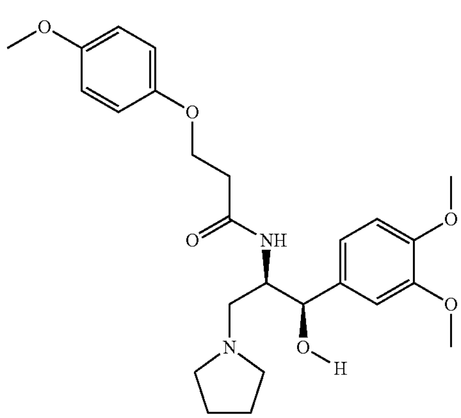 | 274 | C |

TABLE 2-continued

IC 50 Values from GM3 Elisa Assay

| Structure | Compound | IC50_uM_Mean |
|---|---|---|
| 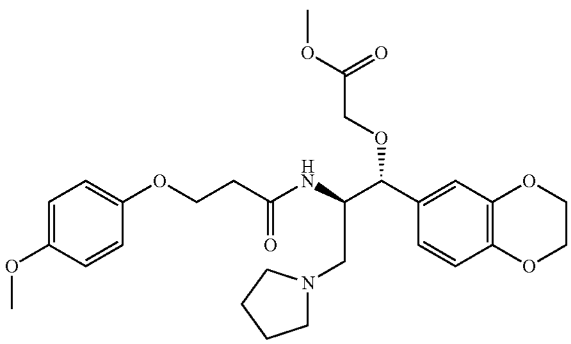 [SMILES: COC(=O)CO[C@H](c1ccc2c(c1)OCCO2)[C@@H](CN1CCCC1)NC(=O)CCOc1ccc(OC)cc1] | 275 | A |
| 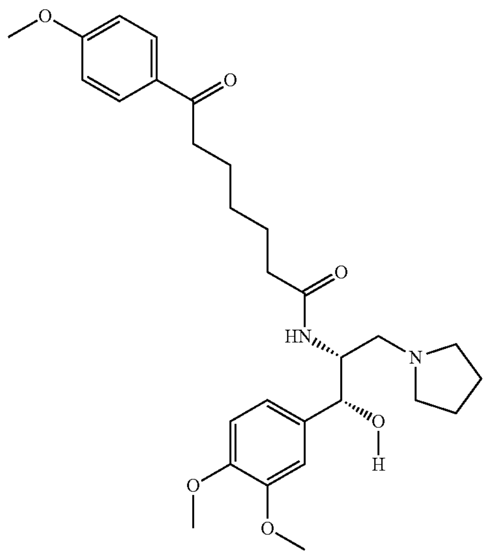 [SMILES: COc1ccc(C(=O)CCCCCC(=O)N[C@H](CN2CCCC2)[C@H](O)c2ccc(OC)c(OC)c2)cc1] | 276 | B |
| 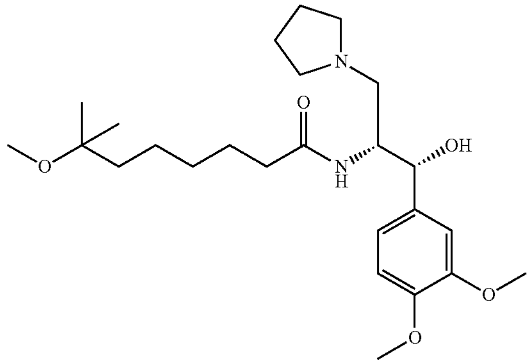 | 277 | D |

TABLE 2-continued

| IC 50 Values from GM3 Elisa Assay | | |
|---|---|---|
| Structure | Compound | IC50_uM_Mean |
| | 278 | E |
| | 279 | C |
| | 282 | C |

TABLE 2-continued

IC 50 Values from GM3 Elisa Assay

| Structure | Compound | IC50_uM_Mean |
|---|---|---|
| 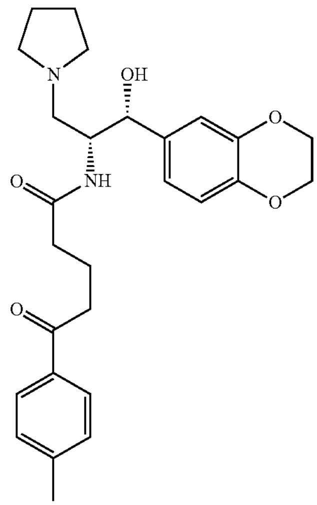 [SMILES: Cc1ccc(C(=O)CCCC(=O)N[C@H](CN2CCCC2)[C@H](O)c2ccc3c(c2)OCCO3)cc1] | 283 | A |
| 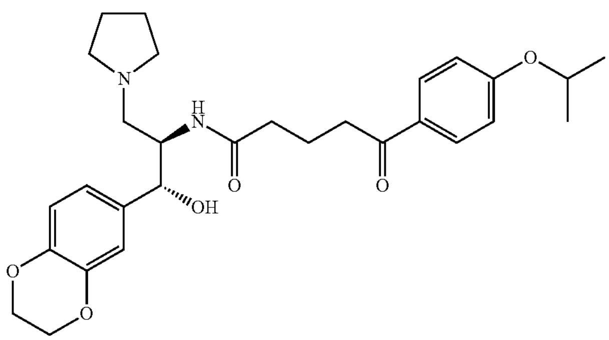 [SMILES: CC(C)Oc1ccc(C(=O)CCCC(=O)N[C@H](CN2CCCC2)[C@H](O)c2ccc3c(c2)OCCO3)cc1] | 284 | A |
| 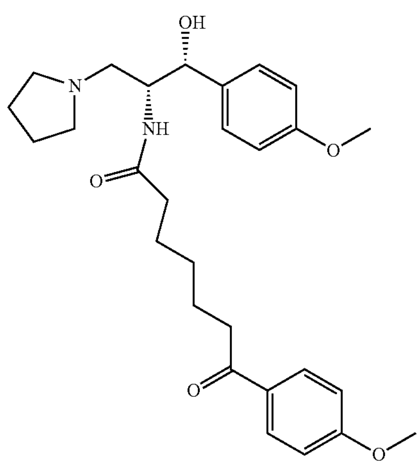 [SMILES: COc1ccc(C(=O)CCCCCC(=O)N[C@H](CN2CCCC2)[C@H](O)c2ccc(OC)cc2)cc1] | 285 | A |
| 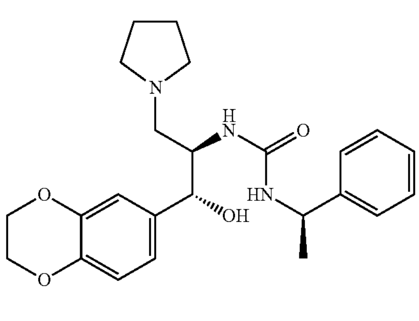 [SMILES: C[C@@H](NC(=O)N[C@H](CN1CCCC1)[C@H](O)c1ccc2c(c1)OCCO2)c1ccccc1] | 286 | D |

TABLE 2-continued

IC 50 Values from GM3 Elisa Assay

| Structure | Compound | IC50_uM_Mean |
|---|---|---|
| 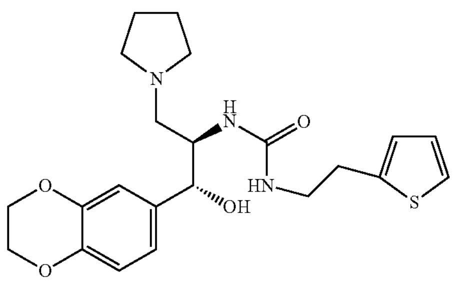 | 287 | C |
| 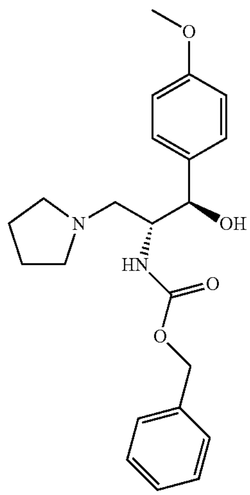 [SMILES: COc1ccc([C@@H](O)[C@@H](CN2CCCC2)NC(=O)OCc2ccccc2)cc1] | 289 | B |
| 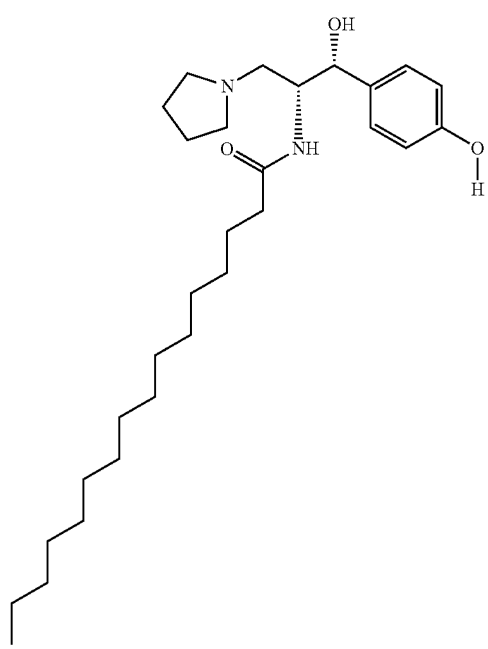 [SMILES: CCCCCCCCCCCCCCCC(=O)N[C@H](CN1CCCC1)[C@H](O)c1ccc(O)cc1] | 309 | A |

TABLE 2-continued

IC 50 Values from GM3 Elisa Assay

| Structure | Compound | IC50_uM_Mean |
|---|---|---|
| 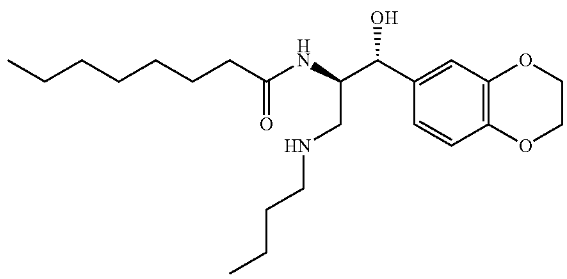 [SMILES: CCCCCCCC(=O)N[C@H](CNCCCC)[C@H](O)c1ccc2c(c1)OCCO2] | 310 | C |
| 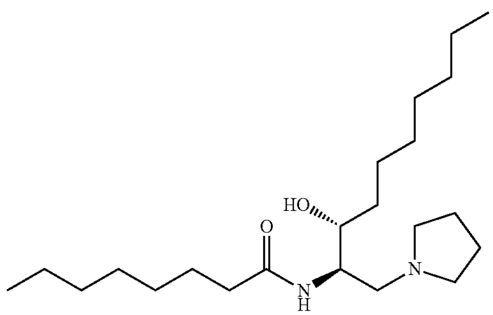 [SMILES: CCCCCCCC(=O)N[C@H](CN1CCCC1)[C@H](O)CCCCCCC] | 311 | C |
| 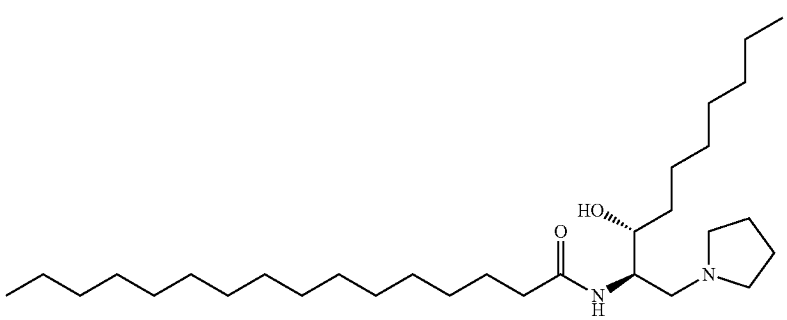 [SMILES: CCCCCCCCCCCCCCCC(=O)N[C@H](CN1CCCC1)[C@H](O)CCCCCCC] | 312 | B |
| 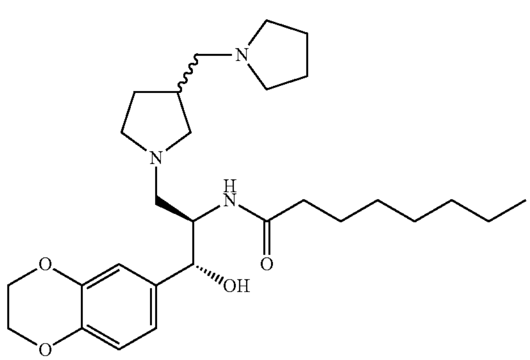 [SMILES: CCCCCCCC(=O)N[C@H](CN1CCC(CN2CCCC2)C1)[C@H](O)c1ccc2c(c1)OCCO2] | 313 | A |

TABLE 2-continued
IC 50 Values from GM3 Elisa Assay
| Structure | Compound | IC50_uM_Mean |
|---|---|---|
| 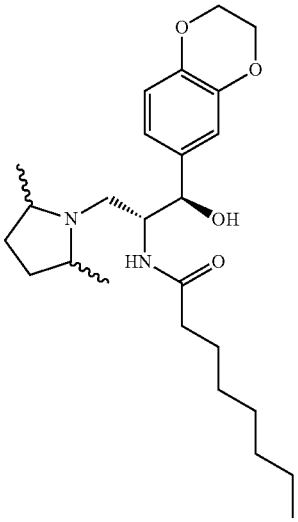 | 314 | C |
| 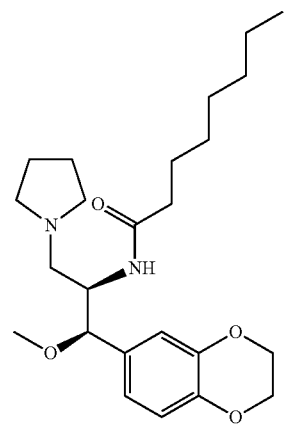 [SMILES: CCCCCCCC(=O)N[C@H](CN1CCCC1)[C@H](OC)c1ccc2c(c1)OCCO2] | 315 | B |
| 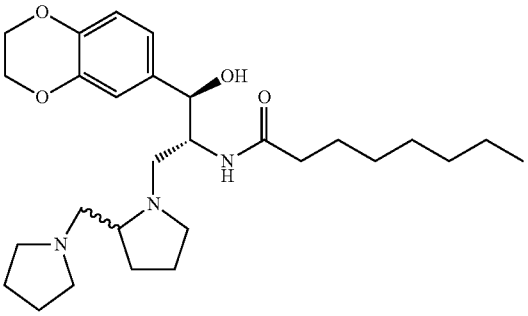 [SMILES: CCCCCCCC(=O)N[C@H](CN1CCCC1CN1CCCC1)[C@H](O)c1ccc2c(c1)OCCO2] | 316 | D |

TABLE 2-continued

IC 50 Values from GM3 Elisa Assay

| Structure | Compound | IC50_uM_Mean |
|---|---|---|
| 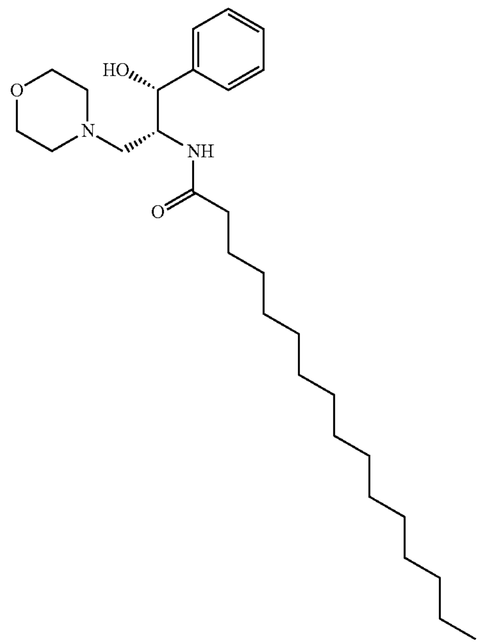 [SMILES: CCCCCCCCCCCCCCCC(=O)N[C@H](CN1CCOCC1)[C@H](O)c1ccccc1] | 317 | B |
| 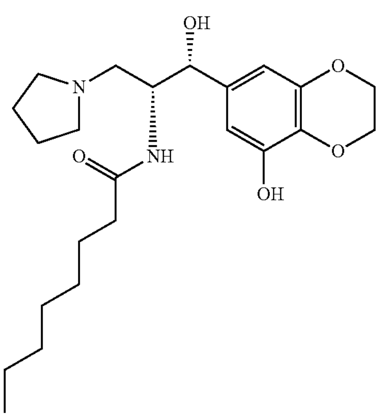 [SMILES: CCCCCCCC(=O)N[C@H](CN1CCCC1)[C@H](O)c1cc(O)c2c(c1)OCCO2] | 318 | B |
| 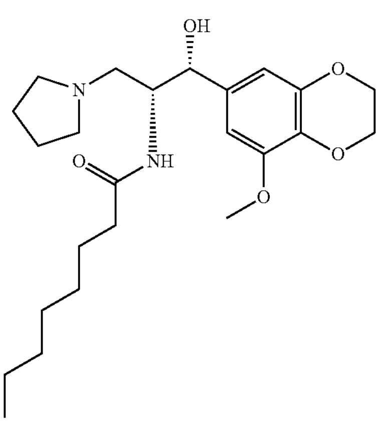 [SMILES: CCCCCCCC(=O)N[C@H](CN1CCCC1)[C@H](O)c1cc(OC)c2c(c1)OCCO2] | 319 | B |

TABLE 2-continued

IC 50 Values from GM3 Elisa Assay

| Structure | Compound | IC50_uM_Mean |
|---|---|---|
| 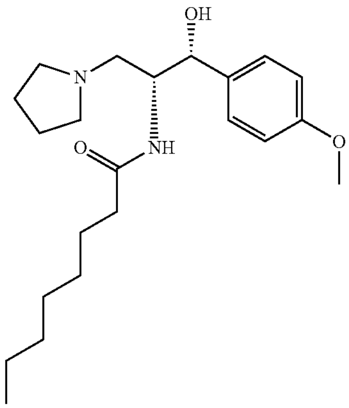 [SMILES: CCCCCCCC(=O)N[C@H](CN1CCCC1)[C@H](O)c1ccc(OC)cc1] | 320 | A |
| 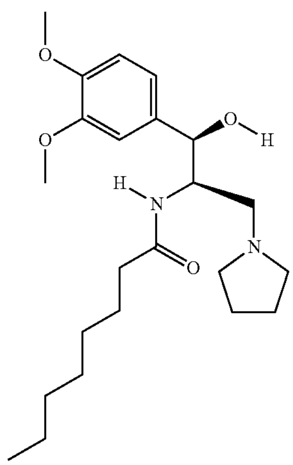 [SMILES: CCCCCCCC(=O)N[C@H](CN1CCCC1)[C@H](O)c1ccc(OC)c(OC)c1] | 321 | C |
| 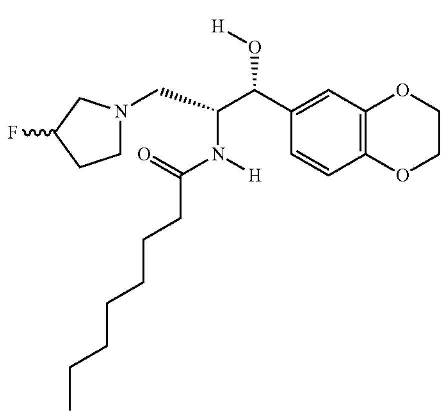 [SMILES: CCCCCCCC(=O)N[C@H](CN1CCC(F)C1)[C@H](O)c1ccc2c(c1)OCCO2] | 322 | B |

TABLE 3
| IC 50 Values | | |
| --- | --- | --- |
| Structure | IC50_uM_Mean | Compound |
| 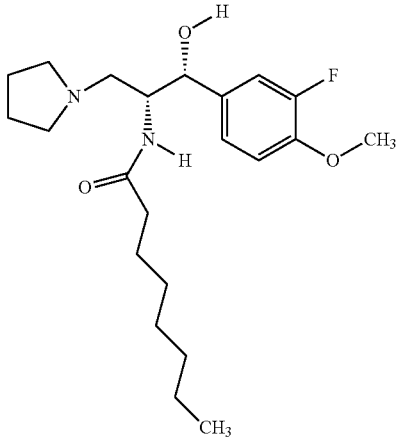 [SMILES: CCCCCCCC(=O)N[C@H](CN1CCCC1)[C@H](O)c1ccc(OC)c(F)c1] | B | 340 |
| 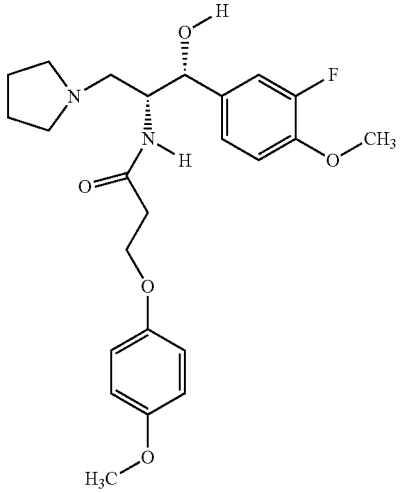 [SMILES: COc1ccc(OCCC(=O)N[C@H](CN2CCCC2)[C@H](O)c2ccc(OC)c(F)c2)cc1] | A | 341 |
| 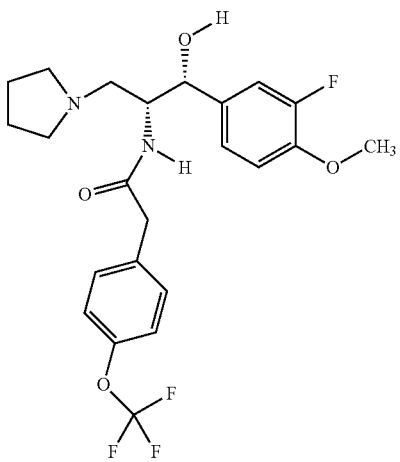 [SMILES: COc1ccc([C@@H](O)[C@@H](CN2CCCC2)NC(=O)Cc2ccc(OC(F)(F)F)cc2)cc1F] | B | 342 |

TABLE 3-continued

IC 50 Values

| Structure | IC50_uM_Mean | Compound |
|---|---|---|
| 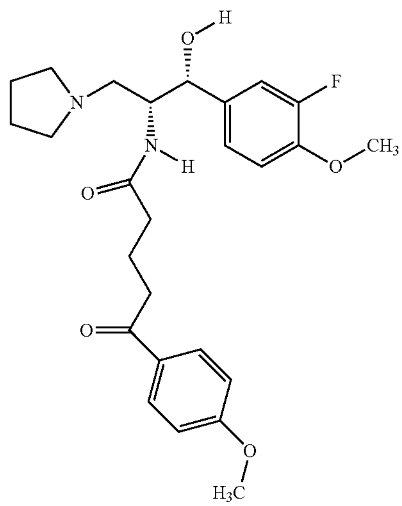 [SMILES: COc1ccc(C(=O)CCCC(=O)N[C@H](CN2CCCC2)[C@H](O)c2ccc(OC)c(F)c2)cc1] | B | 343 |
| | A | 344 |
| | A | 345 |

TABLE 3-continued

IC 50 Values

| Structure | IC50_uM_Mean | Compound |
|---|---|---|
| | B | 346 |
| | B | 347 |
| | B | 348 |

TABLE 3-continued

IC 50 Values

| Structure | IC50_uM_Mean | Compound |
|---|---|---|
| | B | 349 |
| 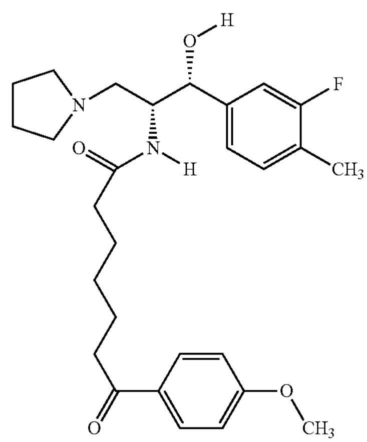 [SMILES: COc1ccc(C(=O)CCCCCC(=O)N[C@H](CN2CCCC2)[C@H](O)c2ccc(C)c(F)c2)cc1] | A | 350 |
| | B | 351 |

TABLE 3-continued

IC 50 Values

| Structure | IC50_uM_Mean | Compound |
|---|---|---|
| 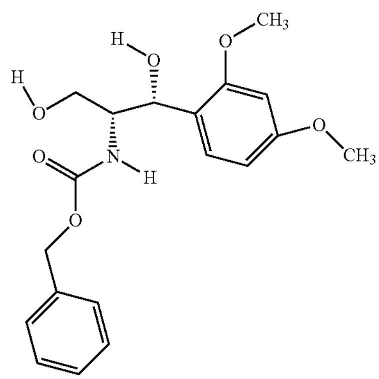 [SMILES: COc1ccc([C@@H](O)[C@@H](CO)NC(=O)OCc2ccccc2)c(OC)c1] | D | 352 |
| | B | 353 |
| | B | 354 |

TABLE 3-continued
IC 50 Values
| Structure | IC50_uM_Mean | Compound |
|---|---|---|
| 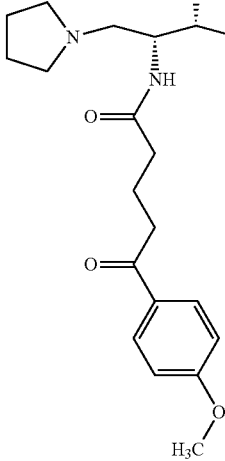 | C | 355 |
|  | C | 356 |
| 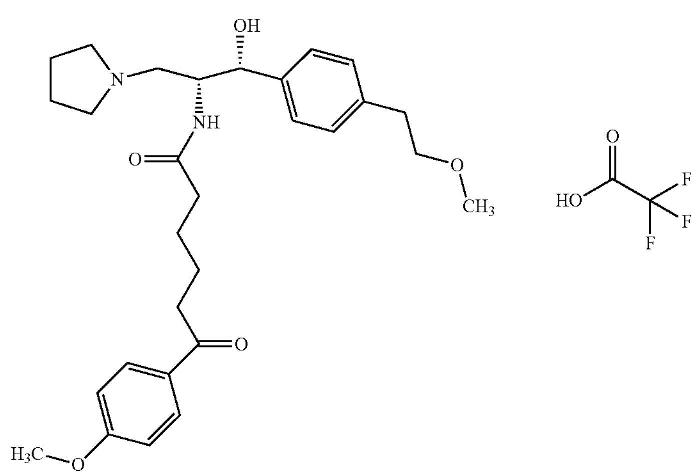 | B | 357 |

TABLE 3-continued

IC 50 Values

| Structure | IC50_uM_Mean | Compound |
|---|---|---|
| 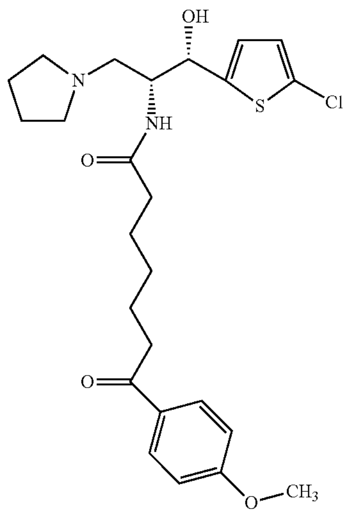 [SMILES: COc1ccc(C(=O)CCCCCC(=O)N[C@H](CN2CCCC2)[C@H](O)c2ccc(Cl)s2)cc1] | A | 358 |
| | B | 359 |
| | B | 360 |

TABLE 3-continued
IC 50 Values
| Structure | IC50_uM_Mean | Compound |
|---|---|---|
| 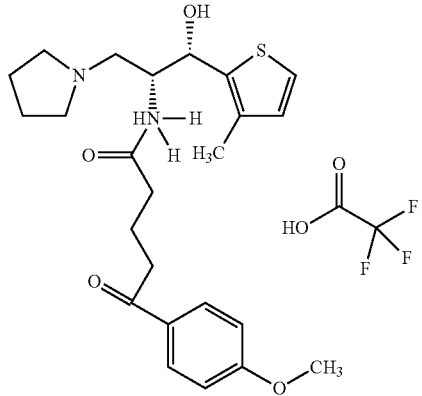 | D | 361 |
| 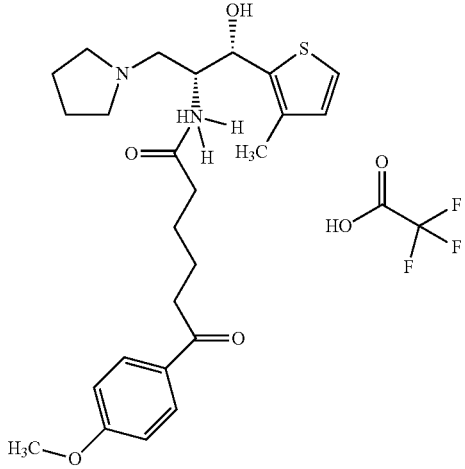 | D | 362 |
| 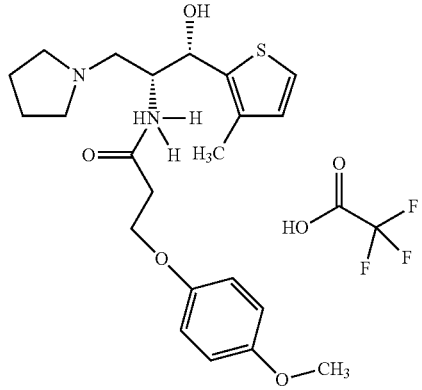 | B | 363 |

TABLE 3-continued
| IC 50 Values | | |
|---|---|---|
| Structure | IC50_uM_Mean | Compound |
| 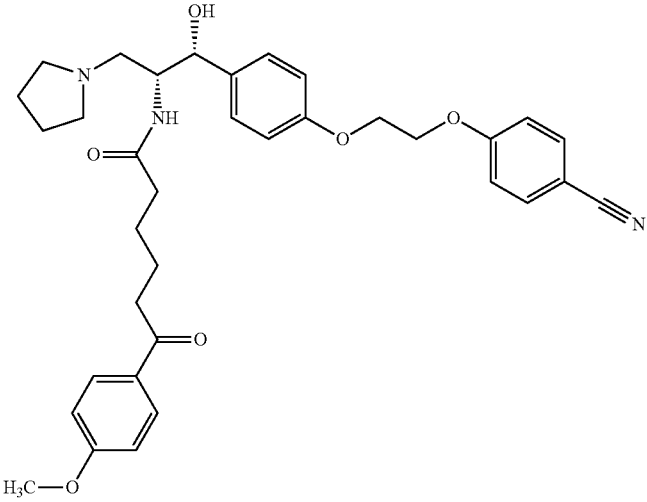 [SMILES: COc1ccc(C(=O)CCCCC(=O)N[C@H](CN2CCCC2)[C@H](O)c2ccc(OCCOc3ccc(C#N)cc3)cc2)cc1] | A | 364 |
| 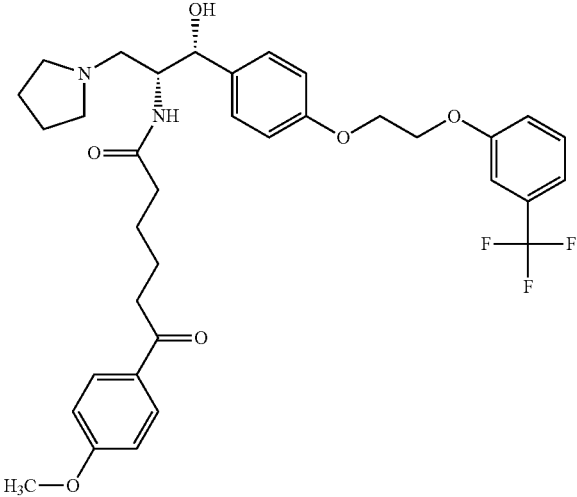 [SMILES: COc1ccc(C(=O)CCCCC(=O)N[C@H](CN2CCCC2)[C@H](O)c2ccc(OCCOc3cccc(C(F)(F)F)c3)cc2)cc1] | A | 365 |
| 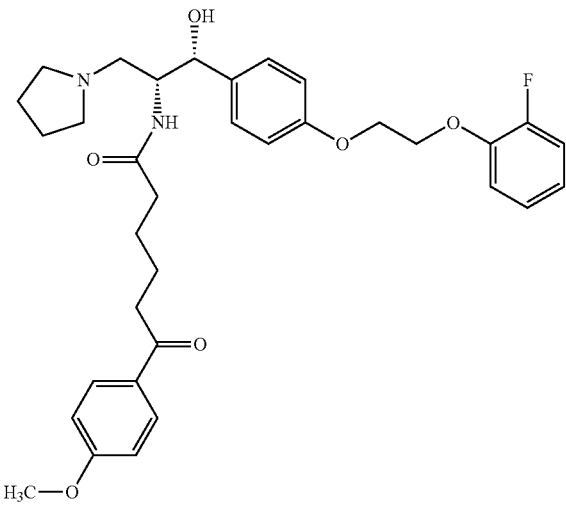 [SMILES: COc1ccc(C(=O)CCCCC(=O)N[C@H](CN2CCCC2)[C@H](O)c2ccc(OCCOc3ccccc3F)cc2)cc1] | A | 366 |

TABLE 3-continued

| Structure | IC50_uM_Mean | Compound |
|---|---|---|
| | A | 367 |
| | A | 368 |
| | A | 369 |

TABLE 3-continued
| Structure | IC50_uM_Mean | Compound |
|---|---|---|
| 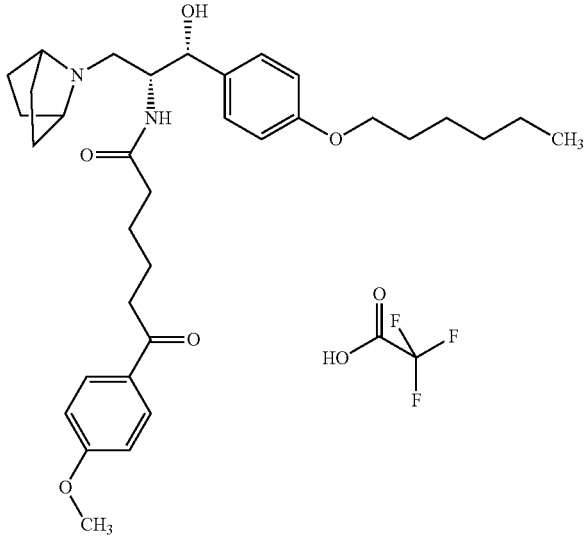 [SMILES: CCCCCCOc1ccc([C@@H](O)[C@@H](CN2C3CCC2CC3)NC(=O)CCCCC(=O)c2ccc(OC)cc2)cc1 ; O=C(O)C(F)(F)F] | A | 370 |
| 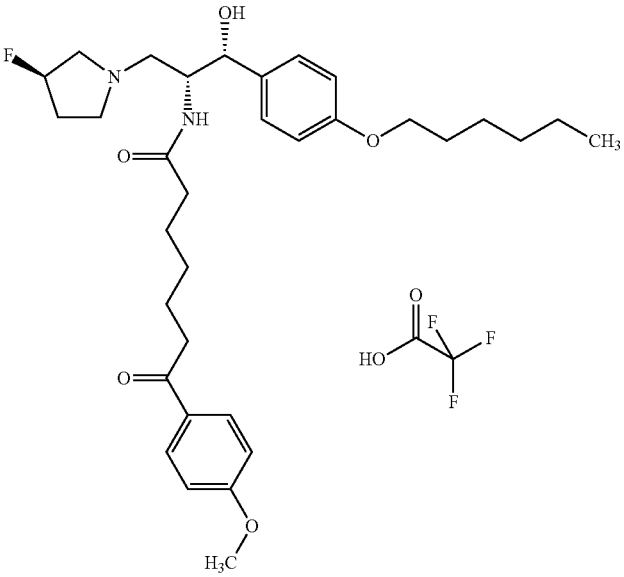 [SMILES: CCCCCCOc1ccc([C@@H](O)[C@@H](CN2CC[C@@H](F)C2)NC(=O)CCCCCC(=O)c2ccc(OC)cc2)cc1 ; O=C(O)C(F)(F)F] | A | 371 |

TABLE 3-continued
IC 50 Values
| Structure | IC50_uM_Mean | Compound |
|---|---|---|
| 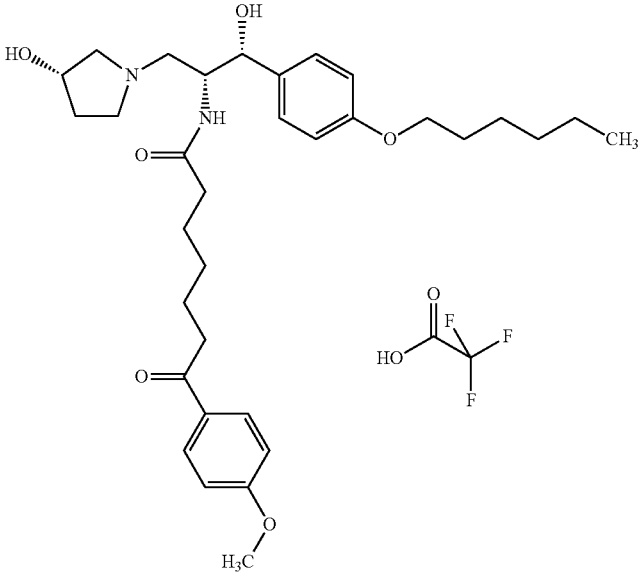 [SMILES: CCCCCCOc1ccc([C@@H](O)[C@@H](CN2CC[C@H](O)C2)NC(=O)CCCCCC(=O)c2ccc(OC)cc2)cc1 ; O=C(O)C(F)(F)F] | A | 372 |
| 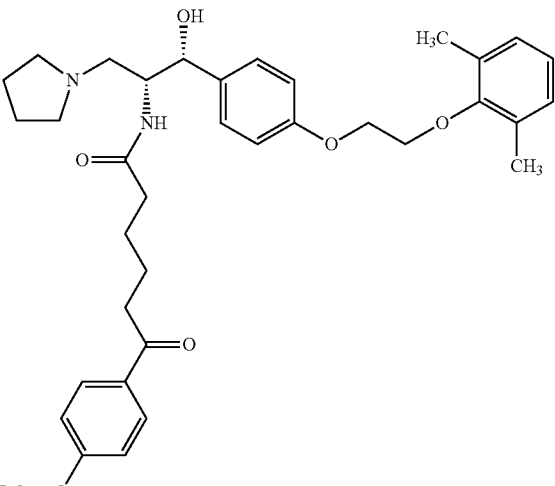 | A | 373 |

TABLE 3-continued

IC 50 Values

| Structure | IC50_uM_Mean | Compound |
|---|---|---|
|  | A | 374 |
| 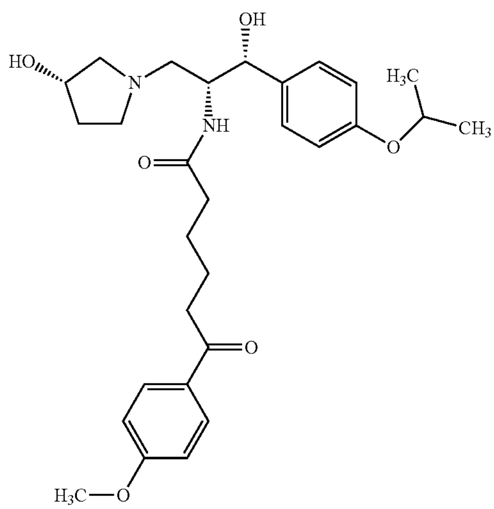 [SMILES: COc1ccc(C(=O)CCCCC(=O)N[C@H](CN2CC[C@H](O)C2)[C@H](O)c2ccc(OC(C)C)cc2)cc1] | B | 375 |
|  | A | 376 |

TABLE 3-continued
IC 50 Values
| Structure | IC50_uM_Mean | Compound |
|---|---|---|
| 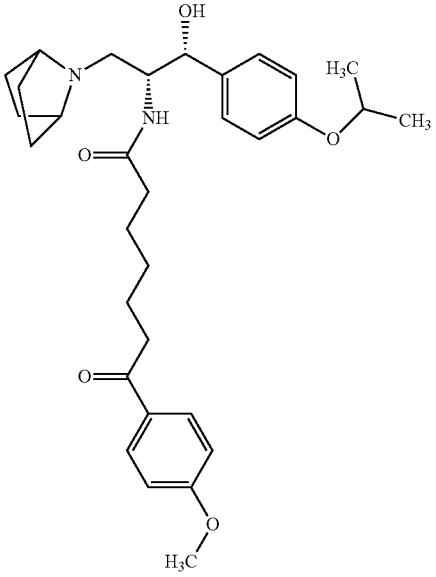 [SMILES: COc1ccc(C(=O)CCCCCC(=O)N[C@H](CN2C3CCC2CC3)[C@H](O)c2ccc(OC(C)C)cc2)cc1] | A | 377 |
| 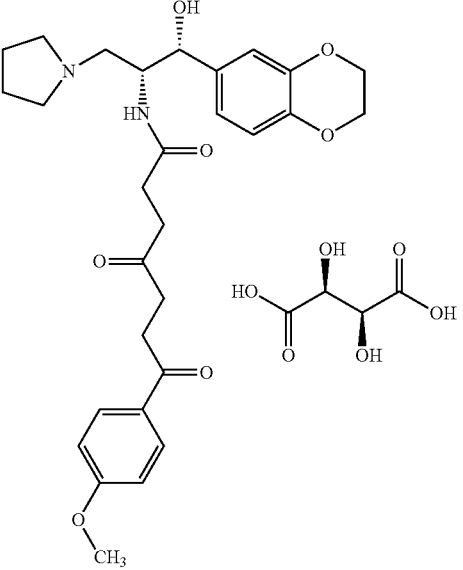 [SMILES: COc1ccc(C(=O)CCC(=O)CCC(=O)N[C@H](CN2CCCC2)[C@H](O)c2ccc3c(c2)OCCO3)cc1 ; O=C(O)[C@@H](O)[C@H](O)C(=O)O] | A | 378 |
| 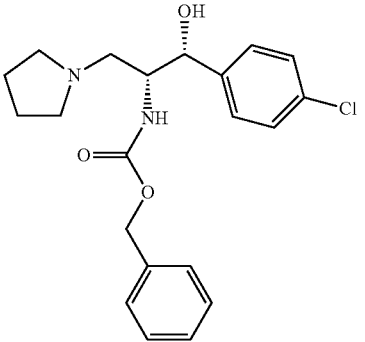 [SMILES: O=C(N[C@H](CN1CCCC1)[C@H](O)c1ccc(Cl)cc1)OCc1ccccc1] | B | 379 |

TABLE 3-continued

| IC 50 Values | | |
|---|---|---|
| Structure | IC50_uM_Mean | Compound |
| | A | 380 |
| | C | 381 |
| | B | 382 |

TABLE 3-continued
IC 50 Values
| Structure | IC50_uM_Mean | Compound |
|---|---|---|
| 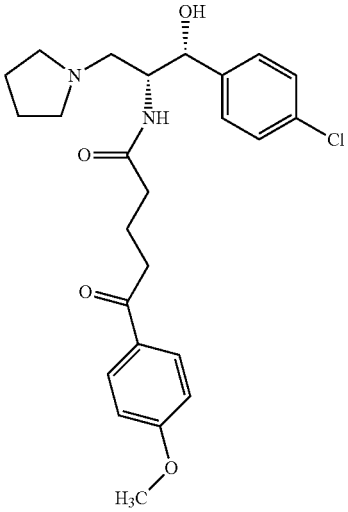 [SMILES: COc1ccc(C(=O)CCCC(=O)N[C@H](CN2CCCC2)[C@H](O)c2ccc(Cl)cc2)cc1] | B | 383 |
| 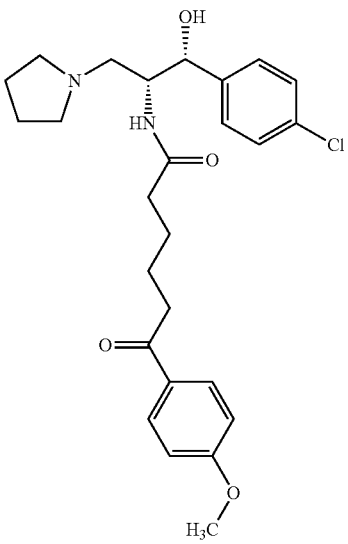 [SMILES: COc1ccc(C(=O)CCCCC(=O)N[C@H](CN2CCCC2)[C@H](O)c2ccc(Cl)cc2)cc1] | B | 384 |
| 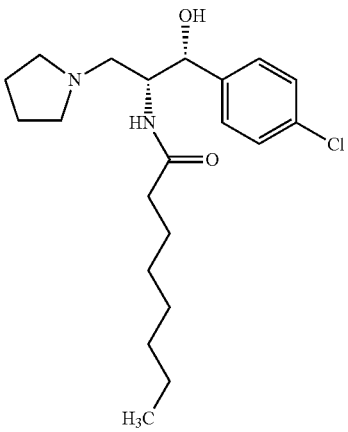 [SMILES: CCCCCCCC(=O)N[C@H](CN1CCCC1)[C@H](O)c1ccc(Cl)cc1] | C | 385 |

TABLE 3-continued

IC 50 Values

| Structure | IC50_uM_Mean | Compound |
|---|---|---|
| | B | 386 |
| | B | 387 |
| 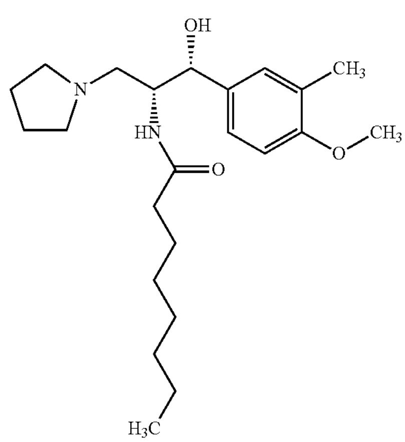 [SMILES: CCCCCCCC(=O)N[C@H](CN1CCCC1)[C@H](O)c1ccc(OC)c(C)c1] | A | 388 |

TABLE 3-continued
| IC 50 Values | | |
|---|---|---|
| Structure | IC50_uM_Mean | Compound |
| 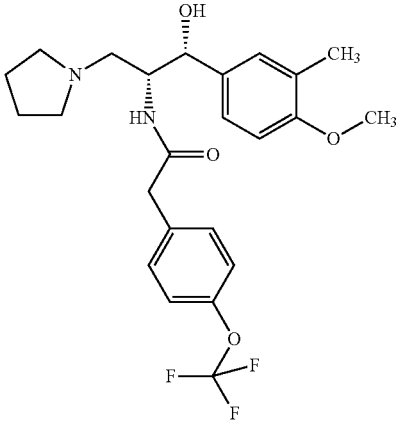 [SMILES: COc1ccc([C@@H](O)[C@@H](CN2CCCC2)NC(=O)Cc2ccc(OC(F)(F)F)cc2)cc1C] | A | 389 |
| 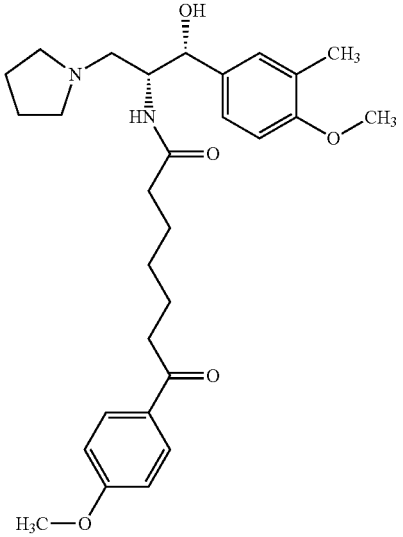 [SMILES: COc1ccc(C(=O)CCCCCC(=O)N[C@H](CN2CCCC2)[C@H](O)c2ccc(OC)c(C)c2)cc1] | A | 390 |
| 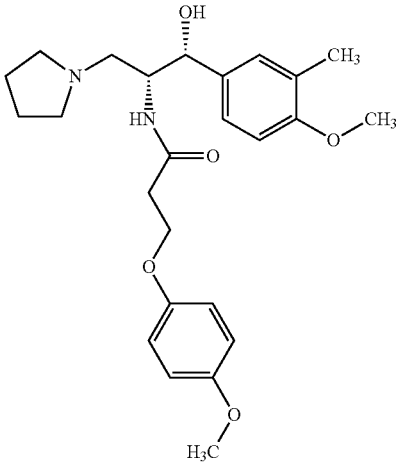 [SMILES: COc1ccc(OCCC(=O)N[C@H](CN2CCCC2)[C@H](O)c2ccc(OC)c(C)c2)cc1] | B | 391 |

TABLE 3-continued
| IC 50 Values | | |
|---|---|---|
| Structure | IC50_uM_Mean | Compound |
| 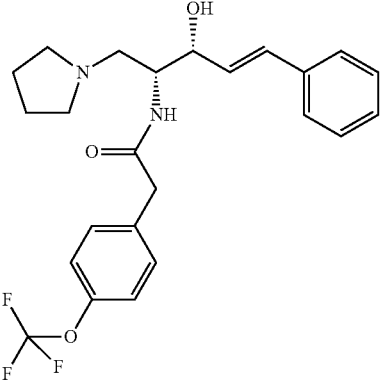 [SMILES: O=C(Cc1ccc(OC(F)(F)F)cc1)N[C@H](CN1CCCC1)[C@H](O)/C=C/c1ccccc1] | D | 392 |
| 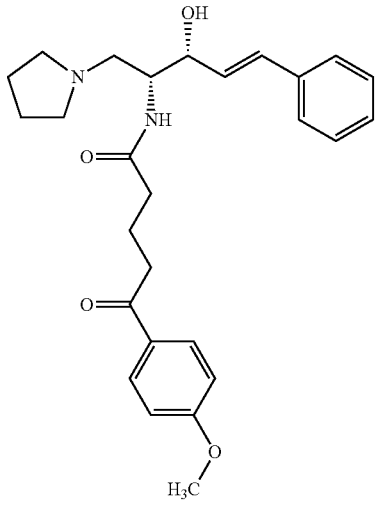 [SMILES: COc1ccc(C(=O)CCCC(=O)N[C@H](CN2CCCC2)[C@H](O)/C=C/c2ccccc2)cc1] | D | 393 |
| 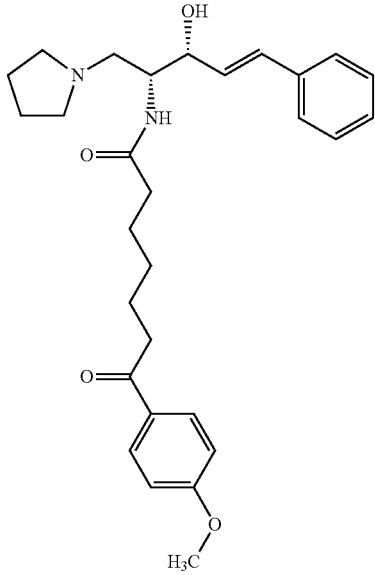 [SMILES: COc1ccc(C(=O)CCCCCC(=O)N[C@H](CN2CCCC2)[C@H](O)/C=C/c2ccccc2)cc1] | C | 394 |

TABLE 3-continued

IC 50 Values

| Structure | IC50_uM_Mean | Compound |
|---|---|---|
| (structure) | D | 395 |
| (structure) | D | 396 |
| (structure) | D | 397 |

TABLE 3-continued

| Structure | IC50_uM_Mean | Compound |
|---|---|---|
| | D | 398 |
| 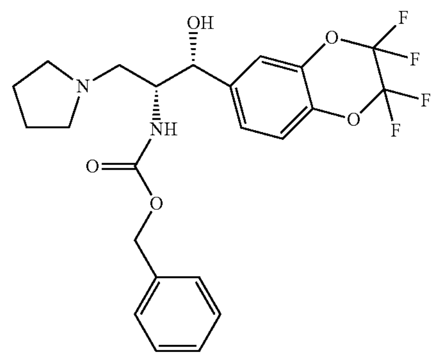 [SMILES: O=C(N[C@H](CN1CCCC1)[C@H](O)c1ccc2c(c1)OC(F)(F)C(F)(F)O2)OCc1ccccc1] | C | 399 |
| | D | 400 |

TABLE 3-continued
| IC 50 Values | | |
|---|---|---|
| Structure | IC50_uM_Mean | Compound |
| 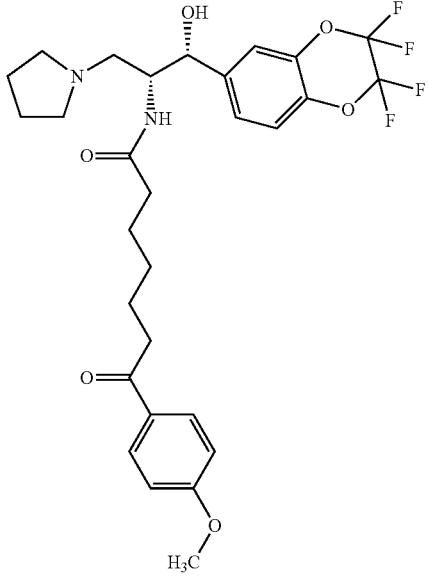 [SMILES: COc1ccc(C(=O)CCCCCC(=O)N[C@H](CN2CCCC2)[C@H](O)c2ccc3c(c2)OC(F)(F)C(F)(F)O3)cc1] | B | 401 |
| 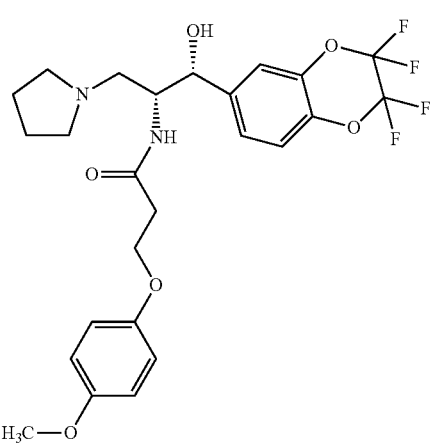 [SMILES: COc1ccc(OCCC(=O)N[C@H](CN2CCCC2)[C@H](O)c2ccc3c(c2)OC(F)(F)C(F)(F)O3)cc1] | D | 402 |
| 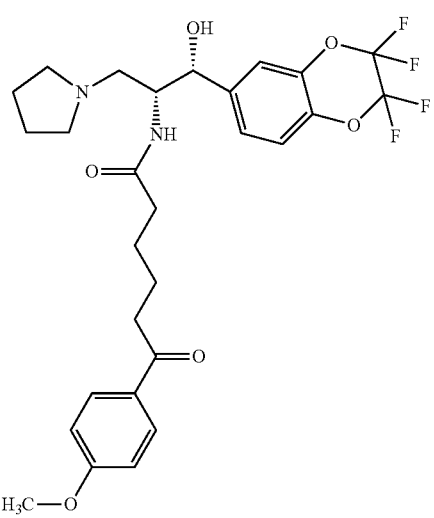 [SMILES: COc1ccc(C(=O)CCCCC(=O)N[C@H](CN2CCCC2)[C@H](O)c2ccc3c(c2)OC(F)(F)C(F)(F)O3)cc1] | C | 403 |

TABLE 3-continued

IC 50 Values

| Structure | IC50_uM_Mean | Compound |
|---|---|---|
| | D | 404 |
| | C | 405 |
| | D | 406 |
| | C | 407 |

TABLE 3-continued
IC 50 Values
| Structure | IC50_uM_Mean | Compound |
|---|---|---|
| 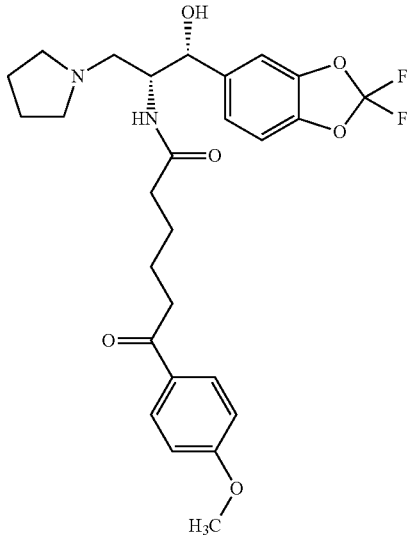 [SMILES: COc1ccc(C(=O)CCCCC(=O)N[C@H](CN2CCCC2)[C@H](O)c2ccc3c(c2)OC(F)(F)O3)cc1] | C | 408 |
| 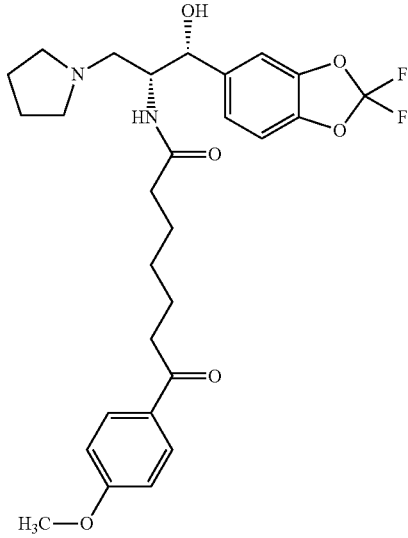 [SMILES: COc1ccc(C(=O)CCCCCC(=O)N[C@H](CN2CCCC2)[C@H](O)c2ccc3c(c2)OC(F)(F)O3)cc1] | B | 409 |
| 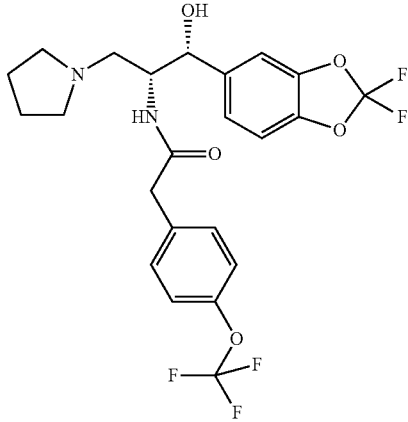 [SMILES: O=C(Cc1ccc(OC(F)(F)F)cc1)N[C@H](CN1CCCC1)[C@H](O)c1ccc2c(c1)OC(F)(F)O2] | D | 410 |

TABLE 3-continued

IC 50 Values

| Structure | IC50_uM_Mean | Compound |
|---|---|---|
| 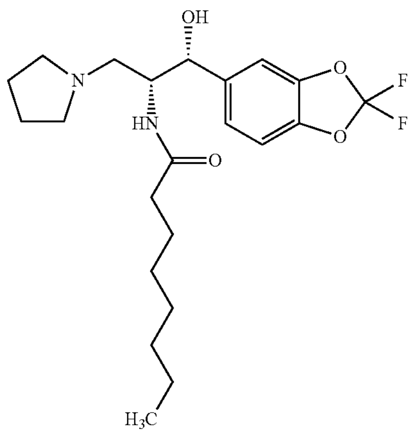 [SMILES: CCCCCCCC(=O)N[C@H](CN1CCCC1)[C@H](O)c1ccc2c(c1)OC(F)(F)O2] | D | 411 |
| | A | 412 |
| | A | 413 |

TABLE 3-continued
IC 50 Values
| Structure | IC50_uM_Mean | Compound |
|---|---|---|
| 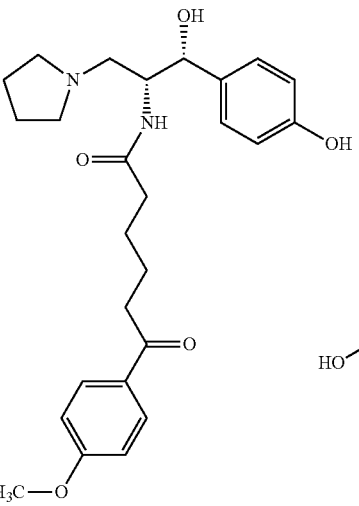 | B | 414 |
|  | B | 415 |
| 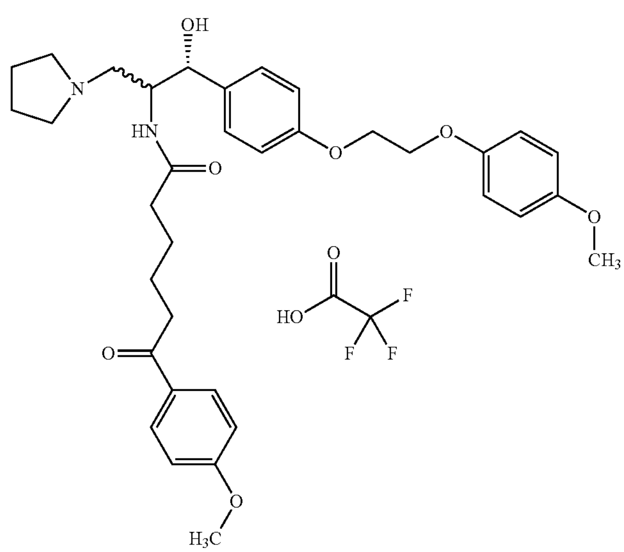 [SMILES: COc1ccc(OCCOc2ccc([C@@H](O)C(CN3CCCC3)NC(=O)CCCCC(=O)c3ccc(OC)cc3)cc2)cc1 ; O=C(O)C(F)(F)F] | A | 416 |

TABLE 3-continued

| | IC 50 Values | |
|---|---|---|
| Structure | IC50_uM_Mean | Compound |
| | A | 417 |
| | A | 418 |
| | A | 419 |

TABLE 3-continued

IC 50 Values

| Structure | IC50_uM_Mean | Compound |
|---|---|---|
| | A | 420 |
| | A | 421 |
| 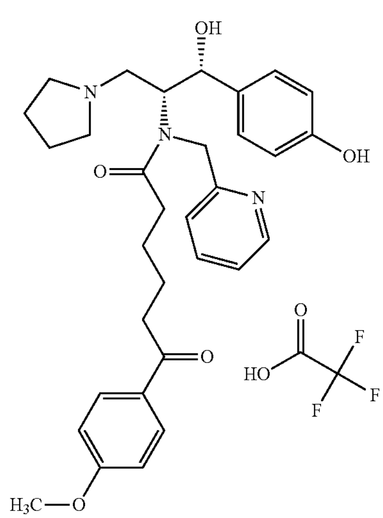 | D | 422 |

TABLE 3-continued

IC 50 Values

| Structure | IC50_uM_Mean | Compound |
|---|---|---|
| 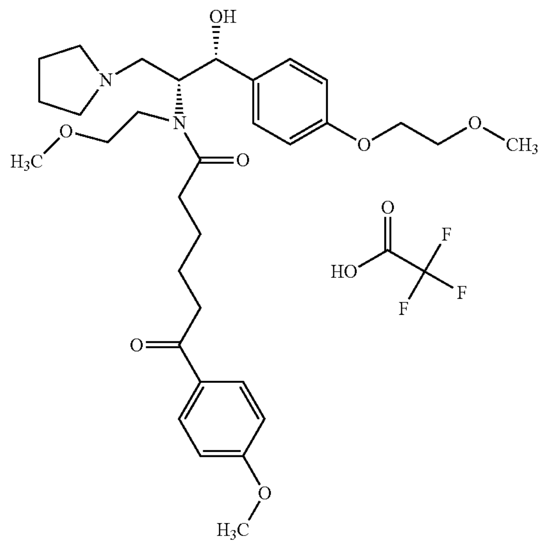 | C | 423 |
| | D | 424 |
| | D | 425 |

TABLE 3-continued

IC 50 Values

| Structure | IC50_uM_Mean | Compound |
|---|---|---|
| | D | 426 |
| | D | 427 |
| | D | 428 |

TABLE 3-continued

IC 50 Values

| Structure | IC50_uM_Mean | Compound |
|-----------|--------------|----------|
| 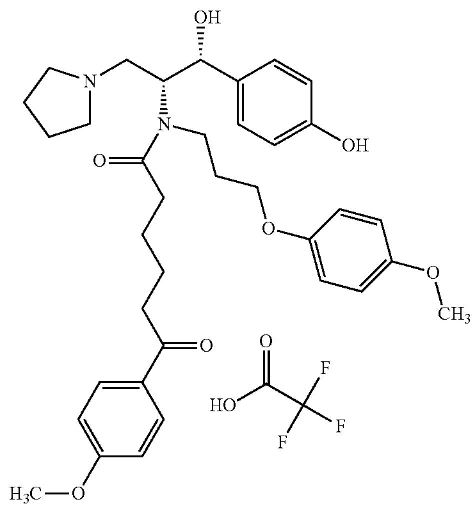 [SMILES: COc1ccc(OCCCN(C(=O)CCCCC(=O)c2ccc(OC)cc2)[C@H](CN2CCCC2)[C@H](O)c2ccc(O)cc2)cc1 ; O=C(O)C(F)(F)F] | D | 429 |
| | A | 430 |
| | A | 431 |

TABLE 3-continued

IC 50 Values

| Structure | IC50_uM_Mean | Compound |
|---|---|---|
| | A | 432 |
| | A | 433 |
| | A | 434 |

TABLE 3-continued

IC 50 Values

| Structure | IC50_uM_Mean | Compound |
|---|---|---|
| | A | 435 |
| | A | 436 |
| | A | 437 |

TABLE 3-continued

IC 50 Values

| Structure | IC50_uM_Mean | Compound |
|---|---|---|
| | A | 438 |
| 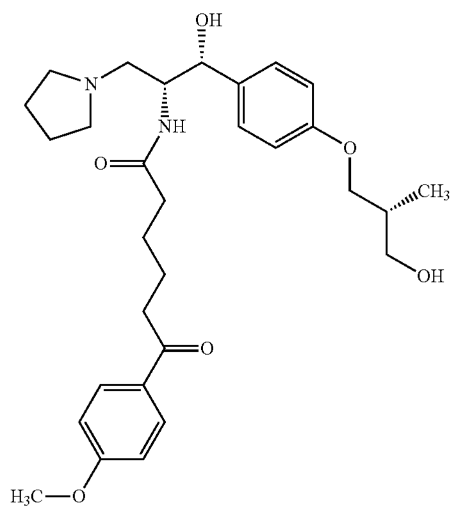 [SMILES: COc1ccc(C(=O)CCCCC(=O)N[C@H](CN2CCCC2)[C@H](O)c2ccc(OC[C@H](C)CO)cc2)cc1] | B | 439 |
| | A | 440 |

TABLE 3-continued
IC 50 Values
| Structure | IC50_uM_Mean | Compound |
|---|---|---|
| 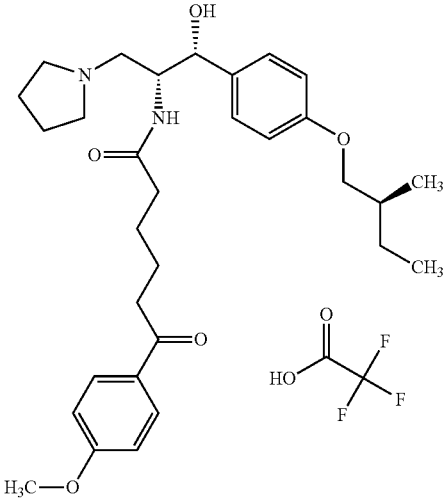 [SMILES: CC[C@H](C)COc1ccc([C@@H](O)[C@@H](CN2CCCC2)NC(=O)CCCCC(=O)c2ccc(OC)cc2)cc1 ; O=C(O)C(F)(F)F] | A | 441 |
| 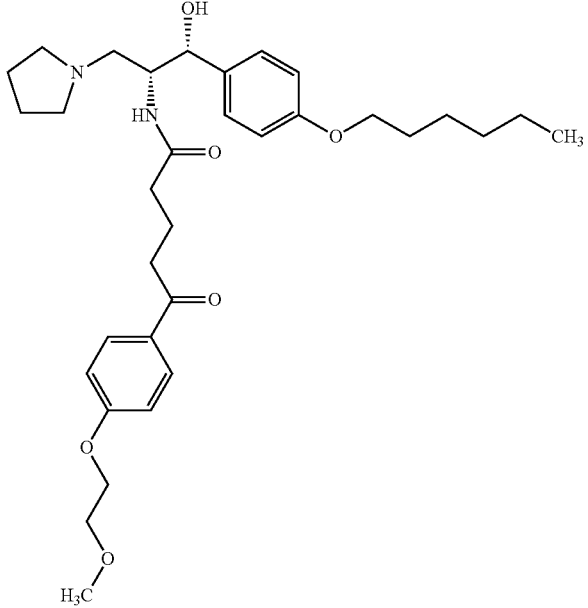 [SMILES: CCCCCCOc1ccc([C@@H](O)[C@@H](CN2CCCC2)NC(=O)CCCC(=O)c2ccc(OCCOC)cc2)cc1] | A | 442 |

TABLE 3-continued
IC 50 Values
| Structure | IC50_uM_Mean | Compound |
|---|---|---|
| 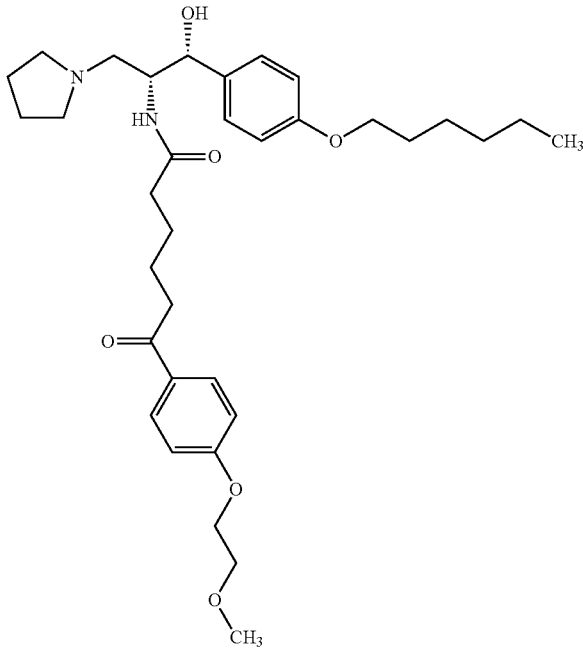 [SMILES: CCCCCCOc1ccc([C@@H](O)[C@@H](CN2CCCC2)NC(=O)CCCCC(=O)c2ccc(OCCOC)cc2)cc1] | A | 443 |
| 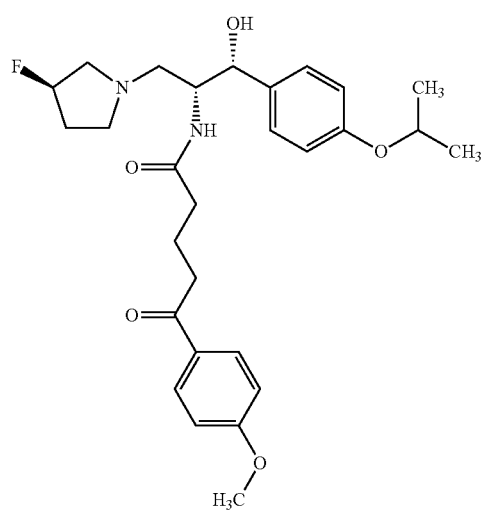 [SMILES: COc1ccc(C(=O)CCCC(=O)N[C@H](CN2CC[C@@H](F)C2)[C@H](O)c2ccc(OC(C)C)cc2)cc1] | B | 444 |

TABLE 3-continued

IC 50 Values

| Structure | IC50_uM_Mean | Compound |
|---|---|---|
| 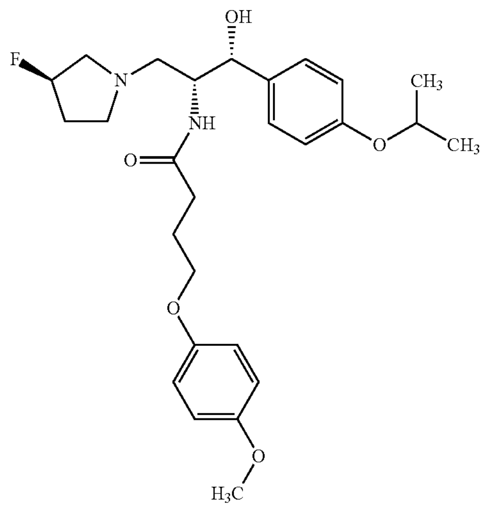 [SMILES: COc1ccc(OCCCC(=O)N[C@H](CN2CC[C@@H](F)C2)[C@H](O)c2ccc(OC(C)C)cc2)cc1] | B | 445 |
|  | A | 446 |
|  | A | 447 |

TABLE 3-continued
IC 50 Values
| Structure | IC50_uM_Mean | Compound |
|---|---|---|
| 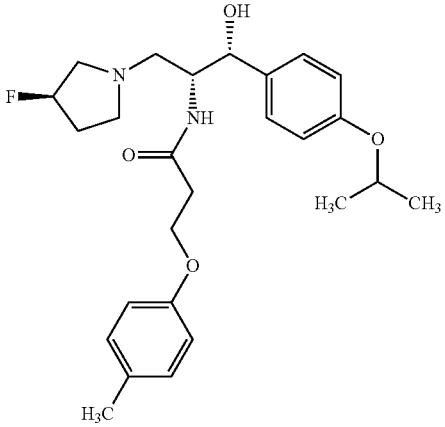 [SMILES: Cc1ccc(OCCC(=O)N[C@H](CN2CC[C@@H](F)C2)[C@H](O)c2ccc(OC(C)C)cc2)cc1] | B | 448 |
| 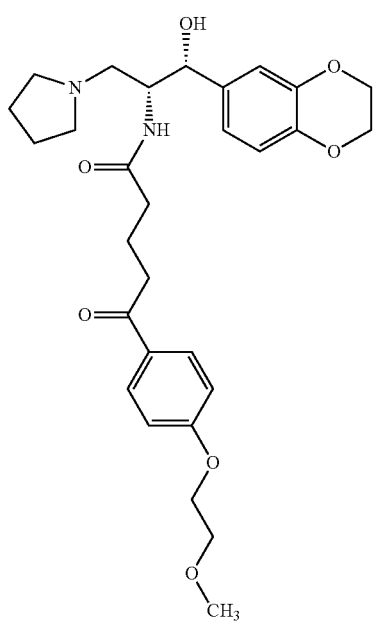 [SMILES: COCCOc1ccc(C(=O)CCCC(=O)N[C@H](CN2CCCC2)[C@H](O)c2ccc3c(c2)OCCO3)cc1] | A | 449 |

TABLE 3-continued
| IC 50 Values | | |
|---|---|---|
| Structure | IC50_uM_Mean | Compound |
| 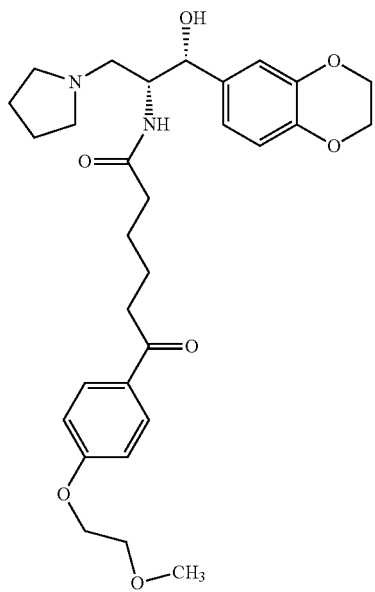 [SMILES: COCCOc1ccc(C(=O)CCCCC(=O)N[C@H](CN2CCCC2)[C@H](O)c2ccc3c(c2)OCCO3)cc1] | A | 450 |
| 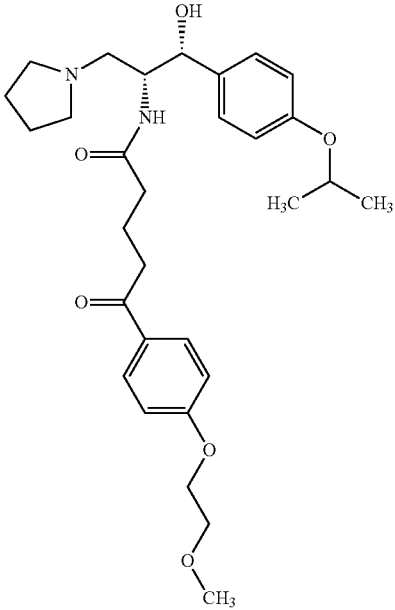 [SMILES: COCCOc1ccc(C(=O)CCCC(=O)N[C@H](CN2CCCC2)[C@H](O)c2ccc(OC(C)C)cc2)cc1] | B | 451 |

TABLE 3-continued

IC 50 Values

| Structure | IC50_uM_Mean | Compound |
|---|---|---|
| 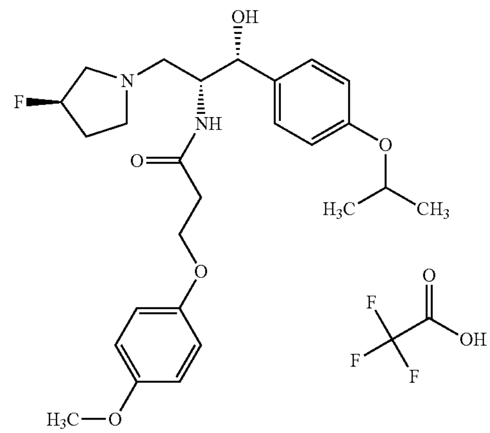 [SMILES: COc1ccc(OCCC(=O)N[C@H](CN2CC[C@@H](F)C2)[C@H](O)c2ccc(OC(C)C)cc2)cc1 ; O=C(O)C(F)(F)F] | B | 452 |
| | A | 453 |
| | A | 454 |

TABLE 3-continued
IC 50 Values
| Structure | IC50_uM_Mean | Compound |
|---|---|---|
| 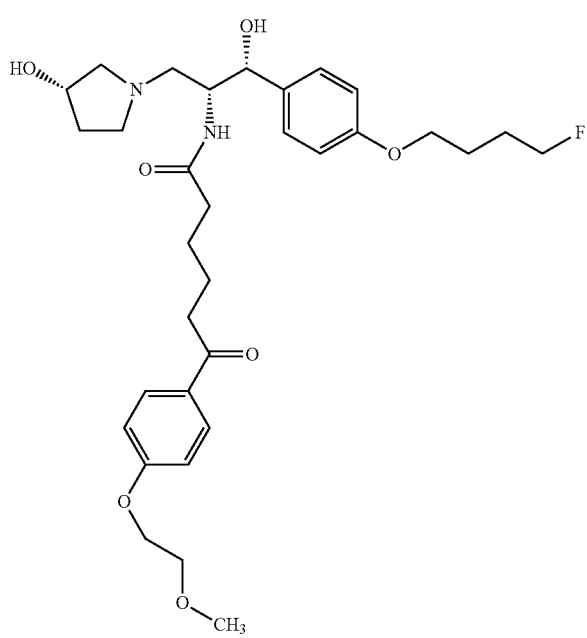 [SMILES: COCCOc1ccc(C(=O)CCCCC(=O)N[C@H](CN2CC[C@H](O)C2)[C@H](O)c2ccc(OCCCCF)cc2)cc1] | A | 455 |
| 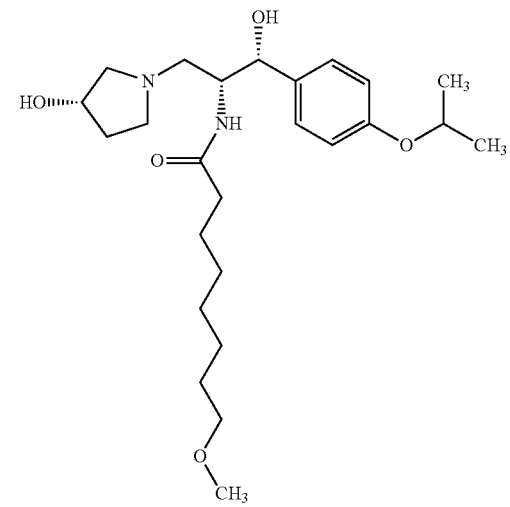 [SMILES: COCCCCCCCC(=O)N[C@H](CN1CC[C@H](O)C1)[C@H](O)c1ccc(OC(C)C)cc1] | A | 456 |

TABLE 3-continued

| Structure | IC50_uM_Mean | Compound |
|---|---|---|
| (structure) | A | 457 |
| Chiral (structure) | D | 458 |

TABLE 3-continued
| | IC 50 Values | |
|---|---|---|
| Structure | IC50_uM_Mean | Compound |
| Chiral 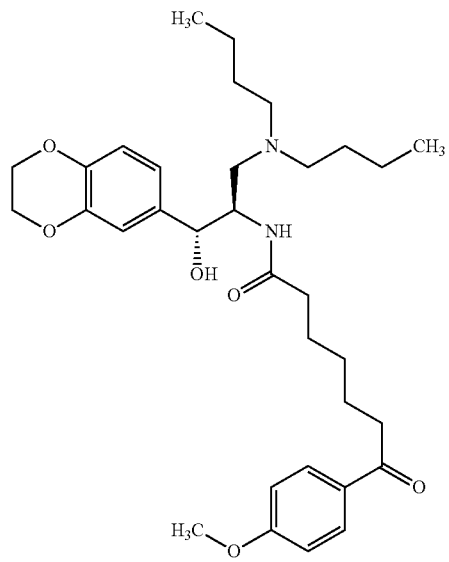 | D | 459 |
| Chiral 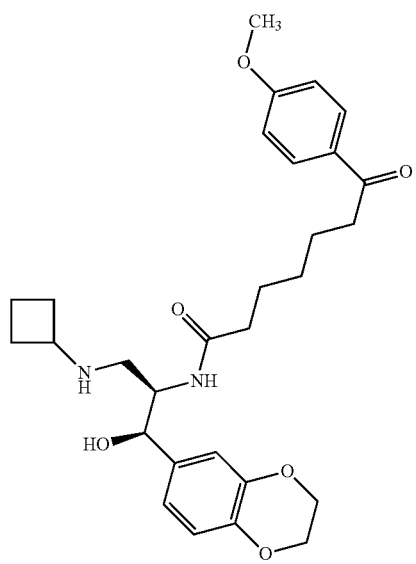 | C | 460 |

TABLE 3-continued
| Structure | IC50_uM_Mean | Compound |
|---|---|---|
| 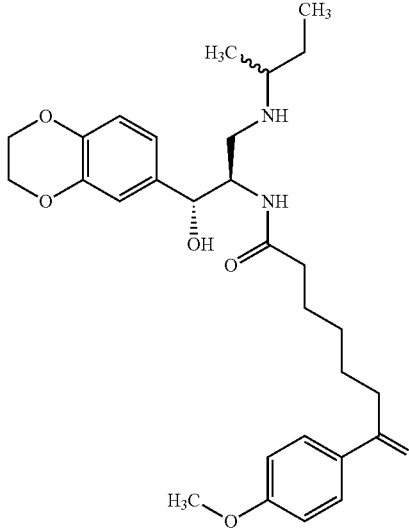 | B | 461 |
| 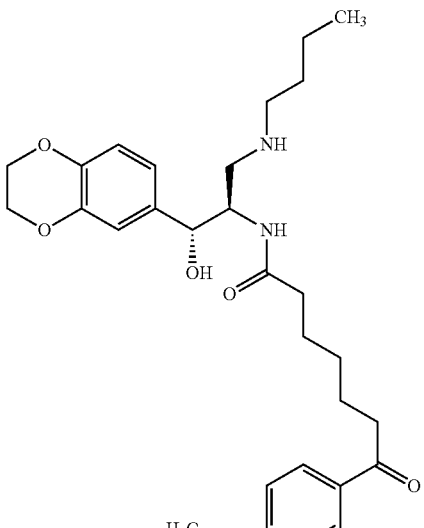 Chiral | C | 462 |

TABLE 3-continued

| Structure | IC50_uM_Mean | Compound |
|---|---|---|
| Chiral | B | 463 |
| Chiral | D | 464 |

TABLE 3-continued
| | IC 50 Values | |
|---|---|---|
| Structure | IC50_uM_Mean | Compound |
| Chiral | B | 465 |
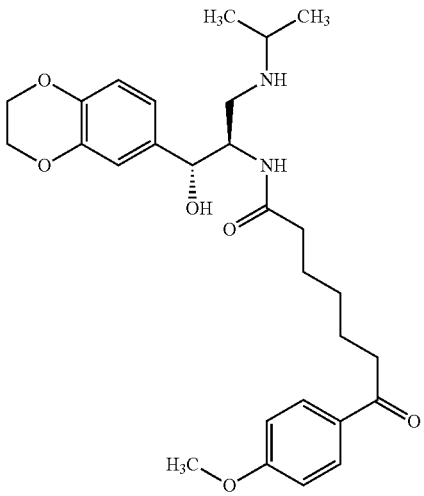
| Chiral | D | 466 |
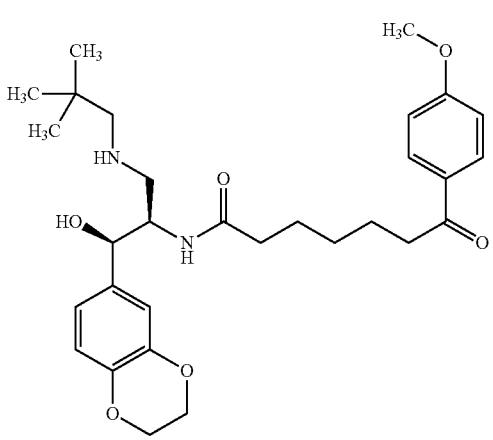

TABLE 3-continued
| Structure | IC50_uM_Mean | Compound |
|---|---|---|
| Chiral 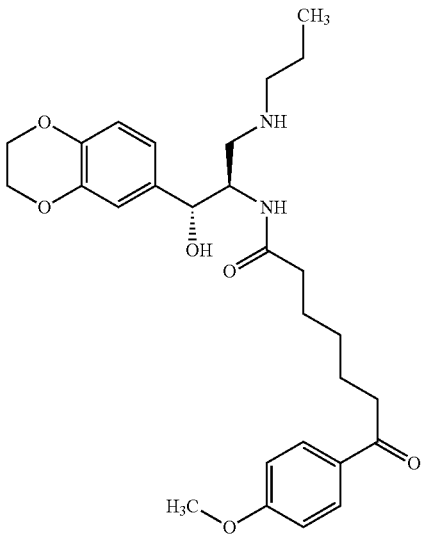 [SMILES: CCC(C)NC[C@@H](NC(=O)CCCCCC(=O)c1ccc(OC)cc1)[C@H](O)c1ccc2c(c1)OCCO2] | B | 467 |
| 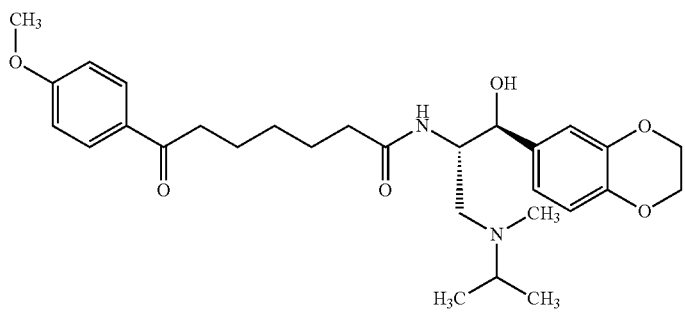 [SMILES: COc1ccc(C(=O)CCCCCC(=O)N[C@@H](CN(C)C(C)C)[C@@H](O)c2ccc3c(c2)OCCO3)cc1] | A | 468 |
| 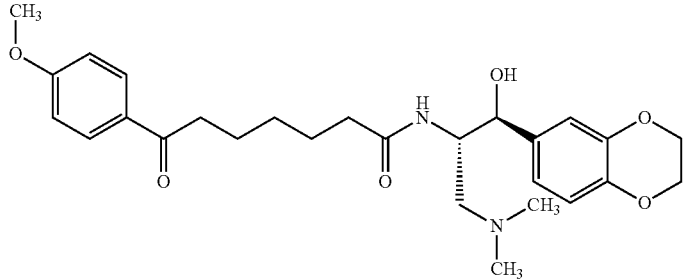 [SMILES: COc1ccc(C(=O)CCCCCC(=O)N[C@@H](CN(C)C)[C@@H](O)c2ccc3c(c2)OCCO3)cc1] | B | 469 |
| 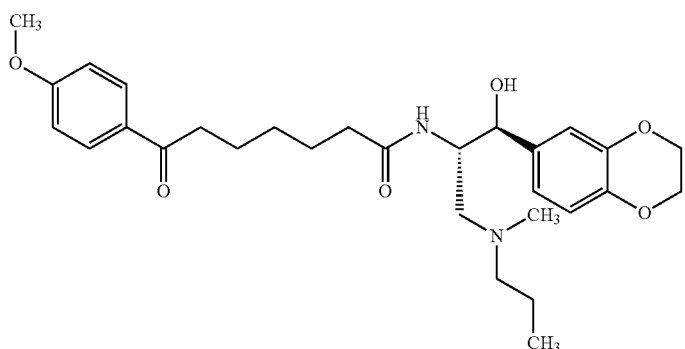 [SMILES: CCCN(C)C[C@H](NC(=O)CCCCCC(=O)c1ccc(OC)cc1)[C@@H](O)c1ccc2c(c1)OCCO2] | B | 470 |

TABLE 3-continued

IC 50 Values

| Structure | IC50_uM_Mean | Compound |
|---|---|---|
| 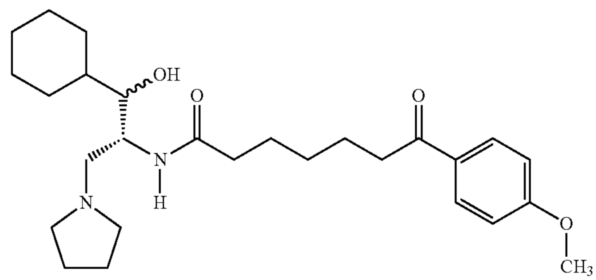 [SMILES: COc1ccc(C(=O)CCCCCC(=O)N[C@H](CN2CCCC2)C(O)C2CCCCC2)cc1] | C | 471 |
| 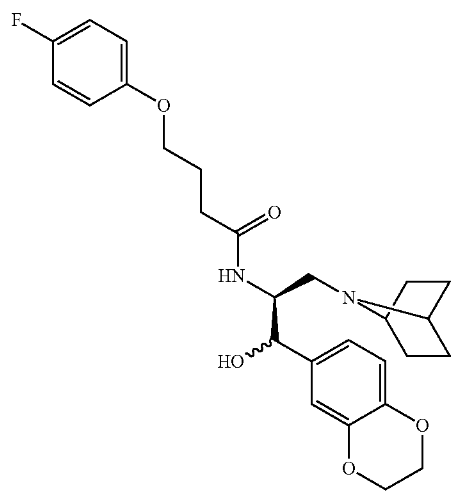 [SMILES: O=C(CCCOc1ccc(F)cc1)N[C@@H](CN1C2CCC1CC2)C(O)c1ccc2c(c1)OCCO2] | B | 472 |
| 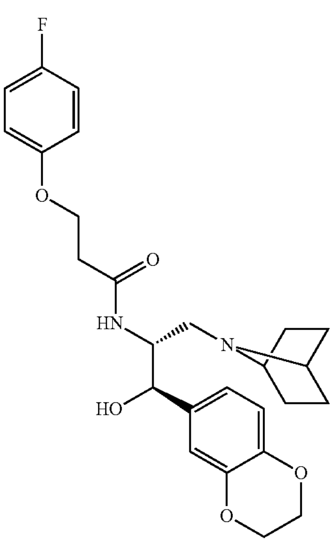 [SMILES: O=C(CCOc1ccc(F)cc1)N[C@H](CN1C2CCC1CC2)[C@H](O)c1ccc2c(c1)OCCO2] | A | 473 |

TABLE 3-continued
| IC 50 Values | | |
|---|---|---|
| Structure | IC50_uM_Mean | Compound |
| 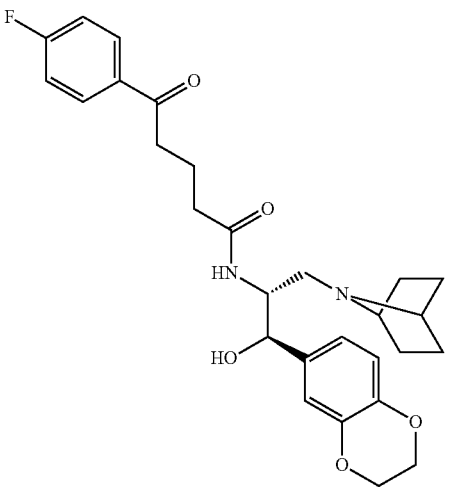 [SMILES: O=C(CCCC(=O)c1ccc(F)cc1)N[C@H](CN1C2CCC1CC2)[C@H](O)c1ccc2c(c1)OCCO2] | B | 474 |
| 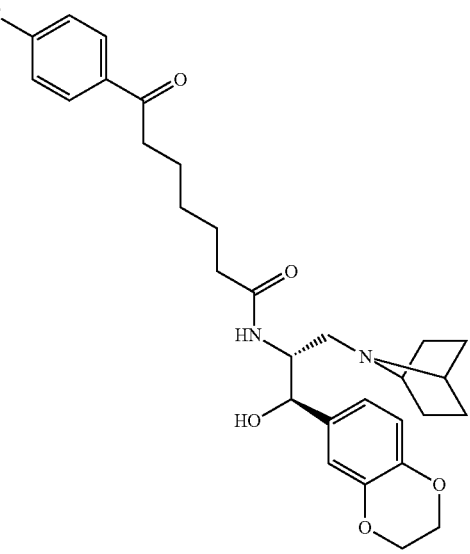 | A | 475 |

TABLE 3-continued
| | IC 50 Values | |
|---|---|---|
| Structure | IC50_uM_Mean | Compound |
| 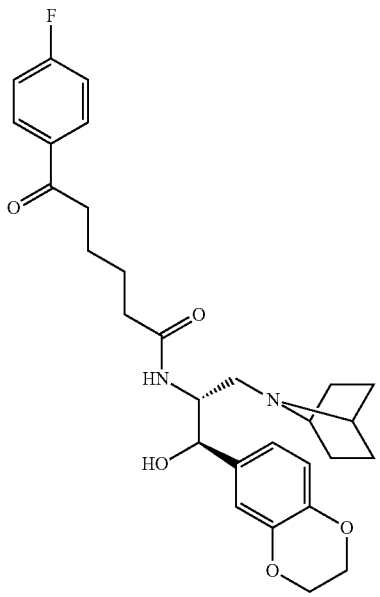 [SMILES: O=C(CCCCC(=O)c1ccc(F)cc1)N[C@H](CN1C2CCC1CC2)[C@H](O)c1ccc2c(c1)OCCO2] | B | 476 |
| 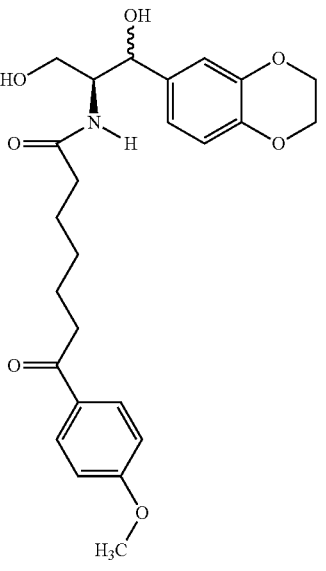 [SMILES: COc1ccc(C(=O)CCCCCC(=O)N[C@@H](CO)C(O)c2ccc3c(c2)OCCO3)cc1] | D | 477 |
| 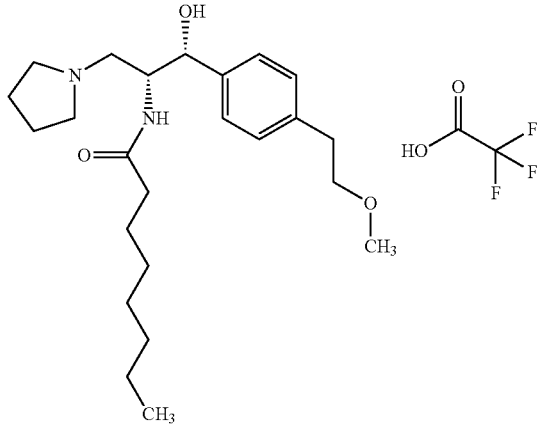 [SMILES: CCCCCCCC(=O)N[C@H](CN1CCCC1)[C@H](O)c1ccc(CCOC)cc1 ; O=C(O)C(F)(F)F] | B | 478 |

TABLE 3-continued

IC 50 Values

| Structure | IC50_uM_Mean | Compound |
|---|---|---|
| 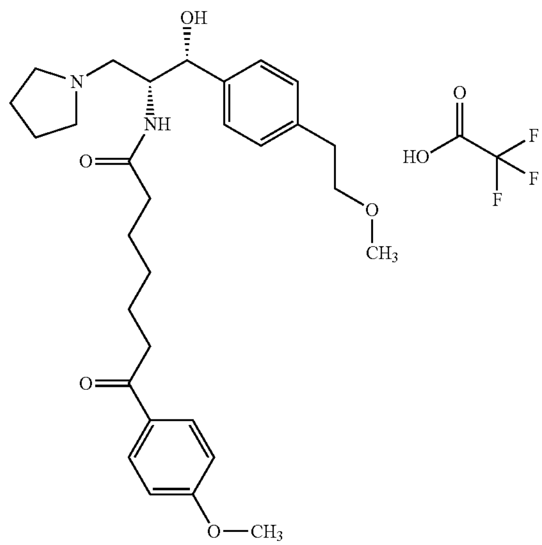 [SMILES: COCCc1ccc([C@@H](O)[C@@H](CN2CCCC2)NC(=O)CCCCCC(=O)c2ccc(OC)cc2)cc1 ; O=C(O)C(F)(F)F] | A | 479 |
| 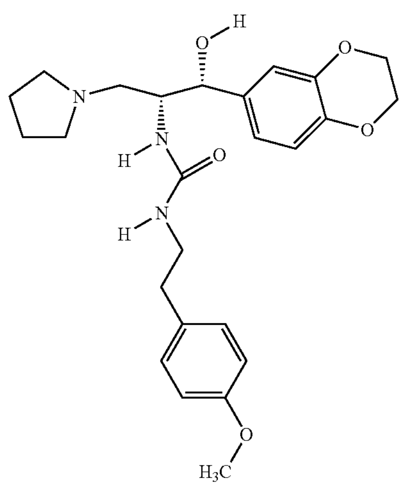 [SMILES: COc1ccc(CCNC(=O)N[C@H](CN2CCCC2)[C@H](O)c2ccc3c(c2)OCCO3)cc1] | C | 480 |
| 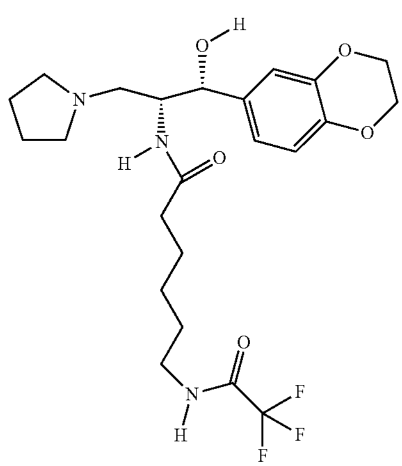 [SMILES: O=C(CCCCCNC(=O)C(F)(F)F)N[C@H](CN1CCCC1)[C@H](O)c1ccc2c(c1)OCCO2] | D | 481 |

TABLE 3-continued

IC 50 Values

| Structure | IC50_uM_Mean | Compound |
|---|---|---|
| (3-fluoro-4-methoxyphenyl with CH(OH)-CH(NHCbz)-CH2OH) | D | 482 |
| (4-trifluoromethylphenyl with CH(OH)-CH(NHCbz)-CH2OH) | D | 483 |
| (4-trifluoromethylphenyl with CH(OH)-CH(NH-CO-(CH2)5-CO-C6H4-OMe)-CH2-pyrrolidine) | C | 484 |

TABLE 3-continued

IC 50 Values

| Structure | IC50_uM_Mean | Compound |
|---|---|---|
| | D | 485 |
| 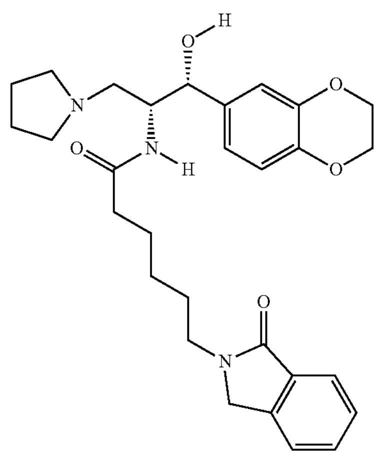 [SMILES: O=C(CCCCCN1Cc2ccccc2C1=O)N[C@H](CN1CCCC1)[C@H](O)c1ccc2c(c1)OCCO2] | C | 486 |
| | D | 487 |

TABLE 3-continued
| Structure | IC50_uM_Mean | Compound |
|---|---|---|
| 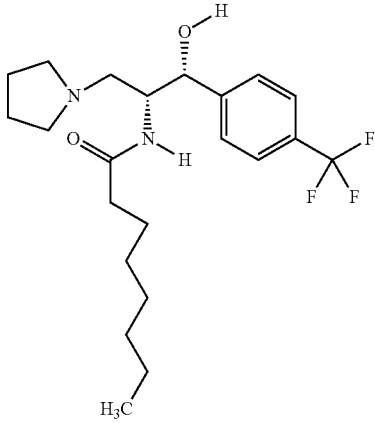 [SMILES: CCCCCCCC(=O)N[C@H](CN1CCCC1)[C@H](O)c1ccc(C(F)(F)F)cc1] | C | 488 |
| 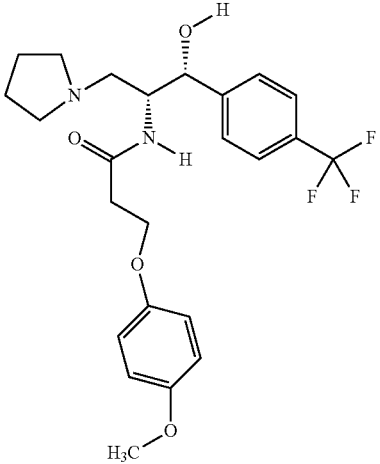 [SMILES: COc1ccc(OCCC(=O)N[C@H](CN2CCCC2)[C@H](O)c2ccc(C(F)(F)F)cc2)cc1] | D | 489 |
| 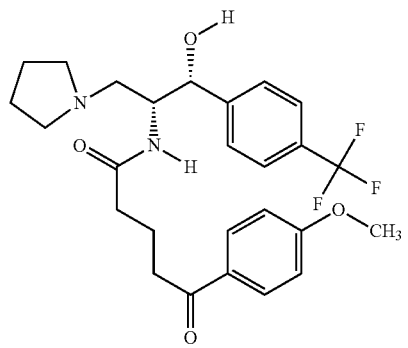 [SMILES: COc1ccc(C(=O)CCCC(=O)N[C@H](CN2CCCC2)[C@H](O)c2ccc(C(F)(F)F)cc2)cc1] | D | 490 |

TABLE 3-continued

| Structure | IC50_uM_Mean | Compound |
|---|---|---|
| | C | 491 |
| 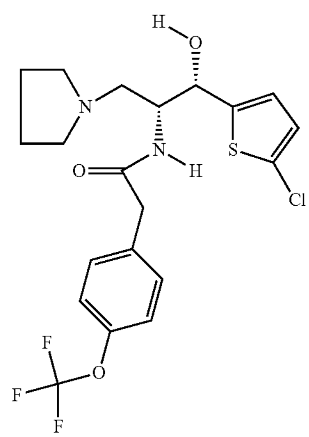 [SMILES: O=C(Cc1ccc(OC(F)(F)F)cc1)N[C@H](CN1CCCC1)[C@H](O)c1ccc(Cl)s1] | D | 492 |
| | C | 493 |

TABLE 3-continued
IC 50 Values
| Structure | IC50_uM_Mean | Compound |
|---|---|---|
| 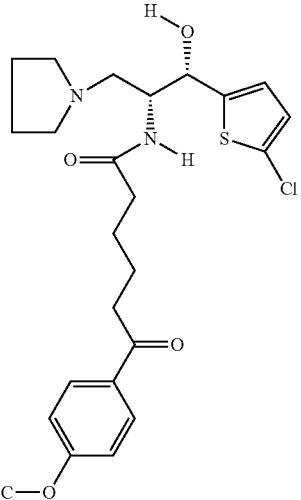 | B | 494 |
| 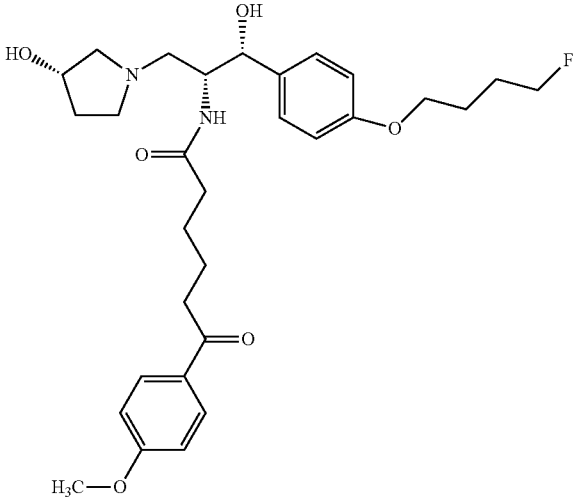 [SMILES: COc1ccc(C(=O)CCCCC(=O)N[C@H](CN2CC[C@H](O)C2)[C@H](O)c2ccc(OCCCCF)cc2)cc1] | A | 495 |
| 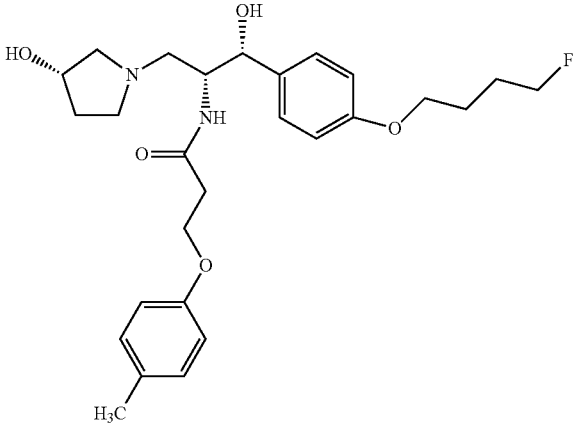 [SMILES: Cc1ccc(OCCC(=O)N[C@H](CN2CC[C@H](O)C2)[C@H](O)c2ccc(OCCCCF)cc2)cc1] | A | 496 |

TABLE 3-continued

IC 50 Values

| Structure | IC50_uM_Mean | Compound |
|---|---|---|
| | A | 497 |
| | A | 498 |
| | A | 499 |

TABLE 3-continued

| Structure | IC50_uM_Mean | Compound |
|---|---|---|
| | A | 500 |
| | A | 501 |
| | A | 502 |

TABLE 3-continued
IC 50 Values
| Structure | IC50_uM_Mean | Compound |
|---|---|---|
| 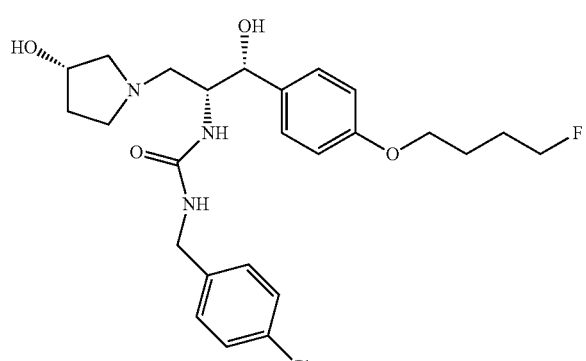 | A | 503 |
| 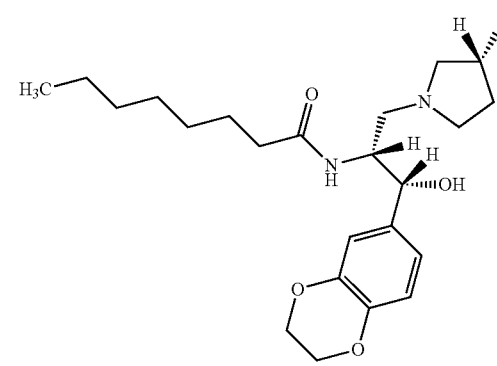 Chiral | B | 504 |
| 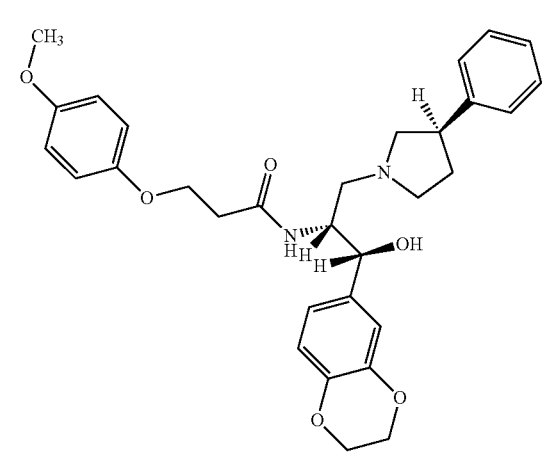 Chiral | D | 505 |

TABLE 3-continued
| | IC 50 Values | | |
| --- | --- | --- | --- |
| Structure | | IC50_uM_Mean | Compound |
| 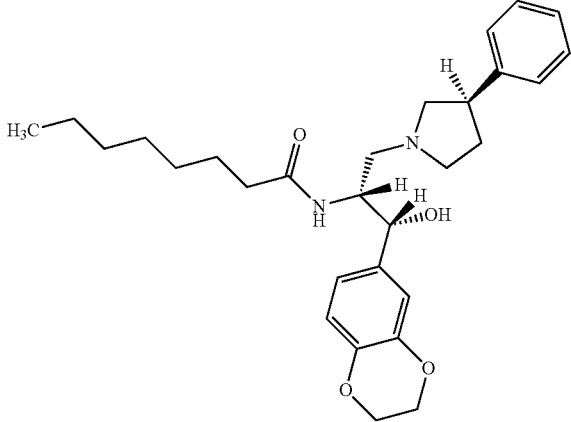 Chiral | | D | 506 |
| 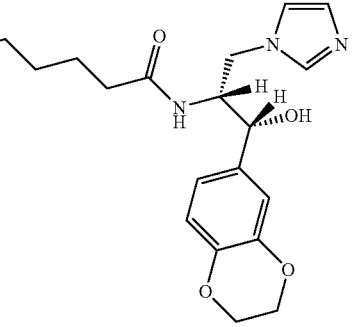 Chiral | | B | 507 |
| 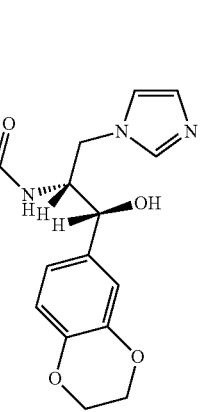 Chiral | | D | 508 |

TABLE 3-continued

| IC 50 Values | | |
|---|---|---|
| Structure | IC50_uM_Mean | Compound |
| Chiral | B | 509 |
| Chiral | D | 510 |
| Chiral | D | 511 |

TABLE 3-continued

| IC 50 Values | | |
|---|---|---|
| Structure | IC50_uM_Mean | Compound |
| (Chiral structure) | C | 512 |
| (Chiral structure) | D | 513 |
| (Chiral structure) | B | 514 |

TABLE 3-continued

IC 50 Values

| Structure | IC50_uM_Mean | Compound |
|---|---|---|
| Chiral | A | 515 |
| | B | 516 |
| | B | 517 |

TABLE 3-continued

| | IC 50 Values | |
|---|---|---|
| Structure | IC50_uM_Mean | Compound |
| Chiral | B | 518 |
| Chiral | D | 519 |

TABLE 3-continued
| | IC 50 Values | |
|---|---|---|
| Structure | IC50_uM_Mean | Compound |
| 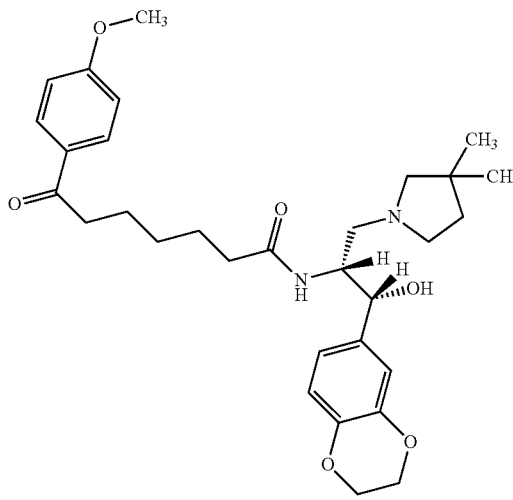 Chiral | C | 520 |
| 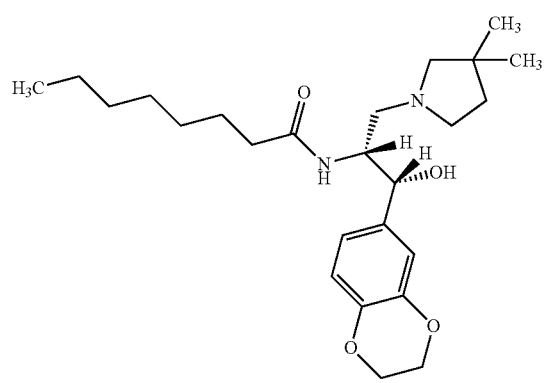 Chiral | D | 521 |

TABLE 3-continued

| | IC 50 Values | |
|---|---|---|
| Structure | IC50_uM_Mean | Compound |
| Chiral | A | 522 |
| Chiral | B | 523 |
| Chiral | B | 524 |

TABLE 3-continued

IC 50 Values

| Structure | IC50_uM_Mean | Compound |
|---|---|---|
| Chiral | A | 525 |
| Chiral | B | 526 |
| Chiral | C | 527 |

TABLE 3-continued

IC 50 Values

| Structure | IC50_uM_Mean | Compound |
|---|---|---|
| (Chiral structure) | C | 528 |
| (Chiral structure) | A | 529 |
| (Chiral structure) | D | 530 |

TABLE 3-continued
| IC 50 Values | | |
|---|---|---|
| Structure | IC50_uM_Mean | Compound |
| Chiral 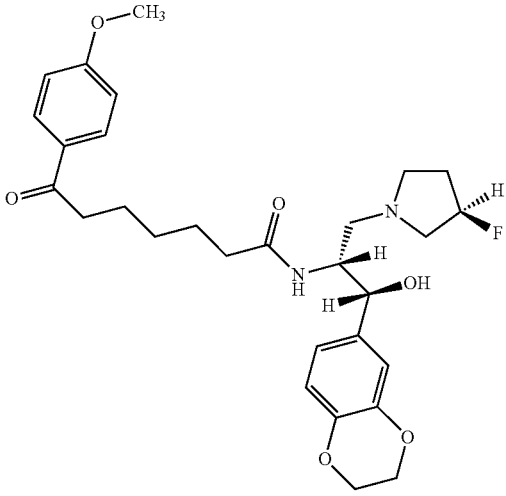 | A | 531 |
| Chiral 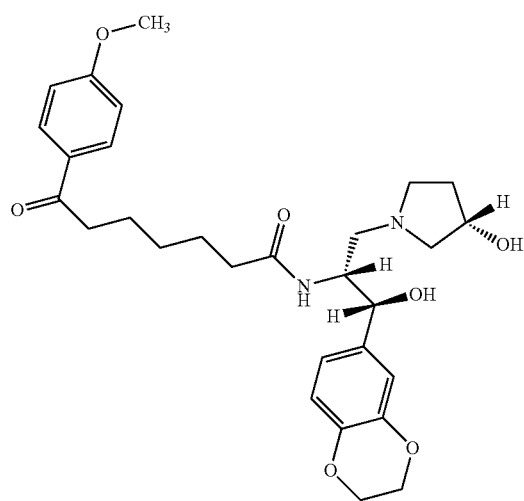 | A | 532 |

TABLE 3-continued

IC 50 Values

| Structure | IC50_uM_Mean | Compound |
|---|---|---|
| Chiral | B | 533 |
| Chiral | D | 534 |
| Chiral | D | 535 |

TABLE 3-continued

IC 50 Values

| Structure | IC50_uM_Mean | Compound |
|---|---|---|
| | D | 536 |
| | A | 537 |
| | D | 538 |

TABLE 3-continued

| | IC 50 Values | |
|---|---|---|
| Structure | IC50_uM_Mean | Compound |
| Chiral (structure) | D | 539 |
| Chiral (structure) | D | 540 |
| Chiral (structure) | D | 541 |

TABLE 3-continued

IC 50 Values

| Structure | IC50_uM_Mean | Compound |
|---|---|---|
| Chiral (structure) | D | 542 |
| Chiral (structure) | D | 543 |
| Chiral (structure) | B | 544 |

TABLE 3-continued
| | IC 50 Values | |
|---|---|---|
| Structure | IC50_uM_Mean | Compound |
| Chiral 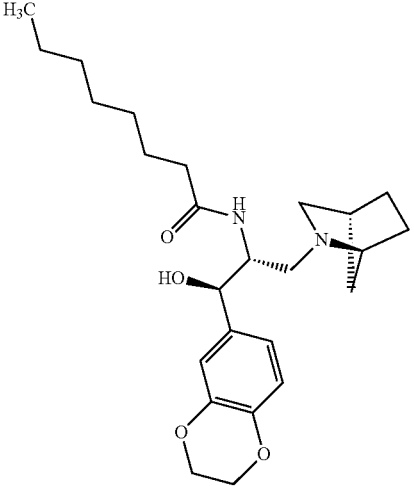 | B | 545 |
| Chiral 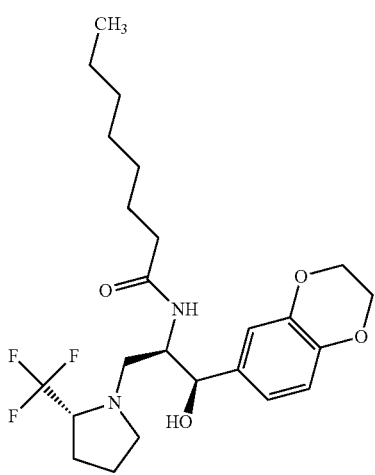 | D | 546 |

TABLE 3-continued
IC 50 Values
| Structure | | IC50_uM_Mean | Compound |
|---|---|---|---|
| | Chiral | A | 547 |
| 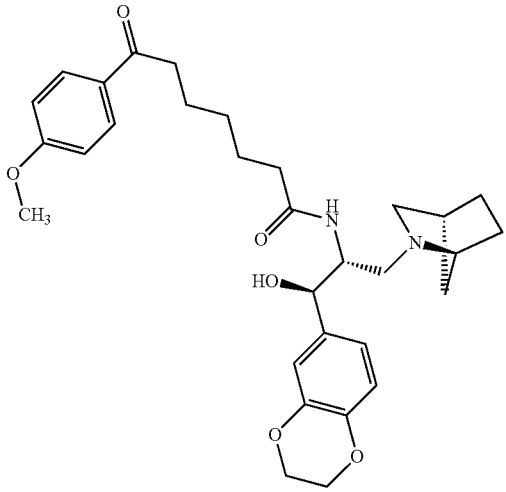 | | | |
| | Chiral | C | 548 |
| 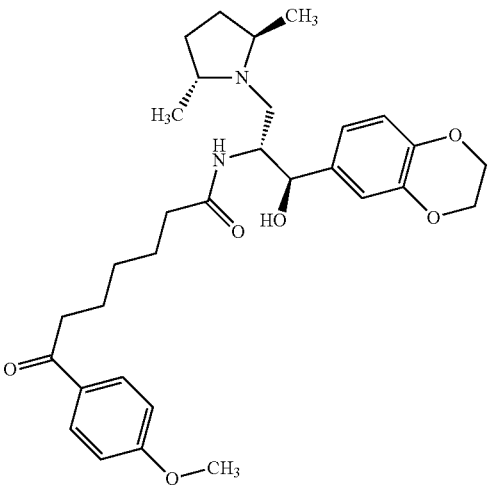 | | | |
| | Chiral | D | 549 |
| 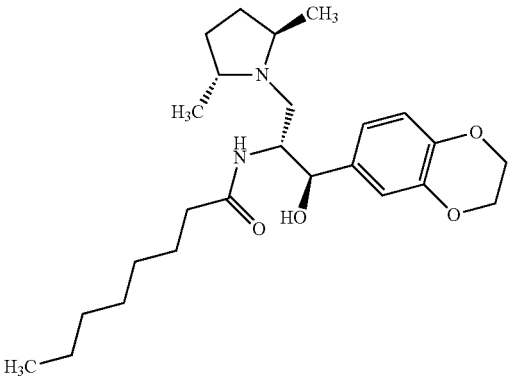 | | | |

TABLE 3-continued
| | IC 50 Values | | |
|---|---|---|---|
| Structure | | IC50_uM_Mean | Compound |
| Chiral 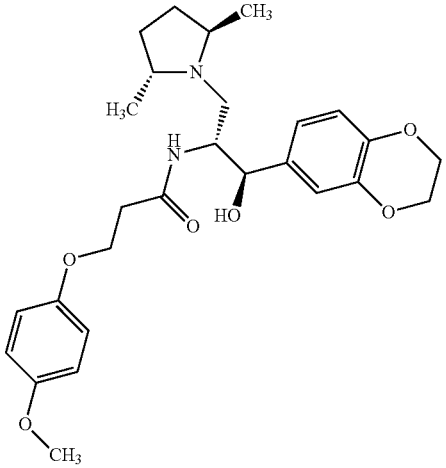 | | D | 550 |
| Chiral 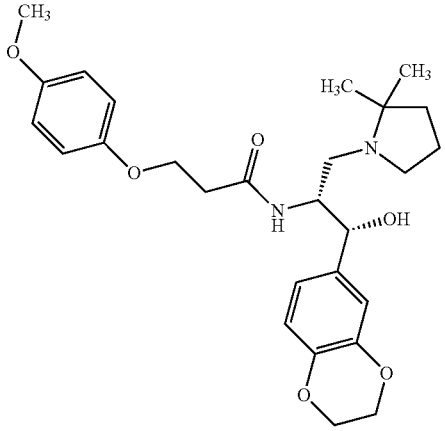 | | D | 551 |

TABLE 3-continued

| Structure | IC50_uM_Mean | Compound |
|---|---|---|
| Chiral | C | 552 |
| Chiral | D | 553 |
| Chiral | D | 554 |

TABLE 3-continued
| IC 50 Values | | |
|---|---|---|
| Structure | IC50_uM_Mean | Compound |
| Chiral 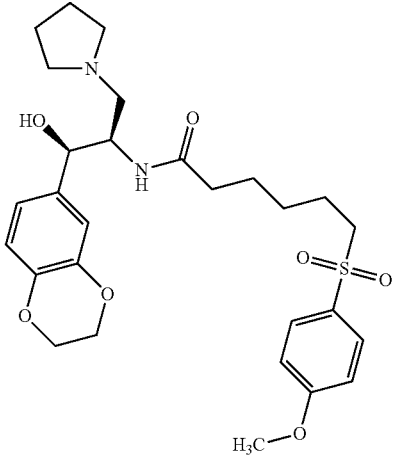 | B | 555 |
| Chiral 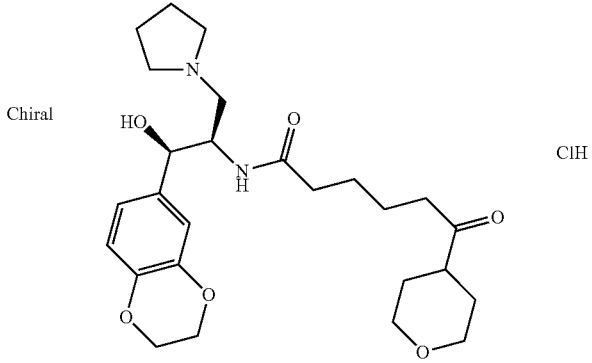 [SMILES: O=C(CCCCC(=O)C1CCOCC1)N[C@H](CN1CCCC1)[C@H](O)c1ccc2c(c1)OCCO2 ; Cl] ClH | D | 556 |
| Chiral 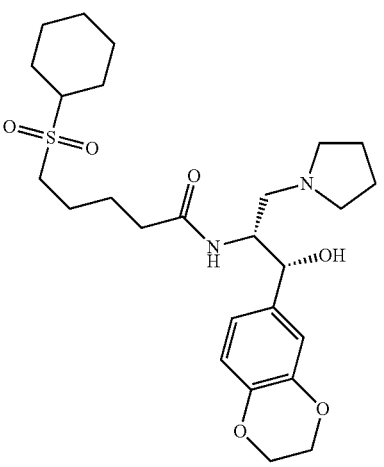 | D | 557 |

TABLE 3-continued

| Structure | IC50_uM_Mean | Compound |
|---|---|---|
| Chiral | C | 558 |
| Chiral | B | 559 |
| Chiral | B | 560 |

TABLE 3-continued
IC 50 Values
| Structure | IC50_uM_Mean | Compound |
|---|---|---|
| Chiral 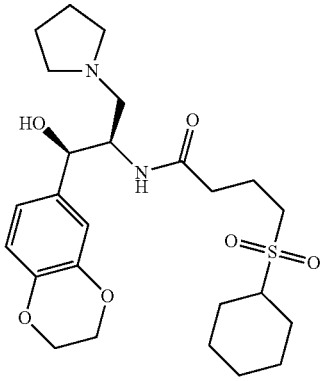 | D | 561 |
| Chiral 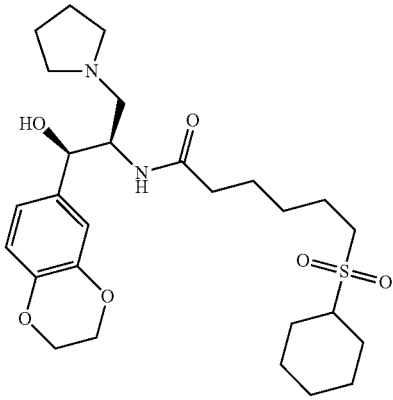 | B | 562 |
| Chiral 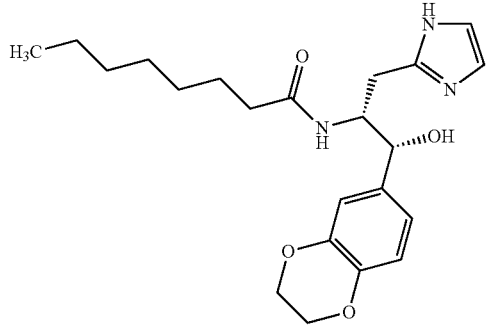 | D | 563 |

TABLE 3-continued
IC 50 Values
| Structure | IC50_uM_Mean | Compound |
|---|---|---|
| Chiral 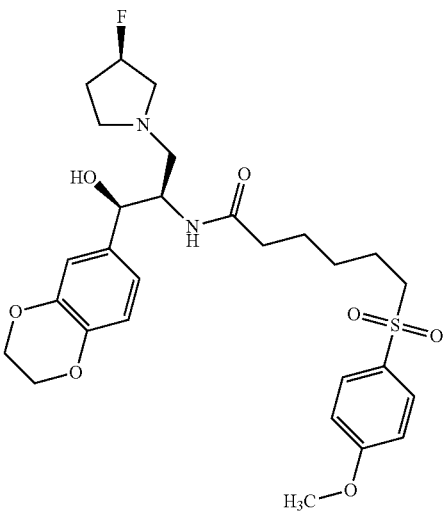 | B | 564 |
| Chiral 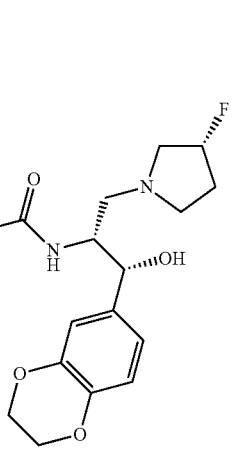 | A | 565 |
| Chiral 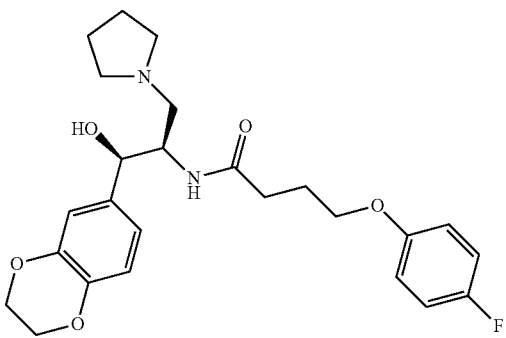 | A | 566 |

TABLE 3-continued
| IC 50 Values | | |
|---|---|---|
| Structure | IC50_uM_Mean | Compound |
| Chiral 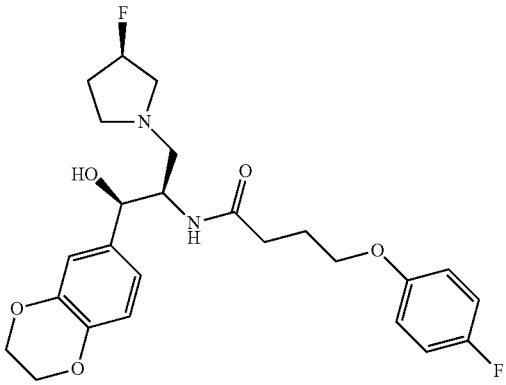 | B | 567 |
| Chiral 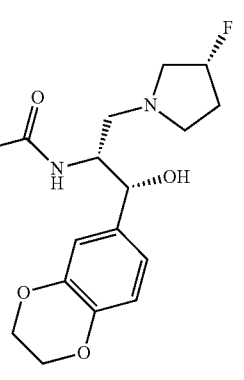 | B | 568 |
| Chiral 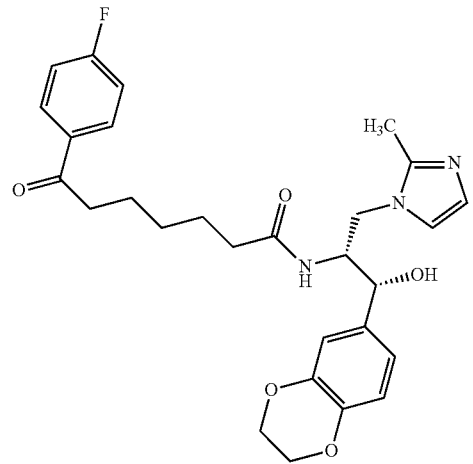 | D | 569 |

TABLE 3-continued
IC 50 Values
| Structure | IC50_uM_Mean | Compound |
|---|---|---|
| Chiral 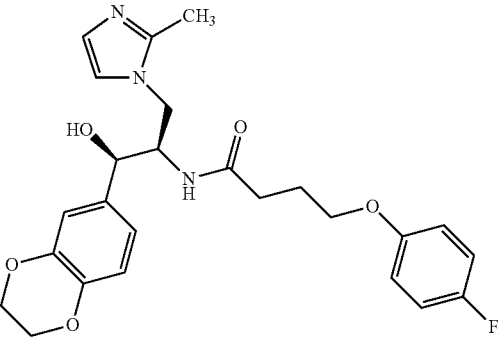 | D | 570 |
| Chiral 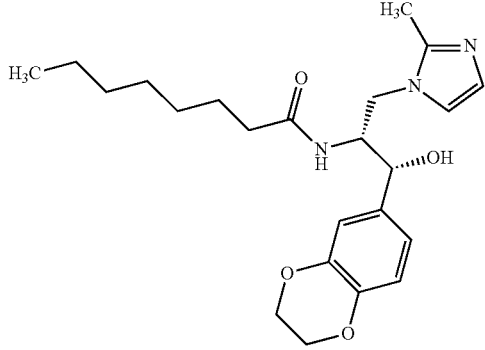 | D | 571 |
| Chiral 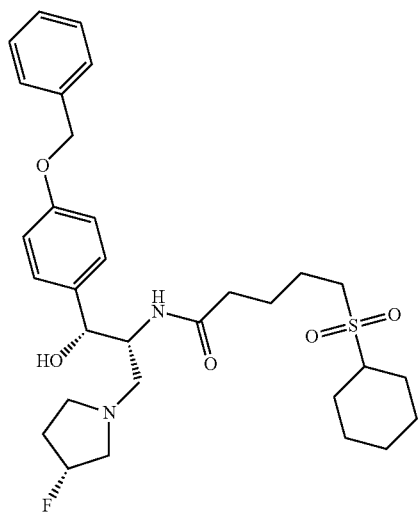 | B | 572 |

TABLE 3-continued

IC 50 Values

| Structure | IC50_uM_Mean | Compound |
|---|---|---|
| Chiral (structure) | B | 573 |
| Chiral (structure) | B | 574 |

TABLE 3-continued
IC 50 Values
| Structure | | IC50_uM_Mean | Compound |
|---|---|---|---|
| 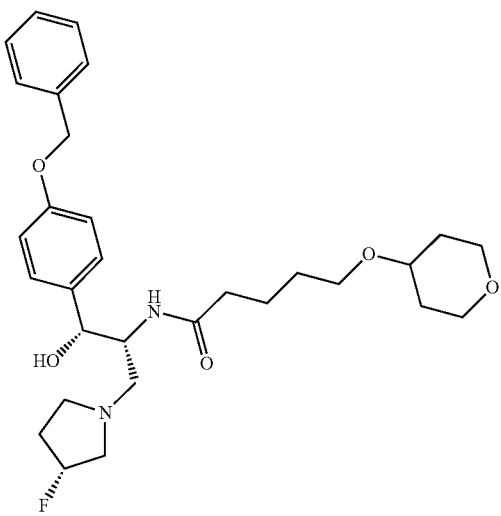 | Chiral | B | 575 |
| 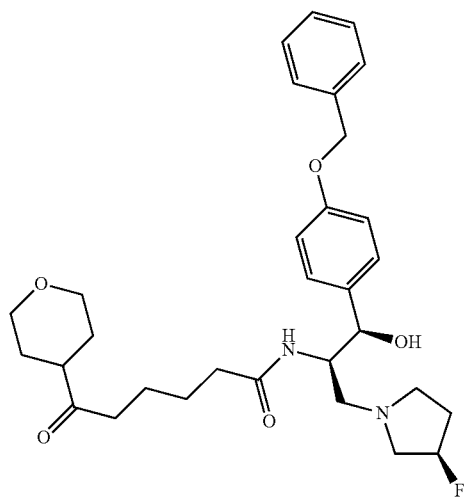 | Chiral | B | 576 |

TABLE 3-continued

IC 50 Values

| Structure | IC50_uM_Mean | Compound |
|---|---|---|
| Chiral (structure) | B | 577 |
| Chiral (structure) | A | 578 |
| Chiral (structure) | D | 579 |

TABLE 3-continued

| | IC 50 Values | |
|---|---|---|
| Structure | IC50_uM_Mean | Compound |
| Chiral | D | 580 |
| Chiral | B | 581 |
| Chiral | D | 582 |

TABLE 3-continued
| | IC 50 Values | |
|---|---|---|
| Structure | IC50_uM_Mean | Compound |
| Chiral | D | 583 |
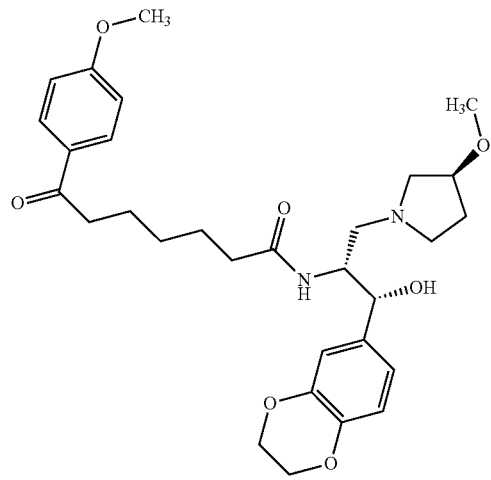
| Chiral | B | 584 |

TABLE 3-continued

| | IC 50 Values | |
|---|---|---|
| Structure | IC50_uM_Mean | Compound |
| Chiral | B | 585 |
| Chiral | A | 586 |

TABLE 3-continued
| | IC 50 Values | |
|---|---|---|
| Structure | IC50_uM_Mean | Compound |
| Chiral | B | 587 |
| 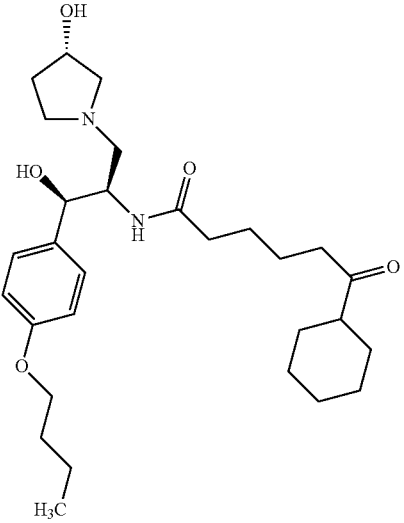 | D | 588 |
| 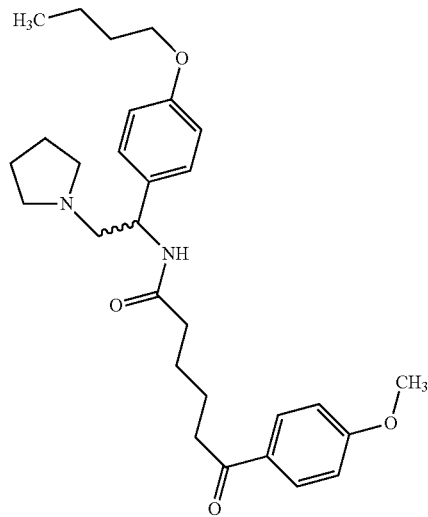 [SMILES: CCCCOc1ccc(C(CN2CCCC2)NC(=O)CCCCC(=O)c2ccc(OC)cc2)cc1] | C | 589 |
| 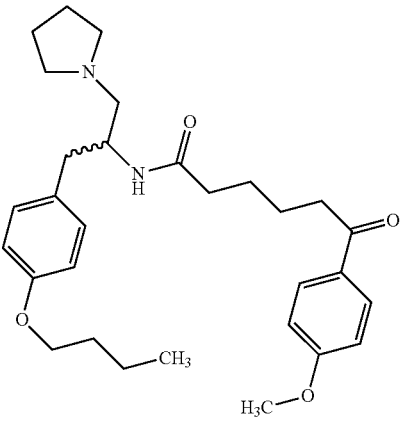 [SMILES: CCCCOc1ccc(CC(CN2CCCC2)NC(=O)CCCCC(=O)c2ccc(OC)cc2)cc1] | | |

TABLE 3-continued
| | IC 50 Values | |
|---|---|---|
| Structure | IC50_uM_Mean | Compound |
| 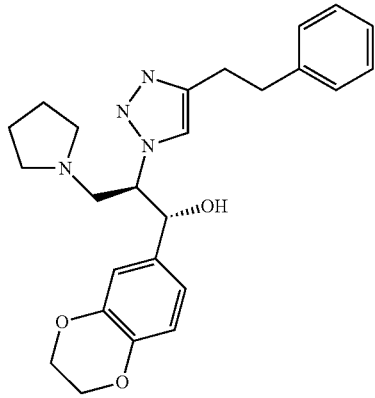 Chiral | D | 590 |
| 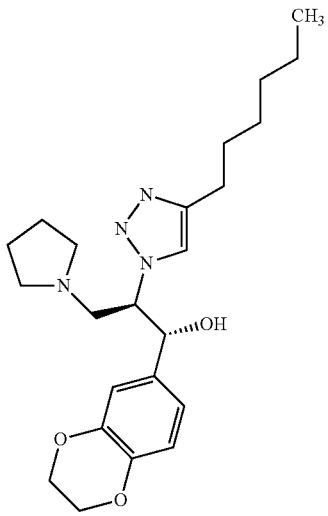 Chiral | D | 591 |
| 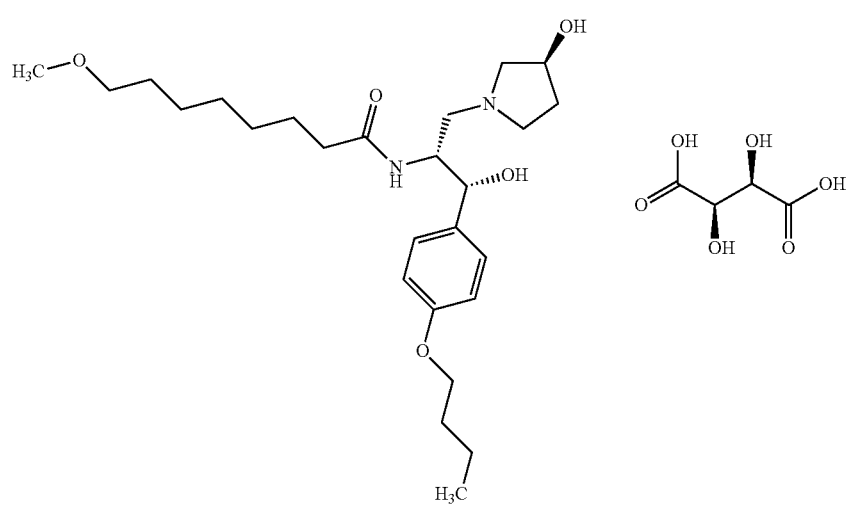 Chiral | A | 592 |

TABLE 3-continued

| Structure | IC50_uM_Mean | Compound |
|---|---|---|
| Chiral | B | 593 |
| Chiral | C | 594 |
| 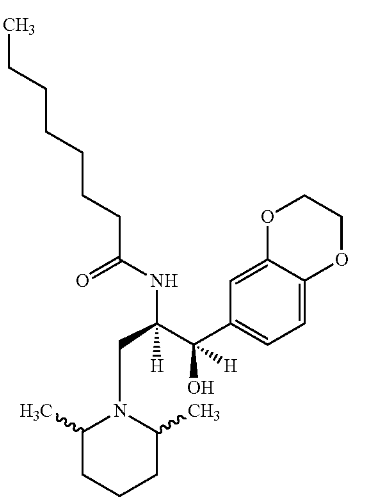 | D | 595 |

TABLE 3-continued

IC 50 Values

| Structure | IC50_uM_Mean | Compound |
|---|---|---|
| Chiral | D | 596 |
| Chiral | D | 597 |
| | D | 598 |

TABLE 3-continued
| Structure | IC50_uM_Mean | Compound |
|---|---|---|
| Chiral 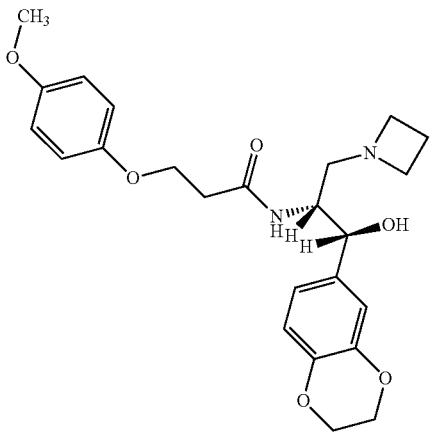 | C | 599 |
| Chiral 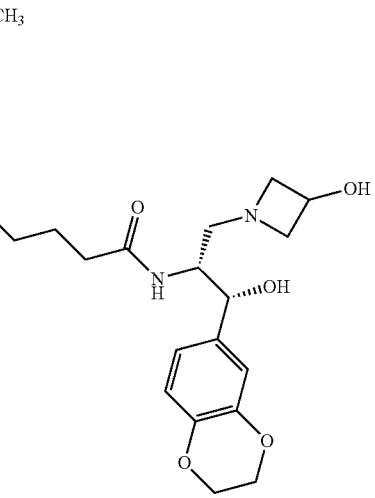 | C | 600 |
| Chiral 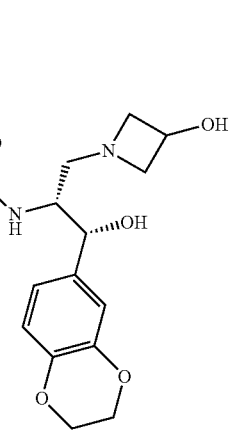 | D | 601 |

TABLE 3-continued

IC 50 Values

| Structure | IC50_uM_Mean | Compound |
|---|---|---|
| 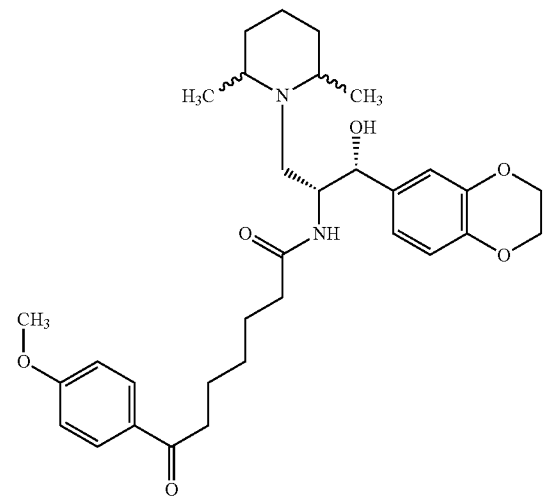 | D | 602 |
| Chiral | B | 603 |

TABLE 3-continued

| | IC 50 Values | |
|---|---|---|
| Structure | IC50_uM_Mean | Compound |
| Chiral | D | 604 |
| | D | 605 |
| | D | 606 |

TABLE 3-continued
IC 50 Values
| Structure | IC50_uM_Mean | Compound |
|---|---|---|
| 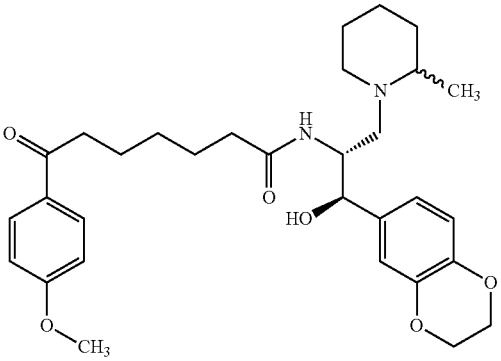 [SMILES: COc1ccc(C(=O)CCCCCC(=O)N[C@H](CN2CCCCC2C)[C@H](O)c2ccc3c(c2)OCCO3)cc1] | C | 607 |
| 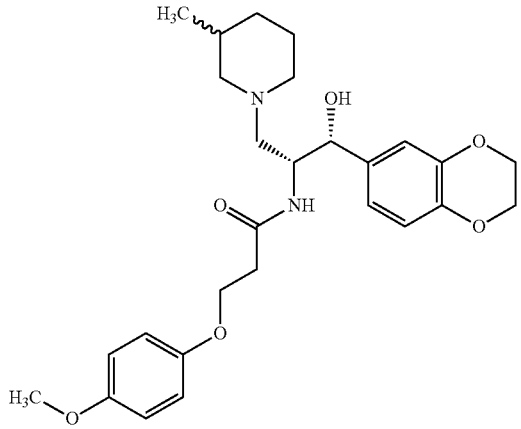 [SMILES: COc1ccc(OCCC(=O)N[C@H](CN2CCCC(C)C2)[C@H](O)c2ccc3c(c2)OCCO3)cc1] | D | 608 |
| 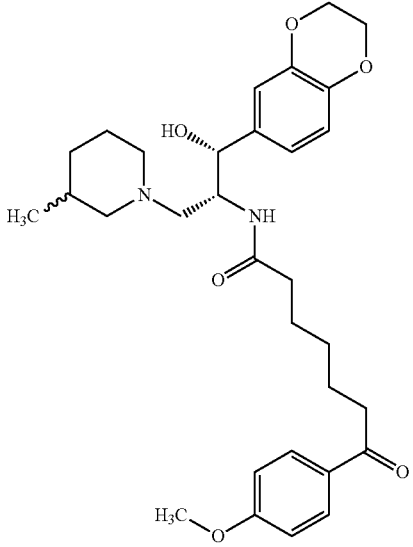 [SMILES: COc1ccc(C(=O)CCCCCC(=O)N[C@H](CN2CCCC(C)C2)[C@H](O)c2ccc3c(c2)OCCO3)cc1] | B | 609 |

TABLE 3-continued
| | IC 50 Values | |
|---|---|---|
| Structure | IC50_uM_Mean | Compound |
| Chiral 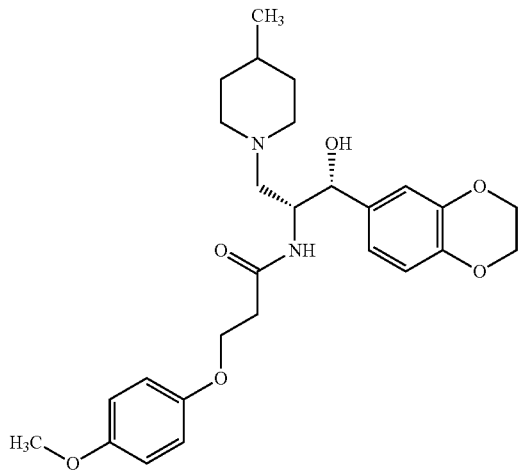 | D | 610 |
| Chiral 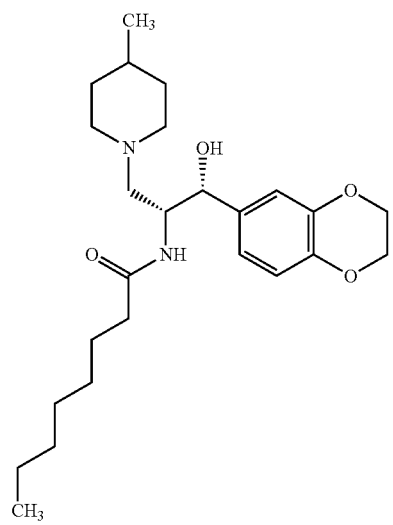 | D | 611 |

TABLE 3-continued

| IC 50 Values | | |
|---|---|---|
| Structure | IC50_uM_Mean | Compound |
| Chiral | D | 612 |
| | D | 613 |
| Chiral | D | 614 |

TABLE 3-continued

IC 50 Values

| Structure | IC50_uM_Mean | Compound |
|---|---|---|
| 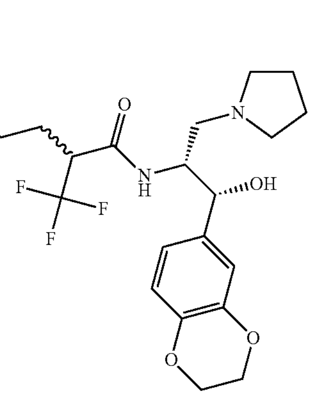 | B | 615 |
| Chiral | D | 616 |
| Chiral | C | 617 |

TABLE 3-continued

| Structure | IC50_uM_Mean | Compound |
|---|---|---|
| Chiral | D | 618 |
| Chiral | C | 619 |
| Chiral | B | 620 |

TABLE 3-continued
| IC 50 Values | | |
|---|---|---|
| Structure | IC50_uM_Mean | Compound |
| Chiral 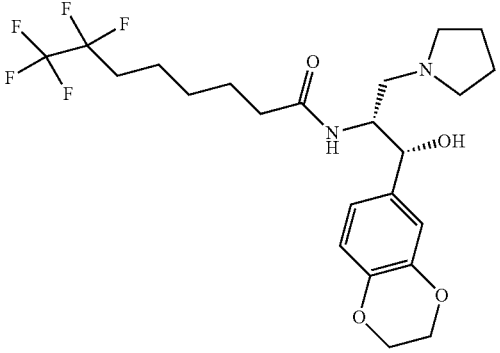 | C | 621 |
| Chiral 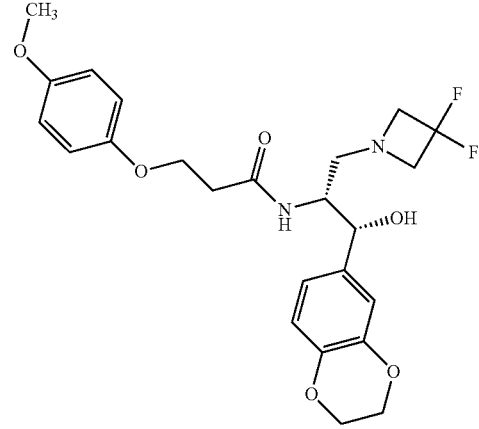 | D | 622 |
| Chiral 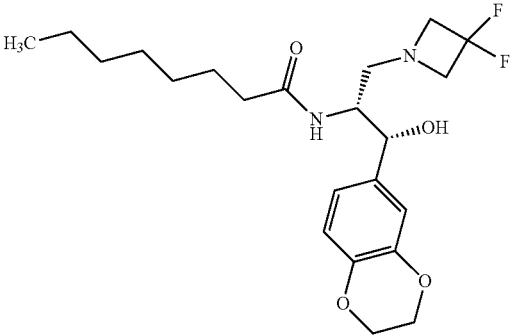 | D | 623 |

TABLE 3-continued
| | IC 50 Values | |
|---|---|---|
| Structure | IC50_uM_Mean | Compound |
| Chiral 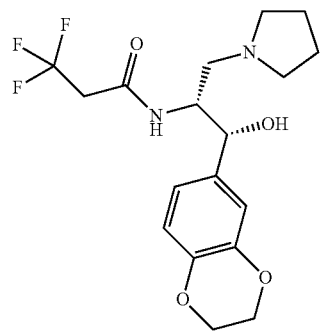 | D | 624 |
| Chiral 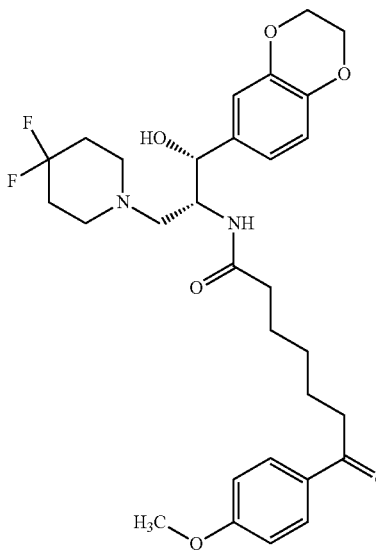 | D | 625 |

TABLE 3-continued
| | IC 50 Values | | |
|---|---|---|---|
| Structure | | IC50_uM_Mean | Compound |
| Chiral | | B | 626 |
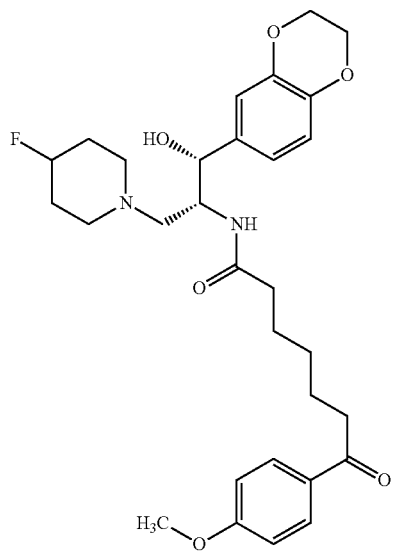
| Chiral | | D | 627 |
|---|---|---|---|
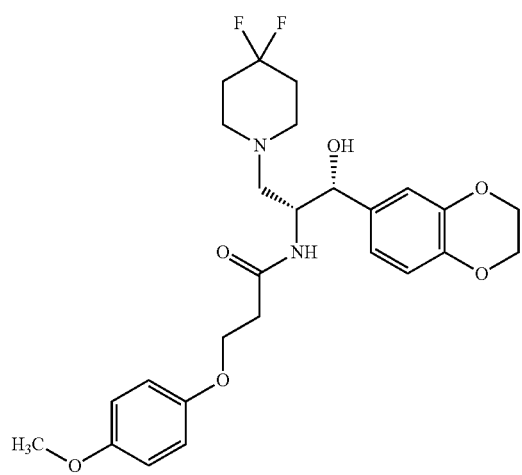

TABLE 3-continued
IC 50 Values
| Structure | IC50_uM_Mean | Compound |
|---|---|---|
| Chiral | A | 628 |
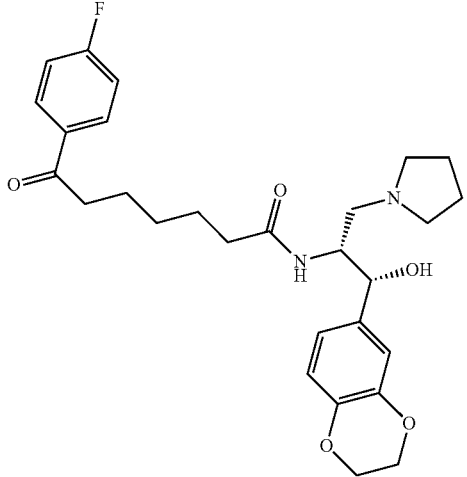
| | B | 629 |
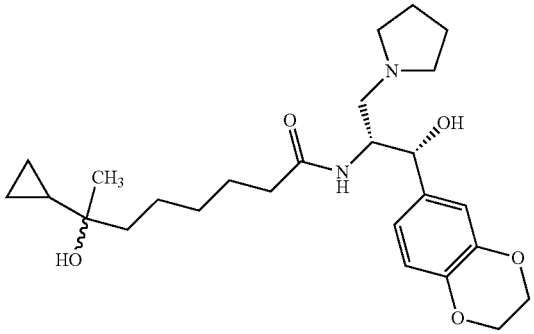 [SMILES: CC(O)(CCCCCC(=O)N[C@H](CN1CCCC1)[C@H](O)c1ccc2c(c1)OCCO2)C1CC1]
| Chiral | B | 630 |
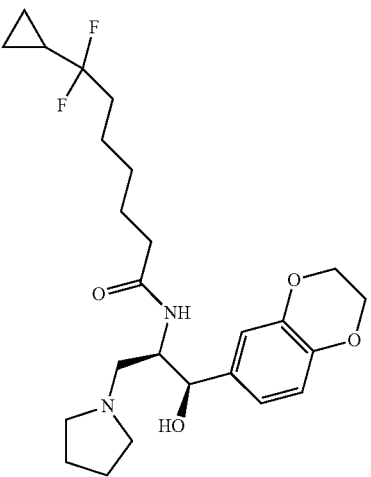

TABLE 3-continued
IC 50 Values
| Structure | IC50_uM_Mean | Compound |
|---|---|---|
| Chiral 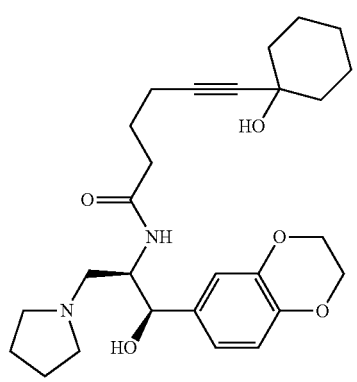 | D | 631 |
| Chiral 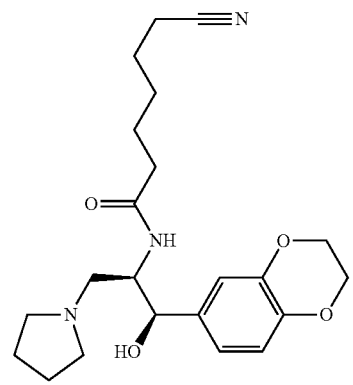 | D | 632 |
| 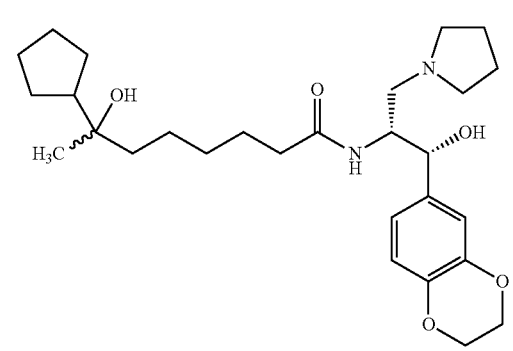 [SMILES: CC(O)(CCCCCC(=O)N[C@H](CN1CCCC1)[C@H](O)c1ccc2c(c1)OCCO2)C1CCCC1] | B | 633 |

TABLE 3-continued

IC 50 Values

| Structure | IC50_uM_Mean | Compound |
|---|---|---|
| Chiral | B | 634 |
| Chiral | D | 635 |
| | D | 636 |

TABLE 3-continued

IC 50 Values

| Structure | IC50_uM_Mean | Compound |
|---|---|---|
| Chiral | B | 637 |
| Chiral | D | 638 |
| Chiral | B | 639 |

TABLE 3-continued
| | IC 50 Values | |
|---|---|---|
| Structure | IC50_uM_Mean | Compound |
| 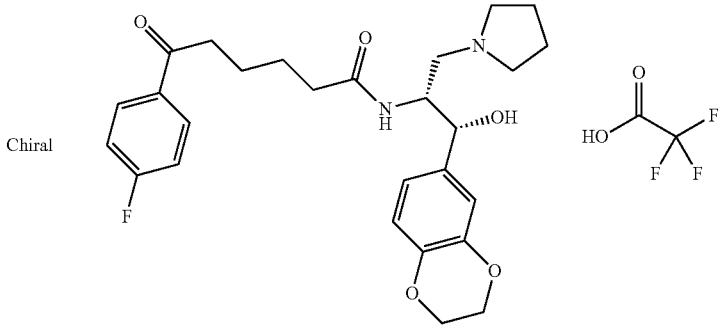 [SMILES: O=C(CCCCC(=O)c1ccc(F)cc1)N[C@H](CN1CCCC1)[C@H](O)c1ccc2c(c1)OCCO2 ; O=C(O)C(F)(F)F] | B | 640 |
| 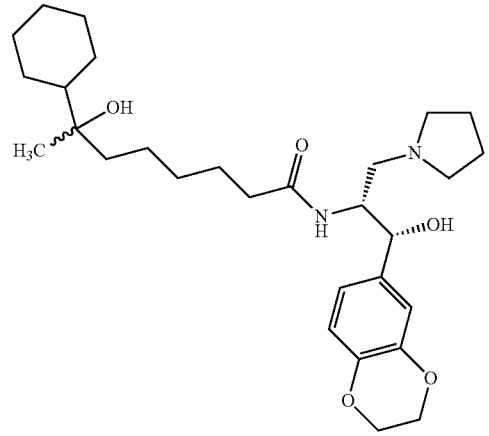 [SMILES: CC(O)(CCCCCC(=O)N[C@H](CN1CCCC1)[C@H](O)c1ccc2c(c1)OCCO2)C1CCCCC1] | A | 641 |
| 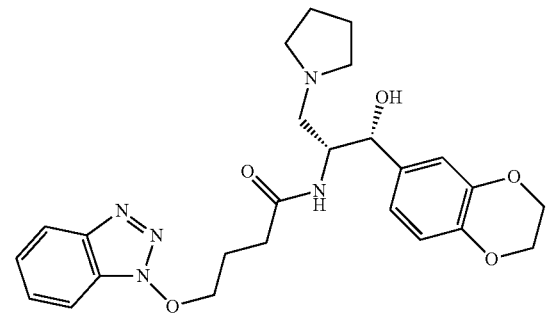 | B | 642 |

TABLE 3-continued
| | IC 50 Values | |
|---|---|---|
| Structure | IC50_uM_Mean | Compound |
| Chiral 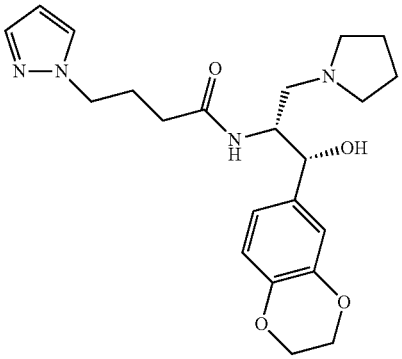 | C | 643 |
| Chiral 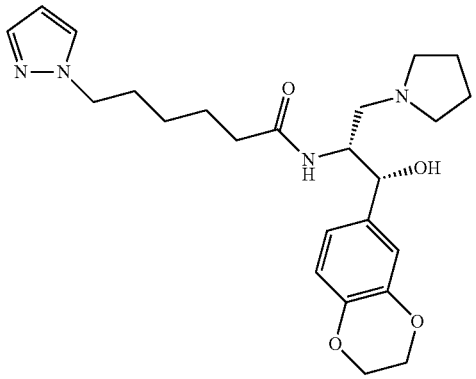 | C | 644 |
| Chiral 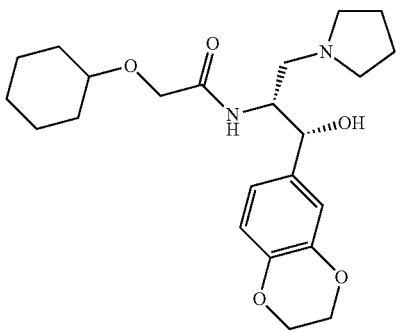 | D | 645 |

451
452
TABLE 3-continued
IC 50 Values
| Structure | IC50_uM_Mean | Compound |
|---|---|---|
| 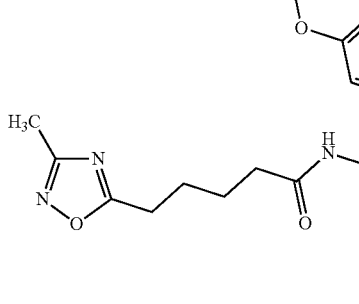 | D | 646 |
| 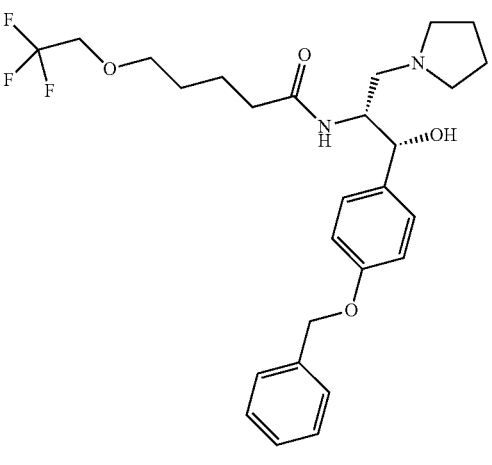 | B | 647 |
| 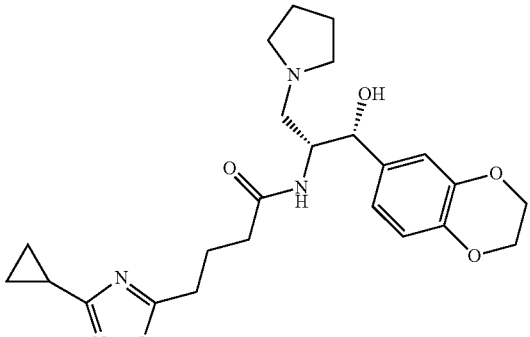 |  | 648 |
| 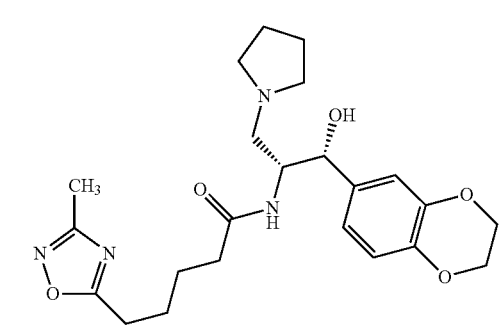 |  | 649 |

TABLE 3-continued
| IC 50 Values | | |
|---|---|---|
| Structure | IC50_uM_Mean | Compound |
| 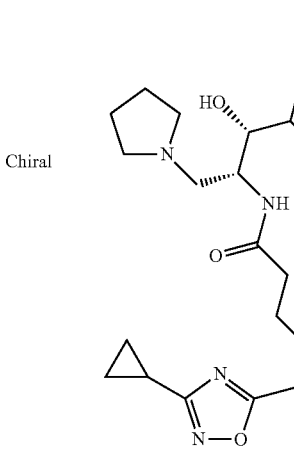 | B | 650 |
| 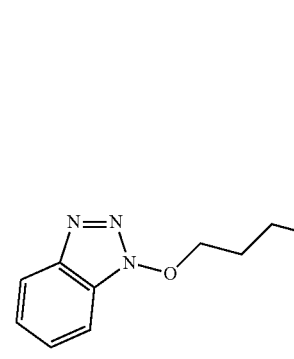 | C | 651 |
| 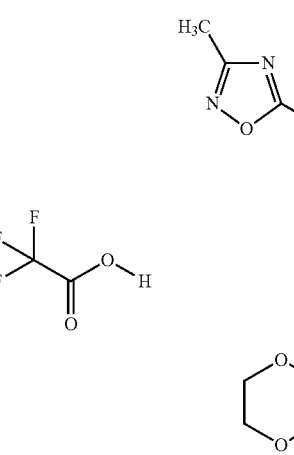 | D | 652 |

TABLE 3-continued

IC 50 Values

| Structure | IC50_uM_Mean | Compound |
|---|---|---|
| (Chiral structure: 4-fluorophenyl ketone-hexanamide linked to aminopropyl-(3-hydroxy)pyrrolidine with benzodioxane and OH; TFA salt) | A | 653 |
| (Chiral structure: isomer with 4-fluorophenyl ketone-hexanamide linked to aminopropyl-(3-hydroxy)pyrrolidine with benzodioxane and OH; TFA salt) | C | 654 |
| (Chiral structure: 4-methoxyphenyl ketone-hexanamide linked to aminopropyl-(3-hydroxy)pyrrolidine with benzodioxane and OH; TFA salt) | B | 655 |

TABLE 3-continued

| Structure | IC50_uM_Mean | Compound |
|---|---|---|
| | A | 656 |
| | B | 657 |
| | B | 658 |

TABLE 3-continued

IC 50 Values

| Structure | IC50_uM_Mean | Compound |
|---|---|---|
| | B | 659 |
| | B | 660 |
| | C | 661 |

TABLE 3-continued
IC 50 Values
| Structure | IC50_uM_Mean | Compound |
|---|---|---|
| 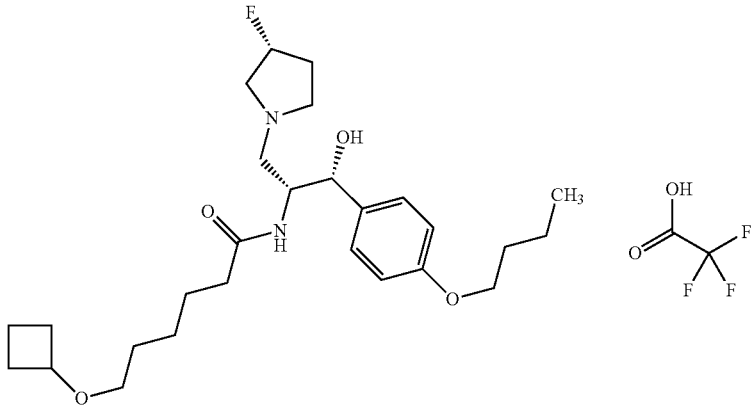 | B | 662 |
| 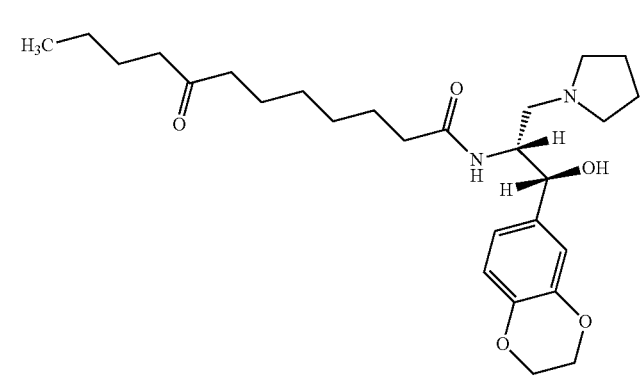 | B | 663 |
| 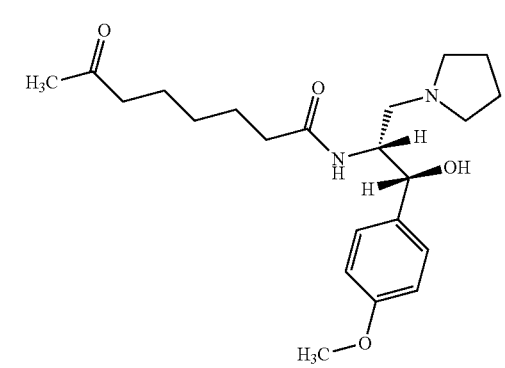 | C | 664 |
Chiral (662)
Chiral (663)
Chiral (664)

TABLE 3-continued

| Structure | IC50_uM_Mean | Compound |
|---|---|---|
| Chiral | D | 665 |
| Chiral | B | 666 |
| Chiral | B | 667 |

TABLE 3-continued

IC 50 Values

| Structure | IC50_uM_Mean | Compound |
|---|---|---|
| Chiral | C | 668 |
| Chiral | D | 669 |
| Chiral | D | 670 |

TABLE 3-continued

| IC 50 Values | | |
|---|---|---|
| Structure | IC50_uM_Mean | Compound |
| Chiral | D | 671 |
| Chiral | D | 672 |
| Chiral | D | 673 |

TABLE 3-continued
IC 50 Values
| Structure | IC50_uM_Mean | Compound |
|---|---|---|
| Chiral 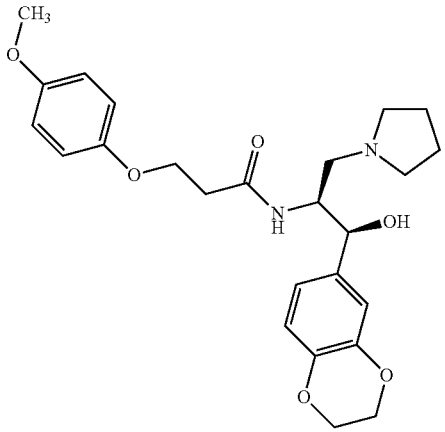 | D | 674 |
| Chiral 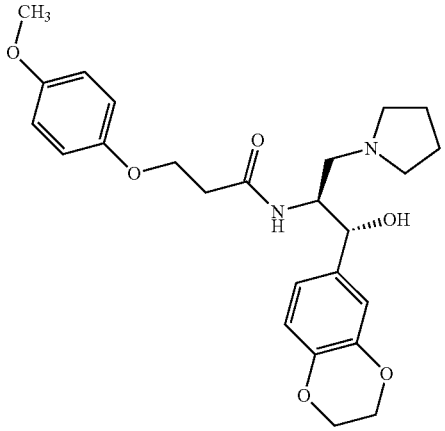 | D | 675 |
| Chiral 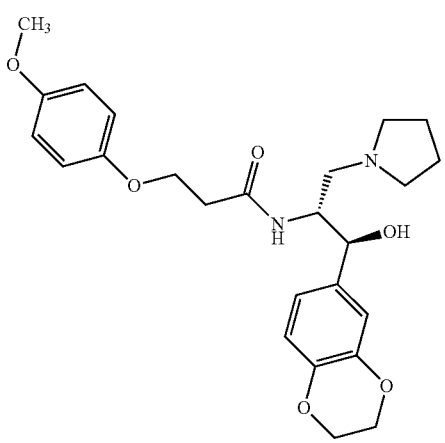 | D | 676 |

TABLE 3-continued

| Structure | IC50_uM_Mean | Compound |
|---|---|---|
| | D | 677 |
| | D | 678 |
| | D | 679 |

TABLE 3-continued
| | IC 50 Values | |
|---|---|---|
| Structure | IC50_uM_Mean | Compound |
| 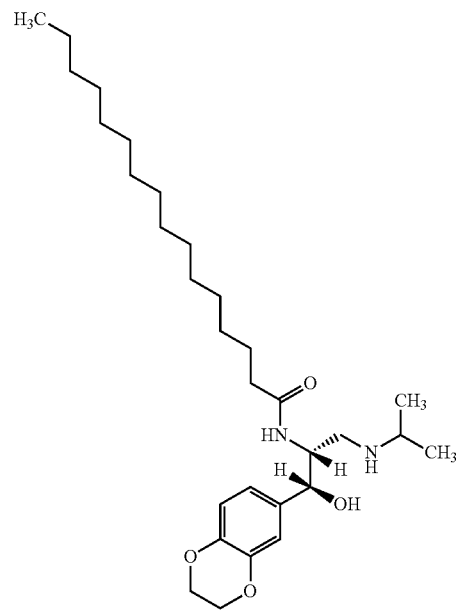 | A | 680 |
| 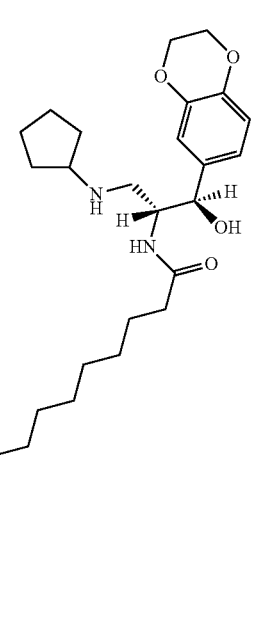 | C | 681 |

TABLE 3-continued
| Structure | IC50_uM_Mean | Compound |
|---|---|---|
| 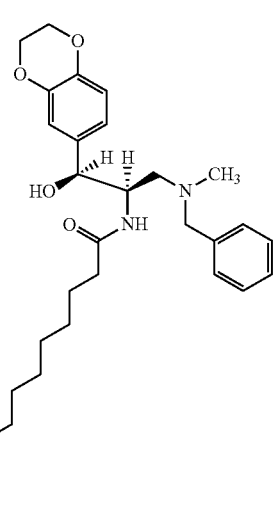 Chiral | D | 682 |
| 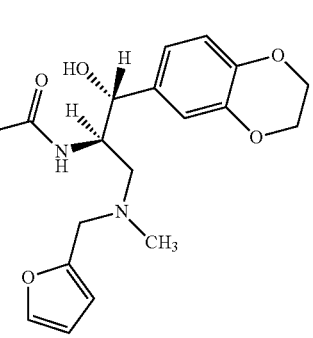 Chiral | D | 683 |

TABLE 3-continued

| Structure | IC50_uM_Mean | Compound |
|---|---|---|
| Chiral (structure) | B | 684 |
| Chiral (structure) | D | 685 |
| (structure) | D | 686 |

TABLE 3-continued
| IC 50 Values | | |
|---|---|---|
| Structure | IC50_uM_Mean | Compound |
| 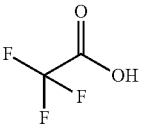 | D | 687 |
| 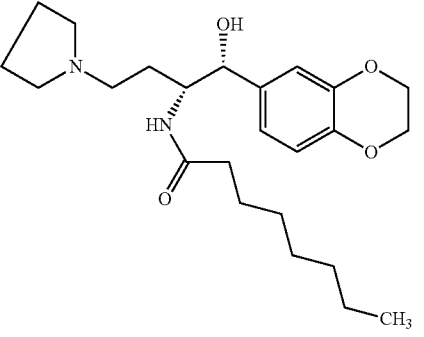 | D | 688 |
| 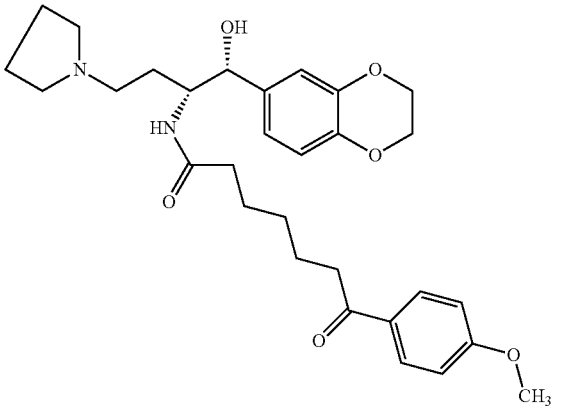 [SMILES: COc1ccc(C(=O)CCCCCC(=O)N[C@H](CCN2CCCC2)[C@H](O)c2ccc3c(c2)OCCO3)cc1] | D | 689 |

TABLE 3-continued
| IC 50 Values | | |
|---|---|---|
| Structure | IC50_uM_Mean | Compound |
| 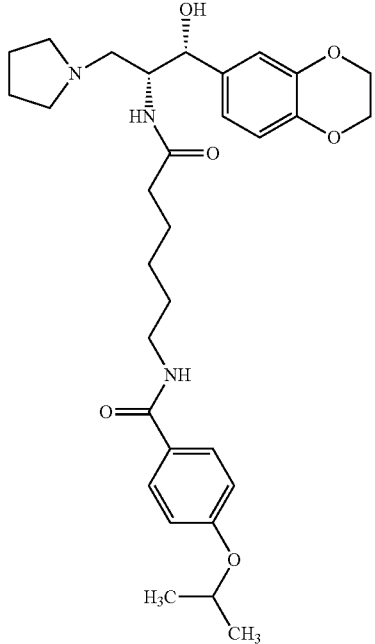 [SMILES: CC(C)Oc1ccc(C(=O)NCCCCCC(=O)N[C@H](CN2CCCC2)[C@H](O)c2ccc3c(c2)OCCO3)cc1] | A | 690 |
| 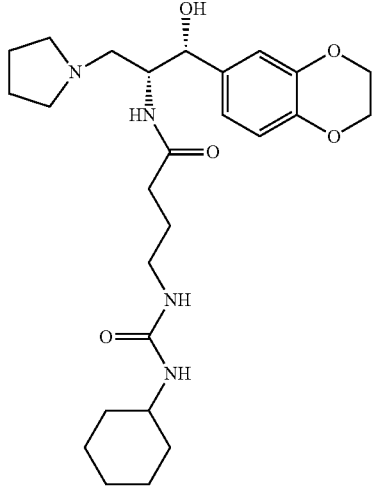 [SMILES: O=C(CCCNC(=O)NC1CCCCC1)N[C@H](CN1CCCC1)[C@H](O)c1ccc2c(c1)OCCO2] | D | 691 |
| 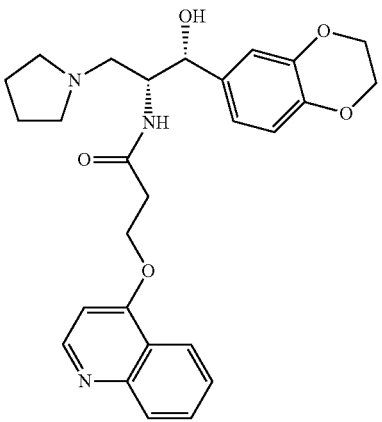 [SMILES: O=C(CCOc1ccnc2ccccc12)N[C@H](CN1CCCC1)[C@H](O)c1ccc2c(c1)OCCO2] | B | 692 |

TABLE 3-continued

| IC 50 Values | | |
|---|---|---|
| Structure | IC50_uM_Mean | Compound |
| | A | 693 |
| | B | 694 |
| | B | 695 |

TABLE 3-continued

IC 50 Values

| Structure | IC50_uM_Mean | Compound |
|---|---|---|
| 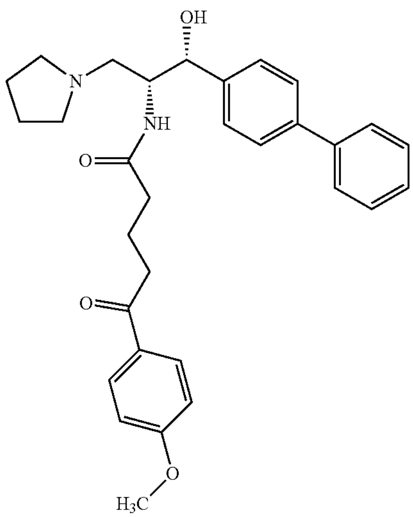 [SMILES: COc1ccc(C(=O)CCCC(=O)N[C@H](CN2CCCC2)[C@H](O)c2ccc(-c3ccccc3)cc2)cc1] | C | 696 |
| | B | 697 |
| | B | 698 |

TABLE 3-continued
| | IC 50 Values | |
|---|---|---|
| Structure | IC50_uM_Mean | Compound |
| 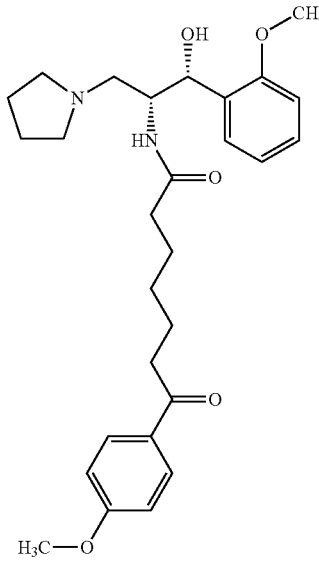 | A | 699 |
| 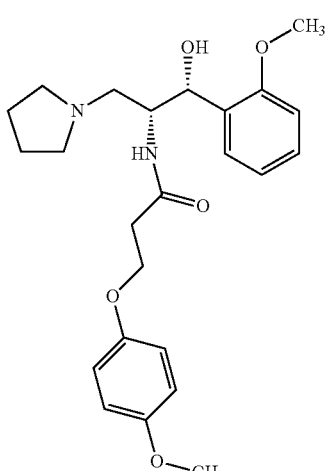 | B | 700 |
| 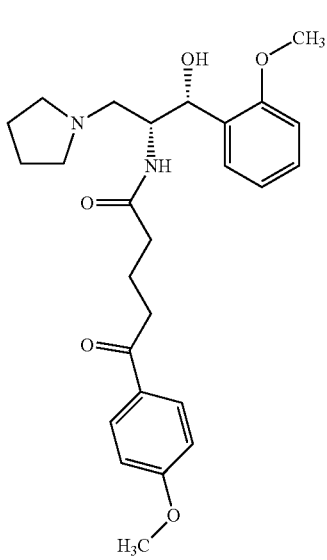 [SMILES: COc1ccc(C(=O)CCCC(=O)N[C@H](CN2CCCC2)[C@H](O)c2ccccc2OC)cc1] | C | 701 |

TABLE 3-continued

IC 50 Values

| Structure | IC50_uM_Mean | Compound |
|---|---|---|
| *(structure)* | A | 702 |
| *(structure)* | A | 703 |
| *(structure)* | A | 704 |

TABLE 3-continued

| Structure | IC50_uM_Mean | Compound |
|---|---|---|
| | A | 705 |
| | A | 706 |
| | A | 707 |

TABLE 3-continued
| Structure | IC50_uM_Mean | Compound |
|---|---|---|
| 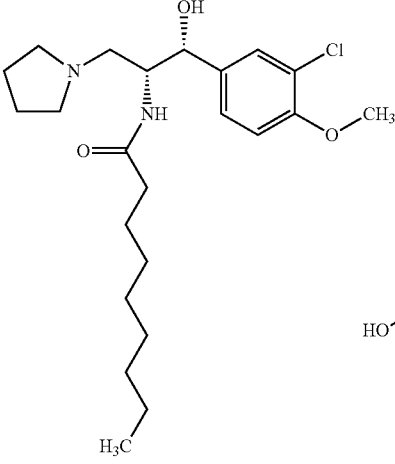 | A | 708 |
| 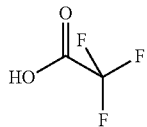 | A | 709 |
| 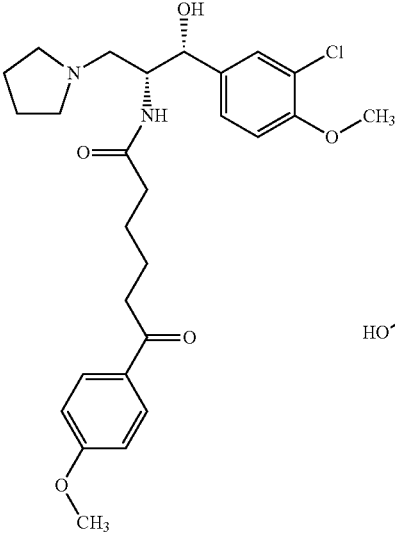 | A | 710 |

TABLE 3-continued

| IC 50 Values | | |
|---|---|---|
| Structure | IC50_uM_Mean | Compound |
| (structure) | A | 711 |
| (structure) | B | 712 |
| (structure) | B | 713 |

TABLE 3-continued

IC 50 Values

| Structure | IC50_uM_Mean | Compound |
|---|---|---|
| | D | 714 |
| | D | 715 |
| | D | 716 |

TABLE 3-continued

IC 50 Values

| Structure | IC50_uM_Mean | Compound |
|---|---|---|
| | D | 717 |
| | D | 718 |
| | D | 719 |

TABLE 3-continued
| Structure | IC50_uM_Mean | Compound |
|---|---|---|
| 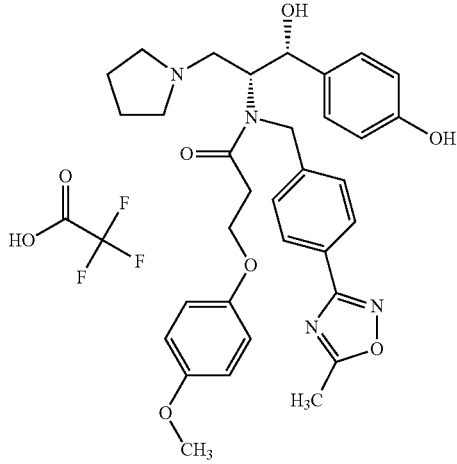 [SMILES: O=C(O)C(F)(F)F ; COc1ccc(OCCC(=O)N(Cc2ccc(-c3noc(C)n3)cc2)[C@H](CN2CCCC2)[C@H](O)c2ccc(O)cc2)cc1] | D | 720 |
| 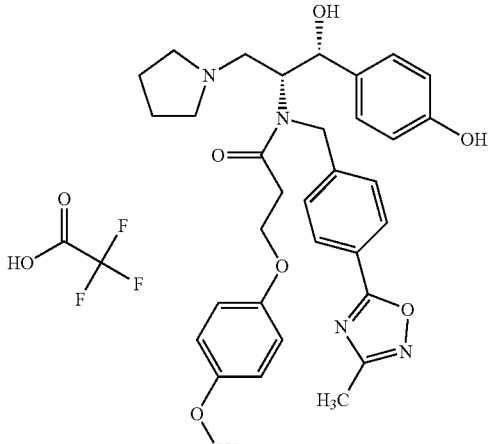 | D | 721 |
| 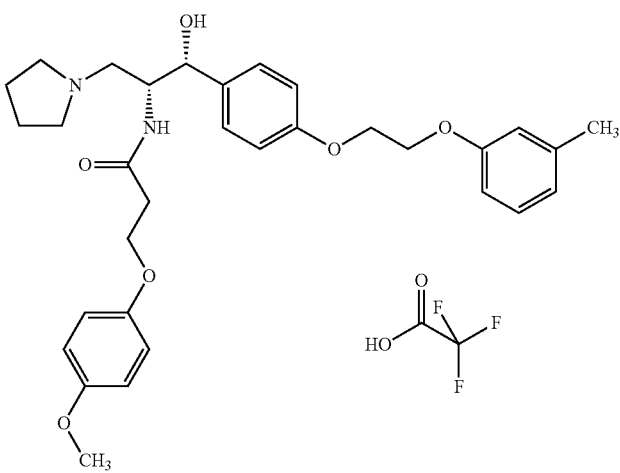 [SMILES: COc1ccc(OCCC(=O)N[C@H](CN2CCCC2)[C@H](O)c2ccc(OCCOc3cccc(C)c3)cc2)cc1 ; O=C(O)C(F)(F)F] | A | 722 |

TABLE 3-continued
| | IC 50 Values | |
|---|---|---|
| Structure | IC50_uM_Mean | Compound |
| 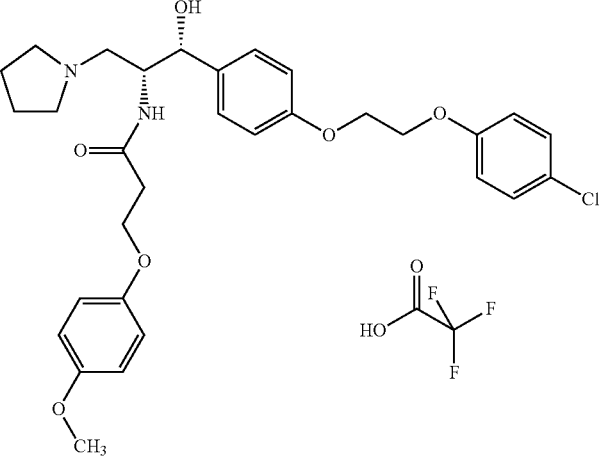 [SMILES: COc1ccc(OCCC(=O)N[C@H](CN2CCCC2)[C@H](O)c2ccc(OCCOc3ccc(Cl)cc3)cc2)cc1 ; O=C(O)C(F)(F)F] | A | 723 |
| 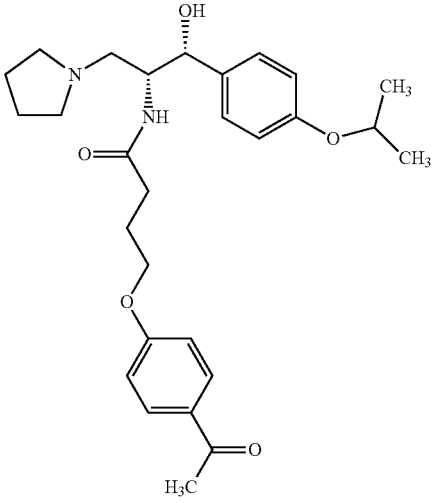 [SMILES: CC(=O)c1ccc(OCCCC(=O)N[C@H](CN2CCCC2)[C@H](O)c2ccc(OC(C)C)cc2)cc1] | B | 724 |
| 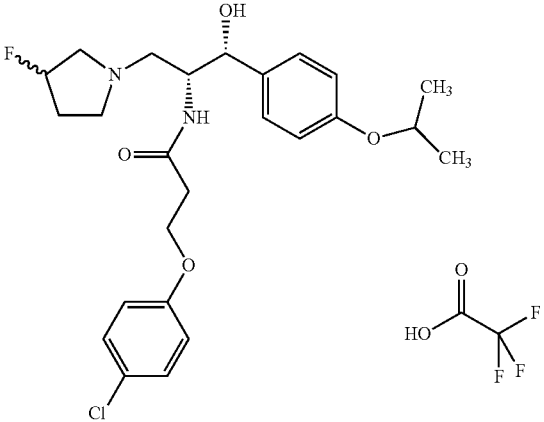 [SMILES: CC(C)Oc1ccc([C@@H](O)[C@@H](CN2CCC(F)C2)NC(=O)CCOc2ccc(Cl)cc2)cc1 ; O=C(O)C(F)(F)F] | B | 725 |

TABLE 3-continued

IC 50 Values

| Structure | IC50_uM_Mean | Compound |
|---|---|---|
| 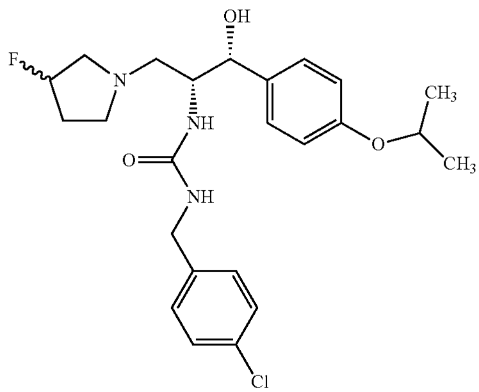 [SMILES: CC(C)Oc1ccc([C@@H](O)[C@@H](CN2CCC(F)C2)NC(=O)NCc2ccc(Cl)cc2)cc1] | B | 726 |
|  | A | 727 |
|  | A | 728 |

TABLE 3-continued

IC 50 Values

| Structure | IC50_uM_Mean | Compound |
|---|---|---|
| | A | 729 |
| | A | 730 |
| | A | 731 |

TABLE 3-continued

IC 50 Values

| Structure | IC50_uM_Mean | Compound |
|---|---|---|
| 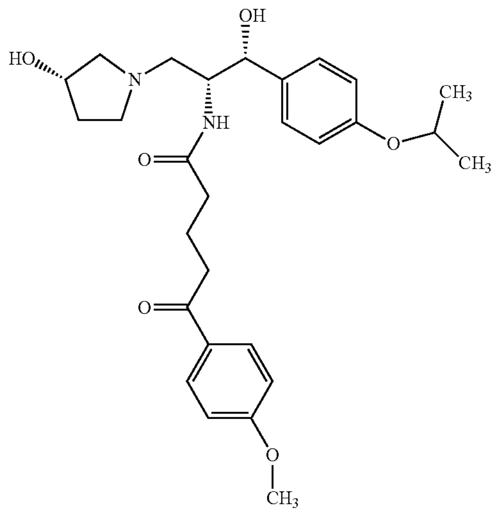 [SMILES: COc1ccc(C(=O)CCCC(=O)N[C@H](CN2CC[C@H](O)C2)[C@H](O)c2ccc(OC(C)C)cc2)cc1] | B | 732 |
| | A | 733 |
| | A | 734 |

TABLE 3-continued
IC 50 Values
| Structure | IC50_uM_Mean | Compound |
|---|---|---|
| 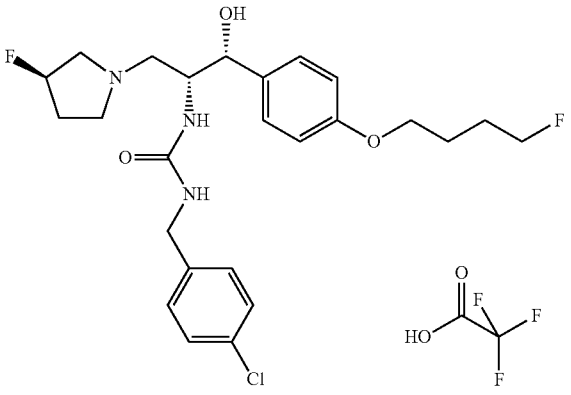 [SMILES: O=C(NCc1ccc(Cl)cc1)N[C@H](CN1CC[C@@H](F)C1)[C@H](O)c1ccc(OCCCCF)cc1 ; O=C(O)C(F)(F)F] | A | 735 |
| 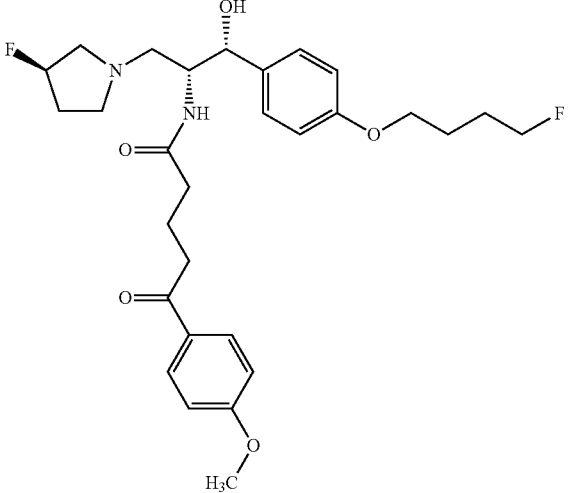 [SMILES: COc1ccc(C(=O)CCCC(=O)N[C@H](CN2CC[C@@H](F)C2)[C@H](O)c2ccc(OCCCCF)cc2)cc1] | A | 736 |
| 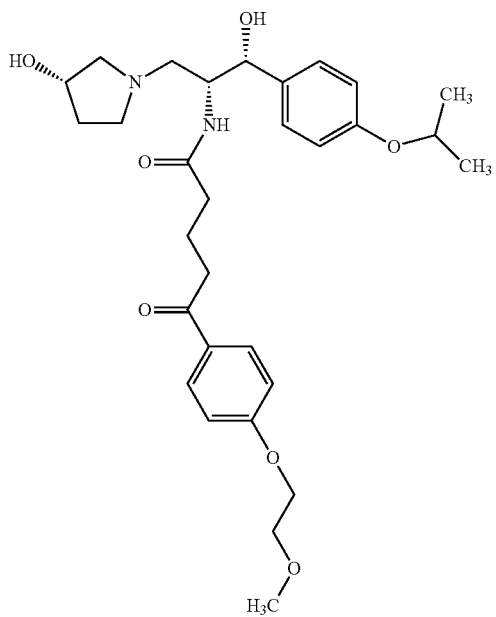 [SMILES: COCCOc1ccc(C(=O)CCCC(=O)N[C@H](CN2CC[C@H](O)C2)[C@H](O)c2ccc(OC(C)C)cc2)cc1] | B | 737 |

TABLE 3-continued

IC 50 Values

| Structure | IC50_uM_Mean | Compound |
|---|---|---|
| | A | 738 |
| | A | 739 |
| | A | 740 |

TABLE 3-continued

IC 50 Values

| Structure | IC50_uM_Mean | Compound |
|---|---|---|
| 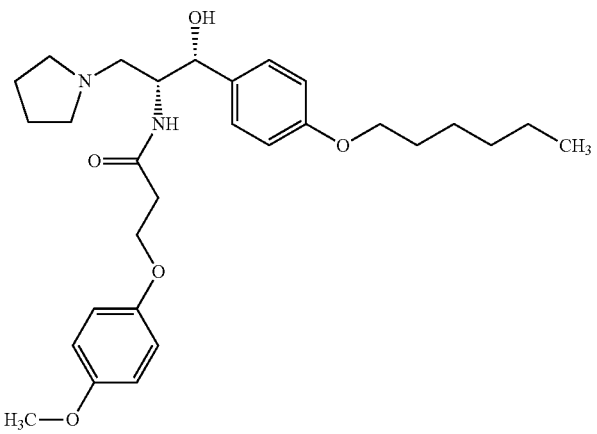 [SMILES: CCCCCCOc1ccc([C@@H](O)[C@@H](CN2CCCC2)NC(=O)CCOc2ccc(OC)cc2)cc1] | A | 741 |

What is claimed is:

1. A compound represented by the following structural formula:

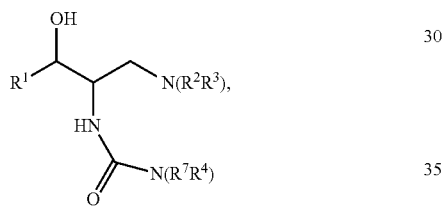

or a pharmaceutically acceptable salt thereof, wherein:

$R^1$ is a phenyl group optionally substituted with one or more substituents selected from halogen, cyano, nitro, C1-C6 alkyl, C1-C6 haloalkyl, —$OR^{30}$, —$SR^{30}$, —$N(R^{31})_2$, $Ar^1$, —$V_o$—$OR^{30}$, —$V_o$—$N(R^{31})_2$, —$V_o$—$Ar^1$, —O—$V_o$—$Ar^1$, —O—$V_1$—$N(R^{31})_2$, —S—$V_o$—$Ar^1$, —S—$V_1$—$N(R^{31})_2$, —$N(R^{31})$—$V_o$—$Ar^1$, —$N(R^{31})$—$V_1$—$N(R^{31})_2$, —O—$[CH_2]_p$—O—, —S—$[CH_2]_p$—S— or —$[CH_2]_q$—;

$Ar^1$ is a phenyl group each optionally substituted with one or more substituents selected from halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl or C1-C6 haloalkyl; and each $R^{30}$ is independently i) hydrogen;

ii) a phenyl group optionally substituted with one or more substituents selected from halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl or C1-C6 haloalkyl; or iii) an C1-C10 alkyl group optionally substituted with one or more substituents selected from halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl or C1-C6 haloalkyl; and each $R^{31}$ is independently $R^{30}$, or —$N(R^{31})_2$ is an optionally substituted non-aromatic heterocyclic group;

—$N(R^2R^3)$ is a pyrrolidinyl group optionally substituted with one or more substituents selected from halogen, alkyl, haloalkyl, —$OR^{40}$, —O(haloalkyl), —$SR^{40}$, —$NO_2$, —CN, —$N(R^{41})_2$, —$NR^{41}C(O)R^{40}$, —$NR^{41}C(O)OR^{42}$, —$N(R^{41})C(O)N(R^{41})_2$, —$C(O)R^{40}$, —$C(S)R^{40}$, —$C(O)OR^{40}$, —$OC(O)R^{40}$, —$C(O)N(R^{41})_2$, —$S(O)_2R^{40}$, —$SO_2N(R^{41})_2$, —$S(O)R^{42}$, —$SO_3R^{40}$, $Ar^2$, $V_2$—$Ar^2$, —$V_2$—$OR^{40}$, —$V_2$—O(haloalkyl), —$V_2$—$SR^{40}$, —$V_2$—$NO_2$, —$V_2$—CN, —$V_2$—N$(R^{41})_2$, —$V_2$—$NR^{41}C(O)R^{40}$, —$V_2$—$NR^{41}CO_2R^{42}$, —$V_2$—$N(R^{41})C(O)N(R^{41})_2$, —$V_2$—$C(O)R^{40}$, —$V_2$—$C(S)R^{40}$, —$V_2$—$CO_2R^{40}$, —$V_2$—$OC(O)R^{40}$, —$V_2$—$C(O)N(R^{41})_2$—, —$V_2$—$S(O)_2R^{40}$, —$V_2$—$SO_2N(R^{41})_2$, —$V_2$—$S(O)R^{42}$, —$V_2$—$SO_3R^{40}$, —O—$V_2$—$Ar^2$ or —S—$V_2$—$Ar^2$;

each $V_2$ is independently a C1-C4 alkylene group;

$Ar^2$ is an aryl group each optionally substituted with one or more substituents selected from halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl or C1-C6 haloalkyl; and each $R^{40}$ is independently i) hydrogen;

ii) an aryl group optionally substituted with one or more substituents selected from halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl or C1-C6 haloalkyl; or iii) an C1-C10 alkyl group optionally substituted with one or more substituents selected from halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl or C1-C6 haloalkyl; and each $R^{41}$ is independently $R^{40}$, —$CO_2R^{40}$, —$SO_2R^{40}$ or —$C(O)R^{40}$; or —$N(R^{41})_2$ taken together is an optionally substituted non-aromatic heterocyclic group; and each $R^{42}$ is independently:

i) an aryl group optionally substituted with one or more substituents selected from halogen, C1-C6 alkyl, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl or C1-C6 haloalkyl; or ii) an C1-C10 alkyl group optionally substituted with one or more substituents selected from halogen, amino, C1-C6 alkylamino, C1-C6 dialkylamino, C1-C6 alkoxy, nitro, cyano, hydroxy, C1-C6 haloalkoxy, C1-C6 alkoxycarbonyl, C1-C6 alkylcarbonyl or C1-C6 haloalkyl;

$R^4$ is an aliphatic group or an aryl group optionally substituted with one or more substituents selected from halogen, alkyl, haloalkyl, $Ar^3$, $Ar^3$—$Ar^3$, —$OR^{50}$, —O(haloalkyl), —$SR^{50}$, —$NO_2$, —CN, —NCS, —$N(R^{51})_2$, —$NR^{51}C(O)R^{50}$, —$NR^{51}C(O)OR^{52}$, —$N(R^{51})C(O)N(R^{51})_2$, —$C(O)R^{50}$, —$C(S)R^{50}$, —$C(O)OR^{50}$, —$OC(O)R^{50}$, —$C(O)N(R^{51})_2$, —$S(O)_2R^{50}$, —$SO_2N(R^{51})_2$, —$S(O)R^{52}$, —$SO_3R^{50}$, —$NR^{51}SO_2N(R^{51})_2$, —$NR^{51}SO_2R^{52}$, —$V_4$—$Ar^3$, —V—$OR^{50}$, —$V_4$—O(haloalkyl), —$V_4$—$SR^{50}$, —$V_4$—$NO_2$, —$V_4$—CN, —$V_4$—$N(R^{51})_2$, —$V_4$—$NR^{51}C(O)R^{50}$, —$V_4$—$NR^{51}CO_2R^{52}$, —$V_4$—$N(R^{51})C(O)N(R^{51})_2$, —$V_4$—$C(O)R^{50}$, —$V_4$—$C(S)R^{50}$, —$V_4$—$CO_2R^{50}$, —$V_4$—$OC(O)R^{50}$, —$V_4$—$C(O)N(R^{51})_2$—, —$V_4$—$S(O)_2R^{50}$, —$V_4$—$SO_2N(R^{51})_2$, —$V_4$—$S(O)R^{52}$, —$V_4$—$SO_3R^{50}$, —$V_4$—$NR^{51}SO_2N(R^{51})_2$, —$V_4$—$NR^{51}SO_2R^{52}$, —O—$V_4$—$Ar^3$, —O—$V_5$—$N(R^{51})_2$, —S—$V_4$—$Ar^3$, —S—$V_5$—$N(R^{51})_2$, —$N(R^{51})$—$V_4$—$Ar^3$, —$N(R^{51})$—$V_5$—$N(R^{51})_2$, —$NR^{51}C(O)$—$V_4$—$N(R^{51})_2$, —$NR^{51}C(O)$—$V_4$—$Ar^3$, —$C(O)$—$V_4$—$N(R^{51})_2$, —$C(O)$—$V_4$—$Ar^3$, —$C(S)$—$V_4$—$N(R^{51})_2$, —$C(S)$—$V_4$—$Ar^3$, —$C(O)O$—$V_5$—$N(R^{51})_2$, —$C(O)O$—$V_4$—$Ar^3$, —O—$C(O)$—$V_5$—$N(R^{51})_2$, —O—$C(O)$—$V_4$—$Ar^3$, —$C(O)N(R^{51})$—$V_5$—$N(R^{51})_2$, —$C(O)N(R^{51})$—$V_4$—$Ar^3$, —$S(O)_2$—$V_4$—$N(R^{51})_2$, —$S(O)_2$—$V_4$—$Ar^3$, —$SO_2N(R^{51})$—$V_5$—$N(R^{51})_2$, —$SO_2N(R^{51})$—$V_4$—$Ar^3$, —$S(O)$—$V_4$—$N(R^{51})_2$, —$S(O)$—$V_4$—$Ar^3$, —$S(O)_2$—O—$V_5$—$N(R^{51})_2$, —$S(O)_2$—O—$V_4$—$Ar^3$, —$NR^{51}SO_2$—$V_4$—$N(R^{51})_2$, —$NR^{51}SO_2$—$V_4$—$Ar^3$, —O—$[CH_2]_{p'}$—O—, —S—$[CH_2]_{p'}$—S—, or —$[CH_2]_{q'}$—;

each $V_4$ is independently a C1-C10 alkylene group;
each $V_5$ is independently a C2-C10 alkylene group;
each $Ar^3$ is independently an aryl group each optionally substituted with one or more substituents selected from halogen, alkyl, amino, alkylamino, dialkylamino, alkoxy, nitro, cyano, hydroxy, haloalkoxy or haloalkyl; and each $R^{50}$ is independently
i) hydrogen;
ii) an aryl group optionally substituted with one or more substituents selected from halogen, alkyl, amino, alkylamino, dialkylamino, alkoxy, nitro, cyano, hydroxy, haloalkoxy, alkoxycarbonyl, alkylcarbonyl or haloalkyl; or
iii) an alkyl group optionally substituted with one or more substituents selected from halogen, amino, alkylamino, dialkylamino, alkoxy, nitro, cyano, hydroxy, haloalkoxy, alkoxycarbonyl, alkylcarbonyl or haloalkyl; and each $R^{51}$ is independently $R^{50}$, —$CO_2R^{50}$, —$SO_2R^{50}$ or —$C(O)R^{50}$; or —$N(R^{51})_2$ taken together is an optionally substituted non-aromatic heterocyclic group; and each $R^{52}$ is independently:
i) an aryl group optionally substituted with one or two substituents selected from halogen, alkyl, amino, alkylamino, dialkylamino, alkoxy, nitro, cyano, hydroxy, haloalkoxy, alkoxycarbonyl, alkylcarbonyl or haloalkyl; or ii) an alkyl group optionally substituted with one or more substituents selected from halogen, amino, alkylamino, dialkylamino, alkoxy, nitro, cyano, hydroxy, haloalkoxy, alkoxycarbonyl, alkylcarbonyl or haloalkyl; and each p' is 1, 2, 3 or 4; and
each q' is 3, 4, 5 or 6; and
$R^7$ is —H or C1-C6 alkyl.

2. The compound of claim 1, wherein —$N(R^2R^3)$ is a pyrrolidinyl group optionally substituted with one or more substituents selected from halogen, C1-C5 alkyl, C1-C5 haloalkyl, hydroxyl, C1-C5 alkoxy, nitro, cyano, C1-C5 alkoxycarbonyl, C1-C5 alkylcarbonyl or C1-C5 haloalkoxy, amino, C1-C5 alkylamino or C1-C5 dialkylamino.

3. The compound of claim 2, represented by the following structural formula:

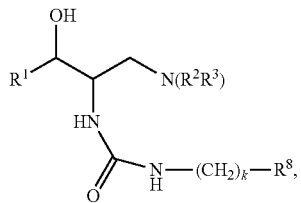

or a pharmaceutically acceptable salt thereof, wherein:
$R^8$ is —H, or an aryl or C1-C6 alkyl group each optionally and independently substituted with one or more substituents selected from halogen, C1-C10 alkyl, C1-C10 haloalkyl, $Ar^3$, —$OR^{50}$, —O(haloalkyl), —$SR^{50}$, —$NO_2$, —CN, —$N(R^{51})_2$, —$NR^{51}C(O)R^{50}$, —$C(O)R^{50}$, —$C(O)OR^{50}$, —$OC(O)R^{50}$, —$C(O)N(R^{51})_2$, —$V_4$—$Ar^3$, —V—$OR^{50}$, —$V_4$—O(haloalkyl), —$V_4$—$SR^{50}$, —$V_4$—$NO_2$, —$V_4$—CN, —$V_4$—$N(R^{51})_2$, —$V_4$—$NR^{51}C(O)R^{50}$, —$V_4$—$C(O)R^{50}$, —$V_4$—$CO_2R^{50}$, —$V_4$—$OC(O)R^{50}$, —$V_4$—$C(O)N(R^{51})_2$—, —O—$V_4$—$Ar^3$, —O—$V_5$—$N(R^{51})_2$, —S—$V_4$—$Ar^3$, —S—$V_5$—$N(R^{51})_2$, —$N(R^{51})$—$V_4$—$Ar^3$, —$N(R^{51})$—$V_5$—$N(R^{51})_2$, —$NR^{51}C(O)$—$V_4$—$N(R^{51})_2$, —$NR^{51}C(O)$—$V_4$—$Ar^3$, —$C(O)$—$V_4$—$N(R^{51})_2$, —$C(O)$—$V_4$—$Ar^3$, —$C(O)O$—$V_5$—$N(R^{51})_2$, —$C(O)O$—$V_4$—$Ar^3$, —O—$C(O)$—$V_5$—$N(R^{51})_2$, —O—$C(O)$—$V_4$—$Ar^3$, —$C(O)N(R^{51})$—$V_5$—$N(R^{51})_2$, —$C(O)N(R^{51})$—$V_4$—$Ar^3$, —O—$[CH_2]_{p'}$—O— or —$[CH_2]_{q'}$—; and
k is 0, 1, 2, 3, 4, 5 or 6.

4. A pharmaceutical composition comprising a pharmaceutically acceptable carrier and the compound of claim 1, or a pharmaceutically acceptable salt thereof.

5. A method of treating a subject having type 2 diabetes, comprising administering to the subject a therapeutically effective amount of the compound of claim 1, or a pharmaceutically acceptable salt thereof.

6. A method of treating a subject having renal hypertrophy or hyperplasia associated with diabetic nephropathy, comprising administering to the subject a therapeutically effective amount of the compound of claim 1, or a pharmaceutically acceptable salt thereof.

7. A method of decreasing plasma TNF-α in a subject in need thereof, comprising administering to the subject a therapeutically effective amount of the compound of claim 1, or a pharmaceutically acceptable salt thereof.

8. A method of lowering blood glucose levels in a subject in need thereof, comprising administering to the subject a therapeutically effective amount of the compound of claim 1, or a pharmaceutically acceptable salt thereof.

9. A method of decreasing glycated hemoglobin levels in a subject in need thereof, comprising administering to the subject a therapeutically effective amount of the compound of claim 1, or a pharmaceutically acceptable salt thereof.

10. A method of inhibiting glucosylceramide synthase or lowering glycosphingolipid concentrations in a subject in need thereof, comprising administering to the subject a therapeutically effective amount of the compound of claim 1, or a pharmaceutically acceptable salt thereof.

11. A method of treating a subject with Tay-Sachs, Gaucher's or Fabry's disease, comprising administering to the subject a therapeutically effective amount of the compound of claim 1, or a pharmaceutically acceptable salt thereof.

12. The compound of claim 1, wherein the compound is a (1R,2R) stereoisomer.

13. The compound of claim 2, wherein $R^7$ is —H, and $R^4$ is an optionally substituted aryl or arylalkyl group.

14. The compound of claim 13, wherein $R^4$ is an aryl or arylalkyl group each optionally and independently substituted with one or more substituents selected from halogen, C1-C10 alkyl, C1-C10 haloalkyl, $Ar^3$, —$OR^{50}$, —O(haloalkyl), —$SR^{50}$, —$NO_2$, —CN, —$N(R^{51})_2$, —$NR^{51}C(O)R^{50}$, —$C(O)R^{50}$, —$C(O)OR^{50}$, —$OC(O)R^{50}$, —$C(O)N(R^{51})_2$, —$V_4$—$Ar^3$, —$V_4$—$OR^{50}$, —$V_4$—O(haloalkyl), —$V_4$—$SR^{50}$, —$V_4$—$NO_2$, —$V_4$—CN, —$V_4$—$N(R^{51})_2$, —$V_4$—$NR^{51}C(O)R^{50}$, —$V_4$—$C(O)R^{50}$, —$V_4$—$CO_2R^{50}$, —$V_4$—$OC(O)R^{50}$, —$V_4$—$C(O)N(R^{51})_2$—, —O—$V_4$—$Ar^3$, —O—$V_5$—$N(R^{51})_2$, —S—$V_4$—$Ar^3$, —S—$V_5$—$N(R^{51})_2$, —$N(R^{51})$—$V_4$—$Ar^3$, —$N(R^{51})$—$V_5$—$N(R^{51})_2$, —$NR^{51}C(O)$—$V_4$—$N(R^{51})_2$, —$NR^{51}C(O)$—$V_4$—$Ar^3$, —C(O)—$V_4$—$N(R^{51})_2$, —C(O)—$V_4$—$Ar^3$, —C(O)O—$V_5$—$N(R^{51})_2$, —C(O)O—$V_4$—$Ar^3$, —O—C(O)—$V_5$—$N(R^{51})_2$, —O—C(O)—$V_4$—$Ar^3$, —C(O)$N(R^{51})$—$V_5$—$N(R^{51})_2$, —C(O)$N(R^{51})$—$V_4$—$Ar^3$, —O—$[CH_2]_{p'}$—O— or —$[CH_2]_{q'}$—, wherein arylalkyl includes straight and branched saturated chains containing one to six carbon atoms.

15. The compound of claim 3, wherein $R^8$ is selected from:

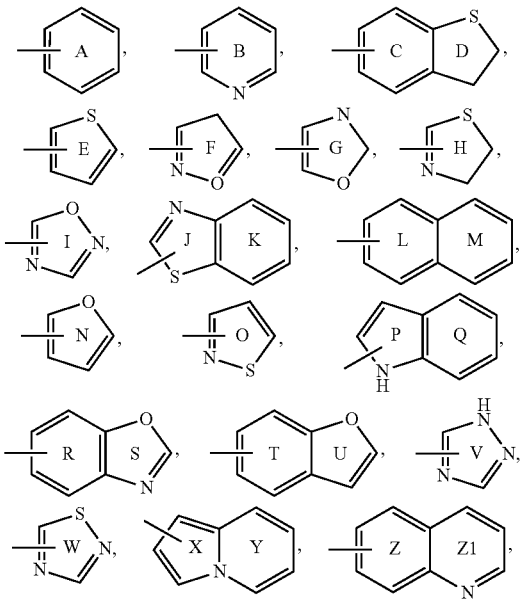

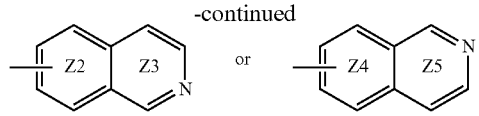

wherein:
each of rings A-Z5 is optionally substituted.

16. The compound of claim 15, wherein —$N(R^2R^3)$ is an unsubstituted pyrrolidinyl group.

17. The compound of claim 16, wherein each of rings A-Z5 is optionally substituted with one or more substituents selected from halogen, cyano, nitro, C1-C10 alkyl, C1-C10 haloalkyl, amino, C1-C10 alkylamino, C1-C10 dialkylamino, aryl, aryloxy, hydroxy, C1-10 alkoxy, —O—$[CH_2]_p$—O— or —$[CH_2]_q$—.

18. The compound of claim 17, wherein:
—$N(R^2R^3)$ is pyrrolidinyl; and
the phenyl group represented by $R^1$ is optionally substituted with one or more substituents selected from —OH, —$OCH_3$, —$OC_2H_5$ or —O—$[CH_2]_p$—O—.

19. The compound of claim 1, represented by one of the following structural formulas:

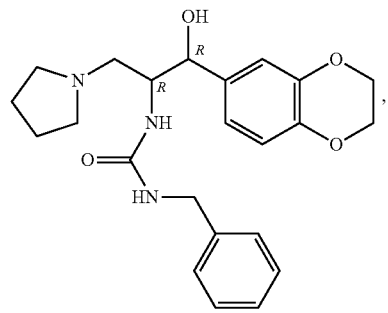

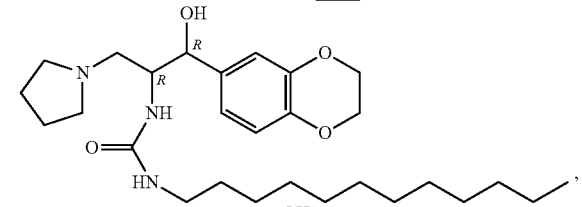

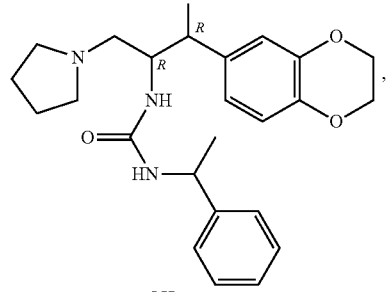

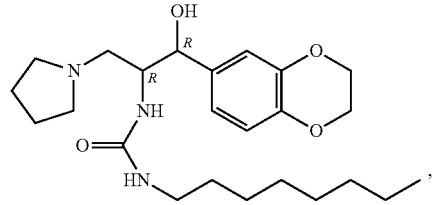

521
-continued
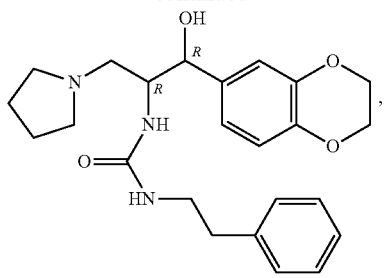,
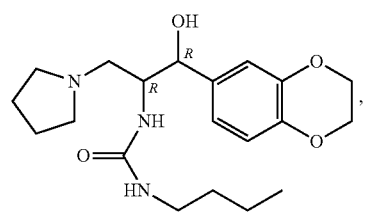,
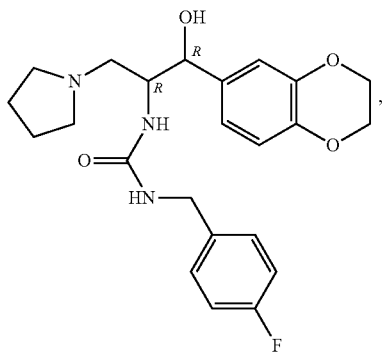,
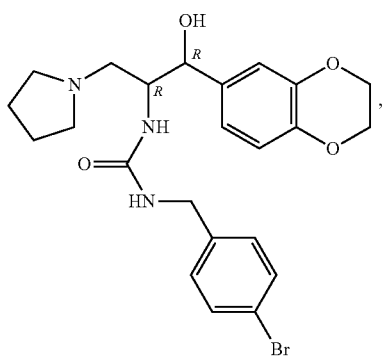,
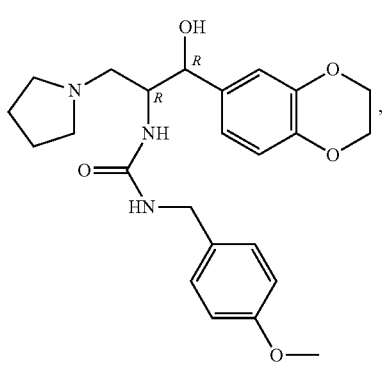,
522
-continued
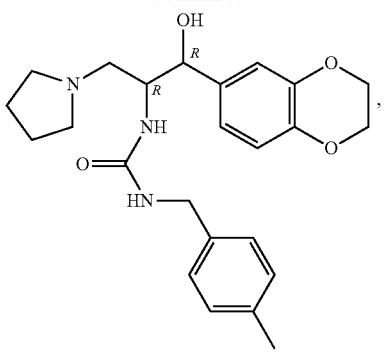,
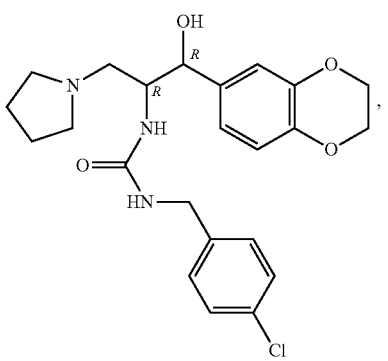,
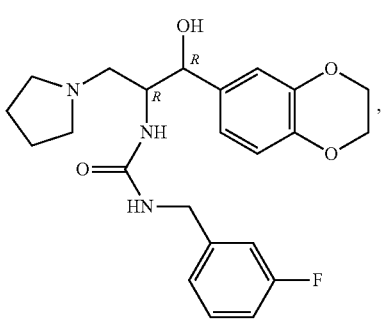,
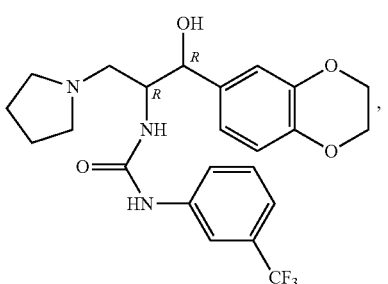,
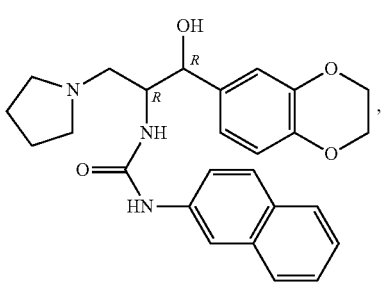, 523
-continued
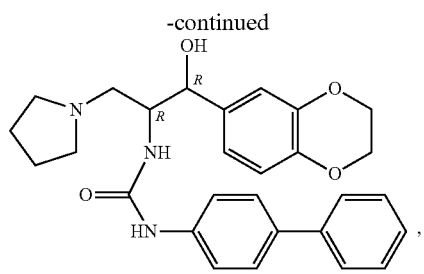,
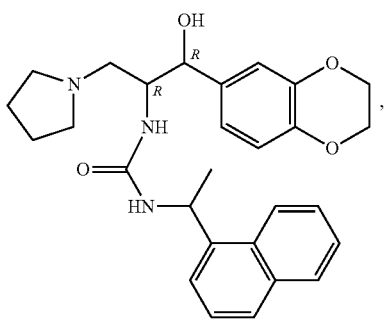,
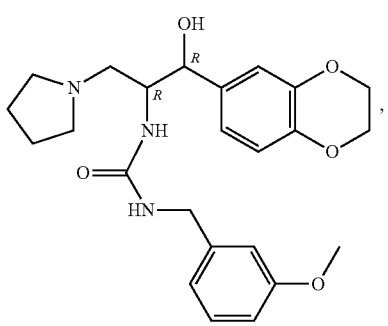,
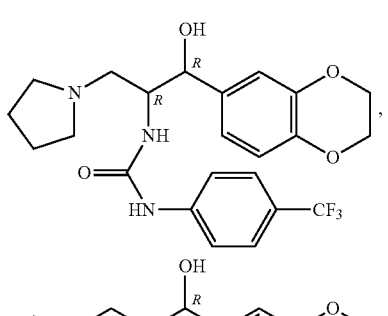,
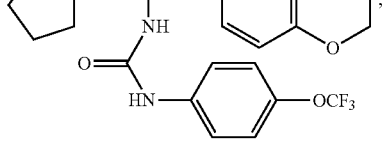,
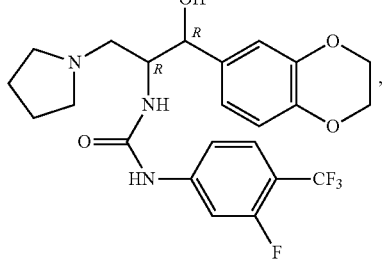,
524
-continued
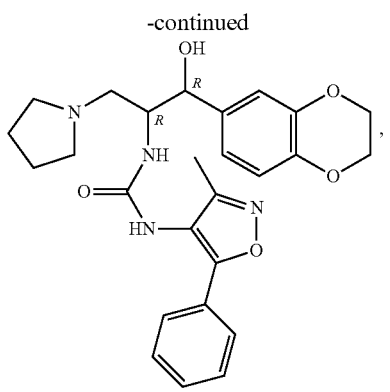,
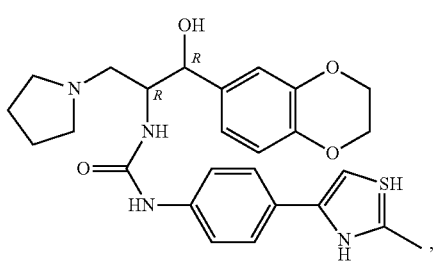,
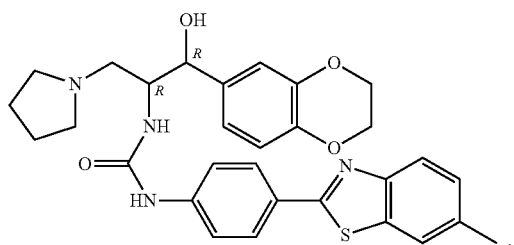,
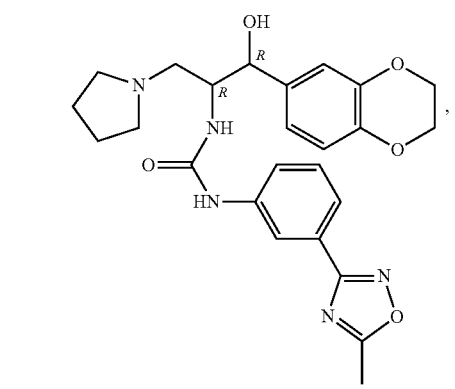,
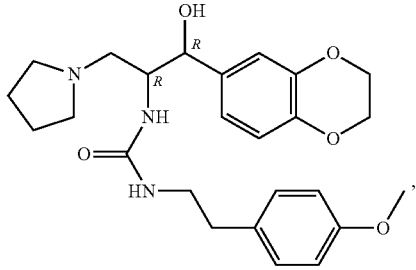, 525
-continued
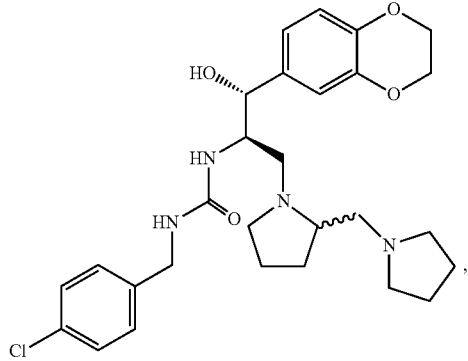
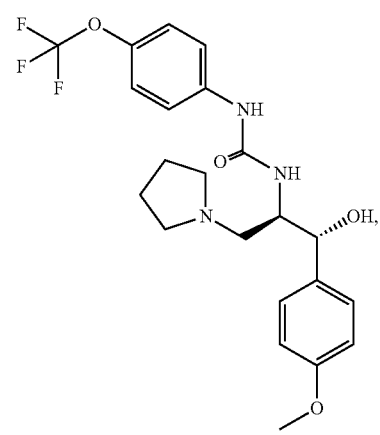
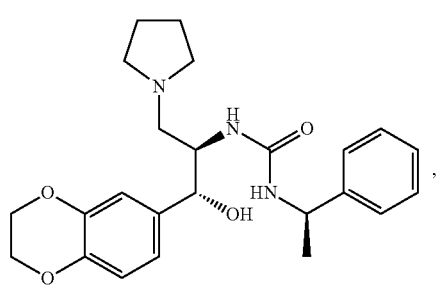
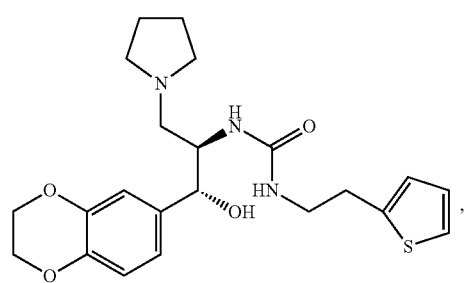
526
-continued
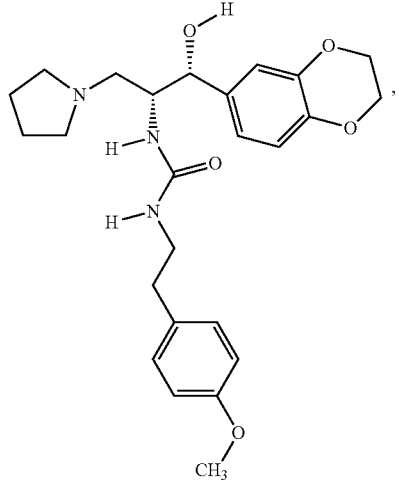
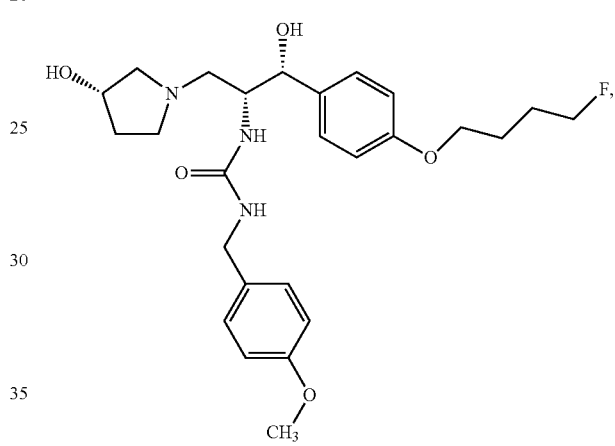
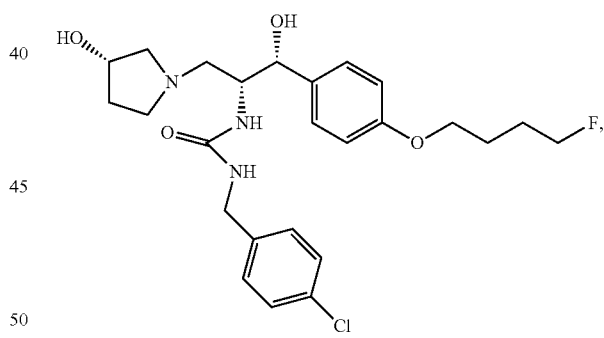
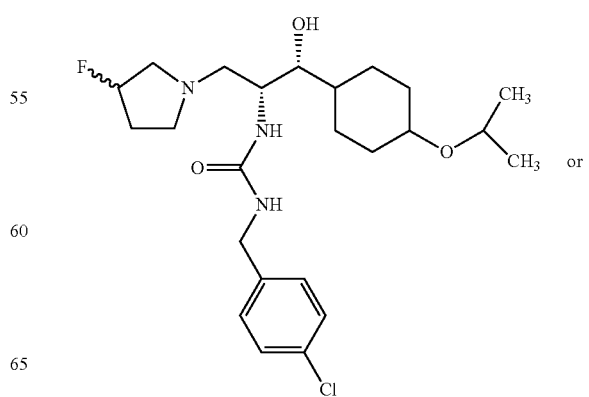

-continued
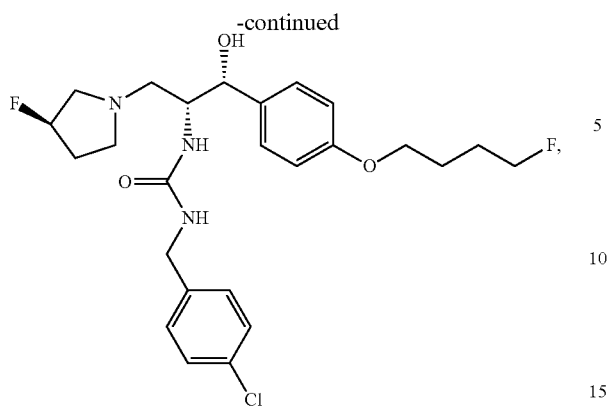
or a pharmaceutically acceptable salt of any of the foregoing.
* * * * *

UNITED STATES PATENT AND TRADEMARK OFFICE
CERTIFICATE OF CORRECTION

PATENT NO. : 8,940,776 B2
APPLICATION NO. : 13/595349
DATED : January 27, 2015
INVENTOR(S) : Craig Siegel et al.

It is certified that error appears in the above-identified patent and that said Letters Patent is hereby corrected as shown below:

In the Claims,

In Claim 15, Column 519, lines 43-50, please remove the structural formulas and insert the following structural formulas:

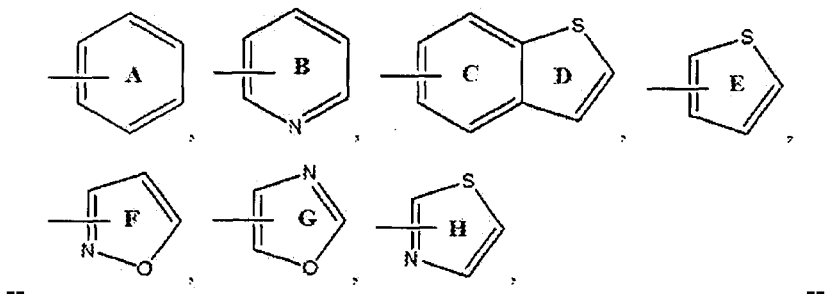

--

In Claim 19, Column 526, lines 21-37, please remove the structural formula and insert the following structural formula:

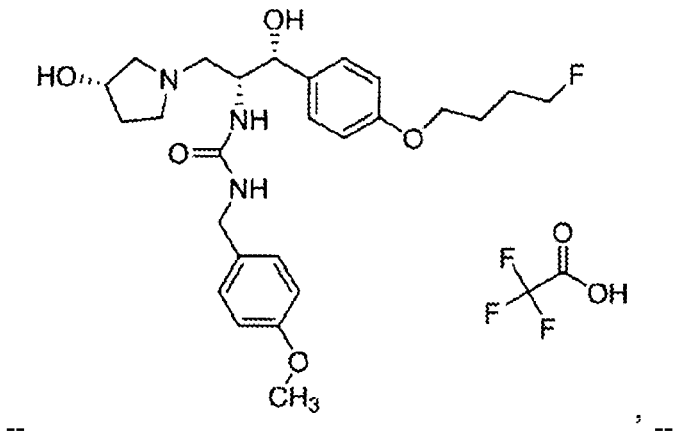

--

Signed and Sealed this
Second Day of June, 2015

Michelle K. Lee
*Director of the United States Patent and Trademark Office*